United States Patent
Ittig et al.

(10) Patent No.: US 12,358,955 B2
(45) Date of Patent: *Jul. 15, 2025

(54) VIRULENCE ATTENUATED BACTERIA BASED PROTEIN DELIVERY

(71) Applicant: UNIVERSITÄT BASEL, Basel (CH)

(72) Inventors: Simon Ittig, Bottmingen (CH); Marlise Amstutz, Basel (CH); Christoph Kasper, Olten (CH)

(73) Assignee: Universitaet Basel, Basel (CH)

(*) Notice: Subject to any disclaimer, the term of this patent is extended or adjusted under 35 U.S.C. 154(b) by 253 days.

This patent is subject to a terminal disclaimer.

(21) Appl. No.: 18/047,586

(22) Filed: Oct. 18, 2022

(65) Prior Publication Data

US 2023/0250138 A1 Aug. 10, 2023

Related U.S. Application Data

(63) Continuation of application No. 16/471,264, filed as application No. PCT/EP2017/083853 on Dec. 20, 2017, now Pat. No. 11,518,789.

(30) Foreign Application Priority Data

Dec. 20, 2016 (EP) ..................... 16205439

(51) Int. Cl.
*C07K 14/24* (2006.01)
*A61K 38/00* (2006.01)
*A61P 35/00* (2006.01)
*C12N 1/20* (2006.01)
*C12N 1/36* (2006.01)
*C12N 15/74* (2006.01)

(52) U.S. Cl.
CPC .............. *C07K 14/24* (2013.01); *A61P 35/00* (2018.01); *C12N 1/20* (2013.01); *C12N 1/36* (2013.01); *C12N 15/74* (2013.01); *A61K 38/00* (2013.01); *C07K 2319/02* (2013.01); *C07K 2319/036* (2013.01); *C07K 2319/21* (2013.01); *C07K 2319/41* (2013.01); *C07K 2319/50* (2013.01)

(58) Field of Classification Search
CPC ...................................... C07K 14/24
See application file for complete search history.

(56) References Cited

U.S. PATENT DOCUMENTS

| | | | |
|---|---|---|---|
| 6,602,506 B1 | 8/2003 | Van et al. | |
| 7,763,420 B2 | 7/2010 | Stritzker et al. | |
| 10,889,823 B2 | 1/2021 | Arrieumerlou et al. | |
| 11,166,987 B2 | 11/2021 | Ittig et al. | |
| 11,518,789 B2 * | 12/2022 | Ittig | C12N 15/74 |
| 2004/0147719 A1 | 7/2004 | Cornelis | |
| 2008/0187520 A1 | 8/2008 | Polack et al. | |
| 2011/0183908 A1 | 7/2011 | Rueter et al. | |
| 2015/0140037 A1 | 5/2015 | Galan et al. | |
| 2017/0198297 A1 | 7/2017 | Arrieumerlou et al. | |
| 2019/0015497 A1 | 1/2019 | Ittig et al. | |
| 2019/0194670 A1 | 6/2019 | Ittig et al. | |
| 2021/0155942 A1 | 5/2021 | Arrieumerlou et al. | |
| 2024/0165169 A1 | 5/2024 | Ittig et al. | |
| 2024/0165265 A1 | 5/2024 | Ittig et al. | |

FOREIGN PATENT DOCUMENTS

| | | |
|---|---|---|
| WO | WO 89/03427 | 4/1989 |
| WO | WO 9945098 | 9/1999 |
| WO | WO 200002996 | 1/2000 |
| WO | WO 0226819 | 4/2002 |
| WO | WO 2002077249 | 10/2002 |
| WO | WO 2007044406 | 4/2007 |
| WO | WO 2008019183 | 2/2008 |
| WO | WO 2009115531 | 9/2009 |
| WO | WO 2014/138324 | 9/2014 |
| WO | WO 2015042705 | 4/2015 |
| WO | WO 2015177197 | 11/2015 |
| WO | 2017024000 A1 | 2/2017 |
| WO | 2017085235 A1 | 5/2017 |
| WO | WO 2018115140 | 6/2018 |
| WO | 2018136617 A2 | 7/2018 |
| WO | 2019203965 A1 | 10/2019 |

OTHER PUBLICATIONS

Covone et al., Infection and Immunity, 1998; 66(1):224-231 (Year: 1998).*
Spreng et al., Vaccine, 2005; 23: 2060-2065 (Year: 2005).*
Dittmann et al., "The Yersinia enterocolitica type three secretion chaperone SycO is integrated into the Yop regulatory network and binds to the Yop secretion protein YscM1", BMC Microbiol., Jul. 5, 2007, 7(67):1-10.
Harrington et al., "Phase I, first-in-human trial evaluating BI 1387446 (stimulator of interferon genes [STING] agonist) alone and combined with BI 754091 (anti-programmed cell death [PD]-1) in solid tumors", The Journal for Immuno Therapy of Cancer, Nov. 9, 2020, 8(Suppl 3)::A433-A433.
Kong et al., "A combination of PD-1/PD-L1 inhibitors: The prospect of overcoming the weakness of tumor immunotherapy (Review)", Mol Med Rep., Mar. 16, 2021, 23(5):362. (16 pages).
Xu et al., "Structural basis for the prion-like MAVS filaments in antiviral innate immunity", Elife, Jan. 1, 2014, 3:e01489. (25 pages).
Ziemann et al., "Gene name errors are widespread in the scientific literature", Genome Biol., Aug. 23, 2016, 17(177): 3 pages.
Ahmed Kamal et al., (2014) "Apoptosi s-inducing agents: a patent review (2010-2013)", Expert Opinion on Therapeutic Patents, 1(3):339-354.

(Continued)

*Primary Examiner* — Brian Gangle
*Assistant Examiner* — Lakia J Jackson-Tongue
(74) *Attorney, Agent, or Firm* — Shweta Chandra; Bozicevic, Field & Francis LLP

(57) ABSTRACT

The present invention relates to recombinant virulence attenuated Gram-negative bacterial strains and its use in a method of treating cancer in a subject.

29 Claims, 68 Drawing Sheets

Specification includes a Sequence Listing.

(56) References Cited

OTHER PUBLICATIONS

Akeda, Y &, Galan J.E. (2005) "Chaperone release and unfolding of substrates in type III secretion"; Nature 437; pp. 911-915.
Bohme et al., (2012) "Concerted Actions of a Thermo-labile Regulator and a Unique Intergenic RNA Thermosensor Control Yersinia Virulence", Plos Pathogens, 8(2): e1002518, XP055365892.
Bowie et al., (1990) "Deciphering the Message in Protein Sequences: Tolerance to Amino Acid Substitutions", Science, 247:1306-1310.
Boyd AP, et al (2000) "Yersinia enterocolitica can deliver Yop proteins into a wide range of cell types: development of a delivery system for heterologous proteins"; Eur J Cell Biol.79(10); pp. 659-671.
Briones et al., (2006) "Cre Reporter System to Monitor the Translocation of Type III Secreted Proteins into Host Cells", Infection and Immunity, 1084-1090.
Burdette et al., (2018) "Developing Gram-negative bacteria for the secretion of heterologous proteins", Microb Cell Fact, 17(196):1-16.
Burgess et al., (1990) "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" The Journal of Cell Biology, 111:2129-2138.
Cardenal-Munoz, and Ramos-Morales (2011) "Analysis of the Expression, Secretion and Translocation of the *Salmonella enterica* Type III Secretion System Effector SteA"; PLOS ONE 6(10); pp. 1-13.
Chamekh et al., (2008) "Delivery of 1 Biologically Active Anti-Inflammatory Cytokines IL-10 and IL-1ra In Vivo by the Shigella Type III Secretion Apparatus", The Journal of Immunology, 180(6):4292-4298.
Chen, Li-Mei, et al., (2006) "Optimization of the Delivery of Heterologous Proteins by the *Salmonella enterica* Serovar Typhimurium Type III Secretion System for Vaccine Development", Infection and Immunity, 74(10):5826-5833.
Corrales et al., (2014) "Direct activation of STING in the tumor microenvironment with synthetic cyclic dinucleotide derivatives leads to potent and systemic tumor-specific immunity", Journal for Immunotherapy of Cancer, 2(3):010, XP021202342.
Culliton, Barbara J. (1986) "NIH considers major change in definition of recombinant DNA"; Science 2344773); pp. 146.
De et al., (2009) "Determinants for the Activation and Autoinhibition of the Diguanylate Cyclase Response Regulator WspR", Journal of Molecular Biology, 393(3):619-633, XP026676221.
Feldman M. et al. (2002) "SycE allows secretion of YopE-DHFR hybrids by the Yersinia enterocolitica type III Ysc system"; Molecular Microbiology 46(4); pp. 1183-1197.
Fensterle J et al, (2008) "Cancer immunotherapy based on recombinant *Salmonella enterica* serovar Typhimurium aroA strains secreting prostate-specific antigen and cholera toxin subunit B", Cancer Gene Therapy, Appleton & Lange, GB, 15(2):85-93.
Garcia, Julie Torruellas, et al., (2006) "Measurement of Effector Protein Injection by Type III and Type IV Secretion Systems by Using a 13-Residue Phosphorylatable Glycogen Synthase Kinase Tag", Infection and Immunity, 74(10):5645-5657.
Gentschev Ivaylo et al, (2005) "Use of a recombinant *Salmonella enterica* serovar Typhimurium strain expressing C-Raf for protection against C-Raf induced lung adenoma in mice", BMC Cancer, Biomed Central, London, GB, 5(1):1-9.
Gosh P. (2004) "Process of Protein Transport by the Type III Secretion System"; Microbiology and Molecular Biology Reviews 68(4); pp. 771-795.
Höppner, (2002) "Clinical Impact of Molecular Diagnostics in Endocrinology", Harm Research, 58(3):7-15.
Iriarte, Maite, et al., (1998) "TyeA, a protein involved in control of Yop release and in translocation of Yersinia Yop effectors", The EMBO Journal, 17(7):1907-1918.
Ittig et al., (2015) "A bacterial type III secretion-based protein delivery tool for broad applications in cell biology", The Journal of Cell Biology : JCB, 211(4):913-931.
Jacobi, C. A. et al. (1998) "In vitro and in vivo expression studies of yopE from Yeresinia enterocolitica using the gfp reporter gene"; Molecular microbiology 30(4); pp. 865-882.
Karavolos et al. (2015) "Type III Secretion of the *Salmonella* Effector Protein SopE is Mediated via an N-Terminal Amino Acid Signal and Not an mRNA Sequence"; Journal of Bacteriology 187(5); pp. 1559-1567.
Lazar et al., (1988) Transforming Growth Factor α: Mutation of Aspartic Acid 47 and Leucine 48 Results in Different Biological Activities, Molecular and Cellular Biology, 8(3):1247-1252.
Lee, V. T. & Schneewind, O. (2002) "Yop Fusions to Tightly Folded Protein Domains and Their Effects on Yersinia enterocolitica Type III Secretion"; Journal of Bacteriology, vol. 184, No. 13; pp. 3740-3745.
Letzelter., (2006) "The discovery of SycO reveals a new function for Type Three Secretion Effector Chaperones", Biozentrum University of Basel, 1-101.
Li et al., (2014) "Tumor suppressor activity of RIG-I", Molecular & Celluar Oncology, 1(4): e968016, XP055366048.
Lloyd et al (2001) "Yersinian YopE is targeted for Type III secretion by N-terminal, not mRNA, signals"; Molecular Microbiology 39(2); pp. 520-531.
Mota and Cornelis (2005) "The bacterial injection kit: type III secretion systems"; Ann Med.37(4); pp. 234-249.
Russmann et al., (2001) "Protection Against Murine Listeriosis by Oral Vaccination with Recombinant *Salmonella* Expressing Hybrid Yersinia Type III Proteins", The Journal of Immunology, 167(1):357-365.
Stadler et al., (2014) "The use of a neutral peptide aptamer scaffold to anchor BH3 peptides constitutes a viable approach to studying their function", Cell Death and Disease, 5(1):1-9.
Viboud et al., "Yersinia Outer Proteins: Role in Modulation of Host Cell Signaling Responses and Pathogensis", Annu. Rev. Microbial. 2005, 59:69-89.
Wiedig, et al. (2005) "Induction of CD8+ T cell responses by Yersinia vaccine carrier strains"; Vaccine.23(42); pp. 4984-4998.
Wu et al., (2014) "Innate Immune Sensing and Signaling of Cytosolic Nucleic Acids", Annual Review of Immunology, 32(1):461-488, XP055366371.
Y. Zhang et al., (2011) "Type III Secretion System-Dependent Translocation of Ectopically Expressed Yop Effectors into Macrophages by Intracellular Yersinia pseudotuberculosis", Infection and Immunity, 79(11):4322-4331.
Letzelter, (2006) The discovery of SycO reveals a new function for Type Three Secretion Effector Chaperones (dissertation).
Blanco-Toribio et al., (2010) "Direct Injection of Functional Single-Domain Antibodies from *E. coli* into Human Cells.", PLOS One,5(12):1-12, e15227.
Colussi et al., (1998) "Conversion of Procaspase-3 to an Autoactivating Caspase by Fusion to the Caspase-2 Prodomain.", Journal of Biological Chemistry, 273(41):26566-26570.
Costantini et al., (2015) "Going Viral with Fluorescent Proteins", Journal of Virology, 89(19):9706-9708.
Hopp et al., (1988) "A Short Polypeptide Marker Sequence Useful for Recombinant Protein Identification and Purification", Biotechnology, 6:1204-1210.
Le Rouzic and Benichou, (2005) "The Vpr protein from HIV-1: distinct roles along the viral life cycle.", Retrovirology, 2(11):1-14.
Li et al., (2006) "Ankyrin repeat: a unique motif mediating protein-protein interactions.", Biochemistry,45:15168-15178.
Lu et al., (2021) "Types of nuclear localization signals and mechanisms of protein import into the nucleus" Cell Commun Signal, 19(60):1-10.
Park et al., (2018) "Structure of TRAF Family: Current Understanding of Receptor Recognition.", Frontiers in Immunology, 9(1999):1-7.
Perron-Savard et al., (2005) "Dimerization and DNA binding of the *Salmonella enterica* PhoP response regulator are phosphorylation independent", Microbiology, 151:3979-3987.

(56) References Cited

OTHER PUBLICATIONS

Reed et al., (2004) "The Domains of Apoptosis: A Genomics Perspective.", Science STKE, 2004(239):re9.
Schweizer et al., (2003) "Crystal Structure of Caspase-2, Apical Initiator of the Intrinsic Apoptotic Pathway.", Journal of Biological Chemistry, 278(43):42441-42447.
Swulius et al., (2012) "The Helical MreB Cytoskeleton in *Escherichia coli* MC1000/pLE7 is an Artifact of the N-Terminal Yellow Fluorescent Protein Tag", Journal of Biology, 194(23):6382-6386.
Uchida (2012) "Databases and software to make your research life easier", Woodhead Publishing Limited, 1-41.
Van Den Berg et al., (2006) "Improved solubility of TEV protease by directed evolution", Journal of Biotechnology, 121:291-298.
U.S. Appl. No. 18/806,599, Titled "Bacteria-Based Protein Delivery", filed Aug. 15, 2024.
Anderson et al., (1999) "Reciprocal secretion of proteins by the bacterial type III machines of plant and animal pathogens suggests universal recognition of mRNA targeting signals", PNAS, 96(22): 12839-12843.
Covone et al., (1998) "Levels of Expression and Immunogenicity of Attenuated Salmonella enterica Serovar Typhimurium Strains Expressing Escherichia coli Mutant Heat-Labile Enterotoxin", Infection and Immunity, 224-231. Not legible; clear copy attached.
Curtiss III et al., (1990) "Stabilization of Recombinant Avirulent Vaccine Strains in Vivio", Res. Microbiol., 141:797-805.
Reeves et al., (2015) "Engineering Escherichia coli into a Protein Delivery System for Mammalian Cells", ACS Synth. Biol., 644-654.
Sory et al., (1990) "Oral Immunization of Mice with a Live Recombinant Yersinia enterocolitica 0:9 Strain That Produces the Cholera Toxin B Subunit", Infection and Immunity, 2420-2428.
Spreng et al., (2005) "Plasmid maintenance systems suitable for GMO-based bacterial vaccines", Vaccine, 23:2060-2065. not legible; clear copy has attached.

\* cited by examiner

Figure 3A

| Strain Name | Background strain | Insert/relevant characteristics | Protein to be delivered by T3SS | Backbone plasmid | Resulting plasmid name | Primers. SI_Nr.: | resistances | Reference |
|---|---|---|---|---|---|---|---|---|
| ΔHOPEMT | Y. enterocolitica | MRS40 pIML421 [yopHΔ1-352, yopOΔ65-558, yopP23, yopE21, yopM23, yopT135] | | | | | Nal | Iriarte and Cornelis, 1998 |
| ΔHOPEMT asd yopB | Y. enterocolitica ΔyopH,O,P,E,M,T | MRS40 pIML421 [yopBΔ89-217, yopHΔ1-352, yopOΔ65-558, yopP23, yopE21, yopM23, yopT135] | | | | | Nal Kan | |
| ΔHOPEMT asd | Y. enterocolitica ΔyopH,O,P,E,M,T | MRS40 asdΔ292-610 pIML421 [yopHΔ1-352, yopOΔ65-558, yopP23, yopE21, yopM23, yopT135] | | | | | Nal | Kudryashev et al., 2013 |
| ΔHOPEMT asd inv | Y. enterocolitica ΔyopH,O,P,E,M,T | MRS40 asdΔ292-610 invAΔ352-2225::aphA-3 pIML421 [yopHΔ1-352, yopOΔ65-558, yopP23, yopE21, yopM23, yopT135] | | | | 445/446, 447/448, 449/450 | Nal Kan | |
| ΔHOPEMT asd inv yadA | Y. enterocolitica ΔyopH,O,P,E,M,T ΔinvA ΔyadA | MRS40 asdΔ292-610 invAΔ587-836 (vector cointegration) yadAΔ89-354::aphA3 pIML421 [yopHΔ1-352, yopOΔ65-558, yopP23, yopE21, yopM23, yopT135] | | | | 352/353, 354/355, 356/357 | Nal Kan Tet | |

Figure 3B

| Strain Name | Background strain | Insert/relevant characteristics | Protein to be delivered by T3SS | Backbone plasmid | Resulting plasmid name | Primers. Si_Nr.: | resistances | Reference |
|---|---|---|---|---|---|---|---|---|
| ΔHOPEMT asd pBad_Si1 | Y. enterocolitica ΔyopH,O,P,E,M,T Δasd | EGFP (Arabinose inducible), SycE-YopE1-138-MycHis fragment | | pBad-MycHisA (Invitrogen) | pBad_Si_1 | 285/286 (EGFP), 287/288 (sycE-YopE1-138) | Nal Amp | |
| ΔHOPEMT asd pBad_Si2 | Y. enterocolitica ΔyopH,O,P,E,M,T Δasd | SycE-YopE1-138-MycHis fragment | YopE1-138-MycHis | pBad-MycHisA (Invitrogen) | pBad_Si_2 | 287/288 (sycE-YopE1-138) | Nal Amp | |
| ΔHOPEMT asd pSi_85 | Y. enterocolitica ΔyopH,O,P,E,M,T Δasd | | YopE1-138-Bid | pBad_Si_2 | pSi_85 | 387/391 | Nal Amp | |
| ΔHOPEMT asd pSi_87 | Y. enterocolitica ΔyopH,O,P,E,M,T Δasd | | YopE1-138-t-Bid | pBad_Si_2 | pSi_87 | 389/391 | Nal Amp | |

Figure 3C

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pSi_120 | Y. enterocolitica ΔyopH,O,P,E,M,T Δasd | | YopE1-138-ET1 | pBad_Si_2 | pSi_120 | 436/437 | Nal Amp | |
| ΔHOPEMT asd pSi_121 | Y. enterocolitica ΔyopH,O,P,E,M,T Δasd | | YopE1-138-z-BIM | pbad_Si_1 | pSi_121 | 438/439 | Nal Amp | |
| ΔHOPEMT asd pSi_132 | Y. enterocolitica ΔyopH,O,P,E,M,T Δasd | | YopE1-138-TEV protease S219V | pBad_Si_2 | pSi_132 | 463/464 | Nal Amp | |
| ΔHOPEMT asd pSi_158 | Y. enterocolitica ΔyopH,O,P,E,M,T Δasd | | YopE1-138 - 2xTEVsite - EGFP | pBad_Si_2 | pSi_158 | 511/476 | Nal Amp | |
| ΔHOPEMT asd pSi_151 | Y. enterocolitica ΔyopH,O,P,E,M,T Δasd | | YopE1-138-Ink4C | pBad_Si_2 | pSi_151 | 494/495 | Nal Amp | |

Figure 3D

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pSi_156 | Y. enterocolitica ΔyopH,O,P,E,M,T Δasd | | YopE1-138-2x TEVsite - ET1 | pBad_Si_2 | pSi_156 | 504/505 | Nal Amp | |
| ΔHOPEMT asd pSi_159 | Y. enterocolitica ΔyopH,O,P,E,M,T Δasd | | YopE1-138-2xTEVsite - EGFP - NLS | pBad_Si_2 | pSi_159 | 511/513 | Nal Amp | |
| ΔHOPEMT asd pSi_160 | Y. enterocolitica ΔyopH,O,P,E,M,T Δasd | | YopE1-138-2xTEVsite - NLS - EGFP | pBad_Si_2 | pSi_160 | 512/476 | Nal Amp | |
| ΔHOPEMT asd pSi_161 | Y. enterocolitica ΔyopH,O,P,E,M,T Δasd | | YopE1-138-2x TEVsite - INK4C | pBad_Si_2 | pSi_161 | 508/509 | Nal Amp | |
| ΔHOPEMT asd pSi_164 | Y. enterocolitica ΔyopH,O,P,E,M,T Δasd | | YopE1-138-2x TEVsite - Flag - INK4C | pBad_Si_2 | pSi_164 | 515/509 | Nal Amp | |

Figure 3E

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pSi_318 | Y. enterocolitica ΔyopH,O,P,E,M,T Δasd | | YopE1-138-Y. enterocolitica codon optimized murine tBid BH3 part | pBad_Si_2 | pSi_318 | 677/678 | Nal Amp | |
| ΔHOPEMT asd pSi_322 | Y. enterocolitica ΔyopH,O,P,E,M,T Δasd | | YopE1-138-Y. enterocolitica codon optimized murine Bax BH3 part | pBad_Si_2 | pSi_322 | 682/683 | Nal Amp | |
| S. enterica SL1344 ΔaroA | S. enterica subsp. enterica serovar Typhimurium SL1344 ΔaroA | | | | | | | Hoiseth and Stocker, 1981 |
| ΔHOPEMT asd pSi_315 | Y. enterocolitica ΔyopH,O,P,E,M,T Δasd | | YopE1-138-Y. enterocolitica codon optimized murine tBid | pBad_Si_2 | pSi_315 | synthetic construct | Nal Amp | |
| ΔHOPEMT asd pSi_236 | Y. enterocolitica ΔyopH,O,P,E,M,T Δasd | | YopE1-138-Ubiquitin | pBad_Si_2 | pSi_236 | 585/586 | Nal Amp | |
| ΔHOPEMT asd pSi_237_II | Y. enterocolitica ΔyopH,O,P,E,M,T Δasd | | YopE1-138-Ubiquitin-Flag-INK4C-MycHis | pSi_236 | pSI_237_II | 588/509 | Nal Amp | |

Figure 3F

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT Or: ΔHOPEMT asd pSi_357 | Y. enterocolitica ΔyopH,O,P,E,M,T (Δasd) | | YopE1-138-Y. enterocolitica codon optimized murine tBid BH3 | pBad_Si_2 | pSi_357 | 733/735 | Nal Amp | |
| ΔHOPEMT Or: ΔHOPEMT asd pSi_358 | Y. enterocolitica ΔyopH,O,P,E,M,T (Δasd) | | YopE1-138-Y. enterocolitica codon optimized murine Bax BH3 | pBad_Si_2 | pSi_358 | 736/738 | Nal Amp | |
| ΔHOPEMT Or: ΔHOPEMT asd pSi_371 | Y. enterocolitica ΔyopH,O,P,E,M,T (Δasd) | | YopE1-138-(Y. enterocolitica codon optimized murine tBid BH3)$_2$ | pSi_357 | pSi_371 | 733/734 | Nal Amp | |
| ΔHOPEMT Or: ΔHOPEMT asd pSi_373 | Y. enterocolitica ΔyopH,O,P,E,M,T (Δasd) | | YopE1-138-Y. enterocolitica codon optimized murine tBid BH3-. enterocolitica codon optimized murine Bax BH3 | pSi_358 | pSi_373 | 733/734 | Nal Amp | |

Figure 3G

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT Or: ΔHOPEMT asd pSi_353 | Y. enterocolitica ΔyopH,O,P,E,M,T (Δasd) | | YopE1-138-Y. enterocolitica codon optimized murine tBid BH3 extended (by 4 Aa) | pBad_Si_2 | pSi_353 | 725/726 | Nal Amp | |
| ΔHOPEMT Or: ΔHOPEMT asd pSi_354 | Y. enterocolitica ΔyopH,O,P,E,M,T (Δasd) | | YopE1-138-10 Aa linker-Y. enterocolitica codon optimized murine tBid BH3 | pBad_Si_2 | pSi_354 | 727/728 | Nal Amp | |
| ΔHOPEMT Or: ΔHOPEMT asd pSi_374 | Y. enterocolitica ΔyopH,O,P,E,M,T (Δasd) | | YopE1-138-Y. enterocolitica codon optimized murine Bax BH3-. enterocolitica codon optimized murine tBid BH3 | pSi_357 | pSi_374 | 736/737 | Nal Amp | |

Figure 3H

| Strain Name | Background strain | Insert/relevant characteristics | Protein to be delivered by T3SS | Backbone plasmid | Resulting plasmid name | Primers. Si_Nr.: | resistances | References |
|---|---|---|---|---|---|---|---|---|
| ΔHOPEMT Or: ΔHOPEMT asd pSi_453 | Y. enterocolitica ΔyopH,O,P,E,M,T (Δasd) | | YopE$_{1-138}$- Y. enterocolitica cod

Figure 3I

| Strain Name | Background strain | Insert/relevant characteristics | Protein to be delivred by T3SS | Backbone plasmid | Resulting plasmid name | Primers. Si Nr.: | resistances | Reference |
|---|---|---|---|---|---|---|---|---|
| ΔHOPEMT Or: ΔHOPEMT asd pSi_428 | Y. enterocolitica ΔyopH,O,P,E,M,T (Δasd) | | YopE$_{1-138

Figure 3J

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pYV-asd | Y. enterocolitica ΔyopH,O,P,E,M,T *Δasd* | MRS40 pIML421 [yopHΔ1–352, yopOΔ65–558, yopP23, yopE21, yopM23, yopT135, pYV-asd] | / | pKNG101 | pSi_417 (Mutator | PCR1: 869/870; PCR2: 871/872; PCR3: 873/874; overlapping PCR 869/874 | Nal | |
| ΔHOPEMT asd pBad-asd | Y. enterocolitica ΔyopH,O,P,E,M,T *Δasd* | MRS40 pIML421 [yopHΔ1–352, yopOΔ65–558, yopP23, yopE21, yopM23, yopT135] | YopE1-138-MycHis | pBad_Si_2 | pSi_397 | 600/601 | Nal | |
| ΔHOPEMT *virF-hairpinI* | Y. enterocolitica ΔyopH,O,P,E,M,T | MRS40 [yopHΔ1–352, yopOΔ65–558, yopP23, yopE21, yopM23, yopT135 virFΔ-111 – -57] | / | pKNG101 | pSI_441 (Mutator) | synthetic construct | Nal | |
| ΔHOPEMT *virF-hairpinI* pSi_371 | Y. enterocolitica ΔyopH,O,P,E,M,T *ΔvirF-hairpinI* | MRS40 [yopHΔ1–352, yopOΔ65–558, yopP23, yopE21, yopM23, yopT135 virFΔ-111 – -57] | YopE1-138-(Y. enterocolitica codon optimized murine tBid $BH3)_2$ | pBad_Si_2 | pSi_371 | 733/734 | Nal Amp | |

Figure 3K

| Strain Name | Background strain | Insert/relevant characteristics | Protein to be delivered by T3SS | Backbone plasmid | Resulting plasmid name | Primers. Si Nr.: | resistances | Reference |
|---|---|---|---|---|---|---|---|---|
| ΔHOPEMT pYV-YopE$_{1-138}$- murine tBID BH3 | Y. enterocolitica ΔyopH,O,P,E,M,T | MRS40 [yopHΔ1-352, yopOΔ65-558, yopP23, yopE21, yopM23, yopT135 yopE::tBID BH3] | YopE$_{1-138}$-tBID BH3 | pKNG101 | pSI_408 (Mutator) | synthetic construct | Nal | |
| ΔHOPEMT pYV-YopE$_{1-138}$- murine (tBID BH3)$_2$ | Y. enterocolitica ΔyopH,O,P,E,M,T | MRS40 [yopHΔ1-352, yopOΔ65-558, yopP23, yopE21, yopM23, yopT135 yopE::(tBID BH3)$_2$] | YopE$_{1-138}$-(tBID BH3)$_2$ | pKNG101 | pSI_437 (Mutator) | synthetic construct | — | |
| ΔHOPEMT pYV-virF-hairpin1 - YopE$_{1-138}$- murine (tBID BH3)$_2$ | Y. enterocolitica ΔyopH,O,P,E,M,T | MRS40 [yopHΔ1-352, yopOΔ65-558, yopP23, yopE21, yopM23, yopT135 yopE::(tBID BH3)$_2$ virFΔ-111 – 57] | YopE$_{1-138}$-(tBID BH3)$_2$ | pKNG101 | pSI_441 (Mutator) | synthetic construct | Nal | |
| ΔHOPEMT asd pYV-asd-YopE$_{1-138}$- murine (tBID BH3)$_2$ | Y. enterocolitica ΔyopH,O,P,E,M,T Δasd pYV-asd | MRS40 pIML421 [yopHΔ1-352, yopOΔ65-558, yopP23, yopE21, yopM23, yopT135, yopE::(tBID BH3)$_2$ pYV-asd] | YopE$_{1-138}$-(tBID BH3)$_2$ | pKNG101 | pSI_437 (Mutator) | synthetic construct | Nal | |

Figure 3L

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT pYV-$YopE_{1-138}$- murine RIG-1 CARD domains | Y. enterocolitica ΔyopH,O,P,E,M,T | MRS40 [yopHΔ1–352, yopOΔ65–558, yopP23, yopE21, yopM23, yopT135 yopE::RIG-1 CARD domains | $YopE_{1-138}$- RIG-1 CARD domains | pKNG101 | pSI_456 (Mutator) | synthetic construct | Nal | |
| ΔHOPEMT pYV-pAra-*virF* | Y. enterocolitica ΔyopH,O,P,E,M,T | MRS40 [yopHΔ1–352, yopOΔ65–558, yopP23, yopE21, yopM23, yopT135 pAra::virF] | / | pKNG101 | pSI_439 (Mutator) | synthetic construct | | |
| ΔHOPEMT pYV-pAra-*virF* pSi_371 | Y. enterocolitica ΔyopH,O,P,E,M,T, pYV-pAra-*virF* | MRS40 [yopHΔ1–352, yopOΔ65–558, yopP23, yopE21, yopM23, yopT135 pAra::virF] | $YopE_{1-138}$-(Y. enterocolitica codon optimized murine tBid $BH3)_2$ | pBad_Si_2 | pSi_371 | 733/734 | Nal Amp | |

Figure 3M

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT pYV-*virF-hairpinI* -$YopE_{1-138}$- murine RIG-1 CARD domains | Y. enterocolitica ΔyopH,O,P,E,M,T yopE::murine RIG-1 CARD domains | MRS40 [yopHΔ1–352, yopOΔ65–558, yopP23, yopE21, yopM23, yopT135 virFΔ-111 – -57 yopE::RIG-1 CARD domains | $YopE_{1-138}$- RIG-1 CARD domains | pKNG101 | pSI_441 (Mutator) | synthetic construct | Nal | |
| ΔHOPEMT Or: ΔHOPEMT asd pSi_521 | Y. enterocolitica ΔyopH,O,P,E,M,T (Δasd) | | $YopE_{1-138}$- Y. enterocolitica codon optimized murine RIG-1 two CARD domains (Aa. 1-229) | pBad_Si_2 | pSi_521 | 1021/1022 | Nal Amp | |

Figure 3N

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT Or: ΔHOPEMT asd pSi_522 | Y. enterocolitica ΔyopH,O,P,E,M,T (Δasd) | | $YopE_{1-138}$- Y. enterocolitica codon optimized murine RIG-1 two CARD domains (Aa. 1-218) | pBad_Si_2 | pSi_522 | 1021/1023 | Nal Amp | |
| ΔHOPEMT Or: ΔHOPEMT asd pSi_517 | Y. enterocolitica ΔyopH,O,P,E,M,T (Δasd) | | $YopE_{1-138}$- Y. enterocolitica codon optimized murine MDA5 two CARD domains (Aa. 1-294) | pBad_Si_2 | pSi_517 | synthetic construct | Nal Amp | |

Figure 3O

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT Or: ΔHOPEMT asd pSi_524 | Y. enterocolitica ΔyopH,O,P,E,M,T (Δasd) | | $YopE_{1-138}$- Y. enterocolitica codon optimized murine MDA5 two CARD domains (Aa. 1-231) | pBad_Si_2 | pSi_524 | 1025/1026 | Nal Amp | |
| ΔHOPEMT Or: ΔHOPEMT asd pSi_515 | Y. enterocolitica ΔyopH,O,P,E,M,T (Δasd) | | $YopE_{1-138}$- Y. enterocolitica codon optimized human cGAS (Aa. 161-522) | pBad_Si_2 | pSi_515 | synthetic construct | Na Ar | |

Figure 3P

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT Or: ΔHOPEMT asd pSi_539 | Y. enterocolitica ΔyopH,O,P,E,M,T (Δasd) | | $YopE_{1-138}$- Y. enterocolitica codon optimized human MAVS CARD (Aa. 1-100) | pBad_Si_2 | pSi_539 | synthetic construct | Nal Amp | |
| ΔHOPEMT Or: ΔHOPEMT asd pSi_503 | Y. enterocolitica ΔyopH,O,P,E,M,T (Δasd) | | $YopE_{1-138}$- Y. enterocolitica codon optimized Anemonae (N. vectensis) cGAS (Aa. 60-422) (Ensembl: A7SFB5.1) | pBad_Si_2 | pSi_484 | 1010/1012 | / | |
| ΔHOPEMT Or: ΔHOPEMT asd pSi_518 | Y. enterocolitica ΔyopH,O,P,E,M,T (Δasd) | | $YopE_{1-138}$- Y. enterocolitica codon optimized Listeria monocytogenes CdaA (Aa. 101-273) | pBad_Si_2 | pSi_518 | synthetic construct | Nal Amp | |

Figure 3Q

| Strain Name | Background strain | Insert/relevant characteristics | Protein to be delivered by T3SS | Backbone plasmid | Resulting plasmid name | Primers. SI_Nr.: | resistances | Reference |
|---|---|---|---|---|---|---|---|---|
| ΔHOPEMT-yopB pSi_539 | Y. enterocolitica ΔyopH,O,P,E,M,T,yopB | Deletion of yopB | YopE$_{1-138}$- Y. enterocolitica codon optimized human MA Figure 11
A
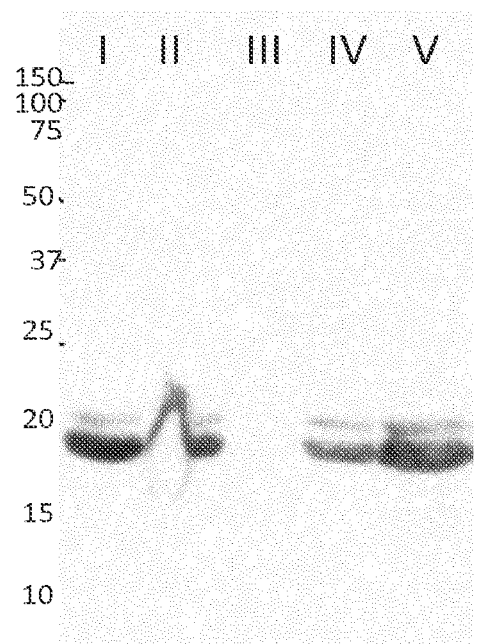
B
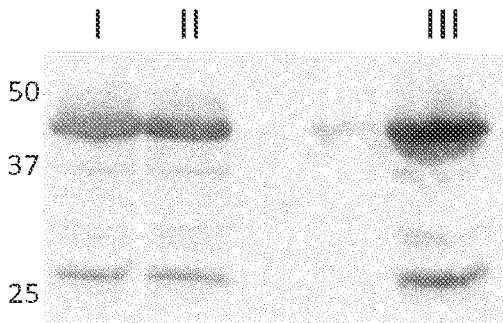

VIRULENCE ATTENUATED BACTERIA BASED PROTEIN DELIVERY

CROSS-REFERENCE TO RELATED APPLICATIONS

This application is a Continuation application and claims priority to U.S. patent application Ser. No. 16/471,264, filed on Jun. 19, 2019; which is a U.S. 371 Application of PCT/EP2017/08353 filed on Dec. 20, 2017; which claims the benefit of European Application 16205439.9, filed Dec. 20, 2016, which are hereby incorporated by reference in their entireties.

INCORPORATION BY REFERENCE OF SEQUENCE LISTING PROVIDED AS A SEQUENCE LISTING XML FILE

A Sequence Listing is provided herewith as a Sequence Listing XML, "LATS-007CON_SEQ_LIST", created on Oct. 18, 2022 and having a size of 187,000 bytes. The contents of the Sequence Listing XML are incorporated herein by reference in their entirety.

THE FIELD OF THE INVENTION

The present invention relates to recombinant virulence attenuated Gram-negative bacterial strains and its use in a method of treating cancer in a subject.

BACKGROUND OF THE INVENTION

Bacteria have evolved different mechanisms to directly inject proteins into target cells [1]. The type III secretion system (T3SS) used by bacteria like *Yersinia, Shigella* and *Salmonella* [2] functions like a nano-syringe that injects so-called bacterial effector proteins into host cells.

T3SS has been exploited to deliver hybrid peptides and proteins into target cells. Heterologous bacterial T3SS effectors have been delivered in case the bacterium under study is hardly accessible by genetics (like *Chlamydia trachomatis*). Often reporter proteins were fused to possible T3SS secretion signals as to study requirements for T3SS dependent protein delivery, such as the *Bordetella pertussis* adenylate cyclase, murine DHFR or a phosphorylatable tag. Peptide delivery was mainly conducted with the aim of vaccination. This includes viral epitopes, bacterial epitopes (listeriolysin O) as well as peptides representing epitopes of human cancer cells. In few cases functional eukaryotic proteins have been delivered to modulate the host cell, as done with nanobodies [3], nuclear proteins (Cre-recombinase, MyoD) [4,5] or IL10 and IL1ra [6]. None of the above-mentioned systems allows single-protein delivery as in each case one or multiple endogenous effector proteins are still encoded. Furthermore, the vectors used have not been designed in a way allowing simple cloning of other DNA fragments encoding proteins of choice, hindering broad application of the system.

Approaches allowing targeted drug delivery are of great interest. For example, antibodies recognizing surface structures of tumor cells and, in an optimal case, selectively bind to tumor cells are used. To improve the mechanism of such antibodies they can be conjugated to therapeutic agents or to lipid vesicles packed with drugs. One of the challenges with such vesicles is the proper release of the active reagent. Even more complex is the delivery of therapeutic proteins or peptides, especially when intracellular mechanisms are targeted. Many alternative ways have been tried to solve the problem of delivering therapeutic proteins into eukaryotic cells, among which are "cell penetrating peptides" (CPP) or similar technologies as well as various nanoparticle-based methodologies. All these technologies have the drawback of low efficacy and that the cargo taken up by the cell via endocytosis is likely to end up being degraded in lysosomes. Furthermore, the conflict between need for stability of cargo-carrier in the human body and the requirement for destabilization and liberation within the target cell constitutes an intrinsic problem of such technologies. Various bacteria have been shown to replicate within malignant solid tumors when administered from a distal site, including *Escherichia coli, Vibrio cholerae, Salmonella enterica, Listeria monocytogenes, Pseudomonas aeruginosa* and Bifidobacteria. Currently, only *bacillus* Calmette-Gudrin (BCG, derived from *Mycobacterium bovis*) is used in clinical practice. BCG is administrated to treat superficial bladder cancer, while the underlying molecular mechanism remains largely unknown. The development of bacterial strains which are capable e.g. to deliver cargo produced inside bacteria to its site of action inside cells like cancer cells, i.e. outside of bacteria, remains a major challenge.

SUMMARY OF THE INVENTION

The present invention relates to recombinant virulence attenuated Gram-negative bacterial strains and its use in a method of treating cancer in a subject. In some embodiments the present invention provides recombinant virulence attenuated Gram-negative bacterial strains and the use thereof for treating cancer in a subject wherein the recombinant virulence attenuated Gram-negative bacterial strains allow the translocation of various type III effectors, but also of type IV effectors, of viral proteins and most importantly of functional eukaryotic proteins into cancer cells e.g. into cells of a malignant solid tumor.

The present invention provides a recombinant virulence attenuated Gram-negative bacterial strain with increased heterologous protein expression and secretion properties and which is surprisingly capable to stably encode the heterologous protein over several days, or even weeks, in vivo.

In a first aspect the present invention relates to a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a deletion of a chromosomal gene coding for an endogenous protein essential for growth and an endogenous virulence plasmid which comprises a nucleotide sequence comprising a gene coding for said endogenous protein essential for growth operably linked to a promoter.

In a further aspect the present invention relates to a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a modulation within a RNA thermosensor region upstream of a gene coding for an endogenous AraC-type DNA binding protein.

In a further aspect the present invention relates to a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the heterologous protein is a protein involved in induction or regulation of an interferon (IFN) response.

In a further aspect the present invention relates to a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a deletion of a chromosomal gene coding for an endogenous protein essential for growth and an endogenous virulence plasmid which comprises a nucleotide sequence comprising a gene coding for said endogenous protein essential for growth operably linked to a promoter for use in a method of treating cancer in a subject, the method comprising administering to the subject said recombinant virulence attenuated Gram-negative bacterial strain, wherein the recombinant virulence attenuated Gram-negative bacterial strain is administered in an amount that is sufficient to treat the subject.

Likewise the present invention relates to a method of treating cancer in a subject, comprising administering to the subject a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a deletion of a chromosomal gene coding for an endogenous protein essential for growth and an endogenous virulence plasmid which comprises a nucleotide sequence comprising a gene coding for said endogenous protein essential for growth operably linked to a promoter, wherein the recombinant virulence attenuated Gram-negative bacterial strain is administered in an amount that is sufficient to treat the subject.

Likewise the present invention relates to the use of a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a deletion of a chromosomal gene coding for an endogenous protein essential for growth and an endogenous virulence plasmid which comprises a nucleotide sequence comprising a gene coding for said endogenous protein essential for growth operably linked to a promoter for the manufacture of a medicament for treating cancer in a subject In a further aspect the present invention relates to a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a modulation within a RNA thermosensor region upstream of a gene coding for an endogenous AraC-type DNA binding protein for use in a method of treating cancer in a subject, the method comprising administering to the subject said recombinant virulence attenuated Gram-negative bacterial strain, wherein the recombinant virulence attenuated Gram-negative bacterial strain is administered in an amount that is sufficient to treat the subject.

Likewise the present invention relates to a method of treating cancer in a subject, comprising administering to the subject a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a modulation within a RNA thermosensor region upstream of a gene coding for an endogenous AraC-type DNA binding protein, wherein the recombinant virulence attenuated Gram-negative bacterial strain is administered in an amount that is sufficient to treat the subject.

Likewise the present invention relates to the use of a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a modulation within a RNA thermosensor region upstream of a gene coding for an endogenous AraC-type DNA binding protein for the manufacture of a medicament for treating cancer in a subject.

In a further aspect the present invention relates to a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the heterologous protein is a protein involved in induction or regulation of an interferon (IFN) response for use in a method of treating cancer in a subject, the method comprising administering to the subject said recombinant virulence attenuated Gram-negative bacterial strain, wherein the recombinant virulence attenuated Gram-negative bacterial strain is administered in an amount that is sufficient to treat the subject.

Likewise the present invention relates to a method of treating cancer in a subject, comprising administering to the subject a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the heterologous protein is a protein involved in induction or regulation of an interferon (IFN) response, wherein the recombinant virulence attenuated Gram-negative bacterial strain is administered in an amount that is sufficient to treat the subject.

Likewise the present invention relates to the use of a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the heterologous protein is a protein involved in induction or regulation of an interferon (IFN) response for the manufacture of a medicament for treating cancer in a subject.

In a further aspect the present invention relates to a pharmaceutical composition comprising a recombinant virulence attenuated Gram-negative bacterial strain and a pharmaceutically acceptable carrier, wherein the recombinant virulence attenuated Gram-negative bacterial strain comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a deletion of a chromosomal gene coding for an endogenous protein essential for growth and an endogenous virulence plasmid which comprises a nucleotide sequence comprising a gene coding for said endogenous protein essential for growth operably linked to a promoter.

In a further aspect the present invention relates to a pharmaceutical composition comprising a recombinant virulence attenuated Gram-negative bacterial strain and a pharmaceutically acceptable carrier, wherein the recombinant virulence attenuated Gram-negative bacterial strain comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a modulation within a RNA thermosensor region upstream of a gene coding for an endogenous AraC-type DNA binding protein.

In a further aspect the present invention relates to a pharmaceutical composition comprising a recombinant virulence attenuated Gram-negative bacterial strain and a pharmaceutically acceptable carrier, wherein the recombinant virulence attenuated Gram-negative bacterial strain comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the heterologous protein is a protein involved in induction or regulation of an interferon (IFN) response.

BRIEF DESCRIPTION OF THE FIGURES

FIGS. 3A to Q: Y. enterocolitica strains used in this study. List of Y. enterocolitica strains used in this study providing information on background strains, plasmids and proteins for T3SS dependent delivery encoded on corresponding plasmids. Further, information on oligonucleotides used for construction of the corresponding plasmid, the backbone plasmid and antibiotic resistances is provided.

FIG. 11: Regulation of T3SS-based secretion by controlling the expression of the master regulator VirF. A: In vitro secretion assay (performed at 37° C.) with *Y. enterocolitica* ΔHOPEMT strains delivering YopE$_{1-138}$(tBID BH3)$_2$. Expression of VirF is under control of its natural promoter (I+II), an arabinose-inducible promoter (III+IV) or its natural promoter with a deletion of its hairpin I region controlling temperature-dependent expression (V). The secretion assay was performed either in the absence of arabinose (I, III and V) or in the presence of 0.2% arabinose (II and IV). Secreted YopE$_{1-138}$(tBID BH3)$_2$ was detected using Western blotting with an antibody recognizing the YopE$_{1-138}$ region. B: In vitro secretion assay (performed at 37° C.) with *Y. enterocolitica* ΔHOPEMT strains delivering YopE$_{1-138}$—murine RIG1 caspase activation and recruitment domain (CARD) domains. Expression of VirF is under control of its natural promoter (I+II), or its natural promoter with a deletion of its hairpin I region controlling temperature-dependent expression (III). The secretion assay was performed either in the absence of arabinose (I, and III) or in the presence of 0.2% arabinose (II). Secreted of YopE$_{1-138}$—murine RIG1 CARD domains was detected using Western blotting with an antibody recognizing the YopE$_{1-138}$ region.

DETAILED DESCRIPTION OF THE INVENTION

Figure 1:
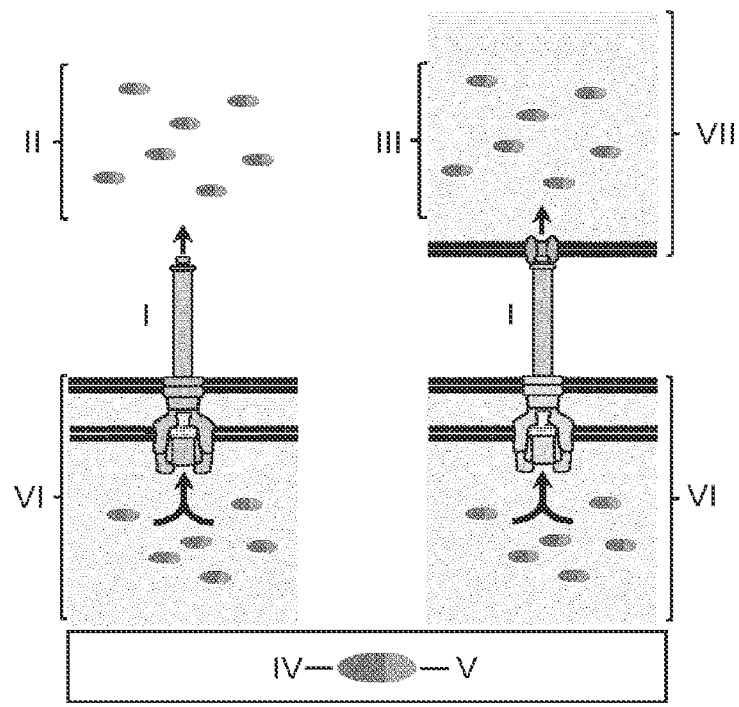
FIG. 1: Characterization of T3SS protein delivery. Schematic representation of T3SS dependent protein secretion into the surrounding medium (in-vitro secretion)(left side) or into eukaryotic cells (right side). I: shows the type 3 secretion system. II indicates proteins secreted into the surrounding medium, III proteins translocated through the membrane into the cytosol of eukaryotic cells (VII). VI shows a stretch of the two bacterial membranes in which the T3SS is inserted and the bacterial cytosol underneath. IV is a fusion protein attached to the YopE$_{1-138}$ N-terminal fragment (V)

The present invention relates to recombinant virulence attenuated Gram-negative bacterial strains and its use in a method of treating cancer e.g. a malignant solid tumor in a subject.

For the purposes of interpreting this specification, the following definitions will apply and whenever appropriate, terms used in the singular will also include the plural and vice versa. It is to be understood that the terminology used herein is for the purpose of describing particular embodiments only and is not intended to be limiting.

The term "Gram-negative bacterial strain" as used herein includes the following bacteria: *Aeromonas salmonicida, Aeromonas hydrophila, Aeromonas veronii, Anaeromyxobacter dehalogenans, Bordetella bronchiseptica, Bordetella parapertussis, Bordetella pertussis, Bradyrhizobium japonicum, Burkholderia cenocepacia, Burkholderia cepacia, Burkholderia mallei, Burkholderia pseudomallei, Chlamydia muridarum, Chlamydia trachmoatis, Chlamydophila abortus, Chlamydophila pneumoniae, Chromobacterium violaceum, Citrobacter rodentium, Desulfovibrio vulgaris, Edwardsiella tarda, Endozoicomonas elysicola, Erwinia amylovora, Escherichia albertii, Escherichia coli, Lawsonia intracellularis, Mesorhizobium loti, Myxococcus xanthus, Pantoea agglomerans, Photobacterium damselae, Photorhabdus luminescens, Photorabdus temperate, Pseudoalteromonas spongiae, Pseudomonas aeruginosa, Pseudomonas plecoglossicida, Pseudomonas syringae, Ralstonia solanacearum, Rhizobium sp, Salmonella enterica* and other *Salmonella sp, Shigella flexneri* and other *Shigella sp, Sodalis glossinidius, Vibrio alginolyticus, Vibrio azureus, Vibrio campellii, Vibrio caribbenthicus, Vibrio harvey, Vibrio parahaemolyticus, Vibrio tasmaniensis, Vibrio tubiashii, Xanthomonas axonopodis, Xanthomonas campestris, Xanthomonas oryzae, Yersinia enterocolitica, Yersinia pestis, Yersinia pseudotuberculosis*. Preferred Gram-negative bacterial strains of the invention are Gram-negative bacterial strains comprised by the family of Enterobacteriaceae and Pseudomonadaceae. The Gram-negative bacterial strain of the present invention is normally used for delivery of heterologous proteins by the bacterial T3SS into eukaryotic cells in vitro and/or in vivo, preferably in vivo.

The term "recombinant virulence attenuated Gram-negative bacterial strain" as used herein refers to a recombinant virulence attenuated Gram-negative bacterial strain genetically transformed with a nucleotide molecule like a vector. Virulence of such a recombinant Gram-negative bacterial strain is usually attenuated by deletion of bacterial effector proteins having virulence activity which are transported by one or more bacterial proteins, which are part of a secretion system machinery. Such effector proteins are delivered by a secretion system machinery into a host cells where they exert their virulence activity toward various host proteins and cellular machineries. Many different effector proteins are known, transported by various secretion system types and displaying a large repertoire of biochemical activities that modulate the functions of host regulatory molecules. Virulence of the recombinant Gram-negative bacterial strain used herein can be attenuated additionally by lack of a siderophore normally or occasionally produced by the Gram-negative bacterial strain so that the strain does not produce the siderophore e.g. is deficient in the production of the siderophore. Thus in a preferred embodiment a recombinant virulence attenuated Gram-negative bacterial strain is used which lacks of a siderophore normally or occasionally produced by the Gram-negative bacterial strain so that the strain does not produce the siderophore e.g. is deficient in the production of a siderophore, more preferably a *Yersinia* strain, in particular *Y. enterocolitica* MRS40 ΔyopH,O,P,E,M,T, *Y. enterocolitica* MRS40 ΔyopH,O,P,E,M,T ΔHairpinI-virF or *Y. enterocolitica* MRS40 ΔyopH,O,P,E,M,T Δasd pYV-asd is used which lack of a siderophore normally or occasionally produced by the Gram-negative bacterial strain so that the strain does not produce the siderophore e.g. is deficient in the production of a siderophore, in particular is deficient in the production of Yersiniabactin. *Y. enterocolitica* MRS40 ΔyopH,O,P,E,M,T which is deficient in the production of Yersiniabactin has been described in WO02077249 and was deposited on 24 Sep. 2001, according to the Budapest Treaty on the International Recognition of the Deposit of Microorganisms for the Purposes of Patent Procedure with the Belgian Coordinated Collections of Microorganisms (BCCM) and was given accession number LMG P-21013. The recombinant virulence attenuated Gram-negative bacterial strain preferably does not produce at least one, preferably at least two siderophores e.g. is deficient in the production of at least one, preferably at least two siderophores, more preferably the recombinant virulence attenuated Gram-negative bacterial strain does not produce any siderophore.

The term "siderophore", "iron siderophore" or "iron chelator" which are used interchangeably herein refer to compounds with high affinity for iron e.g. small compounds with high affinity for iron.

Siderophores of Gram-negative bacteria are e.g. Enterobactin and dihydroxybenzoylserine synthetized by *Salmonella, Escherichia, Klebsiella, Shigella, Serratia* (but used by all enterobacteria), Pyoverdins synthetized by *Pseudomonas*, Vibriobactin synthetized by *Vibrio*, Acinetobactin and Acinetoferrin by *Acinetobacter*, Yersiniabactin and Aerobactin synthetized by *Yersinia*, Ornibactin synthetized by *Burkholderia*, Salmochelin synthetized by *Salmonella*, Aerobactin synthetized by *Escherichia, Shigella, Salmonella,* and *Yersinia,* Alcaligin synthetized by *Bordetella,* Bisucaberin synthetized by *Vibrio.*

Siderophores include hydroxamate, catecholate and mixed ligand siderophores.

Several siderophores have to date been approved for use in humans, mainly with the aim of treating iron overload. Preferred siderophores are Deferoxamine (also known as desferrioxamine B, desferoxamine B, DFO-B, DFOA, DFB or desferal), Desferrioxamine E, Deferasirox (Exjade, Desirox, Defrijet, Desifer) and Deferiprone (Ferriprox).

The term "an endogenous protein essential for growth" used herein refers to proteins of the recombinant virulence attenuated Gram-negative bacterial strain without those the Gram-negative bacterial strain cannot grow. Endogenous proteins essential for growth are e.g. an enzyme essential for amino acid production, an enzyme involved in peptidoglycan biosynthesis, an enzyme involved in LPS biosynthesis, an enzyme involved in nucleotide synthesis or a translation initiation factor.

The term "an enzyme essential for amino acid production" used herein refers to enzymes which are related to the amino acid production of the recombinant virulence attenuated Gram-negative bacterial strain and without those the Gram-negative bacterial strain can not grow. Enzymes essential for amino acid production, are e.g aspartate-beta-semialdehyde dehydrogenase (asd), glutamine synthetase (glnA), tryptophanyl tRNA synthetase (trpS) or serine hydroxymethly transferase (glyA), or Transketolase 1 (tktA), Transketolase 2 (tktB), Ribulose-phosphate 3-epimerase (rpe), Ribose-5-phosphate isomerase A (rpiA), Transaldolase A (talA), Transaldolase B (talB), phosphoribosylpyrophosphate synthase (prs), ATP phosphoribosyltransferase (hisG), Histidine biosynthesis bifunctional protein HisIE (hisI), 1-(5-phosphoribosyl)-5-[(5-phosphoribosylamino)methylideneamino] imidazole-4-carboxamide isomerase (hisA), Imidazole glycerol phosphate synthase subunit HisH (hisH), Imidazole glycerol phosphate synthase subunit HisF (hisF), Histidine biosynthesis bifunctional protein HisB (hisB), Histidinol-phosphate aminotransferase (hisC), Histidinol dehydrogenase (hisD), 3-dehydroquinate synthase (aroB), 3-dehydroquinate dehydratase (aroD), Shikimate dehydrogenase (NADP(+)) (aroE), Shikimate kinase 2 (aroL), Shikimate kinase 1 (aroK), 3-phosphoshikimate 1-carboxyvinyltransferase (aroA), Chorismate synthase (aroC), P-protein (pheA), T-protein (tyrA), Aromatic-amino-acid aminotransferase (tyrB), Phospho-2-dehydro-3-deoxyheptonate aldolase (aroG), Phospho-2-dehydro-3-deoxyheptonate aldolase (aroH), Phospho-2-dehydro-3-deoxyheptonate aldolase (aroF), Quinate/shikimate dehydrogenase (ydiB), ATP-dependent 6-phosphofructokinase isozyme 1 (pfkA), ATP-dependent 6-phosphofructokinase isozyme 2 (pfkB), Fructose-bisphosphate aldolase class 2 (fbaA), Fructose-bisphosphate aldolase class 1 (fbaB), Triosephosphate isomerase (tpiA), Pyruvate kinase I (pykF), Pyruvate kinase II (pykA), Glyceraldehyde-3-phosphate dehydrogenase A (gapA), Phosphoglycerate kinase (pgk), 2,3-bisphosphoglycerate-dependent phosphoglycerate mutase (gpmA), 2,3-bisphosphoglycerate-independent phosphoglycerate mutase (gpmM/yibO), Probable phosphoglycerate mutase (ytjC/gpmB), enolase (eno), D-3-phosphoglycerate dehydrogenase (serA), Phosphoserine aminotransferase (serC), Phosphoserine phosphatase (serB), L-serine dehydratase 1 (sdaA), L-serine dehydratase 2 (sdaB), L-threonine dehydratase catabolic (tdcB), L-threonine dehydratase biosynthetic (ilvA), L-serine dehydratase (tdcG), Serine acetyltransferase (cysE), Cysteine synthase A (cysK), Cysteine synthase B (cysM), beta-cystathionase (malY), Cystathionine beta-lyase (metC), 5-methyltetrahydropteroyltriglutamate-homocysteine methyltransferase (metE), Methionine synthase (metH), S-adenosylmethionine synthase (metK), Cystathionine gamma-synthase (metB), Homoserine O-succinyltransferase (metA), 5'-methylthioadenosine/S-adenosylhomocysteine nucleosidase (mtnN), S-ribosylhomocysteine lyase (luxS), cystathione beta lyase, cystathione gamma lyase, Serine hydroxymethyltransferase (glyA), Glycine hydroxymethyltransferase (itaE), 3-isopropylmalate dehydratase small subunit (leuD), 3-isopropylmalate dehydratase large subunit (leuC), 3-isopropylmalate dehydrogenase (leuB), L-threonine dehydratase biosynthetic (ilvA), Acetolactate synthase isozyme 3 large subunit (ilvI), Acetolactate synthase isozyme 3 small subunit (ilvH), Acetolactate synthase isozyme 1 small subunit (ilvN), Acetolactate synthase isozyme 2 small subunit (ilvM), Ketol-acid reductoisomerase (NADP(+)) (ilvC), Dihydroxy-acid dehydratase (ilvD), Branched-chain-amino-acid aminotransferase (ilvE), Bifunctional aspartokinase/homoserine dehydrogenase 1 (thrA), Bifunctional aspartokinase/homoserine dehydrogenase 2 (metL), 2-isopropylmalate synthase (leuA), Glutamate-pyruvate aminotransferase (alaA), Aspartate aminotransferase (aspC), Bifunctional aspartokinase/homoserine dehydrogenase 1 (thrA), Bifunctional aspartokinase/homoserine dehydrogenase 2 (metL), Lysine-sensitive aspartokinase 3 (lysC), Aspartate-semialdehyde dehydrogenase (asd), 2-keto-3-deoxy-galactonate aldolase (yagE), 4-hydroxy-tetrahydrodipicolinate synthase (dapA), 4-hydroxy-tetrahydrodipicolinate reductase (dapB), 2,3,4,5-tetrahydropyridine-2,6-dicarboxylate N-succinyltransferase (dapD), Succinyl-diaminopimelate desuccinylase (dapE), Diaminopimelate epimerase (dapF), Putative lyase (yjhH), Acetylornithine/succinyldiaminopimelate aminotransferase (argD), Citrate synthase (gltA), Aconitate hydratase B (acnB), Aconitate hydratase A (acnA), uncharacterized putative aconitate hydratase (ybhJ), isocitrate dehydrogenase (icd), Aspartate aminotransferase (aspC), Glutamate-pyruvate aminotransferase (alaA), Glutamate synthase [NADPH] large chain (gltB), Glutamate synthase [NADPH] small chain (gltD), Glutamine synthetase (glnA), Amino-acid acetyltransferase (argA), Acetylglutamate kinase (argB), N-acetyl-gamma-glutamyl-phosphate reductase (argC), Acetylornithine/succinyldiaminopimelate aminotransferase (argD), Acetylornithine deacetylase (argE), Ornithine carbamoyltransferase chain F (argF), Ornithine carbamoyltransferase chain I (argI), Argininosuccinate synthase (argG), Argininosuccinate lyase (argH), Glutamate 5-kinase (proB), Gamma-glutamyl phosphate reductase (proA), pyrroline-5-carboxylate reductase (proC), ornithine cyclodeaminase, Leucine-tRNA ligase (leuS), Glutamine-tRNA ligase (glnS), Serine-tRNA ligase (serS), Glycine-tRNA ligase beta subunit (glyS), Glycine-tRNA ligase alpha subunit (glyQ), Tyrosine-tRNA ligase (tyrS), Threonine-tRNA ligase (thrS), Phenylalanine-tRNA ligase alpha subunit (pheS), Phenylalanine-tRNA ligase beta subunit (pheT), Arginine-tRNA ligase (argS), Histidine-tRNA ligase (hisS), Valine-tRNA ligase (valS), Alanine-tRNA ligase (alaS), Isoleucine-tRNA ligase (ileS), Proline-tRNA ligase (proS), Cystein-tRNA ligase (cysS), Asparagine-tRNA ligase (asnS), Aspartate-tRNA ligase (aspS), Glutamate-tRNA ligase (gltX), Tryptophan-tRNA ligase (trpS), Glycine-tRNA ligase beta subunit (glyS), Methionine-tRNA ligase (metG), Lysine-tRNA ligase (lysS). Preferred enzymes essential for amino acid production are tktA, rpe, prs, aroK, tyrB, aroH, fbaA, gapA, pgk, eno, tdcG, cysE, metK, glyA, asd, dapA/B/D/E/F, argC, proC, leuS, glnS, serS, glyS/Q, tyrS, thrS, pheS/T, argS, hisS, valS, alaS, ileS, proS, cysS, asnS, aspS, gltX, trpS, glyS, metG, lysS, more preferred are asd, glyA, leuS, glnS, serS, glyS/Q, tyrS, thrS, pheS/T, argS, hisS, valS, alaS, ileS, proS, cysS, asnS, aspS, gltX, trpS, glyS, metG, lysS, most preferred is asd.

The terms "Gram-negative bacterial strain deficient to produce an amino acid essential for growth" and "auxotroph mutant" are used herein interchangeably and refer to Gram-negative bacterial strains which can not grow in the absence of at least one exogenously provided essential amino acid or a precursor thereof. The amino acid the strain is deficient to produce is e.g. aspartate, meso-2,6-diaminopimelic acid, aromatic amino acids or leucine-arginine. Such a strain can be generated by e.g. deletion of the aspartate-beta-semialdehyde dehydrogenase gene (Δasd). Such an auxotroph mutant cannot grow in absence of exogenous meso-2,6-diaminopimelic acid. The mutation, e.g. deletion of the aspartate-beta-semialdehyde dehydrogenase gene is preferred herein for a Gram-negative bacterial strain deficient to produce an amino acid essential for growth of the present invention.

The term "Gram-negative bacterial strain deficient to produce adhesion proteins binding to the eukaryotic cell surface or extracellular matrix" refers to mutant Gram-negative bacterial strains which do not express at least one adhesion protein compared to the adhesion proteins expressed by the corresponding wild type strain. Adhesion proteins may include e.g. extended polymeric adhesion molecules like pili/fimbriae or non-fimbrial adhesins. Fimbrial adhesins include type-1 pili (such as *E. coli* Fim-pili with the FimH adhesin), P-pili (such as Pap-pili with the PapG adhesin from *E. coli*), type 4 pili (as pilin protein from e.g. *P. aeruginosa*) or curli (Csg proteins with the CsgA adhesin from *S. enterica*). Non-fimbrial adhesions include trimeric autotransporter adhesins such as YadA from *Y. enterocolitica*, BpaA (*B. pseudomallei*), Hia (*H. influenzae*), BadA (*B. henselae*), NadA (*N. meningitidis*) or UspA1 (*M. catarrhalis*) as well as other autotransporter adhesins such as AIDA-1 (*E. coli*) as well as other adhesins/invasins such as InvA from *Y. enterocolitica* or Intimin (*E. coli*) or members of the Dr-family or Afa-family (*E. coli*). The terms YadA and InvA as used herein refer to proteins from *Y. enterocolitica*. The autotransporter YadA 7 binds to different froms of collagen as well as fibronectin, while the invasin InvA$^8$ binds to β-integrins in the eukaryotic cell membrane. If the Gram-negative bacterial strain is a *Y. enterocolitica* strain the strain is preferably deficient in InvA and/or YadA.

As used herein, the term "family of Enterobacteriaceae" comprises a family of gram-negative, rod-shaped, facultatively anaerobic bacteria found in soil, water, plants, and animals, which frequently occur as pathogens in vertebrates. The bacteria of this family share a similar physiology and demonstrate a conservation within functional elements and genes of the respective genomes. As well as being oxidase negative, all members of this family are glucose fermenters and most are nitrate reducers. Enterobacteriaceae bacteria of the invention may be any bacteria from that family, and specifically includes, but is not limited to, bacteria of the following genera: *Escherichia, Shigella, Edwardsiella, Salmonella, Citrobacter, Klebsiella, Enterobacter, Serratia, Proteus, Erwinia, Morganella, Providencia*, or *Yersinia*. In more specific embodiments, the bacterium is of the *Escherichia coli, Escherichia blattae, Escherichia fergusonii, Escherichia hermanii, Escherichia vuneris, Salmonella enterica, Salmonella bongori, Shigella dysenteriae, Shigella flexneri, Shigella boydii, Shigella sonnei, Enterobacter aerogenes, Enterobacter gergoviae, Enterobacter sakazakii,*

*Enterobacter cloacae, Enterobacter agglomerans, Klebsiella pneumoniae, Klebsiella oxytoca, Serratia marcescens, Yersinia pseudotuberculosis, Yersinia pestis, Yersinia enterocolitica, Erwinia amylovora, Proteus mirabilis, Proteus vulgaris, Proteus penneri, Proteus hauseri, Providencia alcalifaciens,* or *Morganella morganii* species.

Preferably the Gram-negative bacterial strain is selected from the group consisting of the genera *Yersinia, Escherichia, Salmonella, Shigella, Pseudomonas, Chlamydia, Erwinia, Pantoea, Vibrio, Burkholderia, Ralstonia, Xanthomonas, Chromobacterium, Sodalis, Citrobacter, Edwardsiella, Rhizobiae, Aeromonas, Photorhabdus, Bordetella* and *Desulfovibrio*, more preferably from the group consisting of the genera *Yersinia, Escherichia, Salmonella,* and *Pseudomonas*, most preferably from the group consisting of the genera *Yersinia* and *Salmonella*, in particular *Yersinia*.

The term "*Yersinia*" as used herein includes all species of *Yersinia*, including *Yersinia enterocolitica, Yersinia pseudotuberculosis* and *Yersinia pestis*. Preferred is *Yersinia enterocolitica*.

The term "*Salmonella*" as used herein includes all species of *Salmonella*, including *Salmonella enterica* and *S. bongori*. Preferred is *Salmonella enterica*.

"Promoter" as used herein refers to a nucleic acid sequence that regulates expression of a transcriptional unit. A "promoter region" is a regulatory region capable of binding RNA polymerase in a cell and initiating transcription of a downstream (3' direction) coding sequence. Within the promoter region will be found a transcription initiation site (conveniently defined by mapping with nuclease S1), as well as protein binding domains (consensus sequences) responsible for the binding of RNA polymerase such as the putative −35 region and the Pribnow box. The term "operably linked" when describing the relationship between two nucleotide e.g. DNA regions simply means that they are functionally related to each other and they are located on the same nucleic acid fragment. A promoter is operably linked to a structural gene if it controls the transcription of the gene and it is located on the same nucleic acid fragment as the gene. Usually the promoter is functional in said Gram-negative bacterial strain, i.e. the promoter is capable of expressing the fusion protein of the present invention, i.e. the promoter is capable of expressing the fusion protein of the present invention without further genetic engineering or expression of further proteins. Furthermore, a functional promoter must not be naturally counter-regulated to the bacterial T3SS.

The term "extra-chromosomal genetic element" used herein refers to a genetic element other than a chromosome which is endogenously harboured by the Gram-negative bacterial strain of the present invention such as a virulence plasmid or which is an exogenous genetic element with which the Gram-negative bacterial strain is transformed and which is transiently or stably integrated into the chromosome or into a genetic element other than a chromosome which is endogenously harboured such as a virulence plasmid. Such an extra-chromosomal genetic element may be a vector like an expression vector, a vector for homologous recombination or other integration into the chromosome or into a genetic element other than a chromosome which is endogenously harboured such as a virulence plasmid, DNA fragments for homologous recombination or other integration into the chromosome or into a genetic element other than a chromosome which is endogenously harboured such as a virulence plasmid or an RNA element guiding site specific insertion into the chromosome or into a genetic element other than a chromosome which is endogenously harboured such as a virulence plasmid, such as CRISPR/Cas9 and related guide RNA.

The term "RNA thermosensor region" used herein refers to a temperature-sensitive non-coding RNA sequence, which is regulating gene expression of related genes. Usually RNA thermosensor regions function by forming a secondary structure as a RNA hairpin loop, which is stably formed at a repressive temperature and instable at a permissive temperature, and which is masking a RNA sequence essential for translation such as a ribosome binding site, this way regulating expression of a gene related to such a RNA sequence essential for translation.

The term "RNA hairpin structure or parts thereof" used herein refers to a RNA secondary structure formed by intramolecular base-pairing leading to a stem-loop structure. The intramolecular base-paring, generally within the same RNA strand, is formed due to complementary nucleotide sequences or parts thereof.

The term "AraC-type DNA binding protein", also referred as AraC/XylS family, used herein refers to bacterial transcription regulation proteins bind DNA through a helix-turn-helix motif. Most members of the AraC-type DNA binding proteins are positive transcriptional regulators, and can be characterized by a minimal DNA binding domain extending over a 100 residue stretch containing two helix-turn-helix subdomains. AraC-type DNA binding proteins specifically include, but are not limited to: VirF, LcrF, YbtA, Rns, MxiE, AraC, XylS, ExsA, PerA, MmsR, RhaS, TcpN, HrpX, HrpB, GadX, HilC, HilD, MarA, CafR, FapR and InvF. Preferred are AraC-type DNA binding proteins involved in regulation of virulence relevant mechanisms, such as VirF, LcrF, YbtA, Rns, MxiE, ExsA, PerA, HrpX, HrpB, GadX, HilC, HilD, TcpN, CafR, FapR and InvF. More preferred are AraC-type DNA binding proteins involved in regulation of the type three secretion system activity as VirF, LcrF, MxiE, ExsA, PerA, HrpX, HrpB, GadX, HilC, HilD and InvF, most preferred are VirF and/or LcrF.

The term "delivery" used herein refers to the transportation of a protein from a recombinant virulence attenuated Gram-negative bacterial strain to a eukaryotic cell, including the steps of expressing the heterologous protein in the recombinant virulence attenuated Gram-negative bacterial strain, secreting the expressed protein(s) from such recombinant virulence attenuated Gram-negative bacterial strain and translocating the secreted protein(s) by such recombinant virulence attenuated Gram-negative bacterial strain into the cytosol of the eukaryotic cell. Accordingly, the terms "delivery signal" or "secretion signal" which are used interchangeably herein refer to a polypeptide sequence which can be recognized by the secretion and translocation system of the Gram-negative bacterial strain and directs the delivery of a protein from the Gram-negative bacterial strain to eukaryotic cells.

The term "delivery signal from a bacterial effector protein" used herein refers to a delivery signal from a bacterial effector protein functional in the recombinant Gram-negative bacterial strain, i.e. which allows an expressed heterologous protein in the recombinant Gram-negative bacterial strain to be secreted from such recombinant Gram-negative bacterial strain by a secretion system such as the type III, type IV or type VI secretion system or to be translocated by such recombinant Gram-negative bacterial strain into the cytosol of a eukaryotic cell by a secretion system such as the type III, type IV or type VI secretion system. The term "delivery signal from a bacterial effector protein" used herein also comprises a fragment of a delivery signal from a bacterial effector protein i.e. shorter versions of a delivery signal e.g. a delivery signal comprising up to 10, preferably up to 20, more preferably up to 50, even more preferably up to 100, in particular up to 140 amino acids of a delivery signal e.g. of a naturally occurring delivery signal. Thus a nucleotide sequence such as e.g. a DNA sequence encoding a delivery signal from a bacterial effector protein may encode a full length delivery signal or a fragment thereof wherein the fragment usually comprises usually up to 30, preferably up to 60, more preferably up to 150, even more preferably up to 300, in particular up to 420 nucleic acids.

As used herein, the "secretion" of a protein refers to the transportation of a heterologous protein outward across the cell membrane of a recombinant virulence attenuated Gram-negative bacterial strain. The "translocation" of a protein refers to the transportation of a heterologous protein from a recombinant virulence attenuated Gram-negative bacterial strain across the plasma membrane of a eukaryotic cell into the cytosol of such eukaryotic cell.

The term "bacterial protein, which is part of a secretion system machinery" as used herein refers to bacterial proteins constituting essential components of the bacterial type 3 secretion system (T3SS), type 4 secretion system (T4SS) and type 6 secretion system (T6SS), preferably T3SS. Without such proteins, the respective secretion system is non-functional in translocating proteins to host cells, even if all other components of the secretion system and the bacterial effector protein to be translocated are still encoded and produced.

The term "bacterial effector protein" as used herein refers to bacterial proteins transported by secretion systems e.g. by bacterial proteins, which are part of a secretion system machinery into host cells. Such effector proteins are delivered by a secretion system into a host cell where they exert e.g. virulence activity toward various host proteins and cellular machineries. Many different effector proteins are known, transported by various secretion system types and displaying a large repertoire of biochemical activities that modulate the functions of host regulatory molecules. Secretion systems include type 3 secretion system (T3SS), type 4 secretion system (T4SS) and type 6 secretion system (T6SS). Some effector proteins (as *Shigella flexneri* IpaC) as well belong to the class of bacterial protein, which are part of a secretion system machinery and allow protein translocation. The recombinant virulence attenuated Gram-negative bacterial strain used herein usually comprises bacterial proteins constituting essential components of the bacterial type 3 secretion system (T3SS), type 4 secretion system (T4SS) and/or the type 6 secretion system (T6SS), preferably of the type 3 secretion system (T3SS). The term "bacterial proteins constituting essential components of the bacterial T3SS" as used herein refers to proteins, which are naturally forming the injectisome e.g. the injection needle or are otherwise essential for its function in translocating proteins into eukaryotic cells. Proteins forming the injectisome or are otherwise essential for its function in translocating proteins into eukaryotic cells include, but are not limited to: SctC, YscC, MxiD, InvG, SsaC, EscC, HrcC, HrcC (Secretin), SctD, YscD, MxiG, Prg, SsaD, EscD, HrpQ, HrpW, FliG (Outer MS ring protein), SctJ, YscJ, MxiJ, PrgK, SsaJ, EscJ, HrcJ, HrcJ, FliF (Inner MS ring protein), SctR, YscR, Spa24, SpaP, SpaP, SsaR, EscR, HrcR, HrcR, FliP (Minor export apparatus protein), SctS, YscS, Spa9 (SpaQ), SpaQ, SsaS, EscS, HrcS, HrcS, FliQ (Minor export apparatus protein), SctT, YscT, Spa29 (SpaR), SpaR, SsaT, EscT, HrcT, HrcT, FliR (Minor export apparatus protein), SctU, YscU, Spa40, SpaS, SpaS, SsaU, EscU, HrcU, HrcU, FlhB (Export apparatus switch protein), SctV, YscV, MxiA, InvA, SsaV, EscV, HrcV, HrcV, FlhA (Major export apparatus protein), SctK, YscK, MxiK, OrgA, HrpD (Accessory cytosolic protein), SctQ, YscQ, Spa33, SpaO, SpaO, SsaQ, EscQ, HrcQA+B, HrcQ, FliM+FliN (C ring protein), SctL, YscL, MxiN, OrgB, SsaK, EscL, Orf5, HrpE, HrpF, FliH (Stator), SctN, YscN, Spa47, SpaL, InvC, SsaN, EscN, HrcN, HrcN, FliI (ATPase), SctO, YscO, Spa13, SpaM, InvI, SsaO, Orf15, HrpO, HrpD, FliJ (Stalk), SctF, YscF, MxiH, PrgI, SsaG, EscF, HrpA, HrpY (Needle filament protein), SctI, YscI, MxiI, PrgJ, SsaI, EscI, rOrf8, HrpB, HrpJ, (Inner rod protein), SctP, YscP, Spa32, SpaN, InvJ, SsaP, EscP, Orf16, HrpP, HpaP, FliK (Needle length regulator), LcrV, IpaD, SipD (Hydrophilic translocator, needle tip protein), YopB, IpaB, SipB, SseC, EspD, HrpK, PopF1, PopF2 (Hydrophobic translocator, pore protein), YopD, IpaC, SipC, SseD, EspB (Hydrophobic translocator, pore protein), YscW, MxiM, InvH (Pilotin), SctW, YopN, MxiC, InvE, SsaL, SepL, HrpJ, HpaA (Gatekeeper).

The term "T6SS effector protein" or "bacterial T6SS effector protein" as used herein refers to proteins which are naturally injected by T6S systems into the cytosol of eukaryotic cells or bacteria and to proteins which are naturally secreted by T6S systems that might e.g form translocation pores into the eukaryotic membrane. The term "T4SS effector protein" or "bacterial T4SS effector protein" as used herein refers to proteins which are naturally injected by T4S systems into the cytosol of eukaryotic cells and to proteins which are naturally secreted by T4S systems that might e.g form the translocation pore into the eukaryotic membrane.

The term "T3SS effector protein" or "bacterial T3SS effector protein" as used herein refers to proteins which are naturally injected by T3S systems into the cytosol of eukaryotic cells and to proteins which are naturally secreted by T3S systems that might e.g form the translocation pore into the eukaryotic membrane (including pore-forming tranlocators (as *Yersinia* YopB and YopD) and tip-proteins like *Yersinia* LcrV). Preferably proteins which are naturally injected by T3S systems into the cytosol of eukaryotic cells are used. These virulence factors will paralyze or reprogram the eukaryotic cell to the benefit of the pathogen. T3S effectors display a large repertoire of biochemical activities and modulate the function of crucial host regulatory molecules and include AvrA, AvrB, AvrBs2, AvrBS3, AvrBsT, AvrD, AvrD1, AvrPphB, AvrPphC, AvrPphEPto, AvrPpiBPto, AvrPto, AvrPtoB, AvrRpm1, AvrRpt2, AvrXv3, CigR, EspF, EspG, EspH, EspZ, ExoS, ExoT, GogB, GtgA, GtgE, GALA family of proteins, HopAB2, HopAO1, HopI1, HopM1, HopN1, HopPtoD2, HopPtoE, HopPtoF, HopPtoN, HopU1, HsvB, IcsB, IpaA, IpaB, IpaC, IpaH, IpaH7.8, IpaH9.8, IpgB1, IpgB2, IpgD, LcrV, Map, OspC1, OspE2, OspF, OspG, OspI, PipB, PipB2, PopB, PopP2, PthXo1, PthXo6, PthXo7, SifA, SifB, SipA/SspA, SipB, SipC/SspC, SipD/SspD, SlrP, SopA, SopB/SigD, SopD, SopE, SopE2, SpiC/SsaB, SptP, SpvB, SpvC, SrfH, SrfJ, Sse, SseB, SseC, SseD, SseF, SseG, SseI/SrfH, SseJ, SseK1, SseK2, SseK3, SseL, SspH1, SspH2, SteA, SteB, SteC, SteD, SteE, TccP2, Tir, VirA, VirPphA, VopF, XopD, YopB, YopD YopE, YopH, YopJ, YopM, YopO, YopP, YopT, YpkA.

The term "recombinant virulence attenuated Gram-negative bacterial strain accumulating in a malignant solid tumor" or "the recombinant virulence attenuated Gram-negative bacterial strain accumulates in a malignant solid tumor" as used herein refers to a recombinant virulence attenuated Gram-negative bacterial strain which replicates within a malignant solid tumor thereby increasing the bacterial count of this recombinant virulence attenuated Gram-negative bacterial strain inside the malignant solid tumor. Surprisingly it has been found that the recombinant virulence attenuated Gram-negative bacterial strain after administration to the subject accumulates specifically in the malignant solid tumor i.e. accumulates specifically in the organ where the malignant tumor is present, wherein the bacterial counts of the recombinant virulence attenuated Gram-negative bacterial strain in organs where no malignant solid tumor is present is low or not detectable.

In case of extracellular residing bacteria as *Yersinia*, the bacteria mostly accumulate within the intercellular space formed between tumor cells. Intracellular growing bacteria as *Salmonella* will mostly invade tumor cells and reside inside such cells, while extracellular accumulations might still occur. Bacterial counts of the recombinant virulence attenuated Gram-negative bacterial strain accumulated inside the malignant solid tumor can be e.g. in the range of $10^4$ to $10^9$ bacteria per gram of tumor tissue.

The term "cancer" used herein refers to a disease in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue, such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord. The term "cancer" used herein comprises solid tumors i.e. malignant solid tumors such as e.g. sarcomas, carcinomas, and lymphomas and non-solid tumors such as e.g. leukemias (cancers of the blood). Malignant solid tumors are preferred.

The term "malignant solid tumor" or "malignant solid tumor indication" used herein refers to an abnormal mass of tissue that usually does not contain cysts or liquid areas. Solid tumors may be benign (not cancer), or malignant (cancer). Malignant solid tumors are treated with the methods of the present invention. Different types of malignant solid tumors are named for the type of cells that form them. Examples of malignant solid tumors are sarcomas, carcinomas, and lymphomas. Leukemias (cancers of the blood) generally do not form malignant solid tumors (definition according to the national cancer institute of the NIH). Malignant solid tumors include, but are not limited to, abnormal mass of cells which may stem from different tissue types such as liver, colon, colorectum, skin, breast, pancreas, cervix uteri, corpus uteri, bladder, gallbladder, kidney, larynx, lip, oral cavity, oesophagus, ovary, prostate, stomach, testis, thyroid gland or lung and thus include malignant solid liver, colon, colorectum, skin, breast, pancreas, cervix uteri, corpus uteri, bladder, gallbladder, kidney, larynx, lip, oral cavity, oesophagus, ovary, prostate, stomach, testis, thyroid gland or lung tumors. Preferred malignant solid tumors which can be treated with the methods of the present invention are malignant solid tumors which stem from skin, breast, liver, pancreas, bladder, prostate and colon and thus include malignant solid skin, breast, liver, pancreas, bladder, prostate and colon tumors. Equally preferred malignant solid tumors which can be treated with the methods of the present invention are malignant solid tumors associated with liver cancer, such as hepatocellular carcinoma.

The term "bacterial effector protein which is virulent toward eukaryotic cells" as used herein refers to bacterial effector proteins, which are transported by secretion systems into host cells where they exert their virulence activity toward various host proteins and cellular machineries. Many different effector proteins are known, transported by various secretion system types and displaying a large repertoire of biochemical activities that modulate the functions of host regulatory molecules. Secretion systems include type 3 secretion system (T3SS), type 4 secretion system (T4SS) and type 6 secretion system (T6SS). Importantly, some effector proteins which are virulent toward eukaryotic cells (as *Shigella flexneri* IpaC) as well belong to the class of bacterial proteins, which are part of a secretion system machinery. In case the bacterial effector protein which is virulent toward eukaryotic cells is as well essential for the function of the secretion machinery, such a protein is excluded from this definition. T3SS effector proteins which are virulent towards eukaryotic cells refers to proteins as *Y. enterocolitica* YopE, YopH, YopJ, YopM, YopO, YopP, YopT or *Shigella flexneri* OspF, IpgD, IpgB1 or *Salmonella enterica* SopE, SopB, SptP or *P. aeruginosa* ExoS, ExoT, ExoU, ExoY or *E. coli* Tir, Map, EspF, EspG, EspH, EspZ. T4SS effector proteins which are virulent towards eukaryotic cells refers to proteins as *Legionella pneumophila* LidA, SidC, SidG, SidH, SdhA, SidJ, SdjA, SdeA, SdeA, SdeC, LepA, LepB, WipA, WipB, YlfA, YlfB, VipA, VipF, VipD, VpdA, VpdB, DrrA, LegL3, LegL5, LegL7, LegLC4, LegLC8, LegC5, LegG2, Ceg10, Ceg23, Ceg29 or *Bartonella henselae* BepA, BepB, BepC, BepD, BepE, BepF BepG or *Agrobacterium tumefaciens* VirD2, VirE2, VirE3, VirF or *H. pylori* CagA or *Bordetella pertussis* pertussis toxin. T6SS effector proteins which are virulent towards eukaryotic cells refers to proteins as *Vibrio cholerae* VgrG proteins (as VgrG1).

The term "T3SS effector protein which is virulent toward eukaryotic cells" or "bacterial T3SS effector protein which is virulent toward eukaryotic cells" as used herein refers to proteins which are naturally injected by T3S systems into the cytosol of eukaryotic cells and to proteins which are naturally secreted by T3S systems that might e.g form the translocation pore into the eukaryotic membrane, which are virulence factors toward eukaryotic cells i.e. to proteins which paralyze or reprogram the eukaryotic cell to the benefit of the pathogen. Effectors display a large repertoire of biochemical activities and modulate the function of crucial host regulatory mechanisms such as e.g. phagocytosis and the actin cytoskeleton, inflammatory signaling, apoptosis, endocytosis or secretory pathways[2,9] and include AvrA, AvrB, AvrBs2, AvrBS3, AvrBsT, AvrD, AvrD1, AvrPphB, AvrPphC, AvrPphEPto, AvrPpiBPto, AvrPto, AvrPtoB, AvrRpm1, AvrRpt2, AvrXv3, CigR, EspF, EspG, EspH, EspZ, ExoS, ExoT, GogB, GtgA, GtgE, GALA family of proteins, HopAB2, HopAO1, HopI1, HopM1, HopN1, HopPtoD2, HopPtoE, HopPtoF, HopPtoN, HopU1, HsvB, IcsB, IpaA, IpaH, IpaH7.8, IpaH9.8, IpgB1, IpgB2, IpgD, LcrV, Map, OspC1, OspE2, OspF, OspG, OspI, PipB, PipB2, PopB, PopP2, PthXo1, PthXo6, PthXo7, SifA, SifB, SipA/SspA, SlrP, SopA, SopB/SigD, SopD, SopE, SopE2, SpiC/SsaB, SptP, SpvB, SpvC, SrfH, SrfJ, Sse, SseB, SseC, SseD, SseF, SseG, SseI/SrfH, SseJ, SseK1, SseK2, SseK3, SseL, SspH1, SspH2, SteA, SteB, SteC, SteD, SteE, TccP2, Tir, VirA, VirPphA, VopF, XopD, YopE, YopH, YopJ, YopM, YopO, YopP, YopT, YpkA.

T3SS effector genes of *Yersinia* which are virulent to a eukaryotic cell and can be deleted/mutated from e.g. *Y. enterocolitica* are YopE, YopH, YopM, YopO, YopP (also named YopJ), and YopT [10]. The respective effector genes which are virulent to a eukaryotic cell can be deleted/mutated from *Shigella flexneri* (e.g. OspF, IpgD, IpgB1), *Salmonella enterica* (e.g. SopE, SopB, SptP), *P. aeruginosa* (e.g ExoS, ExoT, ExoU, ExoY) or *E. coli* (e.g. Tir, Map, EspF, EspG, EspH, EspZ). The nucleic acid sequences of these genes are available to those skilled in the art, e.g., in the Genebank Database (yopH, yopO, yopE, yopP, yopM, yopT from NC_002120 GI:10955536; *S. flexneri* effector proteins from AF386526.1 GI:18462515; *S. enterica* effectors from NC_016810.1 GI:378697983 or FQ312003.1 GI:301156631; *P. aeruginosa* effectors from AE004091.2 GI:110227054 or CP000438.1 GI:115583796 and *E. coli* effector proteins from NC_011601.1 GI:215485161).

For the purpose of the present invention, genes are denoted by letters of lower case and italicized to be distinguished from proteins. In case the genes (denoted by letters of lower case and italicized) are following a bacterial species name (like *E. coli*), they refer to a mutation of the corresponding gene in the corresponding bacterial species. For example, YopE refers to the effector protein encoded by the yopE gene. *Y. enterocolitica* yopE represents a *Y. enterocolitica* having a mutation in the yopE gene.

As used herein, the terms "polypeptide", "peptide", "protein", "polypeptidic" and "peptidic" are used interchangeably to designate a series of amino acid residues connected to each other by peptide bonds between the alpha-amino and carboxy groups of adjacent residues. Preferred are proteins which have an amino acid sequence comprising at least 10 amino acids, more preferably at least 20 amino acids.

According to the present invention, "a heterologous protein" includes naturally occurring proteins or a part thereof and also includes artificially engineered proteins or a part thereof. As used herein, the term "heterologous protein" refers to a protein or a part thereof other than the T3SS effector protein or N-terminal fragment thereof to which it can be fused. In particular the heterologous protein as used herein refers to a protein or a part thereof, which do not belong to the proteome, i.e. the entire natural protein complement of the specific recombinant virulence attenuated Gram-negative bacterial strain provided and used by the invention, e.g. which do not belong to the proteome, i.e. the entire natural protein complement of a specific bacterial strain of the genera *Yersinia, Escherichia, Salmonella* or *Pseudomonas*. Usually the heterologous protein is of animal origin including human origin. Preferably the heterologous protein is a human protein or a part thereof. More preferably the heterologous protein is selected from the group consisting of proteins involved in induction or regulation of an interferon (IFN) response, proteins involved in apoptosis or apoptosis regulation, cell cycle regulators, ankyrin repeat proteins, cell signaling proteins, reporter proteins, transcription factors, proteases, small GTPases, GPCR related proteins, nanobody fusion constructs and nanobodies, bacterial T3SS effectors, bacterial T4SS effectors and viral proteins. Particular preferably the heterologous protein is selected from the group consisting of proteins involved in induction or regulation of an interferon (IFN) response, proteins involved in apoptosis or apoptosis regulation, cell cycle regulators, ankyrin repeat proteins, reporter proteins, small GTPases, GPCR related proteins, nanobody fusion constructs, bacterial T3SS effectors, bacterial T4SS effectors and viral proteins. Even more particular preferred are heterologous proteins selected from the group consisting of proteins involved in induction or regulation of an interferon (IFN) response, proteins involved in apoptosis or apoptosis regulation, cell cycle regulators, and ankyrin repeat proteins. Most preferred are proteins involved in apoptosis or apoptosis regulation or proteins involved in induction or regulation of an interferon (IFN) response, in particular proteins involved in induction or regulation of an interferon (TFN) response, like animal, preferably human heterologous proteins involved in apoptosis or apoptosis regulation or human proteins involved in induction or regulation of an interferon (IFN) response. Proteins involved in induction or regulation of an interferon (IFN) response are preferably proteins, involved in induction or regulation of a type I interferon (IFN) response, more preferably human proteins involved in induction or regulation of a type I interferon (IFN) response.

In some embodiments the Gram-negative bacterial strain of the present invention comprises two nucleotide sequences encoding the identical or two different heterologous proteins fused independently from each other in frame to the 3'end of a nucleotide sequence encoding a delivery signal from a bacterial effector protein.

In some embodiments the Gram-negative bacterial strain of the present invention comprises three nucleotide sequences encoding the identical or three different heterologous proteins fused independently from each other in frame to the 3'end of a nucleotide sequence encoding a delivery signal from a bacterial effector protein.

The heterologous protein expressed by the recombinant virulence attenuated Gram-negative bacterial strain has usually a molecular weight of between 1 and 150 kD, preferably between 1 and 120 kD, more preferably between 1 and 100 kDa, most preferably between 10 and 80 kDa.

In some embodiments a part of a heterologous protein comprises a domain of a heterologous protein. Thus in some embodiments the Gram-negative bacterial strain of the present invention comprises a nucleotide sequence encoding a domain of a heterologous protein. Preferably the Gram-negative bacterial strain of the present invention comprises a nucleotide sequence encoding one or two domains of a heterologous protein, more preferably two domains of a heterologous protein.

In some embodiments the Gram-negative bacterial strain of the present invention comprises a nucleotide sequence encoding repeated domains of a heterologous protein or two or more domains of different heterologous proteins fused in frame to the 3'end of a nucleotide sequence encoding a delivery signal from a bacterial effector protein.

The term "heterologous proteins which belong to the same functional class of proteins" as used herein refers to heterologous proteins which have the same function e.g. heterologous proteins having enzymatic activity, heterologous proteins which act in the same pathway such as e.g. cell cycle regulation, or share a common specific feature as e.g. belonging to the same class of bacterial effector proteins. Functional classes of proteins are e.g. proteins involved in apoptosis or apoptosis regulation, proteins which act as cell cycle regulators, ankyrin repeat proteins, cell signaling proteins, proteins involved in induction or regulation of an interferon (IFN) response, reporter proteins, transcription factors, proteases, small GTPases, GPCR related proteins, nanobody fusion constructs and nanobodies, bacterial T3SS effectors, bacterial T4SS effectors or viral proteins which act jointly in the biological process of establishing virulence to eukaryotic cells.

According to the present invention, "a domain of a heterologous protein" includes domains of naturally occurring proteins and also includes domains of artificially engineered proteins. As used herein, the term "domain of a heterologous protein" refers to a domain of a heterologous protein other than a domain of a T3SS effector protein or a domain other than a domain comprising the N-terminal fragment thereof to which it can be fused to achieve a fusion protein. In particular the domain of a heterologous protein as used herein refers to a domain of a heterologous protein, which do not belong to the proteome, i.e. the entire natural protein complement of the specific recombinant Gram-negative bacterial strain provided and used by the invention, e.g. which do not belong to the proteome, i.e. the entire natural protein complement of a specific bacterial strain of the genera *Yersinia, Escherichia, Salmonella* or *Pseudomonas*. Usually the domain of the heterologous protein is of animal origin including human origin. Preferably the domain of the heterologous protein is a domain of a human protein. More preferably the domain of the heterologous protein is a domain of a protein selected from the group consisting of proteins involved in apoptosis or apoptosis regulation, proteins involved in induction or regulation of an interferon (IFN) response, cell cycle regulators, ankyrin repeat proteins, cell signaling proteins, reporter proteins, transcription factors, proteases, small GTPases, GPCR related proteins, nanobody fusion constructs and nanobodies, bacterial T3SS effectors, bacterial T4SS effectors and viral proteins. Particular preferably the domain of the heterologous protein is a domain of a protein selected from the group consisting of proteins involved in apoptosis or apoptosis regulation, proteins involved in induction or regulation of an interferon (IFN) response, cell cycle regulators, ankyrin repeat proteins, reporter proteins, small GTPases, GPCR related proteins, nanobody fusion constructs, bacterial T3SS effectors, bacterial T4SS effectors and viral proteins. Even more particular preferred are domains of heterologous proteins selected from the group consisting of proteins involved in apoptosis or apoptosis regulation, proteins involved in induction or regulation of an interferon (IFN) response, cell cycle regulators, and ankyrin repeat proteins. Most preferred are domains of proteins involved in induction or regulation of an interferon (IFN) response, like animal proteins involved in induction or regulation of an interferon (IFN) response, preferably domains of human heterologous proteins involved in induction or regulation of an interferon (IFN) response.

The term "repeated domains of a heterologous protein" as used herein refers to a fusion protein consisting of several repetitions of a domain of a heterologous protein, where these domains might either be directly fused to each other or where a variable linker e.g. a linker between 1 and 30, preferably between 2 and 15, more preferably between 3 and 10 amino acids might be introduced in between the domains. Preferably repeated identical domains or repeated domains which have an amino acid sequence identity of more than 80%, usually more than 85%, preferably more than 90%, even more preferably more than 95%, in particular more than 96%, more particular more than 97%, even more particular more than 98%, most particular more than 99% are used. Also preferred are identical domains which have an amino acid identity of 100%. Preferably two repeated domains, more preferably two repeated identical domains or two repeated domains having an amino acid sequence identity of more than 90%, preferably more than 95%, most preferably 100% are comprised by the fusion protein as referred herein. More than two, e.g. three, four, five or six repeated domains are also contemplated by the present invention.

The term "two or more domains of different heterologous proteins" as used herein refers to a fusion protein consisting of one or several repetitions of at least two domains of different heterologous proteins e.g. at least two domains of heterologous proteins having an amino acid sequence identity of 80% or less, preferably 60% or less, more preferably 40% or less, where these different domains might either be directly fused to each other or where a variable linker e.g. a linker between 1 and 30, preferably between 2 and 15, more preferably between 3 and 10 amino acids might be introduced in between the domains. Preferably two domains of different heterologous proteins are comprised by the fusion protein as referred herein. More than two, e.g. three, four, five or six domains of different heterologous proteins are also contemplated by the present invention.

The domain of a heterologous protein expressed by the recombinant Gram-negative bacterial strain has usually a molecular weight of between 1-50 kDa, preferably between 1-30 kDa, more preferably between 1-20 kDa, most preferably between 1-10 kDa.

According to the present invention "proteins involved in induction or regulation of an IFN response" include, but are not limited to, cGAS, STING, TRIF, TBK1, IKKepsilon, IRF3, TREX1, VPS34, ATG9a, DDX3, LC3, DDX41, IFI16, MRE11, DNA-PK, RIG1, MDA5, LGP2, IPS-1/MAVS/Cardif/VISA, Trim25, Trim32, Trim56, Riplet, TRAF2, TRAF3, TRAF5, TANK, IRF3, IRF7, IRF9, STAT1, STAT2, PKR, TLR3, TLR7, TLR9, DAI, IFI16, IFIX, MRE11, DDX41, LSm14A, LRRFIP1, DHX9, DHX36, DHX29, DHX15, Ku70, IFNAR1, IFNAR2, TYK2, JAK1, ISGF3, IL10R2, IFNLR1, IFNGR1, IFNGR2, JAK2, STAT4, cyclic dinucleotide generating enzymes (cyclic-di-AMP, cyclic-di-GMP and cyclic-di-GAMP cyclases) as WspR, DncV, DisA and DisA-like, CdaA, CdaS and cGAS or a fragment thereof.

According to the present invention "proteins involved in induction or regulation of a type I IFN response" include, but are not limited to, cGAS, STING, TRIF, TBK1, IKKepsilon, IRF3, TREX1, VPS34, ATG9a, DDX3, LC3, DDX41, IFI16, MRE11, DNA-PK, RIG1, MDA5, LGP2, IPS-1/MAVS/Cardif/VISA, Trim25, Trim32, Trim56, Riplet, TRAF2, TRAF3, TRAF5, TANK, IRF3, IRF7, IRF9, STAT1, STAT2, PKR, TLR3, TLR7, TLR9, DAI, IFI16, IFIX, MRE11, DDX41, LSm14A, LRRFIP1, DHX9, DHX36, DHX29, DHX15, Ku70, cyclic dinucleotide generating enzymes (cyclic-di-AMP, cyclic-di-GMP and cyclic-di-GAMP cyclases) as WspR, DncV, DisA and DisA-like, CdaA, CdaS and cGAS or a fragment thereof. Preferred proteins involved in induction or regulation of a type I IFN response are selected from the group consisting of cGAS, STING, TRIF, TBK1, IKKepsilon, IRF3, TREX1, VPS34, ATG9a, DDX3, LC3, DDX41, IFI16, MRE11, DNA-PK, RIG1, MDA5, LGP2, IPS-1/MAVS/Cardif/VISA, Trim25, Trim32, Trim56, Riplet, TRAF2, TRAF3, TRAF5, TANK, IRF3, IRF7, IRF9, STAT1, STAT2, PKR, LSm14A, LRRFIP1, DHX29, DHX15, and cyclic dinucleotide generating enzymes such as cyclic-di-AMP, cyclic-di-GMP and cyclic-di-GAMP cyclases selected from the group consisting of WspR, DncV, DisA and DisA-like, CdaA, CdaS and cGAS or a fragment thereof.

More preferred proteins involved in induction or regulation of a type I IFN response are selected from the group consisting of cGAS (as Uniprot. Q8N884 for the human protein), RIG1 (as Uniprot. O95786 for the human protein), MDA5 (as Uniprot. Q9BYX4 for the human protein), IPS-1/MAVS (as Uniprot. Q7Z434 for the human protein), IRF3 (as Uniprot. Q14653 for the human protein), IRF7 (as Uniprot. Q92985 for the human protein), IRF9 (as Uniprot. Q00978 for the human protein) and cyclic dinucleotide generating enzymes such as cyclic-di-AMP, cyclic-di-GMP and cyclic-di-GAMP cyclases selected from the group consisting of WspR (as Uniprot. Q9HXT9 for the *P. aeruginosa* protein), DncV (as Uniprot. Q9KVG7 for the *V. cholerae* protein), DisA and DisA-like (as Uniprot. Q812L9 for the *B. cereus* protein), CdaA (as Uniprot. Q8Y5E4 for the *L. monocytogenes* protein), CdaS (as Uniprot. 031854 or constitutive active L44F mutation as in Seq ID No.114 for the *B. subtilis* protein) and cGAS (as Uniprot. Q8N884 for the human protein) or a fragment of these proteins.

IPS-1/MAVS/Cardif/VISA refer to the eukaryotic mitochondrial antiviral-signaling protein containing an N-terminal CARD domain and with the Uniprot (uniprot.org) identifier for the human sequence "Q7Z434" and "Q8VCFO" for the murine sequence. The terms "IPS-1/MAVS", "MAVS/IPS-1" and "MAVS" are used herein interchangeably and refer to the eukaryotic mitochondrial antiviral-signaling protein containing an N-terminal CARD domain and with the Uniprot (uniprot.org) identifier for the human sequence "Q7Z434" and "Q8VCFO" for the murine sequence.

In some embodiments the heterologous proteins involved in induction or regulation of a type I IFN response are selected from the group consisting of a CARD domain containing proteins or a fragment thereof and cyclic dinucleotide generating enzymes such as cyclic-di-AMP, cyclic-di-GMP and cyclic-di-GAMP cyclases or a fragment thereof.

A fragment of a heterologous proteins involved in induction or regulation of a IFN response or a type I IFN response contains usually between 25 and 1000 amino acids, preferably between 50 and 600 amino acids, more preferably between 100 and 400 amino acids, even more preferably between 100 and 362 amino acids. In some embodiments a fragment of a heterologous proteins involved in induction or regulation of a IFN response or a type I IFN response comprises a N-terminal fragment of the heterologous proteins involved in induction or regulation of a IFN response or a type I IFN response which contains usually between 25 and 1000 amino acids, preferably between 50 and 600 amino acids, more preferably between 100 and 400 amino acids, even more preferably between 100 and 362 amino acids, in particular between 100 and 246 amino acids or, comprises a N-terminal fragment of the heterologous protein involved in induction or regulation of a IFN response or a type I IFN response which has a deletion of an amino acid sequence containing between amino acid 1 and amino acid 160 of the N-terminal amino acids, preferably a deletion of an amino acid sequence containing N-terminal amino aids 1-59 or N-terminal amino aids 1-160, and wherein the N-terminal fragment of the heterologous protein involved in induction or regulation of a IFN response or a type I IFN response contains usually between 25 and 1000 amino acids, preferably between 50 and 600 amino acids, more preferably between 100 and 400 amino acids, even more preferably between 100 and 362 amino acids.

A fragment of a CARD domain containing heterologous proteins involved in induction or regulation of a IFN response or a type I IFN response contains usually an amino acid sequence from N-terminal amino acid 1 to any of N-terminal amino acid 100-500, preferably an amino acid sequence from N-terminal amino acid 1 to any of N-terminal amino acid 100-400, more preferably an amino acid sequence from N-terminal amino acid 1 to any of N-terminal amino acid 100300, more preferably an amino acid sequence from N-terminal amino acid 1 to any of N-terminal amino acid 100-294, more preferably an amino acid sequence from N-terminal amino acid 1 to any of N-terminal amino acid 100-246.

In some embodiments a fragment of a CARD domain containing heterologous proteins involved in induction or regulation of a IFN response or a type I IFN response contains an amino acid sequence selected from the group consisting of an amino acid sequence comprising at least N-terminal amino acid 1 and no more than N-terminal amino acid 294, an amino acid sequence comprising at least N-terminal amino acid 1 and no more than N-terminal amino acid 246, an amino acid sequence comprising at least N-terminal amino acid 1 and no more than N-terminal amino acid 245, an amino acid sequence comprising at least N-terminal amino acid 1 and no more than N-terminal amino acid 229, an amino acid sequence comprising at least N-terminal amino acid 1 and no more than N-terminal amino acid 228, an amino acid sequence comprising at least N-terminal amino acid 1 and no more than N-terminal amino acid 218, an amino acid sequence comprising at least N-terminal amino acid 1 and no more than N-terminal amino acid 217, an amino acid sequence comprising at least N-terminal amino acid 1 and no more than N-terminal amino acid 100 and an amino acid sequence comprising at least N-terminal amino acid 1 and no more than N-terminal amino acid 101, more particular an amino acid sequence selected from the group consisting of an amino acid sequence comprising at least N-terminal amino acid 1 and no more than N-terminal amino acid 245, an amino acid sequence comprising at least N-terminal amino acid 1 and no more than N-terminal amino acid 228, an amino acid sequence comprising at least N-terminal amino acid 1 and no more than N-terminal amino acid 217 and an amino acid sequence comprising at least N-terminal amino acid 1 and no more than N-terminal amino acid 100 of a human CARD domain.

In some preferred embodiments a fragment of a CARD domain containing heterologous proteins involved in induction or regulation of a IFN response or a type I IFN response contains an amino acid sequence selected from the group consisting of an amino acid sequence from N-terminal amino acid 1 to N-terminal amino acid 294, an amino acid sequence from N-terminal amino acid 1 to N-terminal amino acid 246, an amino acid sequence from N-terminal amino acid 1 to N-terminal amino acid 245, an amino acid sequence from N-terminal amino acid 1 to N-terminal amino acid 229, an amino acid sequence from N-terminal amino acid 1 to N-terminal amino acid 228, an amino acid sequence from N-terminal amino acid 1 to N-terminal amino acid 218, an amino acid sequence from N-terminal amino acid 1 to N-terminal amino acid 217, an amino acid sequence from N-terminal amino acid 1 to N-terminal amino acid 100, an amino acid sequence from N-terminal amino acid 1 to N-terminal amino acid 101, more particular an amino acid sequence selected from the group consisting of an amino acid sequence from N-terminal amino acid 1 to N-terminal amino acid 245, an amino acid sequence from N-terminal amino acid 1 to N-terminal amino acid 228, an amino acid sequence from N-terminal amino acid 1 to N-terminal amino acid 217 and an amino acid sequence from N-terminal amino acid 1 to N-terminal amino acid 100 of a human CARD domain.

A fragment of cyclic dinucleotide generating enzymes such as cyclic-di-AMP, cyclic-di-GMP and cyclic-di-GAMP cyclases contains usually an amino acid sequence from N-terminal amino acid 1 to any of N-terminal amino acid 100-600, preferably an amino acid sequence from N-terminal amino acid 50 to any of N-terminal amino acid 100-550, more preferably an amino acid sequence from N-terminal amino acid 60 to any of N-terminal amino acid 100-530, in particular an amino acid sequence from N-terminal amino acid 60 to N-terminal amino acid 530, an amino acid sequence from N-terminal amino acid 146 to N-terminal amino acid 507 or an amino acid sequence from N-terminal amino acid 161 to N-terminal amino acid 530, more particular an amino acid sequence from N-terminal amino acid 161 to N-terminal amino acid 530 of the human cGAS. In some embodiments a fragment of cGAS contains in particular an amino acid sequence selected from the group consisting of an amino acid sequence comprising at least N-terminal amino acid 60 and no more than N-terminal amino acid N-terminal amino acid 422, an amino acid sequence comprising at least N-terminal amino acid 146 and no more than N-terminal amino acid N-terminal amino acid 507, and an amino acid sequence comprising at least N-terminal amino acid 161 and no more than N-terminal amino acid N-terminal amino acid 522. In some embodiments a fragment of cGAS contains more particular an amino acid sequence selected from the group consisting of an amino acid sequence from N-terminal amino acid 60 to N-terminal amino acid 422, an amino acid sequence from N-terminal amino acid 146 to N-terminal amino acid 507, and an amino acid sequence from N-terminal amino acid 161 to N-terminal amino acid 522.

In a more preferred embodiment the heterologous protein involved in induction or regulation of a type I IFN response is selected from the group consisting of the CARD domain comprising RIG1, MDA5, and MAVS/IPS-1 or a fragment thereof and cGAS and a fragment thereof, in particular selected from the group consisting of the CARD domain comprising RIG1 and a fragment thereof, the CARD domain comprising MAVS/IPS-1 and a fragment thereof, and cGAS and a fragment thereof. Fragments of these proteins are particular preferred. In this more preferred embodiment, the CARD domain comprising RIG1, MDA5, MAVS/IPS-1 comprises the naturally occurring CARD domain(s) and additionally C-terminal amino acids following the naturally occurring CARD domain(s) comprising the naturally occurring helicase domain in case of RIG-1 or a fragment thereof, preferably a fragment containing 1-500, more preferably 1-250, even more preferably 1-150 amino acids wherein the naturally occurring helicase domain or fragment thereof is not functional, i.e. does not bind a CARD domain or, comprises the downstream C-terminal sequence in case of MAVS/IPS-1 or a fragment thereof, preferably a fragment containing 1-500, more preferably 1-250, even more preferably 1-150 amino acids. In these embodiments cGAS and a fragment thereof comprises usually the naturally occurring synthase domain (NTase core and C-terminal domain; amino acids 160-522 of the human cGAS as described in [65] and as Uniprot. Q8N884 for the human protein), preferably cGAS and a fragment thereof comprises the naturally occurring synthase domain, but has a deletion of a part or the complete N-terminal domain, preferably a deletion of the complete N-terminal helical extension (N-terminal helical extension; amino acids 1-160 of the human cGAS as described in [65] and as Uniprot. Q8N884 for the human protein). The deletion of a part or the complete N-terminal domain is preferably a deletion of the amino acids 1-59.

In some embodiments the heterologous proteins involved in induction or regulation of a type I IFN response are selected from the group consisting of the RIG-I-like receptor (RLR) family (as RIG1 and MDA5) and a fragment thereof, other CARD domain containing proteins involved in antiviral signaling and type I IFN induction (as MAVS/IPS-1) and a fragment thereof and cyclic dinucleotide generating enzymes such as cyclic-di-AMP, cyclic-di-GMP and cyclic-di-GAMP cyclases selected from the group consisting of WspR, DncV, DisA and DisA-like, CdaA, CdaS and cGAS, and a fragment thereof, leading to stimulation of STING.

In some embodiments the heterologous proteins involved in induction or regulation of a type I IFN response are selected from the group consisting of RIG1, MDA5, LGP2, MAVS/IPS-1, WspR, DncV, DisA and DisA-like, CdaA, CdaS and cGAS or a fragment thereof, more preferably selected from the group consisting of RIG1, WspR, DncV, DisA-like, and cGAS or a fragment thereof.

In a more preferred embodiment the protein involved in induction or regulation of a type I IFN response is selected from the group consisting of RIG1, MDA5, MAVS/IPS-1, WspR, DncV, DisA and DisA-like, CdaA, and cGAS or a fragment thereof, even more preferably selected from the group consisting of RIG1, MDA5, MAVS/IPS-1, WspR, DncV, DisA-like, CdaA, and cGAS or a fragment thereof, in particular selected from the group consisting of RIG1, MAVS/IPS-1 and cGAS or a fragment thereof. Fragments of these proteins are particular preferred.

In this more preferred embodiment a fragment of RIG1, MDA5, MAVS/IPS-1 usually contains an amino acid sequence from N-terminal amino acid 1 to any of N-terminal amino acid 100-500, preferably an amino acid sequence from N-terminal amino acid 1 to any of N-terminal amino acid 100-400, more preferably an amino acid sequence from N-terminal amino acid 1 to any of N-terminal amino acid 100-300.

In this more preferred embodiment a fragment of RIG1 contains an amino acid sequence selected from the group consisting of an amino acid sequence comprising at least N-terminal amino acid 1 and no more than N-terminal amino acid 246, an amino acid sequence comprising at least N-terminal amino acid 1 and no more than N-terminal amino acid 245, an amino acid sequence comprising at least N-terminal amino acid 1 and no more than N-terminal amino acid 229, an amino acid sequence comprising at least N-terminal amino acid 1 and no more than N-terminal amino acid 228, an amino acid sequence comprising at least N-terminal amino acid 1 and no more than N-terminal amino acid 218, and an amino acid sequence comprising at least N-terminal amino acid 1 and no more than N-terminal amino acid 217; and a fragment of MAVS/IPS-1 contains an amino acid sequence selected from the group consisting of an amino acid sequence comprising at least N-terminal amino acid 1 and no more than N-terminal amino acid 100 and an amino acid sequence comprising at least N-terminal amino acid 1 and no more than N-terminal amino acid 101.

In this more preferred embodiment a fragment of RIG1 contains more particular an amino acid sequence selected from the group consisting of an amino acid sequence from N-terminal amino acid 1 to N-terminal amino acid 246, an amino acid sequence from N-terminal amino acid 1 to N-terminal amino acid 245, an amino acid sequence from N-terminal amino acid 1 to N-terminal amino acid 229, an amino acid sequence from N-terminal amino acid 1 to N-terminal amino acid 228, an amino acid sequence from N-terminal amino acid 1 to N-terminal amino acid 218, and an amino acid sequence from N-terminal amino acid 1 to N-terminal amino acid 217; and a fragment of MAVS/IPS-1 contains more particular an amino acid sequence selected from the group consisting of amino acid sequence from N-terminal amino acid 1 to N-terminal amino acid 100 and an amino acid sequence from N-terminal amino acid 1 to N-terminal amino acid 101.

In this more preferred embodiment a fragment of cGAS contains usually an amino acid sequence from N-terminal amino acid 1 to any of N-terminal amino acid 100-600, preferably an amino acid sequence from N-terminal amino acid 50 to any of N-terminal amino acid 100-550, more preferably an amino acid sequence from N-terminal amino acid 60 to any of N-terminal amino acid 100-530, in particular an amino acid sequence from N-terminal amino acid 60 to N-terminal amino acid 530, an amino acid sequence from N-terminal amino acid 146 to N-terminal amino acid 507 or an amino acid sequence from N-terminal amino acid 161 to N-terminal amino acid 530, more particular an amino acid sequence from N-terminal amino acid 60 to N-terminal amino acid 530, or an amino acid sequence from N-terminal amino acid 161 to N-terminal amino acid 530 of the human cGAS.

In this more preferred embodiment a fragment of cGAS contains in particular an amino acid sequence selected from the group consisting of an amino acid sequence comprising at least N-terminal amino acid 60 and no more than N-terminal amino acid N-terminal amino acid 422, an amino acid sequence comprising at least N-terminal amino acid 146 and no more than N-terminal amino acid N-terminal amino acid 507, and an amino acid sequence comprising at least N-terminal amino acid 161 and no more than N-terminal amino acid N-terminal amino acid 522.

In this more preferred embodiment a fragment of cGAS contains more particular an amino acid sequence selected from the group consisting of an amino acid sequence from N-terminal amino acid 60 to N-terminal amino acid 422, an amino acid sequence from N-terminal amino acid 146 to N-terminal amino acid 507, an amino acid sequence from N-terminal amino acid 161 to N-terminal amino acid 522.

In an even more preferred embodiment the protein involved in induction or regulation of a type I IFN response is selected from the group consisting of human RIG1 CARD domains$_{1-245}$ (SEQ ID NO: 37), human RIG1 CARD domains$_{1-228}$ (SEQ ID NO: 128), human RIG1 CARD domains$_{1-217}$ (SEQ ID NO: 129), murine RIG1 CARD domains$_{1-246}$ (SEQ ID NO: 38), murine RIG1 CARD domains$_{1-229}$ (SEQ ID NO: 110), murine RIG1 CARD domains$_{1-218}$ (SEQ ID NO: 111), human MAVS CARD domain$_{1-100}$ (SEQ ID NO: 116), murine MAVS CARD domain$_{1-101}$ (SEQ ID NO: 130), *N. vectensis* cGAS (SEQ ID NO: 43), human cGAS$_{161-522}$ (SEQ ID NO: 115), murine cGAS$_{146-507}$ (SEQ ID NO: 131) and *N. vectensis* cGAS$_{60-422}$ (SEQ ID NO: 117).

In a particular preferred embodiment the protein involved in induction or regulation of a type I IFN response wherein the protein involved in induction or regulation of a type I IFN response is selected from the group consisting of human RIG1 CARD domains$_{1-245}$, (SEQ ID NO: 37), human RIG1 CARD domains$_{1-228}$ (SEQ ID NO: 128), human RIG1 CARD domains$_{1-217}$ (SEQ ID NO: 129), human MAVS CARD domain$_{1-100}$ (SEQ ID NO: 116), and human cGAS$_{161-522}$ (SEQ ID NO: 115).

In a more particular preferred embodiment the protein involved in induction or regulation of a type I IFN response is selected from the group consisting of human RIG1 CARD domains$_{1-245}$, murine RIG1 CARD domains$_{1-246}$, murine RIG1 CARD domains$_{1-229}$, murine RIG1 CARD domains$_{1-218}$, human MAVS$_{1-100}$, *N. vectensis* cGAS, human cGAS$_{161-522}$ and *N. vectensis* cGAS$_{60-422}$.

The RIG-I-like receptor (RLR) family comprises proteins selected from the group consisting of RIG1, MDA5 and LGP2. Preferred heterologous proteins involved in induction or regulation of a type I IFN response are the CARD domain containing proteins RIG1 and MDA5, in particular the CARD domain containing protein RIG1. Other CARD domain containing proteins involved in type I IFN induction comprises proteins selected form the group consisting of MAVS/IPS-1.

In some preferred embodiments the heterologous proteins involved in induction or regulation of a type I IFN response are selected from the group of proteins comprising a CARD domain of RIG1, a CARD domain of MDA5, and/or a CARD domain of MAVS/IPS-1, and WspR, DncV, DisA and DisA-like, CdaA, CdaS and cGAS and a fragment thereof, preferably selected from the group of proteins comprising of a CARD domain of RIG1 and/or a CARD domain of MAVS/IPS-1, and WspR, DncV, DisA and DisA-like, CdaA, and cGAS or a fragment thereof.

In some preferred embodiments the heterologous proteins involved in induction or regulation of a type I IFN response are selected from the group consisting of a CARD domain of RIG1, a CARD domain of MDA5, a CARD domain of MAVS/IPS-1, WspR, DncV, DisA and DisA-like, CdaA, CdaS and cGAS, more preferably selected from the group consisting of a CARD domain of RIG1, WspR, DncV, DisA-like, and cGAS.

In some preferred embodiments the heterologous proteins involved in induction or regulation of a type I IFN response comprises one or more (e.g. two, three or four) CARD domains, preferably comprises one or more (e.g. two, three or four) CARD domains of RIG1, MDA5, and/or MAVS/IPS-1, preferably of RIG1 and/or MAVS/IPS-1. In a more preferred embodiment the heterologous proteins involved in induction or regulation of a type I IFN response comprises both CARD domains of RIG1 or MDA5, in particular RIG1.

In some embodiments the heterologous proteins involved in induction or regulation of a type I IFN response are selected from the group consisting of a type I IFN response inducing protein without enzymatic function or a type I IFN response inducing protein with enzymatic function. A type I IFN response inducing protein without enzymatic function encompassed by the present invention comprise usually at least one CARD domain preferably two CARD domains. A CARD domain is normally composed of a bundle of six to seven alpha-helices, preferably an arrangement of six to seven antiparallel alpha helices with a hydrophobic core and an outer face composed of charged residues. A type I IFN response inducing protein with enzymatic function encompassed by the present invention comprise usually a cyclic dinucleotide generating enzyme (cyclic-di-AMP, cyclic-di-GMP and cyclic-di-GAMP cyclases) or a domain thereof leading to stimulation of STING, preferably a di-adenylate-cyclase (DAC), di-guanlyate-cyclase (DGC) or GMP-AMP-cylcase (GAC) or domain thereof.

According to the present invention "proteins involved in apoptosis or apoptosis regulation" include, but are not limited to, Bad, Bcl2, Bak, Bmt, Bax, Puma, Noxa, Bim, Bcl-xL, Apaf1, Caspase 9, Caspase 3, Caspase 6, Caspase 7, Caspase 10, DFFA, DFFB, ROCK1, APP, CAD, ICAD, CAD, EndoG, AIF, HtrA2, Smac/Diablo, Arts, ATM, ATR, Bok/Mtd, Bmf, Mcl-1(S), IAP family, LC8, PP2B, 14-3-3 proteins, PKA, PKC, PI3K, Erkl/2, p90RSK, TRAF2, TRADD, FADD, Daxx, Caspase8, Caspase2, RIP, RAIDD, MKK7, JNK, FLIPs, FKHR, GSK3, CDKs and their inhibitors like the INK4-family (p16(Ink4a), p15(Ink4b), p18 (Ink4c), p19(Ink4d)), and the Cip1/Waf1/Kip1-2-family (p21(Cip1/Waf1), p27(Kip1), p57(Kip2).

Preferably Bad, Bmt, Bcl2, Bak, Bax, Puma, Noxa, Bim, Bcl-xL, Caspase9, Caspase3, Caspase6, Caspase7, Smac/Diablo, Bok/Mtd, Bmf, Mel-1(S), LC8, PP2B, TRADD, Daxx, Caspase8, Caspase2, RIP, RAIDD, FKHR, CDKs and their inhibitors like the INK4-family (p16(Ink4a), p15 (Ink4b), p18(Ink4c), p19(Ink4d)), most preferably BIM, Bid, truncated Bid, FADD, Caspase 3 (and subunits thereof), Bax, Bad, Akt, CDKs and their inhibitors like the INK4- family (p16(Ink4a), p15(Ink4b), p18(Ink4c), p19(Ink4d)) are used [11-13]. Additionally proteins involved in apoptosis or apoptosis regulation include DIVA, Bcl-Xs, Nbk/Bik, Hrk/Dp5, Bid and tBid, Egl-1, Bcl-Gs, Cytochrome C, Beclin, CED-13, BNIP1, BNIP3, Bcl-B, Bcl-W, Ced-9, A1, NR13, Bfl-1, Caspase 1, Caspase 2, Caspase 4, Caspase 5, Caspase 8.

Proteins involved in apoptosis or apoptosis regulation are selected from the group consisting of pro-apoptotic proteins, anti-apoptotic proteins, inhibitors of apoptosis-prevention pathways and inhibitors of pro-survival signalling or pathways. Pro-apoptotic proteins comprise proteins selected form the group consisting of Bax, Bak, Diva, Bcl-Xs, Nbk/Bik, Hrk/Dp5, Bmf, Noxa, Puma, Bim, Bad, Bid and tBid, Bok, Apaf1, Smac/Diablo, BNIP1, BNIP3, Bcl-Gs, Beclin 1, Egl-1 and CED-13, Cytochrome C, FADD, the Caspase family, and CDKs and their inhibitors like the INK4-family (p16(Ink4a), p15(Ink4b), p18(Ink4c), p19 (Ink4d)) or selected from the group consisting of Bax, Bak, Diva, Bcl-Xs, Nbk/Bik, Hrk/Dp5, Bmf, Noxa, Puma, Bim, Bad, Bid and tBid, Bok, Egl-1, Apaf1, Smac/Diablo, BNIP1, BNIP3, Bcl-Gs, Beclin 1, Egl-1 and CED-13, Cytochrome C, FADD, and the Caspase family.

Preferred are Bax, Bak, Diva, Bcl-Xs, Nbk/Bik, Hrk/Dp5, Bmf, Noxa, Puma, Bim, Bad, Bid and tBid, Bok, Egl-1, Apaf1, BNIP1, BNIP3, Bcl-Gs, Beclin 1, Egl-1 and CED-13, Smac/Diablo, FADD, the Caspase family, CDKs and their inhibitors like the INK4-family (p16(Ink4a), p15 (Ink4b), p18(Ink4c), p19(Ink4d)). Equally preferred are Bax, Bak, Diva, Bcl-Xs, Nbk/Bik, Hrk/Dp5, Bmf, Noxa, Puma, Bim, Bad, Bid and tBid, Bok, Apaf1, BNIP1, BNIP3, Bcl-Gs, Beclin 1, Egl-1 and CED-13, Smac/Diablo, FADD, the Caspase family.

Anti-apoptotic proteins comprise proteins selected form the group consisting of Bcl-2, Bcl-X1, Bcl-B, Bcl-W, Mcl-1, Ced-9, A1, NR13, IAP family and Bfl-1. Preferred are Bcl-2, Bcl-X1, Bcl-B, Bcl-W, Mcl-1, Ced-9, A1, NR13 and Bfl-1. Inhibitors of apoptosis-prevention pathways comprise proteins selected form the group consisting of Bad, Noxa and Cdc25A. Preferred are Bad and Noxa.

Inhibitors of pro-survival signalling or pathways comprise proteins selected form the group consisting of PTEN, ROCK, PP2A, PHLPP, JNK, p38. Preferred are PTEN, ROCK, PP2A and PHLPP.

In some embodiments, the heterologous proteins involved in apoptosis or apoptosis regulation are selected from the group consisting of BH3-only proteins, caspases and intracellular signalling proteins of death receptor control of apoptosis. BH3-only proteins are preferred.

BH3-only proteins comprise proteins selected form the group consisting of Bad, BIM, Bid and tBid, Puma, Bik/Nbk, Bod, Hrk/Dp5, BNIP1, BNIP3, Bmf, Noxa, Mel-1, Bcl-Gs, Beclin 1, Egl-1 and CED-13. Preferred are Bad, BIM, Bid and tBid, in particular tBid.

Caspases comprise proteins selected form the group consisting of Caspase 1, Caspase 2, Caspase 3, Caspase 4, Caspase 5, Caspase 6, Caspase 7, Caspase 8, Caspase 9, Caspase 10. Preferred are Caspase 3, Caspase 8 and Caspase 9.

Intracellular signalling proteins of death receptor control of apoptosis comprise proteins selected form the group consisting of FADD, TRADD, ASC, BAP31, GULP1/CED-6, CIDEA, MFG-E8, CIDEC, RIPK1/RIP1, CRADD, RIPK3/RIP3, Crk, SHB, CrkL, DAXX, the 14-3-3 family, FLIP, DFF40 and 45, PEA-15, SODD. Preferred are FADD and TRADD.

In some embodiments two heterologous proteins involved in apoptosis or apoptosis regulation are comprised by the Gram-negative bacterial strain, wherein one protein is a pro-apoptotic protein and the other protein is an inhibitor of apoptosis-prevention pathways or wherein one protein is a pro-apoptotic protein and the other protein is an inhibitor of pro-survival signalling or pathways.

Pro-apoptotic proteins encompassed by the present invention have usually an alpha helical structure, preferably a hydrophobic helix surrounded by amphipathic helices and usually comprise at least one of BH1, BH2, BH3 or BH4 domaines, preferably comprise at least one BH3 domain. Usually pro-apoptotic proteins encompassed by the present invention have no enzymatic activity.

Anti-apoptotic proteins encompassed by the present invention have usually an alpha helical structure, preferably a hydrophobic helix surrounded by amphipathic helices and comprises a combination of different BH1, BH2, BH3 and BH4 domains, preferably a combination of different BH1, BH2, BH3 and BH4 domains wherein a BH1 and a BH2 domain is present, more preferably BH4-BH3-BH1-BH2, BH1-BH2, BH4-BH1-BH2 or BH3-BH1-BH2 (from N- to the C-terminus). Additionally, proteins containing at least one BIR domain are also encompassed.

Inhibitors of apoptosis-prevention pathways encompassed by the present invention have usually an alpha helical structure, preferably a hydrophobic helix surrounded by amphipathic helices and usually comprise one BH3 domain.

BH1, BH2, BH3 or BH4 domains are each usually between about 5 to about 50 amino acids in length. Thus in some embodiments the heterologous proteins involved in apoptosis or apoptosis regulation is selected from the group consisting of heterologous proteins involved in apoptosis or apoptosis regulation which are about 5 to about 200, preferably about 5 to about 150, more preferably about 5 to about 100, most preferably about 5 to about 50, in particular about 5 to about 25 amino acids in length.

In some embodiments the Gram-negative bacterial strain of the present invention comprises a nucleotide sequence encoding two domains of a heterologous proteins involved in apoptosis or apoptosis regulation, preferably two repeated, more preferably two identical repeated domains of a protein involved in apoptosis or apoptosis regulation or two domains of different proteins involved in apoptosis or apoptosis regulation, most preferably two identical repeated domains of a protein involved in apoptosis or apoptosis regulation. In some embodiments the Gram-negative bacterial strain of the present invention comprises a nucleotide sequence encoding two domains of a heterologous proteins involved in apoptosis or apoptosis regulation, wherein one is a domain of a pro-apoptotic protein and the other is a domain of a protein which is an inhibitor of apoptosis-prevention pathways or wherein one is a domain of a pro-apoptotic protein and the other domain is a domain of a protein which is an inhibitor of pro-survival signalling or pathways.

A particular preferred heterologous protein is the BH3 domain of apoptosis inducer tBID, more particular the BH3 domain comprising a sequence selected from the group consisting of SEQ ID NOs: 29-32, preferably SEQ ID NO: 31 or SEQ ID NO: 32.

Equally preferred is the BH3 domain of apoptosis regulator BAX, more particular the BAX domain comprising a sequence selected from the group consisting of SEQ ID NOs: 33-36, preferably SEQ ID NO: 35 or SEQ ID NO: 36. The human and murine sequences are given in SEQ ID NOs, but tBID and BAX BH3 domains of all other species are equally included.

In some embodiments the repeated domains of the heterologous proteins are the BH3 domain, preferably repeated BH3 domains of apoptosis inducer tBID, more preferably repeated BH3 domains of the apoptosis inducer tBID comprised by SEQ ID NO: 29-32 or SEQ ID NO: 25 or SEQ ID NO: 19, even more preferably two repeated BH3 domains of apoptosis inducer tBID, most preferably two repeated BH3 domains of the apoptosis inducer tBID comprised by SEQ ID NO: 29-32 or SEQ ID NO: 25 or SEQ ID NO: 19, in particular two repeated BH3 domains of apoptosis inducer tBID comprised by the sequence of SEQ ID NO: 27. Thus in a preferred embodiment the Gram-negative bacterial strain and/or the vector of the present invention comprises a second DNA sequence encoding two repeated domains of a BH3 domain, more preferably two repeated BH3 domains of apoptosis inducer tBID. The two repeated domains may be connected by a linker of 1-30 amino acid length, preferably 2-15 amino acids, more preferred 3-10 amino acids long.

In some embodiments the two or more domains of different heterologous proteins are domains of heterologous proteins which belong to the same functional class of proteins, preferably the different heterologous proteins of the two or more domains are different heterologous proteins from the class of proteins involved in apoptosis or apoptosis regulation. In a preferred embodiment the two or more domains of different heterologous proteins are the BH3 domain of apoptosis inducer tBID and the BH3 domain of apoptosis regulator BAX, in particular the fused BH3 domains comprised by the sequence of SEQ ID NO: 24 and 28. The two domains of different heterologous proteins may be connected by a linker of 1-30 amino acid length, preferably 2-15 amino acids, more preferred 3-10 amino acids long.

Another particular preferred heterologous protein is a domain of a protein involved in induction or regulation of a type I IFN response, more particular a CARD domain of RIG1 comprising a sequence selected from the group consisting of SEQ ID NOs: 37, 38, 110, 111, 128, 129, a CARD domain of MDA5 comprising a sequence selected from the group consisting of SEQ ID NOs: 44-47, 112, 113, preferably SEQ ID NOs: 112 or 113, or a CARD domain of MAVS/IPS-1 comprising a sequence selected from the group consisting of SEQ ID NO: 116, 48-49, preferably SEQ ID NO: 116, full-length cGAS such as N. vectensis cGAS (SEQ ID NO: 43), human cGAS$_{161-522}$ (SEQ ID NO: 115), N. vectensis cGAS$_{60-422}$ (SEQ ID NO: 117) or murine cGAS$_{146-507}$ (SEQ ID NO: 131). Most particular a CARD domain of RIG1 comprising a sequence selected from the group consisting of SEQ ID NOs: 37, 38, 110, 111, 128, 129, a CARD domain protein comprising of MAVS/IPS-1 comprising a sequence selected from the group consisting of SEQ ID NO: 116, 48-49, preferably SEQ ID NO: 116, and full-length cGAS such as N. vectensis cGAS (SEQ ID NO: 43), human cGAS$_{161-522}$ (SEQ ID NO: 115), N. vectensis cGAS$_{60-422}$ (SEQ ID NO: 117) or murine cGAS$_{146-507}$ (SEQ ID NO: 131).

In some embodiments the heterologous proteins is a pro-drug converting enzyme. In these embodiments the recombinant virulence attenuated Gram-negative bacterial strain expresses, preferably expresses and secretes a pro-drug converting enzyme. A prodrug converting enzyme as referred herein comprises enzymes converting non-toxic prodrugs into a toxic drug, preferably enzymes selected from the group consisting of cytosine deaminase, purine nucleoside phosphorylase, thymidine kinase, beta-galactosidase, carboxylesterases, nitroreductase, carboxypeptidases and beta-glucuronidases, more preferably enzymes selected from the group consisting of cytosine deaminase, purine nucleoside phosphorylase, thymidine kinase, and beta-galactosidase.

The term "protease cleavage site" as used herein refers to a specific amino acid motif within an amino acid sequence e.g. within an amino acid sequence of a protein or a fusion protein, which is cleaved by a specific protease, which recognizes the amino acid motif. For review see [14]. Examples of protease cleavage sites are amino acid motifs, which are cleaved by a protease selected from the group consisting of enterokinase (light chain), enteropeptidase, prescission protease, human rhinovirus protease (HRV 3C), TEV protease, TVMV protease, FactorXa protease and thrombin. The following amino acid motif is recognized by the respective protease:

Asp-Asp-Asp-Asp-Lys (SEQ ID NO:132): Enterokinase (light chain)/Enteropeptidase

Leu-Glu-Val-Leu-Phe-Gln/Gly-Pro (SEQ ID NO:133): PreScission Protease/human Rhinovirus protease (HRV 3C)

Glu-Asn-Leu-Tyr-Phe-Gln-Ser (SEQ ID NO:134) and modified motifs based on the Glu-X-X-Tyr-X-Gln-Gly/Ser (SEQ ID NO:135) (where X is any amino acid) recognized by TEV protease (tobacco etch virus)

Glu-Thr-Val-Arg-Phe-Gln-Ser (SEQ ID NO:136): TVMV protease

Ile-(Glu or Asp)-Gly-Arg (SEQ ID NO:137): FactorXa protease

Leu-Val-Pro-Arg/Gly-Ser (SEQ ID NO:138): Thrombin.

Encompassed by the protease cleavage sites as used herein is ubiquitin. Thus in some preferred embodiments ubiquitin is used as protease cleavage site, i.e. a nucleotide sequence encodes ubiquitin as protease cleavage site, which can be cleaved by a specific ubiquitin processing proteases at the N-terminal site, e.g. which can be cleaved by a specific ubiquitin processing proteases called Deubiquitinating enzymes at the N-terminal site endogenously in the cell where the fusion protein has been delivered to. Ubiquitin is processed at its C-terminus by a group of endogenous Ubiquitin-specific C-terminal proteases (Deubiquitinating enzymes, DUBs). The cleavage of Ubiquitin by DUBs is supposed to happen at the very C-terminus of Ubiquitin (after G76).

An "individual," "subject" or "patient" is a vertebrate. In certain embodiments, the vertebrate is a mammal. Mammals include, but are not limited to, primates (including human and non-human primates) and rodents (e.g., mice and rats). In peferred embodiments, a subject is a human.

The term "mutation" is used herein as a general term and includes changes of both single base pair and multiple base pairs. Such mutations may include substitutions, frame-shift mutations, deletions, insertions and truncations.

The term "nuclear localization signal" as used herein refers to an amino acid sequence that marks a protein for import into the nucleus of a eukaryotic cell and includes preferably a viral nuclear localization signal such as the SV40 large T-antigen derived NLS (PPKKKRKV (SEQ ID NO:139)).

The term "multiple cloning site" as used herein refers to a short DNA sequence containing several restriction sites for cleavage by restriction endonucleases such as AclI, HindIII, SspI, MluCI, Tsp509I, PciI, AgeI, BspMI, BfuAI, SexAI, MluI, BceAI, HpyCH4IV, HpyCH4III, BaeI, BsaXI, AflIII, SpeI, BsrI, BmrI, BglII, AfeI, AluI, StuI, ScaI, ClaI, BspDI, PI-SceI, NsiI, AseI, SwaI, CspCI, MfeI, BssSI, BmgBI, PmlI, DraIII, AleI, EcoP15I, PvuII, AlwNI, BtsIMutI, TspRI, NdeI, NlaIII, CviAII, FatI, MslI, FspEI, XcmI, BstXI, PflMI, BccI, NcoI, BseYI, FauI, SmaI, XmaI, TspMI, Nt.CviPII, LpnPI, AciI, SacII, BsrBI, MspI, HpaII, ScrFI, BssKI, StyD4I, BsaJI, BslI, BtgI, NciI, AvrII, MnlI, BbvCI, Nb.BbvCI, Nt.BbvCI, SbfI, Bpu10I, Bsu36I, EcoNI, HpyAV, BstNI, PspGI, StyI, BcgI, PvuI, BstUI, EagI, RsrII, BsiEI, BsiWI, BsmBI, Hpy99I, MspAlI, MspJI, SgrAI, BfaI, BspCNI, XhoI, EarI, AcuI, PstI, BpmI, DdeI, SfcI, AflMI, BpuEI, SmlI, AvaI, BsoBI, MboII, BbsI, XmnI, BsmI, Nb.BsmI, EcoRI, HgaI, AatII, ZraI, Tth111 PflFI, PshAI, AhdI, DrdI, Eco53kI, SacI, BseRI, PleI, Nt.BstNBI, MlyI, HinfI, EcoRV, MboI, Sau3AI, DpnII BfuCI, DpnI, BsaBI, TfiI, BsrDI, Nb.BsrDI, BbvI, BtsI, Nb.BtsI, BstAPI, SfaNI, SphI, NmeAIII, NaeI, NgoMIV, BglI, AsiSI, BtgZI, HinPII, HhaI, BssHII, NotI, Fnu4HI, Cac8I, MwoI, NheI, BmtI, SapI, BspQI, Nt.BspQI, BlpI, TseI, ApeKI, Bsp1286I, AlwI, Nt.AlwI, BamHI, FokI, BtsCI, HaeIII, PhoI, FseI, SfiI, NarI, KasI, SfoI, PluTI, AscI, EciI, BsmFI, ApaI, PspOMI, Sau96I, NlaIV, KpnI, Acc65I, BsaI, HphI, BstEII, AvaII, BanI, BaeGI, BsaHI, BanII, RsaI, CviQI, BstZ17I, BciVI, SalI, Nt.BsmAI, BsmAI, BcoDI, ApaLI, BsgI, AccI, Hpy166II, Tsp45I, HpaI, PmeI, HincII, BsiHKAI, ApoI, NspI, BsrFI, BstYI, HaeII, CviKI-1, EcoO109I, PpuMI, I-CeuI, SnaBI, I-SceI, BspHI, BspEI, MmeI, TaquI, NruI, Hpy188I, Hpy188III, XbaI, BclI, HpyCH4V, FspI, PI-PspI, MscI, BsrGI, MseI, PacI, PsiI, BstBI, DraI, PspXI, BsaWI, BsaAI, EaeI, preferably XhoI, XbaI, HindIII, NcoI, NotI, EcoRI, EcoRV, BamHI, NheI, SacI, SalI, BstBI. The term "multiple cloning site" as used herein further refers to a short DNA sequence used for recombination events as e.g in Gateway cloning strategy or for methods such as Gibbson assembly or topo cloning.

The term "wild type strain" or "wild type of the Gram-negative bacterial strain" as used herein refers to a naturally occurring variant or a naturally occurring variant containing genetic modifications allowing the use of vectors, such as deletion mutations in restriction endonucleases or antibiotic resistance genes. These strains contain chromosomal DNA as well as in some cases (e.g. *Y. enterocolitica, S. flexneri*) an unmodified virulence plasmid.

The term "*Yersinia* wild type strain" as used herein refers to a naturally occurring variant (as *Y. enterocolitica* E40) or a naturally occurring variant containing genetic modifications allowing the use of vectors, such as deletion mutations in restriction endonucleases or antibiotic resistance genes (as *Y. enterocolitica* MRS40, the Ampicillin sensitive derivate of *Y. enterocolitica* E40) These strains contain chromosomal DNA as well as an unmodified virulence plasmid (called pYV).

*Y. enterocolitica* subspecies *palearctica* refers to the low-pathogenic *Y. enterocolitica* strains, which are in contrast to the higher virulent strains of subspecies *enterocolitica* [15,16] *Y. enterocolitica* subsp. *palearctica* lack, in comparison to *Y. enterocolitica* subsp. *enterocolitica*, a high-pathogenicity island (HPI). This HPI encodes the iron siderophore called yersiniabactin [17]. The lack of yersiniabactin in *Y. enterocolitica* subsp. *palearctica* renders this subspecies less pathogenic and dependent on induced systemic accessible iron for persistent infection in e.g. liver or spleen [17]. Iron can be made accessible for the bacteria in an individual e.g by pretreatment with deferoxamine, an iron chelator used to treat iron overload in patients [18].

The term "comprise" is generally used in the sense of include, that is to say permitting the presence of one or more features or components.

The term "about" refers to a range of values ±10% of a specified value. For example, the phrase "about 200" includes ±10% of 200, or from 180 to 220.

In one aspect the present invention provides a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a deletion of a chromosomal gene coding for an endogenous protein essential for growth and an endogenous virulence plasmid which comprises a nucleotide sequence comprising a gene coding for said endogenous protein essential for growth operably linked to a promoter.

In a further aspect the present invention provides a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a modulation within a RNA within a RNA thermosensor region upstream of a gene coding for an endogenous AraC-type DNA binding protein.

In a further aspect the present invention provides a recombinant virulence attenuated Gram-negative bacterial strain which comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the heterologous protein is a protein involved in induction or regulation of an interferon (IFN) response.

In a further aspect, the present invention provides a recombinant virulence attenuated Gram-negative bacterial strain as described herein, for use in a method of treating cancer in a subject, the method comprising administering to the subject said recombinant virulence attenuated Gram-negative bacterial strain, wherein the recombinant virulence attenuated Gram-negative bacterial strain is administered in an amount that is sufficient to treat the subject. Preferably the present invention provides a recombinant virulence attenuated Gram-negative bacterial strain as described herein for use in a method of treating a malignant solid tumor cancer in a subject, wherein the recombinant virulence attenuated Gram-negative bacterial strain accumulates in the malignant solid tumor, the method comprising administering to the subject said recombinant virulence attenuated Gram-negative bacterial strain, wherein the recombinant virulence attenuated Gram-negative bacterial strain is administered in an amount that is sufficient to treat the subject.

In some embodiments the recombinant virulence attenuated Gram-negative bacterial strain is deficient in the production of at least one bacterial effector protein which is virulent toward eukaryotic cells.

In one embodiment of the present invention the recombinant virulence attenuated Gram-negative bacterial strain is transformed with a nucleotide molecule e.g. a vector which comprises in the 5' to 3' direction:

a promoter;
a first nucleotide sequence encoding a delivery signal from a bacterial effector protein, operably linked to said promoter;
a second nucleotide sequence encoding a heterologous protein fused in frame to the 3'end of said first nucleotide sequence.

In one embodiment of the present invention the recombinant virulence attenuated Gram-negative bacterial strain is transformed with a nucleotide molecule e.g. a vector which comprises in the 5' to 3' direction:
a first nucleotide sequence encoding a delivery signal or a fragment thereof from a bacterial effector protein;
a second nucleotide sequence encoding a heterologous protein fused in frame to the 3'end of said first nucleotide sequence.

Preferably the nucleotide sequence encoding a heterologous protein is flanked on its 3' end by a nucleotide sequence homologous to the nucleotide sequence of the chromosome or of the endogenous virulence plasmid at the 3' end of a delivery signal from a bacterial effector protein or to a fragment thereof. More preferably, this nucleotide sequence flanking the homologous protein on its 3' end is homologous to a nucleotide sequence lying within 10 kbp on the chromosome or on an endogenous virulence plasmid at the 3' end of the delivery signal from a bacterial effector protein or to a fragment thereof. In particular, this nucleotide sequence flanking the homologous protein on its 3' end is homologous to a nucleotide sequence within the same operon on the chromosome or on an endogenous virulence plasmid as the delivery signal from a bacterial effector protein or a fragment thereof. In this embodiment, transformation is usually performed so that the fused nucleotide sequence is inserted by homologous recombination on an endogenous virulence plasmid or a chromosome, preferably on an endogenous virulence plasmid, of the recombinant virulence attenuated Gram-negative bacterial strain, and the fused nucleotide sequence is operably linked to a promoter of an endogenous virulence plasmid or of a chromosome e.g. of a chromosomal pathogenicity island. Preferably the fused nucleotide sequence is operably linked to a promoter of an endogenous virulence plasmid. In this embodiment the nucleotide sequence comprises a delivery signal or fragment thereof from a bacterial effector protein, preferably a fragment thereof, which provides for homologous recombination at the homologous site at the chromosome or at an endogenous virulence plasmid, preferably on an endogenous virulence plasmid, to result in the nucleotide sequence be placed in frame to the 3'end of the chromosomal or endogenous virulence plasmid delivery signal which is operatively linked to the endogenous promoter.

In a further embodiment of the present invention the recombinant virulence attenuated Gram-negative bacterial strain or the recombinant virulence attenuated Gram-negative bacterial strain, is transformed with a nucleotide molecule, preferably a DNA nucleotide molecule, comprising a nucleotide sequence encoding a heterologous protein and a nucleotide sequence which is homologous or identical to a nucleotide sequence encoding a delivery signal from a bacterial effector protein or which is homologous or identical to a nucleotide sequence encoding a fragment of a delivery signal from a bacterial effector protein, wherein the delivery signal from a bacterial effector protein or a fragment thereof is encoded on the chromosome or on an endogenous virulence plasmid of the recombinant virulence attenuated Gram-negative bacterial strain. Preferably the nucleotide sequence which is homologous or identical to a nucleotide sequence of a delivery signal from a bacterial effector protein or to a fragment thereof is located on the 5' end of the nucleotide sequence encoding a heterologous protein. More preferably the nucleotide sequence encoding a heterologous protein is flanked on its 3' end by a nucleotide sequence homologous to the nucleotide sequence of the chromosome or of the endogenous virulence plasmid at the 3' end of the delivery signal from a bacterial effector protein or to a fragment thereof. Even more preferably, this nucleotide sequence flanking the homologous protein on its 3' end is homologous to the nucleotide sequence lying within 10 kbp on the chromosome or on an endogenous virulence plasmid at the 3' end of the delivery signal from a bacterial effector protein or to a fragment thereof. In particular, this nucleotide sequence flanking the homologous protein on its 3' end is homologous to the nucleotide sequence and is within the same operon on the chromosome or on an endogenous virulence plasmid as the delivery signal from a bacterial effector protein or a fragment thereof. In this embodiment, transformation is usually performed so that the nucleotide sequence encoding a heterologous protein is inserted on an endogenous virulence plasmid or a chromosome of the recombinant virulence attenuated Gram-negative bacterial strain, preferably on an endogenous virulence plasmid, at the 3'end of a delivery signal from a bacterial effector protein encoded by the chromosome or the endogenous virulence plasmid, wherein the heterologous protein fused to the delivery signal is expressed and secreted.

In one embodiment of the present invention the recombinant virulence attenuated Gram-negative bacterial strain comprises a deletion of a chromosomal gene coding for an endogenous protein essential for growth and an endogenous virulence plasmid which comprises a nucleotide sequence comprising a gene coding for said endogenous protein essential for growth operably linked to a promoter. Normally the gene coding for the endogenous protein essential for growth on the endogenous virulence plasmid codes for the same endogenous protein essential for growth as encoded by the deleted chromosomal gene. Preferably the gene coding for an endogenous enzyme essential for growth located on the endogenous virulence plasmid comprises its endogenous promoter and its endogenous transcriptional terminator. In case the recombinant virulence attenuated Gram-negative bacterial strain is a *Yersinia* strain, the gene coding for an endogenous enzyme essential for growth is located on the endogenous virulence plasmid pYV and preferably comprises its endogenous promoter and its endogenous transcriptional terminator. The gene coding for the endogenous enzyme essential for growth, the endogenous promoter and the endogenous transcriptional terminator is preferably located 122 bp upstream of the start of orf155 (SycO) on the endogenous virulence plasmid e.g. on pYV. The gene coding for the endogenous enzyme essential for growth, the endogenous promoter and the endogenous transcriptional terminator usually replaces an insertion sequence found in pYVe40, the virulence plasmid of *Y. enterocolitica* MRS40 and E40 strains, but not in pYVe227, the virulence plasmid of *Y. enterocolitica* W22703 (Genbank: AF102990.1).

In case the recombinant virulence attenuated Gram-negative bacterial strain is a *Yersinia* strain the endogenous virulence plasmid is pYV (plasmid of *Yersinia* Virulence). In case the recombinant virulence attenuated Gram-negative bacterial strain is a *Salmonella* strain, the endogenous location for insertion is one of the gene clusters called SpiI or SpiI (for *Salmonella* pathogenicity island), a position where an effector protein is elsewhere encoded or alternatively one of the *Salmonella* virulence plasmids (SVPs).

Preferably the nucleotide sequence encoding a heterologous protein fused in frame to the 3'end of a nucleotide sequence encoding a delivery signal from a bacterial effector protein is inserted on an endogenous virulence plasmid at the native site of a bacterial effector protein e.g. at the native site of a virulence factor, preferably in case the recombinant virulence attenuated Gram-negative bacterial strain is a *Yersinia* strain, at the native site of YopE or another Yop (YopH, YopO, YopP, YopM, YopT), preferably at the native site of YopE or in case the recombinant virulence attenuated Gram-negative bacterial strain is a *Salmonella* strain at the native site of an effector protein encoded within SpiI, SpiII or encoded elsewhere, preferably at the native site of an effector protein encoded within SpiI or SpiII, more preferably at the native site of SopE or SteA. Preferably the nucleotide sequence encoding a heterologous protein fused in frame to the 3'end of a nucleotide sequence encoding a delivery signal from a bacterial effector protein is operably linked to a native promoter of a bacterial effector protein present on an endogenous virulence plasmid e.g. in case the recombinant virulence attenuated Gram-negative bacterial strain is a *Yersinia* strain to a native promoter from a *Yersinia* virulon gene as outlined below, more preferably to the native YopE promoter or another Yop (YopH, YopO, YopP, YopM, YopT) promoter, preferably to the native YopE promoter or in case the recombinant virulence attenuated Gram-negative bacterial strain is a *Salmonella* strain to a native promoter from SpiI or SpiII pathogenicity island or from an effector protein elsewhere encoded as outlined below, more preferably to the native SopE, InvB or SteA promoter.

In one embodiment of the present invention the recombinant virulence attenuated Gram-negative bacterial strain comprises a deletion of a chromosomal gene coding for an endogenous protein essential for growth and an endogenous virulence plasmid which comprises a nucleotide sequence comprising a gene coding for said endogenous protein essential for growth operably linked to a promoter, wherein the gene coding for an endogenous protein essential for growth is selected from a gene coding for an enzyme essential for amino acid production, a gene coding for an enzyme involved in peptidoglycan biosynthesis, a gene coding for an enzyme involved in LPS biosynthesis, a gene coding for an enzyme involved in nucleotide synthesis and a gene coding for a translation initiation factor.

In one embodiment of the present invention the recombinant virulence attenuated Gram-negative bacterial strain comprises a deletion of a chromosomal gene coding for an endogenous protein essential for growth and an endogenous virulence plasmid which comprises a nucleotide sequence comprising a gene coding for said endogenous protein essential for growth operably linked to a promoter, and wherein the gene coding for an endogenous enzyme essential for growth is a gene coding for an enzyme essential for amino acid production, wherein the enzyme essential for amino acid production is selected from the group consisting of aspartate-beta-semialdehyde dehydrogenase (asd), glutamine synthetase (glnA), tryptophanyl tRNA synthetase (trpS) or serine hydroxymethly transferase (glyA), or Transketolase 1 (tktA), Transketolase 2 (tktB), Ribulose-phosphate 3-epimerase (rpe), Ribose-5-phosphate isomerase A (rpiA), Transaldolase A (talA), Transaldolase B (talB), phosphoribosylpyrophosphate synthase (prs), ATP phosphoribosyltransferase (hisG), Histidine biosynthesis bifunctional protein HisIE (hisI), 1-(5-phosphoribosyl)-5-[(5-phosphoribosylamino)methylideneamino] imidazole-4-carboxamide isomerase (hisA), Imidazole glycerol phosphate synthase subunit HisH (hisH), Imidazole glycerol phosphate synthase subunit HisF (hisF), Histidine biosynthesis bifunctional protein HisB (hisB), Histidinol-phosphate aminotransferase (hisC), Histidinol dehydrogenase (hisD), 3-dehydroquinate synthase (aroB), 3-dehydroquinate dehydratase (aroD), Shikimate dehydrogenase (NADP(+)) (aroE), Shikimate kinase 2 (aroL), Shikimate kinase 1 (aroK), 3-phosphoshikimate 1-carboxyvinyltransferase (aroA), Chorismate synthase (aroC), P-protein (pheA), T-protein (tyrA), Aromatic-amino-acid aminotransferase (tyrB), Phospho-2-dehydro-3-deoxyheptonate aldolase (aroG), Phospho-2-dehydro-3-deoxyheptonate aldolase (aroH), Phospho-2-dehydro-3-deoxyheptonate aldolase (aroF), Quinate/shikimate dehydrogenase (ydiB), ATP-dependent 6-phosphofructokinase isozyme 1 (pfkA), ATP-dependent 6-phosphofructokinase isozyme 2 (pfkB), Fructose-bisphosphate aldolase class 2 (fbaA), Fructose-bisphosphate aldolase class 1 (fbaB), Triosephosphate isomerase (tpiA), Pyruvate kinase I (pykF), Pyruvate kinase II (pykA), Glyceraldehyde-3-phosphate dehydrogenase A (gapA), Phosphoglycerate kinase (pgk), 2,3-bisphosphoglycerate-dependent phosphoglycerate mutase (gpmA), 2,3-bisphosphoglycerate-independent phosphoglycerate mutase (gpmM/yibO), Probable phosphoglycerate mutase (ytjC/gpmB), enolase (eno), D-3-phosphoglycerate dehydrogenase (serA), Phosphoserine aminotransferase (serC), Phosphoserine phosphatase (serB), L-serine dehydratase 1 (sdaA), L-serine dehydratase 2 (sdaB), L-threonine dehydratase catabolic (tdcB), L-threonine dehydratase biosynthetic (ilvA), L-serine dehydratase (tdcG), Serine acetyltransferase (cysE), Cysteine synthase A (cysK), Cysteine synthase B (cysM), beta-cystathionase (malY), Cystathionine beta-lyase (metC), 5-methyltetrahydropteroyltriglutamate-homocysteine methyltransferase (metE), Methionine synthase (metH), S-adenosylmethionine synthase (metK), Cystathionine gamma-synthase (metB), Homoserine O-succinyltransferase (metA), 5'-methylthioadenosine/S-adenosylhomocysteine nucleosidase (mtnN), S-ribosylhomocysteine lyase (luxS), cystathione beta lyase, cystathione gamma lyase, Serine hydroxymethyltransferase (glyA), Glycine hydroxymethyltransferase (itaE), 3-isopropylmalate dehydratase small subunit (leuD), 3-isopropylmalate dehydratase large subunit (leuC), 3-isopropylmalate dehydrogenase (leuB), L-threonine dehydratase biosynthetic (ilvA), Acetolactate synthase isozyme 3 large subunit (ilvI), Acetolactate synthase isozyme 3 small subunit (ilvH), Acetolactate synthase isozyme 1 small subunit (ilvN), Acetolactate synthase isozyme 2 small subunit (ilvM), Ketol-acid reductoisomerase (NADP(+)) (ilvC), Dihydroxy-acid dehydratase (ilvD), Branched-chain-amino-acid aminotransferase (ilvE), Bifunctional aspartokinase/homoserine dehydrogenase 1 (thrA), Bifunctional aspartokinase/homoserine dehydrogenase 2 (metL), 2-isopropylmalate synthase (leuA), Glutamate-pyruvate aminotransferase (alaA), Aspartate aminotransferase (aspC), Bifunctional aspartokinase/homoserine dehydrogenase 1 (thrA), Bifunctional aspartokinase/homoserine dehydrogenase 2 (metL), Lysine-sensitive aspartokinase 3 (lysC), Aspartate-semialdehyde dehydrogenase (asd), 2-keto-3-deoxy-galactonate aldolase (yagE), 4-hydroxy-tetrahydrodipicolinate synthase (dapA), 4-hydroxy-tetrahydrodipicolinate reductase (dapB), 2,3,4,5-tetrahydropyridine-2,6-dicarboxylate N-succinyltransferase (dapD), Succinyl-diaminopimelate desuccinylase (dapE), Diaminopimelate epimerase (dapF), Putative lyase (yjhH), Acetylornithine/succinyldiaminopimelate aminotransferase (argD), Citrate synthase (gltA), Aconitate hydratase B (acnB), Aconitate hydratase A (acnA), uncharacterized putative aconitate hydratase (ybhJ), isocitrate dehydrogenase (icd), Aspartate aminotransferase (aspC), Glutamate-pyruvate aminotransferase (alaA), Glutamate synthase [NADPH] large chain (gltB), Glutamate synthase [NADPH] small chain (gltD), Glutamine synthetase (glnA), Aminoacid acetyltransferase (argA), Acetylglutamate kinase (argB), N-acetyl-gamma-glutamyl-phosphate reductase (argC), Acetylornithine/succinyldiaminopimelate aminotransferase (argD), Acetylornithine deacetylase (argE), Ornithine carbamoyltransferase chain F (argF), Ornithine carbamoyltransferase chain I (argI), Argininosuccinate synthase (argG), Argininosuccinate lyase (argH), Glutamate 5-kinase (proB), Gamma-glutamyl phosphate reductase (proA), pyrroline-5-carboxylate reductase (proC), ornithine cyclodeaminase, Leucine-tRNA ligase (leuS), Glutamine-tRNA ligase (glnS), Serine-tRNA ligase (serS), Glycine-tRNA ligase beta subunit (glyS), Glycine-tRNA ligase alpha subunit (glyQ), Tyrosine-tRNA ligase (tyrS), Threonine-tRNA ligase (thrS), Phenylalanine-tRNA ligase alpha subunit (pheS), Phenylalanine-tRNA ligase beta subunit (pheT), Arginine-tRNA ligase (argS), Histidine-tRNA ligase (hisS), Valine-tRNA ligase (valS), Alanine-tRNA ligase (alaS), Isoleucine-tRNA ligase (ileS), Proline-tRNA ligase (proS), Cystein-tRNA ligase (cysS), Asparagine-tRNA ligase (asnS), Aspartate-tRNA ligase (aspS), Glutamate-tRNA ligase (gltX), Tryptophan-tRNA ligase (trpS), Glycine-tRNA ligase beta subunit (glyS), Methionine-tRNA ligase (metG), Lysine-tRNA ligase (lysS). Preferred enzymes essential for amino acid production are tktA, rpe, prs, aroK, tyrB, aroH, fbaA, gapA, pgk, eno, tdcG, cysE, metK, glyA, asd, dapA/B/D/E/F, argC, proC, leuS, glnS, serS, glyS/Q, tyrS, thrS, pheS/T, argS, hisS, valS, alaS, ileS, proS, cysS, asnS, aspS, gltX, trpS, glyS, metG, lysS, more preferred are asd, glyA, leuS, glnS, serS, glyS/Q, tyrS, thrS, pheS/T, argS, hisS, valS, alaS, ileS, proS, cysS, asnS, aspS, gltX, trpS, glyS, metG, lysS, most preferred is asd.

In one embodiment of the present invention the recombinant virulence attenuated Gram-negative bacterial strain further comprises a modulation within a RNA thermosensor region upstream of a gene coding for an endogenous AraC-type DNA binding protein. The modulation within a RNA thermosensor region upstream of a gene coding for an endogenous AraC-type DNA binding protein can be a deletion, an insertion, or a substitution within the RNA thermosensor region. A deletion or an insertion comprises usually a deletion or an insertion of one or several, preferably between about 30 and about 100 nucleotides, more preferably between about 40 and about 60 nucleotides. A substitution comprises usually a substitution of one or several, preferably between about 3 and about 30 nucleotides, more preferably between about 3 and about 15 nucleotides. Preferably, the modulation within a RNA thermosensor region upstream of a gene coding for an endogenous AraC-type DNA binding protein is a deletion, preferably a deletion of between about 30 and about 100 nucleotides, more preferably of between about 40 and about 60 nucleotides within a RNA thermosensor region upstream of a gene coding for an endogenous AraC-type DNA binding protein. The endogenous AraC-type DNA binding protein and the RNA thermosensor region upstream of a gene coding for the AraC-type DNA binding protein are usually located on the endogenous virulence plasmid comprised by the recombinant virulence attenuated Gram-negative bacterial strain. The AraC-type DNA binding protein is preferably selected form the group consisting of VirF, LcrF, MxiE, ExsA, PerA, HrpX, HrpB, GadX, HilC, HilD and InvF. More preferably, the AraC-type DNA binding protein is selected form the group consisting of VirF and LcrF. In some embodiments the recombinant virulence attenuated Gram-negative bacterial strain is *Yersinia enterocolitica* the AraC-type DNA binding protein is VirF. Preferably the modulation within a RNA thermosensor region upstream of a gene coding for an endogenous AraC-type DNA binding protein comprises a modulation that interferes with a RNA hairpin, preferably with Hairpin I, upstream of the gene coding for an endogenous AraC-type DNA binding protein. More preferably the modulation within a RNA thermosensor region upstream of a gene coding for an endogenous AraC-type DNA binding protein comprises a deletion which removes a RNA hairpin structure or parts thereof, preferably parts of hairpin I, upstream of the gene coding for an endogenous AraC-type DNA binding protein. A deletion which removes a RNA hairpin structure or parts thereof, comprises usually a deletion of between about 30 and about 100 nucleotides, preferably of between about 40 and about 60 nucleotides. In some embodiments the recombinant virulence attenuated Gram-negative bacterial strain is *Yersinia enterocolitica* the deletion comprises a deletion of the nucleotides at position −111 to −57 upstream of the coding sequence of virF (where −1 is 1 base upstream of the A of the ATG start codon of the virF coding sequence).

In one embodiment of the present invention the recombinant virulence attenuated Gram-negative bacterial strain is selected from the group consisting of the genera *Yersinia, Escherichia, Salmonella* and *Pseudomonas*. In one embodiment the recombinant virulence attenuated Gram-negative bacterial strain is selected from the group consisting of the genera *Yersinia* and *Salmonella*. Preferably the recombinant virulence attenuated Gram-negative bacterial strain is a *Yersinia* strain, more preferably a *Yersinia enterocolitica* strain. Most preferred is *Yersinia enterocolitica* E40 (0:9, biotype 2)[19] or Ampicilline sensitive derivates thereof as *Y. enterocolitica* MRS40 (also named *Y. enterocolitica* subsp. *palearctica* MRS40) as described in [20]. *Y. enterocolitica* E40 and its derivate *Y. enterocolitica* MRS40 as described in [20] is identical to *Y. enterocolitica* subsp. *palearctica* E40 and its derivate *Y. enterocolitica* subsp. *palearctica* MRS40 as described in [5,17,21]. Also preferably the recombinant virulence attenuated Gram-negative bacterial strain is a *Salmonella* strain, more preferably a *Salmonella enterica* strain. Most preferred is *Salmonella enterica* Serovar *Typhimurium* SL1344 as described by the Public health England culture collection (NCTC 13347).

In some embodiments of the present invention the recombinant virulence attenuated Gram-negative bacterial strain is a strain which does not produce a siderophore e.g. is deficient in the production of a siderophore, preferably does not produce siderophores e.g. is deficient in the production of any siderophore. Such a strain is for example *Y. enterocolitica* subsp. *palearctica* MRS40 as described in [15,17,20,21] which does not produce yersiniabactin and which is preferred.

In one embodiment of the present invention the delivery signal from a bacterial effector protein comprises a bacterial effector protein or a N-terminal fragment thereof, preferably a bacterial effector protein which is virulent toward eukaryotic cells or a N-terminal fragment thereof.

In one embodiment of the present invention the delivery signal from a bacterial effector protein is a bacterial T3SS effector protein comprising a bacterial T3SS effector protein or a N-terminal fragment thereof wherein the T3SS effector protein or a N-terminal fragment thereof may comprise a chaperone binding site. A T3SS effector protein or a N-terminal fragment thereof which comprises a chaperone binding site is particular useful as delivery signal in the present invention. Preferred T3SS effector proteins or N-terminal fragments thereof are selected from the group consisting of SopE, SopE2, SptP, YopE, ExoS, SipA, SipB, SipD, SopA, SopB, SopD, IpgB1, IpgD, SipC, SifA, SseJ, Sse, SrfH, YopJ, AvrA, AvrBsT, YopT, YopH, YpkA, Tir, EspF, TccP2, IpgB2, OspF, Map, OspG, OspI, IpaH, SspH1, VopF, ExoS, ExoT, HopAB2, XopD, AvrRpt2, HopAO1, HopPtoD2, HopU1, GALA family of proteins, AvrBs2, AvrD1, AvrBS3, YopO, YopP, YopE, YopM, YopT, EspG, EspH, EspZ, IpaA, IpaB, IpaC, VirA, IcsB, OspC1, OspE2, IpaH9.8, IpaH7.8, AvrB, AvrD, AvrPphB, AvrPphC, AvrPphEPto, AvrPpiBPto, AvrPto, AvrPtoB, VirPphA, AvrRpm1, HopPtoE, HopPtoF, HopPtoN, PopB, PopP2, AvrBs3, XopD, and AvrXv3. More preferred T3SS effector proteins or N-terminal fragments thereof are selected from the group consisting of SopE, SptP, YopE, ExoS, SopB, IpgB1, IpgD, YopJ, YopH, EspF, OspF, ExoS, YopO, YopP, YopE, YopM, YopT, whereof most preferred T3SS effector proteins or N-terminal fragments thereof are selected from the group consisting of IpgB1, SopE, SopB, SptP, OspF, IpgD, YopH, YopO, YopP, YopE, YopM, YopT, in particular YopE or an N-terminal fragment thereof.

Equally preferred T3SS effector proteins or N-terminal fragments thereof are selected from the group consisting of SopE, SopE2, SptP, SteA, SipA, SipB, SipD, SopA, SopB, SopD, IpgB1, IpgD, SipC, SifA, SifB, SseJ, Sse, SrfH, YopJ, AvrA, AvrBsT, YopH, YpkA, Tir, EspF, TccP2, IpgB2, OspF, Map, OspG, OspI, IpaH, VopF, ExoS, ExoT, HopAB2, AvrRpt2, HopAO1, HopU1, GALA family of proteins, AvrBs2, AvrD1, YopO, YopP, YopE, YopT, EspG, EspH, EspZ, IpaA, IpaB, IpaC, VirA, IcsB, OspC1, OspE2, IpaH9.8, IpaH7.8, AvrB, AvrD, AvrPphB, AvrPphC, AvrPphEPto, AvrPpiBPto, AvrPto, AvrPtoB, VirPphA, AvrRpm1, HopPtoD2, HopPtoE, HopPtoF, HopPtoN, PopB, PopP2, AvrBs3, XopD, and AvrXv3. Equally more preferred T3SS effector proteins or N-terminal fragments thereof are selected from the group consisting of SopE, SptP, SteA, SifB, SopB, IpgB1, IpgD, YopJ, YopH, EspF, OspF, ExoS, YopO, YopP, YopE, YopT, whereof equally most preferred T3SS effector proteins or N-terminal fragments thereof are selected from the group consisting of IpgB1, SopE, SopB, SptP, SteA, SifB, OspF, IpgD, YopH, YopO, YopP, YopE, and YopT, in particular SopE, SteA, or YopE or an N-terminal fragment thereof, more particular SteA or YopE or an N-terminal fragment thereof, most particular YopE or an N-terminal fragment thereof.

In some embodiments the delivery signal from a bacterial effector protein is encoded by a nucleotide sequence comprising the bacterial effector protein or an N-terminal fragment thereof, wherein the N-terminal fragment thereof includes at least the first 10, preferably at least the first 20, more preferably at least the first 100 amino acids of the bacterial T3SS effector protein.

In some embodiments the delivery signal from the bacterial effector protein is encoded by a nucleotide sequence comprising the bacterial T3SS effector protein or an N-terminal fragment thereof, wherein the bacterial T3SS effector protein or the N-terminal fragment thereof comprises a chaperone binding site.

Preferred T3SS effector proteins or a N-terminal fragment thereof, which comprise a chaperone binding site comprise the following combinations of chaperone binding site and T3SS effector protein or N-terminal fragment thereof: SycE-YopE, InvB-SopE, SicP-SptP, SycT-YopT, SycO-YopO, SycN/YscB-YopN, SycH-YopH, SpcS-ExoS, CesF-EspF, SycD-YopB, SycD-YopD. More preferred are SycE-YopE, InvB-SopE, SycT-YopT, SycO-YopO, SycN/YscB-YopN, SycH-YopH, SpcS-ExoS, CesF-EspF.

Most preferred is a YopE or an N-terminal fragment thereof comprising the SycE chaperone binding site such as an N-terminal fragment of a YopE effector protein containing the N-terminal 138 amino acids of the YopE effector protein designated herein as $YopE_{1-138}$ and as shown in SEQ ID NO. 2 or a SopE or an N-terminal fragment thereof comprising the InvB chaperone binding site s as such an N-terminal fragment of a SopE effector protein containing the N-terminal 81 or 105 amino acids of the SopE effector protein designated herein as $SopE_{1-81}$ or $SopE_{1-105}$ respectively, and as shown in SEQ ID NOs.: 6 and 7.

In one embodiment of the present invention the recombinant virulence attenuated Gram-negative bacterial strain is a Yersinia strain and the delivery signal from the bacterial effector protein comprises a YopE effector protein or an N-terminal part, preferably the Y. enterocolitica YopE effector protein or an N-terminal part thereof. Preferably the SycE binding site is comprised within the N-terminal part of the YopE effector protein. In this connection an N-terminal fragment of a YopE effector protein may comprise the N-terminal 12, 16, 18, 52, 53, 80 or 138 amino acids [22-24]. Most preferred is an N-terminal fragment of a YopE effector protein containing the N-terminal 138 amino acids of the YopE effector protein e.g. as described in Forsberg and Wolf-Watz [25] designated herein as $YopE_{1-138}$ and as shown in SEQ ID NO.: 2.

In one embodiment of the present invention the recombinant virulence attenuated Gram-negative bacterial strain is a Salmonella strain and the delivery signal from the bacterial effector protein encoded by anucleotide sequence comprises a SopE or SteA effector protein or an N-terminal part thereof, preferably the Salmonella enterica SopE or SteA effector protein or an N-terminal part thereof. Preferably the chaperon binding site is comprised within the N-terminal part of the SopE effector protein. In this connection an N-terminal fragment of a SopE effector protein may comprise the N-terminal 81 or 105 amino acids. Most preferred is the full length SteA (SEQ ID NO: 5) and an N-terminal fragment of a SopE effector protein containing the N-terminal 105 amino acids of the effector protein e.g. as described in SEQ ID NO.: 7.

One skilled in the art is familiar with methods for identifying the polypeptide sequences of an effector protein that are capable of delivering a protein. For example, one such method is described by Sory et al. [19]. Briefly, polypeptide sequences from e.g. various portions of the Yop proteins can be fused in-frame to a reporter enzyme such as the calmodulin-activated adenylate cyclase domain (or Cya) of the Bordetella pertussis cyclolysin. Delivery of a Yop-Cya hybrid protein into the cytosol of eukaryotic cells is indicated by the appearance of cyclase activity in the infected eukaryotic cells that leads to the accumulation of cAMP. By employing such an approach, one skilled in the art can determine, if desired, the minimal sequence requirement, i.e., a contiguous amino acid sequence of the shortest length, that is capable of delivering a protein, see, e.g. [19]. Accordingly, preferred delivery signals of the present invention consists of at least the minimal sequence of amino acids of a T3SS effector protein that is capable of delivering a protein.

In one embodiment, the present invention provides a recombinant virulence attenuated Gram-negative bacterial strain which is deficient in producing at least one bacterial effector protein, more preferably which is deficient in producing at least one bacterial effector protein which is virulent toward eukaryotic cells, even more preferably which is deficient in producing at least one T3SS effector protein, most preferably which is deficient in producing at least one T3SS effector protein which is virulent toward eukaryotic cells. In some embodiments the recombinant virulence attenuated Gram-negative bacterial strains are deficient in producing at least one, preferably at least two, more preferably at least three, even more preferably at least four, in particular at least five, more particular at least six, most particular all bacterial effector proteins which are virulent toward eukaryotic cells. In some embodiments the recombinant virulence attenuated Gram-negative bacterial strains are deficient in producing at least one preferably at least two, more preferably at least three, even more preferably at least four, in particular at least five, more particular at least six, most particular all functional bacterial effector proteins which are virulent toward eukaryotic cells such that the resulting recombinant virulence attenuated Gram-negative bacterial strain produces less bacterial effector proteins or produces bacterial effector proteins to a lesser extent compared to the non virulence attenuated Gram-negative bacterial wild type strain i.e. compared to the Gram-negative bacterial wild type strain which normally produces bacterial effector proteins or such that the resulting recombinant virulence attenuated Gram-negative bacterial strain no longer produce any functional bacterial effector proteins which are virulent toward eukaryotic cells.

According to the present invention, such a mutant Gram-negative bacterial strain i.e. such a recombinant virulence attenuated Gram-negative bacterial strain which is deficient in producing at least one bacterial effector protein e.g. which is deficient in producing at least one bacterial effector protein which is virulent toward eukaryotic cells e.g. such a mutant Yersinia strain can be generated by introducing at least one mutation into at least one effector-encoding gene. Preferably, such effector-encoding genes include YopE, YopH, YopO/YpkA, YopM, YopP/YopJ and YopT as far as a Yersinia strain is concerned. Preferably, such effector-encoding genes include AvrA, CigR, GogB, GtgA, GtgE, PipB, SifB, SipA/SspA, SipB, SipC/SspC, SipD/SspD, SlrP, SopB/SigD, SopA, SpiC/SsaB, SseB, SseC, SseD, SseF, SseG, SseI/SrfH, SopD, SopE, SopE2, SspH1, SspH2, PipB2, SifA, SopD2, SseJ, SseK1, SseK2, SseK3, SseL, SteC, SteA, SteB, SteD, SteE, SpvB, SpvC, SpvD, SrfJ, SptP, as far as a *Salmonella* strain is concerned. Most preferably, all effector-encoding genes are deleted. The skilled artisan may employ any number of standard techniques to generate mutations in these T3SS effector genes. Sambrook et al. describe in general such techniques. See Sambrook et al. [26].

In accordance with the present invention, the mutation can be generated in the promoter region of an effector-encoding gene so that the expression of such effector gene is abolished.

The mutation can also be generated in the coding region of an effector-encoding gene such that the catalytic activity of the encoded effector protein is abolished. The "catalytic activity" of an effector protein refers normally to the anti-target cell function of an effector protein, i.e., toxicity. Such activity is governed by the catalytic motifs in the catalytic domain of an effector protein. The approaches for identifying the catalytic domain and/or the catalytic motifs of an effector protein are well known by those skilled in the art. See, for example, [27,28].

Accordingly, one preferred mutation of the present invention is a deletion of the entire catalytic domain. Another preferred mutation is a frameshift mutation in an effector-encoding gene such that the catalytic domain is not present in the protein product expressed from such "frameshifted" gene. A most preferred mutation is a mutation with the deletion of the entire coding region of the effector protein. Other mutations are also contemplated by the present invention, such as small deletions or base pair substitutions, which are generated in the catalytic motifs of an effector protein leading to destruction of the catalytic activity of a given effector protein.

The mutations that are generated in the genes of the functional bacterial effector proteins may be introduced into the particular strain by a number of methods. One such method involves cloning a mutated gene into a "suicide" vector which is capable of introducing the mutated sequence into the strain via allelic exchange. An example of such a "suicide" vector is described by [29].

In this manner, mutations generated in multiple genes may be introduced successively into a Gram-negative bacterial strain giving rise to polymutant, e.g a sixtuple mutant recombinant strain. The order in which these mutated sequences are introduced is not important. Under some circumstances, it may be desired to mutate only some but not all of the effector genes. Accordingly, the present invention further contemplates polymutant *Yersinia* other than sixtuple-mutant *Yersinia*, e.g., double-mutant, triple-mutant, quadruple-mutant and quintuple-mutant strains. For the purpose of delivering proteins, the secretion and translocation system of the instant mutant strain needs to be intact.

A preferred recombinant virulence attenuated Gram-negative bacterial strain of the present invention is a sixtuple-mutant *Yersinia* strain in which all the effector-encoding genes are mutated such that the resulting *Yersinia* no longer produce any functional effector proteins. Such sixtuple-mutant *Yersinia* strain is designated as ΔyopH,O,P,E,M,T for *Y. enterocolitica*. As an example such a sixtuple-mutant can be produced from the *Y. enterocolitica* MRS40 strain giving rise to *Y. enterocolitica* MRS40 ΔyopH,O,P,E,M,T, (also named *Y. enterocolitica* subsp. *palearctica* MRS40 ΔyopH,O,P,E,M,T or *Y. enterocolitica* ΔyopH,O,P,E,M,T herein) which is preferred. *Y. enterocolitica* MRS40 ΔyopH,O,P,E,M,T which is deficient in the production of Yersiniabactin has been described in WO02077249 and was deposited on 24 Sep. 2001, according to the Budapest Treaty on the International Recognition of the Deposit of Microorganisms for the Purposes of Patent Procedure with the Belgian Coordinated Collections of Microorganisms (BCCM) and was given accession number LMG P-21013.

More preferred is *Y. enterocolitica* MRS40 ΔyopH,O,P,E,M,T which comprises a deletion on the endogenous virulence plasmid pYV which removes a RNA hairpin structure or parts thereof such as a deletion of Hairpin I upstream of the gene coding for an endogenous AraC-type DNA binding protein (ΔHairpinI-virF) such as *Y. enterocolitica* MRS40 ΔyopH,O,P,E,M,T ΔHairpinI-virF (also named *Y. enterocolitica* ΔyopH,O,P,E,M,T ΔHairpinI-virF). Equally preferred is *Y. enterocolitica* MRS40 ΔyopH,O,P,E,M,T which comprises a deletion of a chromosomal gene coding for asd and the endogenous virulence plasmid pYV which comprises a nucleotide sequence comprising a gene coding for asd operably linked to a promoter (pYV-asd) such as *Y. enterocolitica* MRS40 ΔyopH,O,P,E,M,T Δasd pYV-asd (also named *Y. enterocolitica* ΔyopH,O,P,E,M,T Δasd pYV-asd herein).

Particular preferred is *Y. enterocolitica* MRS40 ΔyopH,O,P,E,M,T Δasd ΔHairpinI-virF pYV-asd which comprises both modifications as described above (also named *Y. enterocolitica* ΔyopH,O,P,E,M,T Δasd ΔHairpinI-virF pYV-asd herein). Particular preferred strains are *Y. enterocolitica* MRS40 ΔyopH,O,P,E,M,T ΔHairpinI-virF (also named *Y.*

*enterocolitica* ΔyopH,O,P,E,M,T ΔHairpinI-virF), *Y. enterocolitica* MRS40 ΔyopH,O,P,E,M,T Δasd pYV-asd (also named *Y. enterocolitica* ΔyopH,O,P,E,M,T Δasd pYV-asd herein) or *Y. enterocolitica* MRS40 ΔyopH,O,P,E,M,T Δasd ΔHairpinI-virF pYV-asd (also named *Y. enterocolitica* ΔyopH,O,P,E,M,T Δasd ΔHairpinI-virF pYV-asd herein) which are deficient in the production of a siderophore, preferably does not produce siderophores e.g. are deficient in the production of any siderophore, as is the case for all *Y. enterocolitica* subsp. *palearctica* strains. Thus, equally particular preferred strains are *Y. enterocolitica* subsp. *palearctica* ΔyopH,O,P,E,M,T ΔHairpinI-virF (also named *Y. enterocolitica* subsp. *palearctica* ΔyopH,O,P,E,M,T ΔHairpinI-virF), *Y. enterocolitica* subsp. *palearctica* ΔyopH,O,P,E,M,T Δasd pYV-asd also named *Y. enterocolitica* ΔyopH,O,P,E,M,T Δasd pYV-asd herein) or *Y. enterocolitica* subsp. *palearctica* ΔyopH,O,P,E,M,T Δasd ΔHairpinI-virF pYV-asd (also named *Y. enterocolitica* ΔyopH,O,P,E,M,T Δasd ΔHairpinI-virF pYV-asd herein).

Nucleotide molecules like vectors which can be used according to the invention to transform a Gram-negative bacterial strain may depend on the Gram-negative bacterial strains used as known to the skilled person. Nucleotide molecules which can be used according to the invention include expression vectors (including synthetic or otherwise generated modified versions of endogenous virulence plasmids), vectors for chromosomal or virulence plasmid insertion and nucleotide sequences such as e.g. DNA fragments for chromosomal or virulence plasmid insertion. Expression vectors which are useful in e.g. *Yersinia, Escherichia, Salmonella* or *Pseudomonas* strain are e.g pUC, pBad, pACYC, pUCP20 and pET plasmids. Vectors for chromosomal or virulence plasmid insertion which are useful in e.g. *Yersinia, Escherichia, Salmonella* or *Pseudomonas* strain are e.g pKNG101. DNA fragments for chromosomal or virulence plasmid insertion refer to methods used in e.g. *Yersinia, Escherichia, Salmonella* or *Pseudomonas* strain as e.g. lambda-red genetic engineering. Vectors for chromosomal or virulence plasmid insertion or DNA fragments for chromosomal or virulence plasmid insertion may insert the nucleotide sequences of the present invention so that e.g. the nucleotide sequence encoding a heterologous protein fused in frame to the 3'end of a nucleotide sequence encoding a delivery signal from a bacterial effector protein is operably linked to an endogenous promoter of the recombinant virulence attenuated Gram-negative bacterial strain. Thus if a vector for chromosomal or virulence plasmid insertion or a DNA fragment for chromosomal or virulence plasmid insertion is used, an endogenous promoter can be encoded on the endogenous bacterial DNA (chromosomal or plasmid DNA) and only the respective nucleotide sequence will be provided by the engineered vector for chromosomal or virulence plasmid insertion or DNA fragment for chromosomal or virulence plasmid insertion. Alternatively, if a vector for chromosomal or virulence plasmid insertion or a nucleotide molecule such as e.g. a nucleotide sequence for chromosomal or virulence plasmid insertion is used, an endogenous promoter and the delivery signal from a bacterial effector protein can be encoded on the endogenous bacterial DNA (chromosomal or plasmid DNA) and only the nucleotide molecule such as e.g. a nucleotide sequence encoding the heterologous protein will be provided by a vector for chromosomal or virulence plasmid insertion or by a nucleotide molecule such as e.g. a nucleotide sequence for chromosomal or virulence plasmid insertion. Thus a promoter is not necessarily needed to be comprised by the vector used for transformation of the recombinant virulence attenuated Gram-negative bacterial strains i.e. the recombinant virulence attenuated Gram-negative bacterial strains of the present invention may be transformed with a vector which dose not comprise a promoter.

In a preferred embodiment the nucleotide molecule e.g. the vector of the present invention comprises in the 5' to 3' direction:

- a first nucleotide sequence encoding a delivery signal or a fragment thereof from a bacterial effector protein;
- a second nucleotide sequence encoding a heterologous protein fused in frame to the 3'end of said first nucleotide sequence.

A preferred vector e.g. a preferred expression vector for *Yersinia* is selected from the group consisting of pBad_Si_1 and pBad_Si_2. pBad_Si2 was constructed by cloning of the SycE-YopE$_{1-138}$ fragment containing endogenous promoters for YopE and SycE from purified pYV40 into KpnI/HindIII site of pBad-MycHisA (Invitrogen).

Additional modifications include removal of the NcoI/BglII fragment of pBad-MycHisA by digest, Klenow fragment treatment and religation. Further at the 3' end of YopE$_{1-138}$ the following cleavage sites were added: XbaI-XhoI-BstBI-(HindIII). pBad_Si1 is equal to pBad_Si2 but encodes EGFP amplified from pEGFP-C1 (Clontech) in the NcoI/BglII site under the Arabinose inducible promoter. Equally preferred is the use of modified versions of the endogenous *Yersinia* virulence plasmid pYV encoding heterologous proteins as fusions to a T3SS signal sequence.

A preferred vector e.g. a preferred expression vector for *Salmonella* is selected from the group consisting of pSi_266, pSi_267, pSi_268 and pSi_269. Plasmids pSi_266, pSi_267, pSi_268 and pSi_269 containing the corresponding endogenous promoter and the SteA1-20 fragment (pSi_266), the full length SteA sequence (pSi_267), the SopE$_{1-81}$ fragment (pSi_268) or the SopE$_{1-105}$ fragment (pSi_269) were amplified from *S. enterica* SL1344 genomic DNA and cloned into NcoI/KpnI site of pBad-MycHisA (Invitrogen).

The nucleotide molecules e.g. the vectors of the instant invention may include other sequence elements such as a 3' termination sequence (including a stop codon and a poly A sequence), or a gene conferring a drug resistance which allows the selection of transformants having received the instant vector.

The nucleotide molecules e.g. the vectors of the present invention may be transformed by a number of known methods into the recombinant virulence attenuated Gram-negative bacterial strains. For the purpose of the present invention, the methods of transformation for introducing a vector include, but are not limited to, electroporation, calcium phosphate mediated transformation, conjugation, or combinations thereof.

For example, a nucleotide molecules e.g. a vector can be transformed into a first bacteria strain by a standard electroporation procedure. Subsequently, such a nucleotide molecules e.g. a vector can be transferred from the first bacteria strain into the desired strain by conjugation, a process also called "mobilization". Transformant (i.e., Gram-negative bacterial strains having taken up the vector) may be selected, e.g., with antibiotics. These techniques are well known in the art. See, for example, [19] In accordance with the present invention, the promoter operably linked to the bacterial effector protein of the recombinant virulence attenuated Gram-negative bacterial strain of the invention can be a native promoter of a T3SS effector protein of the respective strain or a compatible bacterial strain or a promoter used in expression vectors which are useful in e.g. *Yersinia, Escherichia, Salmonella* or *Pseudomonas* strain e.g pUC and pBad.

Such promoters are the T7 promoter, Plac promoter or the arabinose inducible Ara-bad promoter.

If the recombinant virulence attenuated Gram-negative bacterial strain is a *Yersinia* strain the promoter can be from a *Yersinia* virulon gene. A "*Yersinia* virulon gene" refers to genes on the *Yersinia* pYV plasmid, the expression of which is controlled both by temperature and by contact with a target cell. Such genes include genes coding for elements of the secretion machinery (the Ysc genes), genes coding for translocators (YopB, YopD, and LcrV), genes coding for the control elements (YopN, TyeA and LcrG), genes coding for T3SS effector chaperones (SycD, SycE, SycH, SycN, SycO and SycT), and genes coding for effectors (YopE, YopH, YopO/YpkA, YopM, YopT and YopP/YopJ) as well as other pYV encoded proteins as VirF and YadA.

In a preferred embodiment of the present invention, the promoter is the native promoter of a T3SS functional effector encoding gene. If the recombinant virulence attenuated Gram-negative bacterial strain is a *Yersinia* strain the promoter is selected from any one of YopE, YopH, YopO/YpkA, YopM and YopP/YopJ. More preferably, the promoter is from YopE or SycE. Most preferred is the YopE promoter.

If the recombinant virulence attenuated Gram-negative bacterial strain is a *Salmonella* strain the promoter can be from SpiI or SpiII pathogenicity island or from an effector protein elsewhere encoded. Such genes include genes coding for elements of the secretion machinery, genes coding for translocators, genes coding for the control elements, genes coding for T3SS effector chaperones, and genes coding for effectors as well as other proteins encoded by SPI-1 or SPI-2. In a preferred embodiment of the present invention, the promoter is the native promoter of a T3SS functional effector encoding gene. If the recombinant virulence attenuated Gram-negative bacterial strain is a *Salmonella* strain the promoter is selected from any one of the effector proteins. More preferably, the promoter is from SopE, InvB or SteA.

In some embodiments the promoter is an artificially inducible promoter, as e.g. the arabinose inducible promoter, which is preferred. In this case, arabinose is usually provided to the bacteria and will then induce the bacterial expression of the protein to be delivered.

In one embodiment of the present invention the recombinant virulence attenuated Gram-negative bacterial strain comprises a nucleotide sequence encoding a protease cleavage site. The protease cleavage site is usually located on the nucleotide molecule comprising a nucleotide sequence encoding a heterologous protein fused in frame to the 3'end of a nucleotide sequence encoding a delivery signal from a bacterial effector protein between the nucleotide sequence encoding a heterologous protein and the nucleotide sequence encoding a delivery signal. Generation of a functional and generally applicable cleavage site allows cleaving off the delivery signal after translocation. As the delivery signal can interfere with correct localization and/or function of the translocated protein within the target cells the introduction of a protease cleavage site between the delivery signal and the protein of interest provides delivery of almost native proteins into eukaryotic cells. Preferably the protease cleavage site is an amino acid motif which is cleaved by a protease or the catalytic domains thereof selected from the group consisting of enterokinase (light chain), enteropeptidase, prescission protease, human rhinovirus protease 3C, TEV protease, TVMV protease, FactorXa protease and thrombin, more preferably an amino acid motif which is cleaved by TEV protease. Equally preferable the protease cleavage site is an amino acid motif which is cleaved by a protease or the catalytic domains thereof selected from the group consisting of enterokinase (light chain), enteropeptidase, prescission protease, human rhinovirus protease 3C, TEV protease, TVMV protease, FactorXa protease, ubiquitin processing protease, called Deubiquitinating enzymes, and thrombin. Most preferred is an amino acid motif which is cleaved by TEV protease or by an ubiquitin processing protease.

Thus in a further embodiment of the present invention, the heterologous protein is cleaved from the delivery signal from a bacterial effector protein by a protease.

Preferred methods of cleavage are methods wherein:
a) the protease is translocated into the eukaryotic cell by a recombinant virulence attenuated Gram-negative bacterial strain as described herein which expresses a fusion protein which comprises the delivery signal from the bacterial effector protein and the protease as heterologous protein; or
b) the protease is expressed constitutively or transiently in the eukaryotic cell.

Usually the recombinant virulence attenuated Gram-negative bacterial strain used to deliver a desired protein into a eukaryotic cell and the recombinant virulence attenuated Gram-negative bacterial strain translocating the protease into the eukaryotic cell are different.

In one embodiment of the present invention the recombinant virulence attenuated Gram-negative bacterial strain comprises a further nucleotide sequence encoding a labelling molecule or an acceptor site for a labelling molecule. The further nucleotide sequence encoding a labelling molecule or an acceptor site for a labelling molecule is usually fused to the 5' end or to the 3' end of the nucleotide sequence encoding a heterologous protein. A preferred labelling molecule or an acceptor site for a labelling molecule is selected from the group consisting of enhanced green fluourescent protein (EGFP), coumarin, coumarin ligase acceptor site, resorufin, resurofin ligase acceptor site, the tetra-Cysteine motif in use with FlAsH/ReAsH dye (life technologies). Most preferred is resorufin and a resurofin ligase acceptor site or EGFP. The use of a labelling molecule or an acceptor site for a labelling molecule will lead to the attachment of a labelling molecule to the heterologous protein of interest, which will then be delivered as such into the eukaryotic cell and enables tracking of the protein by e.g. live cell microscopy.

In one embodiment of the present invention the recombinant virulence attenuated Gram-negative bacterial strain comprises a further nucleotide sequence encoding a peptide tag. The further nucleotide sequence encoding a peptide tag is usually fused to the 5' end or to the 3' end of the nucleotide sequence encoding a heterologous protein. A preferred peptide tag is selected from the group consisting of Myc-tag, His-tag, Flag-tag, HA tag, Strep tag or V5 tag or a combination of two or more tags out of these groups. Most preferred is Myc-tag, Flag-tag, His-tag and combined Myc- and His-tags. The use of a peptide tag will lead to traceability of the tagged protein e.g by immunofluorescence or Western blotting using anti-tag antibodies. Further, the use of a peptide tag allows affinity purification of the desired protein either after secretion into the culture supernatant or after translocation into eukaryotic cells, in both cases using a purification method suiting the corresponding tag (e.g. metal-chelate affinity purification in use with a His-tag or anti-Flag antibody based purification in use with the Flag-tag).

In one embodiment of the present invention the recombinant virulence attenuated Gram-negative bacterial strain comprises a further nucleotide sequence encoding a nuclear localization signal (NLS). The further nucleotide sequence encoding a nuclear localization signal (NLS) is usually fused to the 5'end or to the 3'end of the nucleotide sequence encoding a heterologous protein wherein said further nucleotide sequence encodes a nuclear localization signal (NLS). A preferred NLS is selected from the group consisting of SV40 large T-antigen NLS and derivates thereof 3° as well as other viral NLS. Most preferred is SV40 large T-antigen NLS and derivates thereof.

In one embodiment of the present invention the recombinant virulence attenuated Gram-negative bacterial strain comprises a multiple cloning site. The multiple cloning site is usually located at the 3'end of the nucleotide sequence encoding a delivery signal from a bacterial effector protein and/or at the 5'end or 3'end of the nucleotide sequence encoding a heterologous protein. One or more than one multiple cloning sites can be comprised by the vector. A preferred multiple cloning site is selected from the group of restriction enzymes consisting of XhoI, XbaI, HindIII, NcoI, NotI, EcoRI, EcoRV, BamHI, NheI, SacI, SalI, BstBI. Most preferred is XbaI, XhoI, BstBI and HindIII.

The fused protein expressed by the recombinant virulence attenuated Gram-negative bacterial strain of the present invention is also termed as a "fusion protein" or a "hybrid protein", i.e., a fused protein or hybrid of delivery signal and a heterologous protein. The fusion protein can also comprise e.g. a delivery signal and two or more different heterologous proteins.

The present invention contemplates methods for treating cancer in a subject e.g. treating malignant solid tumors including delivering heterologous proteins as hereinabove described into cancer cells e.g. to cells of a malignant solid tumor. The proteins may be delivered i.e. translocated into the cancer cell e.g. to cells of a malignant solid tumor at the time of administering the recombinant virulence attenuated Gram-negative bacterial strain to a subject or may be delivered i.e. translocated into the cancer cell e.g. to cells of a malignant solid tumor at a later time e.g. after the recombinant virulence attenuated Gram-negative bacterial strain has reached a cancer cell e.g. the site of the malignant solid tumor and/or has reached a cancer cell e.g. the site of the malignant solid tumor and has replicated as described above. The time of delivery can be regulated e.g by the promoter used to express the heterologous proteins in the recombinant virulence attenuated Gram-negative bacterial strain. In the first case, either a constitutive promoter or, more preferred, an endogenous promoter of a bacterial effector protein might drive the heterologous protein. In the case of delayed protein delivery, an artificially inducible promoter, as the arabinose inducible promoter, might drive the heterologous protein. In this case, arabinose will be administered to a subject once bacteria have reached and accumulated at the desired site. Arabinose will then induce the bacterial expression of the protein to be delivered.

Thus in one embodiment the method of treating cancer comprises
  i) culturing the recombinant virulence attenuated Gram-negative bacterial strain as described herein;
  ii) administering to the subject said recombinant virulence attenuated Gram-negative bacterial strain by contacting a cancer cell with the recombinant virulence attenuated Gram-negative bacterial strain of i) wherein a fusion protein which comprises a delivery signal from a bacterial effector protein and the heterologous protein is expressed by the recombinant virulence attenuated Gram-negative bacterial strain and is translocated into the cancer cell; and optionally
  iii) cleaving the fusion protein so that the heterologous protein is cleaved from the delivery signal from the bacterial effector protein inside of the cancer cell,
  wherein the recombinant virulence attenuated Gram-negative bacterial strain is administered in an amount that is sufficient to treat the subject.

The cancer cells for delivering heterologous proteins are usually cancer cells from cancers selected from non-solid tumors selected from the group consisting of Sarcoma, Leukemia, Lymphoma, multiple myeloma, Central nervous system cancers, and malignant solid tumors, which include, but are not limited to, abnormal mass of cells which may stem from different tissue types such as liver, colon, colorectum, skin, breast, pancreas, cervix uteri, corpus uteri, bladder, gallbladder, kidney, larynx, lip, oral cavity, oesophagus, ovary, prostate, stomach, testis, thyroid gland or lung and thus include malignant solid liver, colon, colorectum, skin, breast, pancreas, cervix uteri, corpus uteri, bladder, gallbladder, kidney, larynx, lip, oral cavity, oesophagus, ovary, prostate, stomach, testis, thyroid gland or lung tumors. Preferably the cancer cells for delivering heterologous proteins are malignant solid tumors.

Thus in one preferred embodiment the cancer is a malignant solid tumor and the method r comprises
  i) culturing the recombinant virulence attenuated Gram-negative bacterial strain as described herein;
  ii) administering to the subject said recombinant virulence attenuated Gram-negative bacterial strain by contacting a cell of a malignant solid tumor with the recombinant virulence attenuated Gram-negative bacterial strain of i) wherein a fusion protein which comprises a delivery signal from a bacterial effector protein and the heterologous protein is expressed by the recombinant virulence attenuated Gram-negative bacterial strain and is translocated into the cell of a malignant solid tumor; and optionally
  iii) cleaving the fusion protein so that the heterologous protein is cleaved from the delivery signal from the bacterial effector protein inside of the cell of a malignant solid tumor,
  wherein the recombinant virulence attenuated Gram-negative bacterial strain is administered in an amount that is sufficient to treat the subject.

In some embodiments at least two fusion proteins which comprise each a delivery signal from a bacterial effector protein and a heterologous protein are expressed by the recombinant virulence attenuated Gram-negative bacterial strain and are translocated into the eukaryotic cell e.g the cancer cell by the methods of the present inventions.

The recombinant virulence attenuated Gram-negative bacterial strain can be cultured so that a fusion protein is expressed which comprises the delivery signal from the bacterial effector protein and the heterologous protein according to methods known in the art (e.g. FDA, Bacteriological Analytical Manual (BAM), chapter 8: *Yersinia enterocolitica*). Preferably the recombinant virulence attenuated Gram-negative bacterial strain can be cultured in Brain Heart infusion broth e.g. at 28° C. For induction of expression of T3SS and e.g. YopE/SycE promoter dependent genes, bacteria can be grown at 37° C.

In one embodiment, the cancer cell e.g the cell of a malignant solid tumor is contacted with two recombinant virulence attenuated Gram-negative bacterial strains of i), wherein the first recombinant virulence attenuated Gram-negative bacterial strain expresses a first fusion protein which comprises the delivery signal from the bacterial effector protein and a first heterologous protein and the second recombinant virulence attenuated Gram-negative bacterial strain expresses a second fusion protein which comprises the delivery signal from the bacterial effector protein and a second heterologous protein, so that the first and the second fusion protein are translocated into the cell of a malignant solid tumor. This embodiment provided for co-infection of a cancer cell e.g a cell of a malignant solid tumor with two bacterial strains as a valid method to deliver e.g. two different hybrid proteins into single cells to address their functional interaction.

Those skilled in the art can also use a number of assays to determine whether the delivery of a fusion protein is successful. For example, the fusion protein may be detected via immunofluorescence using antibodies recognizing a fused tag (like Myc-tag). The determination can also be based on the enzymatic activity of the protein being delivered, e.g., the assay described by [19].

The present invention also provides a pharmaceutical composition comprising a recombinant virulence attenuated Gram-negative bacterial strain as described herein optionally comprising a suitable pharmaceutically acceptable carrier. Thus the present invention also provides a pharmaceutical composition comprising a recombinant virulence attenuated Gram-negative bacterial strain as described herein for use in a method of treating cancer e.g. a malignant solid tumor in a subject.

The recombinant virulence attenuated Gram-negative bacteria can be compounded for convenient and effective administration in an amount that is sufficient to treat the subject as pharmaceutical composition with a suitable pharmaceutically acceptable carrier. A unit dosage form of the recombinant virulence attenuated Gram-negative bacteria or of the pharmaceutical composition to be administered can, for example, contain the recombinant virulence attenuated Gram-negative bacteria in an amount from about $10^5$ to about $10^9$ bacteria per ml, preferably about $10^6$ to about $10^8$ bacteria per ml, more preferably about $10^7$ to about $10^8$ bacteria per ml, most preferably about $10^8$ bacteria per ml.

By "amount that is sufficient to treat the subject" or "effective amount" which are used herein interchangeably is meant to be an amount of a bacterium or bacteria, high enough to significantly positively modify the condition to be treated but low enough to avoid serious side effects (at a reasonable benefit/risk ratio), within the scope of sound medical judgment. An effective amount of a bacterium will vary with the particular goal to be achieved, the age and physical condition of the subject being treated, the duration of treatment, the nature of concurrent therapy and the specific bacterium employed. The effective amount of a bacterium will thus be the minimum amount, which will provide the desired effect. Usually an amount from about $10^5$ to about $10^9$ bacteria e.g. from about $10^5$ to about $10^9$ bacteria/m$^2$ body surface, preferably from about $10^6$ to about $10^8$ bacteria e.g. from about $10^6$ to about $10^8$ bacteria/m$^2$ body surface, more preferably from about $10^7$ to about $10^8$ bacteria e.g. from about $10^7$ to about $10^8$ bacteria/m$^2$ body surface, most preferably $10^8$ bacteria e.g. $10^8$ bacteria/m$^2$ body surface are administered to the subject.

A single dose of the recombinant virulence attenuated Gram-negative bacterial strain to administer to a subject, e.g. to a human to treat cancer e.g. a malignant solid tumor is usually from about $10^4$ to about $10^{10}$ bacteria e.g. from about $10^4$ bacteria/m$^2$ body surface to about $10^{10}$ bacteria/m$^2$ body surface, preferably from about $10^5$ to about $10^9$ bacteria e.g. from about $10^5$ to about $10^9$ bacteria/m$^2$ body surface, more preferably from about $10^6$ to about $10^8$ bacteria e.g. from about $10^6$ to about $10^8$ bacteria/m$^2$ body surface, even more preferably from about $10^7$ to about $10^8$ bacteria e.g. from about $10^7$ to about $10^8$ bacteria/m$^2$ body surface, most preferably $10^8$ bacteria e.g. $10^8$ bacteria/m$^2$ body surface of total recombinant virulence attenuated Gram-negative bacteria.

Examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; calcium carbonate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; cranberry extracts and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tabletting agents, stabilizers, anti-oxidants and preservatives, can also be present.

Modes of administration of the recombinant virulence attenuated Gram-negative bacteria to a subject may be selected from the group consisting of intravenous, intratumoral, intraperitoneal and per-oral administration. Although this invention is not intended to be limited to any particular mode of application, intravenous or intratumoral administration of the bacteria or the pharmaceutical compositions is preferred.

Depending on the route of administration, the active ingredients which comprise bacteria may be required to be coated in a material to protect said organisms from the action of enzymes, acids and other natural conditions which may inactivate said organisms. In order to administer bacteria by other than parenteral administration, they should be coated by, or administered with, a material to prevent inactivation. For example, bacteria may be co-administered with enzyme inhibitors or in liposomes. Enzyme inhibitors include pancreatic trypsin inhibitor, diisopropylfluorophosphate (DFP) and trasylol. Liposomes include water-in-oil-in-water P40 emulsions as well as conventional and specifically designed liposomes which transport bacteria, such as *Lactobacillus*, or their by-products to an internal target of a host subject. One bacterium may be administered alone or in conjunction with a second, different bacterium. Any number of different bacteria may be used in conjunction. By "in conjunction with" is meant together, substantially simultaneously or sequentially. The compositions may be also administered in the form of tablet, pill or capsule, for example, such as a freeze-dried capsule comprising the bacteria or the pharmaceutical compositions of the present invention or as frozen solution of bacteria or the pharmaceutical compositions of the present invention containing DMSO or glycerol. Another preferred form of application involves the preparation of a lyophilized capsule of the bacteria or the pharmaceutical compositions of the present invention. Still another preferred form of application involves the preparation of a heat dried capsule of the bacteria or the pharmaceutical compositions of the present invention.

The recombinant virulence attenuated Gram-negative bacteria or the pharmaceutical composition to be administered can be administered by injection. Forms suitable for injectable use include monoseptic or sterile aqueous solutions (where water soluble) or dispersions and sterile powders for the extemporaneous preparation of sterile injectable solutions or dispersion. In all cases the form must be monoseptic or sterile and must be fluid to the extent that easy syringability exists. It must be stable under the conditions of manufacture and storage. The carrier can be a solvent or dispersion medium containing, for example, water, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

In some embodiments of the present invention the recombinant virulence attenuated Gram-negative bacterial strain is co-administered with a siderophore to the subject. These embodiments are preferred. Siderophores which can be co-administered are siderophores including hydroxamate, catecholate and mixed ligand siderophores. Preferred siderophores are Deferoxamine (also known as desferrioxamine B, desferoxamine B, DFO-B, DFOA, DFB or desferal), Desferrioxamine E, Deferasirox (Exjade, Desirox, Defrijet, Desifer) and Deferiprone (Ferriprox), more preferred is Deferoxamine. Deferoxamine is a bacterial siderophore produced by the Actinobacteria *Streptomyces pilosus* and is commercially available from e.g. Novartis Pharma Schweiz AG (Switzerland).

Co-administration with a siderophore can be before, simultaneous to or after administration of the recombinant virulence attenuated Gram-negative bacterial strain.

Preferably a siderophore is administered before the administration of recombinant virulence attenuated Gram-negative bacterial strain, more preferably is administered at least 1 hour, preferably at least 6 hours, more preferably at least 12, hours, in particular at least 24 hours before the administration of the recombinant virulence attenuated Gram-negative bacterial strain to the subject. In a particular embodiment the subject is pretreated with desfreoxamine 24 h prior to infection with the recombinant virulence attenuated Gram-negative bacterial strain in order to allow bacterial growth. Usually a siderophore is co-administered at a single dose from about $0.5 \times 10^{-5}$ Mol to about $1 \times 10^{-3}$ Mol, more preferably from about $1 \times 10^{-5}$ Mol to about $1 \times 10^{-4}$ Mol preferably from about $3.5 \times 10^{-5}$ Mol to about $1.1 \times 10^{-4}$ Mol per kg of body weight. Usually desferoxamine is co-administered at single dose from about 20 mg to about 60 mg preferably from about 20 mg to about 60 mg per kg of body weight.

Dosis regimens of the administration of the recombinant virulence attenuated Gram-negative bacterial strain or the pharmaceutical composition described herein will vary with the particular goal to be achieved, the age and physical condition of the subject being treated, the duration of treatment, the nature of concurrent therapy and the specific bacterium employed, as known to the skilled person. The recombinant virulence attenuated Gram-negative bacterial strain is usually administered to the subject according to a dosing regimen consisting of a single dose every 1-20 days, preferably every 1-10 days, more preferably every 1-7 days. The period of administration is usually about 20 to about 60 days, preferably about 30-40 days. Alternatively the period of administration is usually about 8 to about 32 weeks, preferably about 8 to about 24 weeks, more preferably about 12 to about 16 weeks.

In a further embodiment the present invention provides a kit for treating cancer e.g. such as malignant solid tumors, preferably in human. Such kits generally will comprise the recombinant virulence attenuated Gram-negative bacterial strain or the pharmaceutical composition described herein, and instructions for using the kit. In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

EXAMPLES

Example 1

A) Materials and Methods

Bacterial strains and growth conditions. The strains used in this study are listed in FIGS. 3A to M. *E. coli* Top10, used for plasmid purification and cloning, and *E. coli* Sm10 k pir, used for conjugation, as well as *E. coli* BW19610 [31], used to propagate pKNG101, were routinely grown on LB agar plates and in LB broth at 37° C. Ampicillin was used at a concentration of 200 μg/ml (*Yersinia*) or 100 μg/ml (*E. coli*) to select for expression vectors. Streptomycin was used at a concentration of 100 μg/ml to select for suicide vectors. *Y. enterocolitica* MRS40 (0:9, biotype 2) [20] a non Ampicillin resistant E40-derivate [19] and strains derived thereof were routinely grown on Brain Heart Infusion (BHI; Difco) at RT. To all *Y. enterocolitica* strains Nalidixic acid was added (35 μg/ml) and all *Y. enterocolitica* asd strains were additionally supplemented with 100 μg/ml meso-2,6-Diaminopimelic acid (mDAP, Sigma Aldrich). *S. enterica* SL1344 were routinely grown on LB agar plates and in LB broth at 37° C. Ampicillin was used at a concentration of 100 μg/ml to select for expression vectors in *S. enterica*.

Genetic manipulations of *Y. enterocolitica*. Genetic manipulations of *Y. enterocolitica* has been described [32,33]. Briefly, mutators for modification or deletion of genes in the pYV plasmids or on the chromosome were constructed by 2-fragment overlapping PCR using purified pYV40 plasmid or genomic DNA as template, leading to 200-250 bp of flanking sequences on both sides of the deleted or modified part of the respective gene. Resulting fragments were cloned in pKNG101 [29] in *E. coli* BW19610 [31]. Sequence verified plasmids were transformed into *E. coli* Sm10 k pir, from where plasmids were mobilized into the corresponding *Y. enterocolitica* strain. Mutants carrying the integrated vector were propagated for several generations without selection pressure. Then sucrose was used to select for clones that have lost the vector. Finally mutants were identified by colony PCR. Specific mutators (pSi_408, pSi_419) are listed in Table III.

Figure 2:
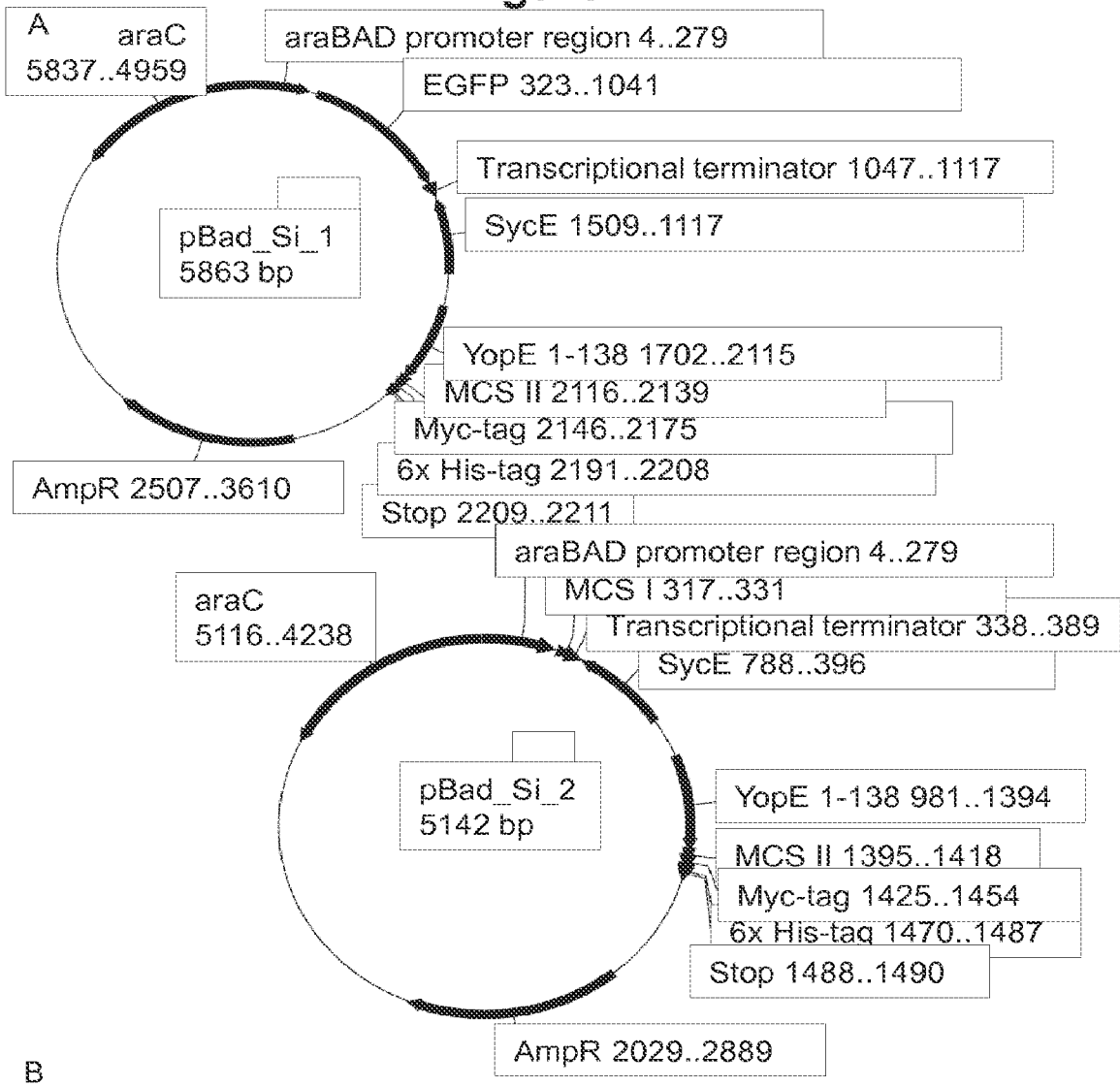
FIG. 2: Description of the type III secretion-based delivery toolbox. (A) Vector maps of the cloning plasmids pBad_Si1 and pBad_Si2 used to generate fusion constructs with YopE$_{1-138}$. The chaperone SycE and the YopE$_{1-138}$—fusion are under the native Y. enterocolitica promoter. The two plasmids only differ in presence of an arabinose inducible EGFP present on pBad_Si1 (B) Multiple cloning site directly following the yopE$_{1-138}$ fragment on pBad_Si1 and pBad_Si2 plasmids (SEQ ID NO:109).
Figure 4:
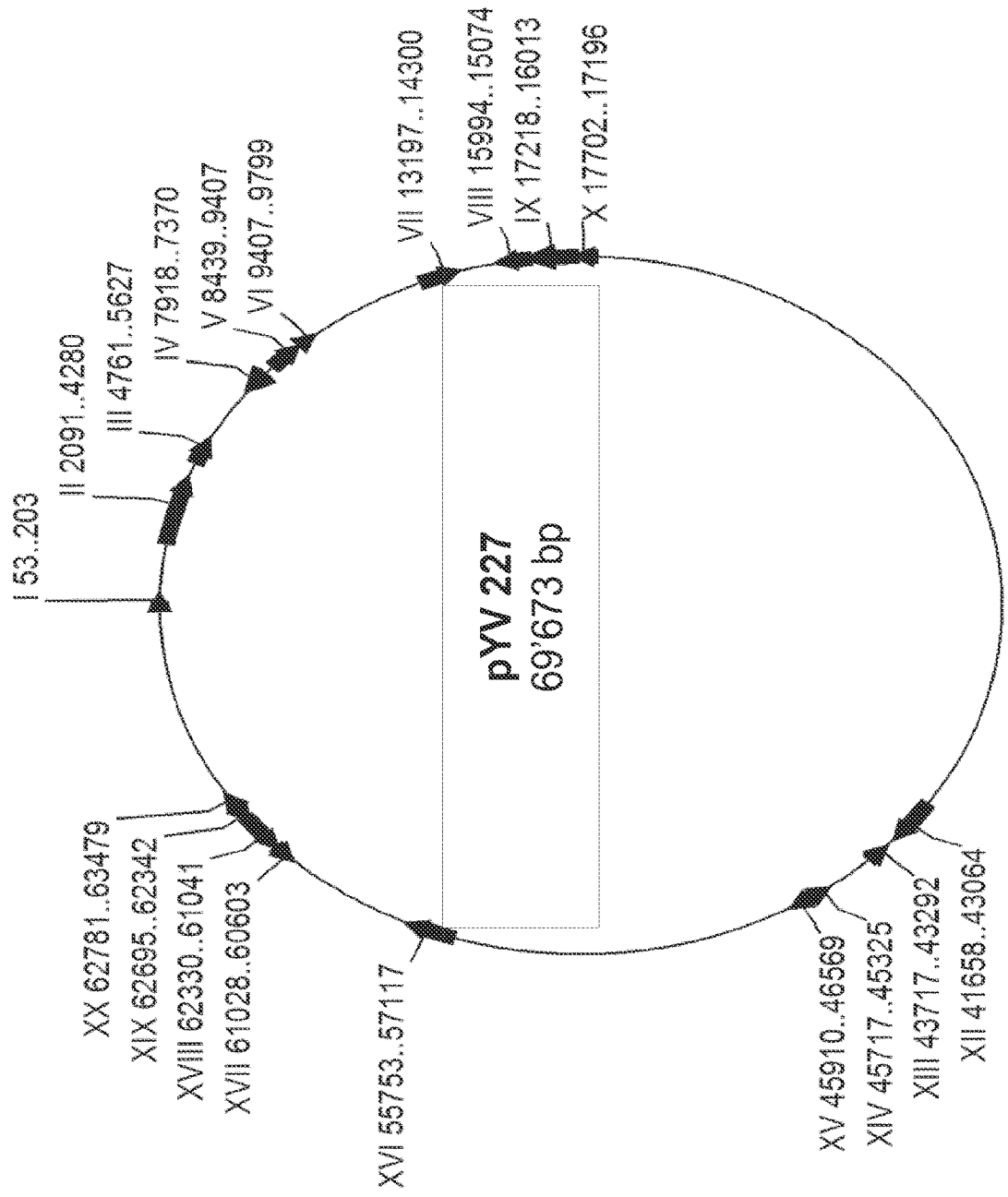
FIG. 4: The *Yersinia enterocolitica* W227 virulence plasmid, pYV. The 69'673 bp plasmid of *Yersinia* virulence (pYV) of strain W227 drawn to scale. T3SS effector proteins, origin of replication and the arsenic resistance (encoded by genes arsC, B, R and H) are indicated:
  I: origin of replication, II: yopO, III: yopP, IV: yopQ, V: yopT, VI: sycT,
  VII: yopM, VIII: yopD, IX: yopB, X: sycD, XII: yopH, XIII: sycH, XIV: sycE,
  XV: yopE, XVI: yadA, XVII-XVXX: arsC, B, R and H.

Construction of plasmids. Plasmid pBad_Si2 or pBad_Si1 (FIG. 2) were used for cloning of fusion proteins with the N-terminal 138 amino acids of YopE (SEQ ID No. 2). pBad_Si2 was constructed by cloning of the SycE-YopE$_{1-138}$ fragment containing endogenous promoters for YopE and SycE from purified pYV40 into KpnI/HindIII site of pBad-MycHisA (Invitrogen). Additional modifications include removal of the NcoI/BglII fragment of pBad-MycHisA by digestion, Klenow fragment treatment and relegation. A bidirectional transcriptional terminator (BBa_B1006; iGEM foundation) was cloned into KpnI cut and Klenow treated (pBad_Si2) or BglII cut site (pBad_Si1). Further at the 3' end of YopE$_{1-138}$ the following cleavage sites were added: XbaI-XhoI-BstBI-(HindIII) (FIG. 2 B). pBad_Si1 is equal to pBad_Si2 but encodes EGFP amplified from pEGFP-C1 (Clontech) in the NcoI/BglII site under the Arabinose inducible promoter. Plasmids pSi_266, pSi_267, pSi_268 and pSi_269 containing the corresponding endogenous promoter and the SteA$_{1-20}$ fragment (pSi_266), the full length SteA sequence (pSi_267), the SopE$_{1-81}$ fragment (pSi_268) or the SopE$_{1-105}$ fragment (pSi_269) were amplified from *S. enterica* SL1344 genomic DNA and cloned into NcoI/KpnI site of pBad-MycHisA (Invitrogen).

Full length genes or fragments thereof were amplified with the specific primers listed in Table I below and cloned as fusions to YopE$_{1-138}$ into plasmid pBad_Si2 or in case of z-BIM (SEQ ID No. 16) into pBad_Si1 (see Table II below). For fusion to SteA or SopE, synthetic DNA constructs were cleaved by KpnI/HindII and cloned into pSi_266, pSi_267, pSi_268 or pSi_269 respectively. In case of genes of bacterial species, purified genomic DNA was used as template (*S. flexneri* M90T, *Salmonella enterica* subsp. *enterica* serovar *Typhimurium* SL1344, *Bartonella henselae* ATCC 49882). For human genes a universal cDNA library (Clontech) was used if not otherwise stated (FIGS. 3A to M, zebrafish genes were amplified from a cDNA library (a kind gift of M. Affolter). Ligated plasmids were cloned in *E. coli* Top10. Sequenced plasmids were electroporated into the desired *Y. enterocolitica* or *S. enterica* strain using settings as for standard *E. coli* electroporation.

TABLE I (Primer Nr. Si_:Sequence)

Seq_Id_No_51: Primer No.: Si_285
CATACCATGGGAGTGAGCAAGGGCGAG

Seq_Id_No_52: Primer No.: Si_286
GGAAGATCTttACTTGTACAGCTCGTCCAT

Seq_Id_No_53: Primer No.: Si_287
CGGGGTACCTCAACTAAATGACCGTGGTG

Seq_Id_No_54: Primer No.: Si_288
GTTAAAGCTTttcgaatctagactcgagCGTGGCGAACTGGTC

Seq_Id_No_55: Primer No.: Si_387
CGTAtctagaATGGACTGTGAGGTCAACAA

Seq_Id_No_56: Primer No.: Si_391
CGTAtctagaGGCAACCGCAGCA

Seq_Id_No_57: Primer No.: Si_389
GTTAAAGCTTTCAGTCCATCCCATTTCTg

Seq_Id_No_58: Primer No.: Si_436
CGTAtctagaATGCCCCGCCCC

Seq_Id_No_59: Primer No.: Si_437
GTTAAAGCTTCTACCCACCGTACTCGTCAAT

Seq_Id_No_60: Primer No.: Si_438
CGTAtctagaATGTCTGACACGTCCAGAGAG

Seq_Id_No_61: Primer No.: Si_439
GTTAAAGCTTTCATCTTCTTCGCAGGAAAAG

Seq_Id_No_62: Primer No.: Si_463
CAGTctcgaggaaagcttgtttaagggc

TABLE I-continued (Primer Nr. Si_:Sequence)

Seq_Id_No_63: Primer No.: Si_464
cagtTTCGAAttagcgacggcgacg

Seq_Id_No_64: Primer No.: Si_476
GTTAAAGCTTttACTTGTACAGCTCGTCCAT

Seq_Id_No_65: Primer No.: Si_494
CGTAtctagaATGGCCGAGCCTTG

Seq_Id_No_66: Primer No.: Si_495
GTTAAAGCTTttaTTGAAGATTTGTGGCTCC

Seq_Id_No_67: Primer No.: Si_504
CGTAtctagaGAAAATCTGTATTTTCAAAGTGAAAATCTGTATTTTCAAA
GTATGCCCCGCCCC Seq_Id_No_68: Primer No.: Si_505
GTTAAAGCTTCCCACCGTACTCGTCAATtc Seq_Id_No_69: Primer No.: Si_508
CGTAtctagaGAAAATCTGTATTTTCAAAGTGAAAATCTGTATTTTCAAA
GTATGGCCGAGCCTTG Seq_Id_No_70: Primer No.: Si_509
GTTAAAGCTTTTGAAGATTTGTGGCTCCc Seq_Id_No_71: Primer No.: Si_511
CGTAtctagaGAAAATCTGTATTTTCAAAGTGAAAATCTGTATTTTCAAA
GTGTGAGCAAGGGCGAG Seq_Id_No_72: Primer No.: Si_512
CGTAtctagaGAAAATCTGTATTTTCAAAGTGAAAATCTGTATTTTCAAA
GTCCGCCGAAAAAAAAACGTAAAGTTGTGAGCAAGGGCGAG Seq_Id_No_73: Primer No.: Si_513
GTTAAAGCTTttAAACTTTACGTTTTTTTTTCGGCGGCTTGTACAGCTCG
TCCAT Seq_Id_No_74: Primer No.: Si_515
CGTAtctagaGAAAATCTGTATTTTCAAAGTGAAAATCTGTATTTTCAAA
GTGATTATAAAGATGATGATGATAAAATGGCCGAGCCTTG Seq_Id_No_75: Primer No.: Si_677
TTACTATTCGAAGAAATTATTCATAATATTGCCCGCCATCTGGCCCAAAT
TGGTGATGAAATGGATCATTAAGCTTGGAGTA Seq_Id_No_76: Primer No.: Si_678
TACTCCAAGCTTAATGATCCATTTCATCACCAATTTGGGCCAGATGGCGG
GCAATATTATGAATAATTTCTTCGAATAGTAA Seq_Id_No_77: Primer No.: Si_682
TTACTACTCGAGAAAAAACTGAGCGAATGTCTGCGCCGCATTGGTGATGA
ACTGGATAGCTAAGCTTGGAGTA Seq_Id_No_78: Primer No.: Si_683
TACTCCAAGCTTAGCTATCCAGTTCATCACCAATGCGGCGCAGACATTCG
CTCAGTTTTTTCTCGAGTAGTAA Seq_Id_No_79: Primer No.: Si_580
catgccatggatttatggtcatagatatgacctc Seq_Id_No_80: Primer No.: Si_612
CGGGGTACCatgaggtagcttatttcctgataaag Seq_Id_No_81: Primer No.: Si_613
CGGGGTACCataattgtccaaatagttatggtagc Seq_Id_No_82: Primer No.: Si_614
catgccatggCGGCAAGGCTCCTC Seq_Id_No_83: Primer No.: Si_615
cggggtaccTTTATTTGTCAACACTGCCC Seq_Id_No_84: Primer No.: Si_616
cggggtaccTGCGGGGTCTTTACTCG

TABLE I-continued (Primer Nr. Si_:Sequence)

Seq_Id_No_85: Primer No.: Si_585
CAGTctcgagATGCAGATCTTCGTCAAGAC

Seq_Id_No_86: Primer No.: Si_586
GTTAAAGCTTgctagcttcgaaACCACCACGTAGACGTAAGAC

Seq_Id_No_87: Primer No.: Si_588
cagtTTCGAAGATTATAAAGATGATGATGATAAAATGGCCGAGCCTTG Seq_Id_No_88: primer No. 733
TTACTACTCGAGGGTGCCATCGATGCCGAAGAAATTATTCATAATATTGCCCG Seq_Id_No_89: primer No. 735
TACTCCTTCGAATTAATGATCCATTTCATCACCAATTTG Seq_Id_No_90: primer No. 736
TTACTACTCGAGGGTGCCATCGATGCCAAAAAACTGAGCGAATGTCTGCG Seq_Id_No_91: primer No. 738
TACTCCTTCGAATTAGCTATCCAGTTCATCACCAATG Seq_Id_No_92: primer No. 734
TACTCCTTCGAAGGCACCATGATCCATTTCATCACCAATTTGG Seq_ID_No_93: primer No. 725:
TTACTATTCGAAGAAATTATTCATAATATTGCC Seq_ID_No_94: primer No. 726:
TACTCCAAGCTTACGGTTGAATATTATGATCCATTTCATCACCAATTTGG Seq_ID_No_95: primer No. 727:
TTACTATTCGAAGCCGGTGGTGCCGAAGAAATTATTCATAATATTGCCC Seq_ID_No_96: primer No. 728:
TACTCCAAGCTTAATGATCCATTTCATCA Seq_ID_No_97: primer No. 737:
TACTCCTTCGAAGGCACCGCTATCCAGTTCATCACCAATG Seq_ID_No_101: primer No. 869:
gatcgtcgacTTAAGTTCAATGGAGCGTTTAATATC Seq_ID_No_102: primer No. 870:
ctttgactggcgagaaacgcTCTTAACATGAGGCTGAGCTC Seq_ID_No_103: primer No. 871:
GAGCTCAGCCTCATGTTAAGAgcgtttctcgccagtcaaag Seq_ID_No_104: primer No. 872:
gatagcccccgagcctgtGCACTTTGTCATTAACCTCAGC Seq_ID_No_105: primer No. 873:
GCTGAGGTTAATGACAAAGTGCacaggctcgggggctatc Seq_ID_No_106: primer No. 874:
catgtctagaCCCTCAGCATAATAACGACTC Seq_ID_No_107: primer No. 600:
catgacatgtTGGCGTTTCTCGCC Seq_ID_No_108: primer No. 601:
catgacatgtATTAACCTCAGCCCTGACTATAAG Seq_ID_No_119: primer No. 1010:
cacatgtctagaCAACCGTTTCCGAAAGGTGATCTG Seq_ID_No_120: primer No. 1012:
atccCAagctTATTGGCGTTGGGTGGTAAAAATTTTG Seq_ID_No_121: primer No. 1021:
cacatgtctagaATGACCGCCGAACAACGC Seq_ID_No_122: primer No. 1022:
catgaagcttaCGGACCCGGATTTTGGCTC >Seq_ID_No_123: primer No. 1023:
catgaagcttaCGGTTCTTCTTGAATAAAAATTTGAATG Seq_ID_No_124: primer No. 1024:
catgaagcttaTTGCAGCACTTTCGGCCAATTT Seq_ID_No_125: primer No. 1025:
cacatgtctagaATGAGCATTGTGTGTAGCGC Seq_ID_No_126: primer No. 1026:
catgaagcttaGCTTTCATCCACGGCCGG Seq_ID_No_127: primer No. 1027:
catgaagcttaATTACCGGTTTGGCGCAGC

TABLE II

Cloned fusion proteins

| Protein to be delivred by T3SS | Protein Seq. ID. No. | Backbone plasmid | Resulting plasmid name | Primers. Si_Nr.: | Primer Seq. ID No. |
|---|---|---|---|---|---|
| YopE1-138-MycHis | 3 | pBad-MycHisA (Invitrogen) | pBad_Si_1 | 285/286 (EGFP), 287/288 (sycE-YopE1-138) | 51/52 and 53/54 |
| YopE1-138-MycHis | 3 | pBad-MycHisA (Invitrogen) | pBad_Si_2 | 287/288 (sycE-YopE1-138) | 53/54 |
| YopE1-138-human Bid | 16 | pBad_Si_2 | pSi_85 | 387/391 | 55/56 |
| YopE1-138-human tBid | 17 | pBad_Si_2 | pSi_87 | 389/391 | 55/57 |
| YopE1-138-ET1 | 9 | pBad_Si_2 | pSi_120 | 436/437 | 58/59 |
| YopE1-138-z-BIM | 16 | pBad_Si_1 | pSi_121 | 438/439 | 60/61 |
| YopE1-138-TEV protease S219V | 12 | pBad_Si_2 | pSi_132 | 463/464 | 62/63 |
| YopE1-138-Ink4C | 8 | pBad_Si_2 | pSi_151 | 494/495 | 65/66 |
| YopE1-138-2x TEVsite-ET1 | 11 | pBad_Si_2 | pSi_156 | 504/505 | 67/68 |

TABLE II-continued

Cloned fusion proteins

| Protein to be delivred by T3SS | Protein Seq. ID. No. | Backbone plasmid | Resulting plasmid name | Primers. Si_Nr.: | Primer Seq. ID No. |
|---|---|---|---|---|---|
| YopE1-138-2xTEVsite-EGFP | 98 | pBad_Si_2 | pSi_158 | 511/476 | 71/64 |
| YopE1-138-2xTEVsite-EGFP-NLS | 99 | pBad_Si_2 | pSi_159 | 511/513 | 71/73 |
| YopE1-138-2xTEVsite-NLS-EGFP | 100 | pBad_Si_2 | pSi_160 | 512/476 | 72/64 |
| YopE1-138-2x TEVsite-INK4C | 10 | pBad_Si_2 | pSi_161 | 508/509 | 69/70 |
| YopE1-138-2x TEVsite-Flag-INK4C | 13 | pBad_Si_2 | pSi_164 | 515/509 | 74/70 |
| YopE1-138-*Y. enterocolitica* codon optimized murine tBid BH3 part | 19 | pBad_Si_2 | pSi_318 | 677/678 | 75/76 |
| YopE1-138-*Y. enterocolitica* codon optimized murine Bax BH3 part | 20 | pBad_Si_2 | pSi_322 | 682/683 | 77/78 |
| SteA1-20 | 5 | pBad-MycHisA (Invitrogen) | pSi_266 | 580/612 | 79/80 |
| SteA | 4 | pBad-MycHisA (Invitrogen) | pSi_267 | 580/613 | 79/81 |
| SopE1-81 | 6 | pBad-MycHisA (Invitrogen) | pSi_268 | 614/615 | 82/83 |
| SopE1-105 | 7 | pBad-MycHisA (Invitrogen) | pSi_269 | 614/616 | 82/84 |
| YopE1-138-*Y. enterocolitica* codon optimized murine tBid | 21 | pBad_Si_2 | pSi_315 | synthetic construct | / |
| YopE1-138-Ubiquitin | 14 | pBad_Si_2 | pSi_236 | 585/586 | 85/86 |
| YopE1-138-Ubiquitin-Flag-INK4C-MycHis | 15 | pSi_236 | pSi_237_II | 588/509 | 87/70 |
| YopE1-138-(*Y. enterocolitica* codon optimized murine tBid BH3 part) ready for insertion of further domains | 25 | pBad_Si_2 | pSi_357 | 733/735 | 88/89 |
| YopE1-138-(*Y. enterocolitica* codon optimized murine BAX BH3 part) ready for insertion of further domains | 26 | pBad_Si_2 | pSi_358 | 736/738 | 90/91 |
| YopE1-138-(*Y. enterocolitica* codon optimized murine tBid BH3 part)$_2$ | 27 | pSi_357 | pSi_371 | 733/734 | 88/92 |
| YopE1-(138-*Y. enterocolitica* codon optimized murine tBid BH3 part-*Y. enterocolitica* codon optimized murine BAX BH3 part | 28 | pSi_358 | pSi_373 | 733/734 | 88/92 |
| YopE$_{1-138}$-codon optimized murine tBid BH3 extended part | 22 | pBad_Si_2 | pSi_353 | 725/726 | 93/94 |
| YopE$_{1-138}$-10 Aa linker-*Y. enterocolitica* codon optimized murine tBid BH3 part | 23 | pBad_Si_2 | pSi_354 | 727/728 | 95/96 |
| YopE$_{1-138}$-*Y. enterocolitica* codon optimized murine Bax | 24 | pSi_357 | pSi_374 | 736/737 | 90/97 |

TABLE II-continued

Cloned fusion proteins

| Protein to be delivred by T3SS | Protein Seq. ID. No. | Backbone plasmid | Resulting plasmid name | Primers. Si_Nr.: | Primer Seq. ID No. |
|---|---|---|---|---|---|
| BH3 part-*Y. enterocolitica* codon optimized murine tBid BH3 part | | | | | |
| YopE$_{1-138}$-*Y. enterocolitica* codon optimized human RIG-1 two CARD domains (Aa. 1-245) | 37 | pBad_Si_2 | pSi_453 | synthetic construct | / |
| YopE$_{1-138}$-*Y. enterocolitica* codon optimized murine RIG-1 two CARD domains (Aa. 1-246) | 38 | pBad_Si_2 | pSi_454 | synthetic construct | / |
| YopE$_{1-138}$-*Y. enterocolitica* codon optimized *S. cerevisiae* GCN4 (Aa. 249-278)-*Y. enterocolitica* codon optimized *P. aeruginosa* WspR (Aa. 172-347) | 39 | pBad_Si_2 | pSi_452 | synthetic construct | / |
| YopE$_{1-138}$-*Y. enterocolitica* codon optimized murine IRF3 S397D | 40 | pBad_Si_2 | pSi_428 | synthetic construct | / |
| YopE$_{1-138}$-*Y. enterocolitica* codon optimized *V. cholerae* DncV (M3toL413) | 41 | pBad_Si_2 | pSi_482 | synthetic construct | / |
| YopE$_{1-138}$-*Y. enterocolitica* codon optimized *B. cereus*_DisA TABLE II-continued Cloned fusion proteins

| Protein to be delivred by T3SS | Protein Seq. ID. No. | Backbone plasmid | Resulting plasmid name | Primers. Si_Nr.: | Primer Seq. ID No. |
|---|---|---|---|---|---|
| YopE$_{1-138}$-Y. enterocolitica codon optimized Anemonae (N. vectensis) cGAS (Aa. 60-422) (Ensembi: A7SFB5.1) | 117 | pBad_Si_2 | pSi_503 | 1010/1012 | 120/121 |
| YopE$_{1-138}$-Y. enterocolitica codon optimized Listeria CdaA (Aa. 101-273) | 118 | pBad_Si_2 | pSi_518 | synthetic construct | / |

TABLE III

Mutators for genetic modification

| Mutator/Construct | To be inserted onto: | Backbone plasmid | Resulting plasmid name | Primers Si_Nr.: | Primers Seq.Id No. | used with special parent strain |
|---|---|---|---|---|---|---|
| YopE$_{1-138}$-murine tBID BH3 | pYV | pKNG101 | pSi_408 | Synthetic gene | / | / |
| YopE$_{1-138}$-(murine tBID BH3)$_2$ | pYV | pKNG101 | pSi_437 | Synthetic gene | / | Strain mutated with pSi_408 |
| YopE$_{1-138}$- Y. enterocolitica codon optimized murine RIG-1 two CARD domains (Aa. 1-246) | pYV | pKNG101 | pSi_456 (Seq ID No 50) | Synthetic gene | / | / |
| pYV-asd | pYV | pKNG101 | pSi_417 | PCR1: 869/870; PCR2: 871/872; PCR3: 873/874; overlapping PCR 869/874 | PCR1: 101/102; PCR2: 103/104; PCR3: 105/106; overlapping PCR 101/106 | Δasd |
| pYV-virF-hairpinI | pYV | pKNG101 | pSi_441 | Synthetic gene | / | / |
| PYV-pAra-VirF | pYV | pKNG101 | pSi_439 | Synthetic gene | / | / |

Yop secretion. Induction of the yop regulon was performed by shifting the culture to 37° C. in BHI-Ox (secretion-permissive conditions) [34]. As carbon source glucose was added (4 mg/ml).

Total cell and supernatant fractions were separated by centrifugation at 20 800 g for 10 min at 4° C. The cell pellet was taken as total cell fraction. Proteins in the supernatant were precipitated with trichloroacetic acid 10% (w/v) final for 1 h at 4° C. After centrifugation (20 800 g for 15 min) and removal of the supernatant, the resulting pellet was washed in ice-cold Acetone over-night. The samples were centrifuged again, the supernatant was discarded and the pellet was air-dried and resuspended in 1×SDS loading dye.

Secreted proteins were analysed by SDS-PAGE; in each case, proteins secreted by 3×10$^8$ bacteria were loaded per lane. Detection of specific secreted proteins by immunoblotting was performed using 12.5% SDS-PAGE gels. For detection of proteins in total cells, 2×10$^8$ bacteria were loaded per lane, if not stated otherwise, and proteins were separated on 12.5% SDS-PAGE gels before detection by immunoblotting.

Immunoblotting was carried out using rat monoclonal antibodies against YopE (MIPA193—13A9; 1:1000, [35]). The antiserum was preabsorbed twice overnight against Y. enterocolitica ΔHOPEMT asd to reduce background staining. Detection was performed with secondary antibodies directed against rat antibodies and conjugated to horseradish peroxidase (1:5000; Southern biotech), before development with ECL chemiluminescent substrate (LumiGlo, KPM).

Cell culture and infections. HeLa Ccl2 and B16F10 cells were cultured in Dulbecco's modified Eagle's medium (DMEM) supplemented with 10% FCS and 2 mM L-Glutamine (cDMEM). 4T1 cells were cultured in RPMI 1640 supplemented with 10% FCS and 2 mM L-Glutamine. Y. enterocolitica were grown in BHI with additives overnight at RT, diluted in fresh BHI to an OD$_{600}$ of 0.2 and grown for 2 h at RT before a temperature shift to a 37° C. waterbath shaker for further 30 min or for 1 h in case of delivery of EGFP. Finally, the bacteria were collected by centrifugation (6000 rcf, 30 sec) and washed once with DMEM supplemented with 10 mM HEPES and 2 mM L-glutamine. Finally, the bacteria were collected by centrifugation (6000 rcf, 30 sec) and washed once with DMEM supplemented with 10 mM HEPES and 2 mM L-glutamine. Cells seeded in 96-well (for Immunofluorescence) or 6-well (for Western blotting) plates were infected at indicated MOIs in DMEM supplemented with 10 mM HEPES and 2 mM L-glutamine. After adding bacteria, plates were centrifuged for 1 min at 1750 rpm and placed at 37° C. for indicated time periods. Extracellular bacteria were killed by gentamicin (100 mg/ml) if indicated. In case of immunofluorescence analysis, infection assays were stopped by 4% PFA fixation. For Western blot analysis cells were washed twice with ice-cold PBS and Phospho-safe lysis buffer (Novagen) was added to lyse the cells. After incubation on ice, the cells were centrifuged (16 000 rcf, 25 min, 4° C.). Supernatants were collected and analyzed for total protein content by Bradford BCA assay (Pierce) before SDS PAGE and Western blotting using anti-Actin (Millipore), Anti-Bid (Cell Signaling), anti-Myc (Santa Cruz), anti-Caspase-3 p17 (Cell Signaling) and anti-Ink4C (Cell Signaling) antibody.

Western blotting of T3SS translocated proteins from infected cells. HeLa cells in 6-well plates were infected at an MOI of 100 as described above. In case of coinfection with the TEV protease translocating *Y. enterocolitica* strain, the $OD_{600}$ of the strains was set and the two bacterial suspensions were mixed in a tube at a ratio of 1:1 (if not otherwise indicated) before addition to the cells. At the end of the infection, the cells were washed twice with ice-cold PBS and collected by scraping in a small volume of ice-cold PBS. After centrifugation (16 000 rcf, 5 min, 4° C.) the pellet was dissolved in 0.002% digitonin supplemented with a protease inhibitor cocktail (Roche complete, Roche). The dissolved pellets were incubated for 5 minutes on ice and then centrifuged (16 000 rcf, 25 min, 4° C.). Supernatants were collected and analyzed for total protein content by Bradford BCA assay (Pierce) before SDS PAGE and Western blotting using an anti-Myc (Santa Cruz, 9E11) or anti-Ink4C (Cell Signaling) antibody.

Automated Microscopy and Image Analysis. Images were automatically acquired with an ImageXpress Micro (Molecular devices, Sunnyvale, USA). Quantification of anti-Myc staining intensities was performed using MetaXpress (Molecular devices, Sunnyvale, USA). Regions within cells excluding nuclear regions and regions containing bacteria were manually chosen (circles with an area of 40 pixels) and average intensity was recorded.

Biodistribution in B16-F10 and 4T1 Tumor Allograft Mouse Models

All animal experiments were approved (license 1908; Kantonales Veterinäramt Basel-Stadt) and performed according to local guidelines (Tierschutz-Verordnung, Basel-Stadt) and the Swiss animal protection law (Tierschutz-Gesetz). 6 week old C57Bl/6 and BALB/c mice were ordered from Janvier Labs. After at least one week of accommodation, mice were anesthetized using isoflurane and 100 ul B16-F10 or 4T1 cells ($1\times10^5$-$1\times10^6$ cells) were subcutaneously injected into the flank of C57Bl/6 and BALB/c, respectively. Throughout the experiment, mice were scored for behavior and physical appearance, and surface temperature, as well as body weight was measured.

Once tumors had developed, mice were administered an 8 mg/ml desferal solution (10 ml/kg) through i.p. injection. On the following day, mice were infected with *Y. enterocolitica* MRS40 or *Y. enterocolitica* MRS40 ΔHOPEMT ($2\times10^5$, $1\times10^6$ or $1\times10^7$ bacteria) by injection into the tail vein. The inoculum i.v. administered to the mice was validated by dilution plating. In some experiments, tumor progression was followed by daily measurements of tumor length and width with digital calipers. Tumor volume was determined as $0.523\times length \times width^2$. On respective days postinfection, mice were sacrificed by $CO_2$ inhalation. A blood sample was immediately isolated through aspiration from the heart. Liver, spleen, lung and the tumor were isolated and their weight determined. The organs and the tumor were homogenized. CFU in each sample was determined by spotting of serial dilutions onto LB agar plates containing nalidixic acid (35 ug/ml).

Direct type I Interferon activation assay. Murine B16F10 melanoma cells, murine RAW264.7 wildtype or MAVS knockout macrophages stably expressing secreted embryonic alkaline phosphatase (SEAP) or secreted Lucia luciferase under the control of the I-ISG54 promoter which is comprised of the IFN-inducible ISG54 promoter enhanced by a multimeric ISRE were purchased from InvivoGen (B16-Blue ISG, RAW-Blue ISG, RAW-Lucia ISG and RAW-Lucia ISG-KO-MAVS). Growth conditions and type I IFN assay were adapted from the protocols provided by InvivoGen. Briefly, 12'500 B16-Blue ISG cells or 30'000 RAW-Blue, RAW-Lucia or RAW-Lucia KO-MAVS ISG cells in 150 μl test medium (RPMI+2 mM L-glutamine+10% FCS for B16-Blue ISG cells; DMEM+2 mM L-glutamine+10% FCS for RAW-Blue, RAW-Lucia and RAW-Lucia KO-MAVS ISG cells) per well were seeded in a flat-bottom 96-well plate (NUNC or Corning). The next day, the cells were infected with the bacterial strains to be assessed by adding 15 μl per well of the desired multiplicity of infection (MOI, diluted in test medium). After 2 hours of incubation (37° C. and 5% $CO_2$) the bacteria were killed by adding test medium containing penicillin (100 U/ml) and streptomycin (100 ug/ml). The incubation was continued for 20-24 h. Detection of SEAP and luciferase followed the QUANTI-Blue™ and QUANTI-Luc™ protocol (InvivoGen), respectively. For SEAP detection: 20 μl of the cell supernatant was incubated with 180 μl detection reagent (QUANTI-Blue™, InvivoGen). The plate was incubated at 37° C. and SEAP activity was measured by reading the OD at 650 nm using a microplate reader (Molecular Devices). As a positive control murine IFNγ (stock: 1'000'000 U/ml) diluted to the respective concentrations in test medium was used. For luciferase detection: To 20 μl of the cell supernatant 50 μl detection reagent (QUANTI-Luc™, InvivoGen) was added in opaque plates (ThermoScientific). Luminescence was measured immediately using a plate reader (BioTek).

Indirect type I Interferon activation assay. Murine B16F10 or 4T1 cells were infected with indicated multiplicities of infection (MOI) of the bacterial strains to be assessed for a total of 4 h as described above. Cell supernatant was then transferred onto murine B16F10 melanoma cells stably expressing secreted embryonic alkaline phosphatase (SEAP) under the control of the I-ISG54 promoter (comprised of the IFN-inducible ISG54 promoter enhanced by a multimeric ISRE; purchased from InvivoGen, B16-Blue ISG cells). Growth conditions and type I IFN assay were adapted from the protocols provided by InvivoGen. Briefly, 12'500 B16-Blue ISG cells in 150 μl test medium (RPMI+2 mM L-glutamine+10% FCS) per well were seeded in a flat-bottom 96-well plate (NUNC). The next day, the entire medium was removed and 100 ul of the cell supernatant of previously infected B16F10 or 4T1 was added. The plate was incubated for 20-24 h at 37° C. and 5% $CO_2$. Detection of SEAP followed the QUANTI-Blue™ protocol (InvivoGen). 20 µl of the cell supernatant was incubated with 180 µl detection reagent (QUANTI-Blue™, Invivo-Gen). The plate was incubated at 37° C. and SEAP activity was measured by reading the OD at 650 nm using a microplate reader (Molecular Devices).

Study of tumor progression in the B16F10 tumor allograft mouse model upon intratumoral treatment. All animal experiments were approved by the responsible authorities and performed according to local guidelines and animal protection laws. 5-7 weeks old female C57Bl/6 mice were ordered from Charles River (L'Arbresles). After at least one week of accommodation, mice were anesthetized using isoflurane and $1\times10^6$ B16-F10 cells in 200 µL of RPMI 1640 were subcutaneously injected into the right flank of the mice. At regular intervals, mice were monitored for behaviour and physical appearance and the body weight was measured.

Treatments started once tumors had reached a volume of 60-130 $mm^3$ (defined as day 0). Mice were administered with the bacterial strains to be assessed on days 0, 1, 2, 3, 6 and 9 by intratumoral injection ($7.5\times10^7$ bacteria in 50 ul PBS per administration) under isoflurane anaesthesia. The inoculum intratumorally administered to the mice was validated by dilution plating. As control, mice were injected with endotoxin-free PBS only. 24 hours before the last bacterial treatment (day 8) mice were administered an 8 mg/ml desferal solution (10 ml/kg) through i.p. injection. Tumor progression was followed by measurements of tumor length and width with digital calipers. Tumor volume was determined as $0.5\times length\times width^2$. A tumor volume exceeding 1500 $mm^3$ was defined as humane endpoint.

Study of tumor progression and rechallenge in the EMT-6 tumor allograft mouse models upon intratumoral treatment. All animal experiments were approved by the responsible authorities and performed according to local guidelines and animal protection laws. 5-7 weeks old female BALB/c (BALB/cByJ) mice were ordered from Charles River (L'Arbresles). After at least one week of accommodation, mice were anesthetized using isoflurane and $1\times10^6$ EMT-6 cells in 200 µL of RPMI 1640 were subcutaneously injected into the right flank of the mice. At regular intervals, mice were monitored for behaviour and physical appearance and the body weight was measured.

Treatments started once tumors had reached a volume of 60-130 $mm^3$ (defined as day 0). Mice were administered with the bacterial strains to be assessed on days 0, 1, 5, 6, 10 and 11 by intratumoral injection ($7.5\times10^7$ bacteria in 50 ul PBS per administration) under isoflurane anaesthesia. The inoculum intratumorally administered to the mice was validated by dilution plating. As control, mice were injected with endotoxin-free PBS only. 24 hours before the last bacterial treatment (day 10) mice were administered an 8 mg/ml desferal solution (10 ml/kg) through i.p. injection. Tumor progression was followed by measurements of tumor length and width with digital calipers. Tumor volume was determined as $0.5\times length\times width^2$. A tumor volume exceeding 1500 $mm^3$ was defined as humane endpoint. Mice displaying a complete tumor regression at day 54 after treatment start, were anesthetized using isoflurane and $1\times10^6$ EMT-6 cells in 200 µL of RPMI 1640 were subcutaneously injected into the contralateral (left) flank in relation to the first tumor cell injection. As control group, naïve mice that have not been grafted with EMT-6 cells before were included. Tumor progression was followed by measurements of tumor length and width with digital calipers. Tumor volume was determined as $0.5\times length\times width^2$. A tumor volume exceeding 1500 $mm^3$ was defined as humane endpoint.

Study of tumor progression in the EMT-6 tumor allograft mouse models upon intravenous treatment. All animal experiments were approved by the responsible authorities and performed according to local guidelines and animal protection laws. 5-6 weeks old female BALB/c (BALB/cByJ) mice were ordered from Charles River (L'Arbresles). After at least one week of accommodation, mice were anesthetized using isoflurane and $1\times10^6$ EMT-6 cells in 200 µL of RPMI 1640 were subcutaneously injected into the right flank of the mice. At regular intervals, mice were monitored for behaviour and physical appearance and the body weight was measured.

Mice were randomized into treatment groups once tumors had reached a volume of 80-250 $mm^3$ (defined as day 0). 24 hours before randomization (D-1) mice were administered an 8 mg/ml desferal solution (10 ml/kg) through i.p. injection. On day 0, mice were administered with the bacterial strains to be assessed by intravenous injection ($5\times10^6$ bacteria in 100 ul PBS per administration) under isoflurane anaesthesia. The inoculum intravenously administered to the mice was validated by dilution plating. As control, mice were injected with endotoxin-free PBS only. Tumor progression was followed by measurements of tumor length and width with digital calipers. Tumor volume was determined as $0.5\times length\times width^2$. A tumor volume exceeding 1500 $mm^3$ was defined as humane endpoint.

Measurement of IFNβ secretion upon infection of tumor cell isolates. All animal experiments were approved (license 1908; Kantonales Veterinäramt Basel-Stadt) and performed according to local guidelines (Tierschutz-Verordnung, Basel-Stadt) and the Swiss animal protection law (Tierschutz-Gesetz). 6 week old BALB/c mice were ordered from Janvier Labs. After one week of accommodation, mice were anesthetized using isoflurane and 100 ul EMT-6 cells ($1\times10^6$ cells) were subcutaneously injected into the flank of the mice. Throughout the experiment, mice were scored for behavior and physical appearance, and surface temperature, and the body weight was measured. Tumor progression was followed by measurements of tumor length and width with digital calipers. Tumor volume was determined as $0.5\times length\times width^2$. On the day of the assay, tumors were isolated, cut to small pieces of 1-2 mm, digested for 1-1.5 hours and passed through a 70 µm nylon mesh to obtain a single cell suspension. Cell count of this crude cell isolate was determined and 300'000 cells per well were seeded in a flat-bottom 24-well plate (Corning) in growth medium (DMEM+L-Glutamine+non-essential amino acids+10% FCS). After 1 hour of incubation at 37° C. and 5% $CO_2$, the cells were infected with the bacterial strains to be assessed by adding 100 µl per well of a titration of bacteria (different MOI, diluted in growth medium). After 1 hour of incubation (37° C. and 5% $CO_2$) the bacteria were killed by adding growth medium containing penicillin (100 U/ml) and streptomycin (100 ug/ml). The incubation was continued for another 3 hours. The plate was centrifuged to collect all cells at the well bottom and the supernatant was analyzed for IFNβ concentration by the LumiKine™ Xpress murine IFN-β ELISA (Invivogen) according to manufacturer's instructions.

B) Results

A Protein Delivery System Based on Type 3 Secretion of YopE Fusion Proteins

While the very N-terminus of the *Y. enterocolitica* T3SS effector YopE (SEQ ID No. 1) contains the secretion signal sufficient to translocate heterologous proteins [22], the chaperone-binding site (CBS) for its chaperone (SycE) is not included [36]. We selected the N-terminal 138 amino acids of YopE (SEQ ID No. 2) to be fused to proteins to be delivered, as this had been shown to give best results for translocation of other heterologous T3S substrates [24]. As these N-terminal 138 amino acids of YopE contain the CBS, we further decided to coexpress SycE. The SycE-YopE$_{1-138}$ fragment cloned from purified *Y. enterocolitica* pYV40 virulence plasmid contains the endogenous promoters of YopE and of its chaperone SycE (FIG. 2). Therfore, SycE and any Yop$E_{1-138}$ fusion protein are induced by a rapid temperature shift from growth at RT to 37° C. Culture time at 37° C. will affect fusion protein amount present in bacteria. A multiple cloning site (MCS) was added at the 3' end of Yop$E_{1-138}$ (FIG. 2 B) followed by a Myc and a 6×His tag and a Stop codon.

The background strain was carefully selected. First, to limit the translocation of endogenous effectors, we used a *Y. enterocolitica* strain that was deleted for all known effectors, Yop H, O, P, E, M and T (named ΔHOPEMT) 37. In addition, we occasionally used an auxotroph mutant that cannot grow in absence of exogenous meso-2,6-diaminopimelic acid [38]. This strain was deleted for the aspartate-beta-semialdehyde dehydrogenase gene (Δasd), and classified as biosafety level 1 by the Swiss safety agency (amendment to A010088/2). In addition, we deleted the adhesion proteins YadA and/or InvA to offer a larger choice of background strains. While the use of the yadA or yadA/invA strains reduce the background signalling induced 39, the delivered protein amount is affected as well [40].

Removal of the Yop$E_{1-138}$ Appendage after Translocation of the Fusion Protein to the Eukaryotic Cell While for bacterial delivery the Yop$E_{1-138}$ fragment is of great benefit, it might hamper the fusion proteins function and/or localization. Therefore, its removal after protein delivery would be optimal. To this end, we introduced two TEV cleavage sites (ENLYFQS) [41-43] in between Yop$E_{1-138}$ and a fusion partner (the transcriptional regulator ET1-Myc (SEQ ID No. 9 and 11) 44 and human INK4C (SEQ ID No. 8 and SEQ ID No. 10)). To keep the advantages of the presented method, we further fused the TEV protease (S219V variant; [45]) to Yop$E_{1-138}$ (SEQ ID No. 12) in another *Y. enterocolitica* strain. HeLa cells were infected with both strains at once. To allow analysis of the translocated fraction of proteins only, infected HeLa cells were lysed at 2 h p.i. with Digitonin, which is known not to lyse the bacteria ([46];). Western blot analysis revealed the presence of the Yop$E_{1-138}$—2×TEV-cleavage-site-ET1-Myc or Yop$E_{1-138}$—2×TEV-cleavage-site-Flag-INK4C-Myc only when cells had been infected with the corresponding strain. Upon overnight digestion of this cell-lysate with purified TEV protease, a shifted band could be observed. This band corresponds to ET1-Myc or Flag-INK4C with the N-terminal remnants of the TEV cleavage site, most likely only one Serine. Upon coinfection of cells with the strain delivering the TEV protease, the same cleaved ET1-Myc or Flag-INK4C fragment became visible, indicating that the TEV protease delivered via T3SS is functional and that single cells had been infected by both bacterial strains. While cleavage is not complete, the majority of translocated protein is cleaved already 2 h post infection and even over-night digestion with purified TEV protease did not yield better cleavage rates. As reported, TEV protease dependent cleavage might need optimization dependent on the fusion protein [47,48]. TEV protease dependent removal of the Yop$E_{1-138}$ appendage after translocation hence provides for the first time a T3SS protein delivery of almost native heterologous proteins, changing the amino acid composition by only one N-terminal amino acid.

An alternative approach to the TEV protease dependent cleavage of the YopE fragment consisted in incorporating Ubiquitin into the fusion protein of interest. Indeed, Ubiquitin is processed at its C-terminus by a group of endogenous Ubiquitin-specific C-terminal proteases (Deubiquitinating enzymes, DUBs). As the cleavage is supposed to happen at the very C-terminus of Ubiquitin (after G76), the protein of interest should be free of additional amino acid sequence. This method was tested on the Yop$E_{1-138}$—Ubiquitin-Flag-INK4C-MycHis fusion protein. In control cells infected by Yop$E_{1-138}$—Flag-INK4C-MycHis-expressing bacteria, a band corresponding to Yop$E_{1-138}$—Flag-INK4C-MycHis was found, indicative of efficient translocation of the fusion protein. When cells were infected for 1 h with Yop$E_{1-138}$—Ubiquitin-Flag-INK4C-MycHis-expressing bacteria, an additional band corresponding to the size of Flag-INK4C-MycHis was visible, indicating that part of the fusion protein was cleaved. This result shows that the introduction of Ubiquitin into the fusion protein enables to cleave off the Yop$E_{1-138}$ fragment without a need for an exogenous protease.

Virulence Attenuation by Deletion/Mutation of Bacterial Effector Proteins with Virulence Activity Towards Eukaryotic Cells In case of *Y. enterocolitica*, the virulence was reduced by deletion of the six endogenous effector proteins, called "*Yersinia* outer proteins" (Yops), in detail YopH, O, P, E, M, T (MRS40 pIML421 [yopHΔ1-352, yopOΔ65-558, yopP23, yopE21, yopM23, yopT135]) 37. These Yops are encoded on the "*Yersinia* virulence plasmid" (pYV), a about 70 kbp sized plasmid, on which the complete type 3 secretion system (T3SS) as well as other virulence players are encoded (FIG. 4). YopH, O, P, E, M and T are the six effector proteins, which are delivered to host cells by the bacterial type three secretion system in order to modulate and dampen the immune system. Each Yop has a specific biochemical activity in the host cell. YopT cleaves off the C-terminal Cysteine of Rho GTPases and thus removes the isoprenyl group anchoring the GTPases to the membrane. This inactivation of the Rho due to mislocalization avoids phagocytosis by immune cells as macrophages and neutrophils [49]. In the same pathway, YopE acts as GTPase activating protein (GAP) for Rho GTPases, deactivating them. This results in decreased phagocytosis and inhibition of release of IL-1 beta by immune cells [49]. Furthermore, YopO acts as guanidine nucleotide dissociation inhibitor (GDI), deactivating Rho GTPases. YopO further has a serine/threonine kinase domain acting in a not yet defined way on the actin cytoskeleton [49]. YopH is a tyrosine phsophatase acting on focal adhesion proteins as Focal adhesion kinase (Fak), paxillin and others, thus strongly preventing phagocytosis by macrophages and neutrophils [49]. YopP, termed YopJ in *Y. pseudotuberculosis* or *Y. pestis*, was found to inactivate the MAPK/NFkB pathway in immune cells, preventing TNFa and IL-8 release from immune cells stimulated by the presence of the bacteria. Furthermore, YopP was found to induce apoptosis in immune cells, which might be related to the effect sin the MAPK pathway, which in its activated state protects cells from apoptosis 49. The role of YopM is not yet completely clear, but it was found associated with ribosomal S6 kinase 1 (RSK1) and protein kinase C-like 2 (PRK2). It seems as if YopM could stimulate phosphorylation of RSK1 and thus affects downstream targets, as e.g cell cycle progression 49. By deleting one or several of these Yops, the defense mechanism of the bacteria against the immune system are dramatically affected [50]. Mutation of respective yops was confirmed by PCR on the respective region, and by in vitro secretion assay. Analysis of in vitro secretion by SDS-PAGE and Coomassie-blue staining confirmed absence of full-length YopH,O,M and YopE.

Furthermore, a *Y. enterocolitica* strain with deletions in asd (aspartate semialdehyde dehydrogenase) was constructed. The mutation in asd leads to a complete loss of growth capability without addition of meso-diamino-pimelic acid. This allows generating antibiotic free plasmid maintenance systems based on the presence of asd on the respective plasmid. In a similar way, other auxotroph mutants might be used.

Generation of Enhanced Pro-Apoptotic Bacteria

In order to optimize the delivery or pro-apoptotic proteins, strains transformed with different pro-apoptotic proteins have been generated according to Table IV.

Figure 5:
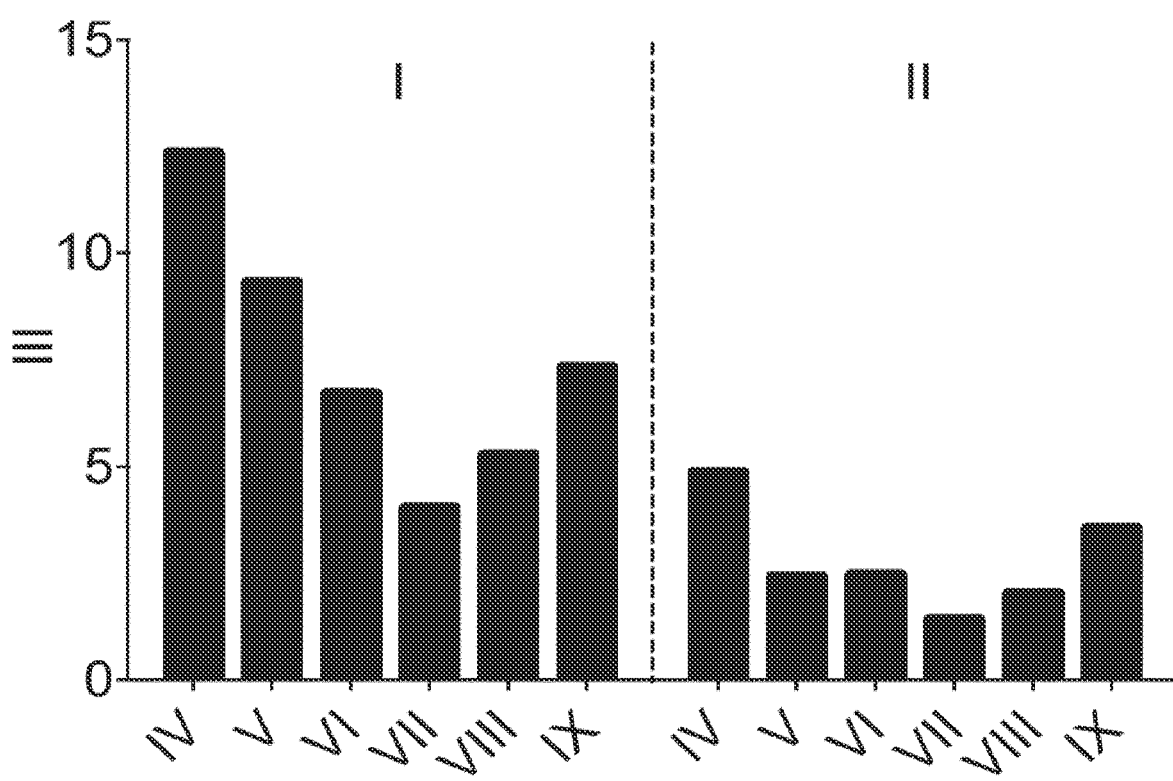
FIG. 5: Delivery of synthetic increased pro-apoptotic proteins. Delivery of single synthetic proteins consisting of single or tandem repeats of BH3 domains originating from pro-apoptotic proteins t-BID or BAX leads to enhanced apoptosis induction in 4T1 and B16F10 cancerous cells. 4T1 (I) or B16F10 (II) cells were infected with Y. enterocolitica ΔyopHOPEMT encoding on pBad-MycHisA IV: YopE$_{1-138}$—tBID BH3 extended domain, V: YopE$_{1-138}$—linker-tBID BH3, VI: YopE$_{1-138}$—tBID BH3, VII: YopE$_{1-138}$—(tBID BH3)$_2$, VIII: YopE$_{1-138}$—tBID BH3-BAX BH3 or IX: YopE$_{1-138}$—BAX BH3-tBID BH3. A titration of the bacteria added to the cells (MOI) was performed for each strain, cell counts determined and IC50 calculated using non-linear regression. IC50 MOI is indicated as (III).
Figure 6:
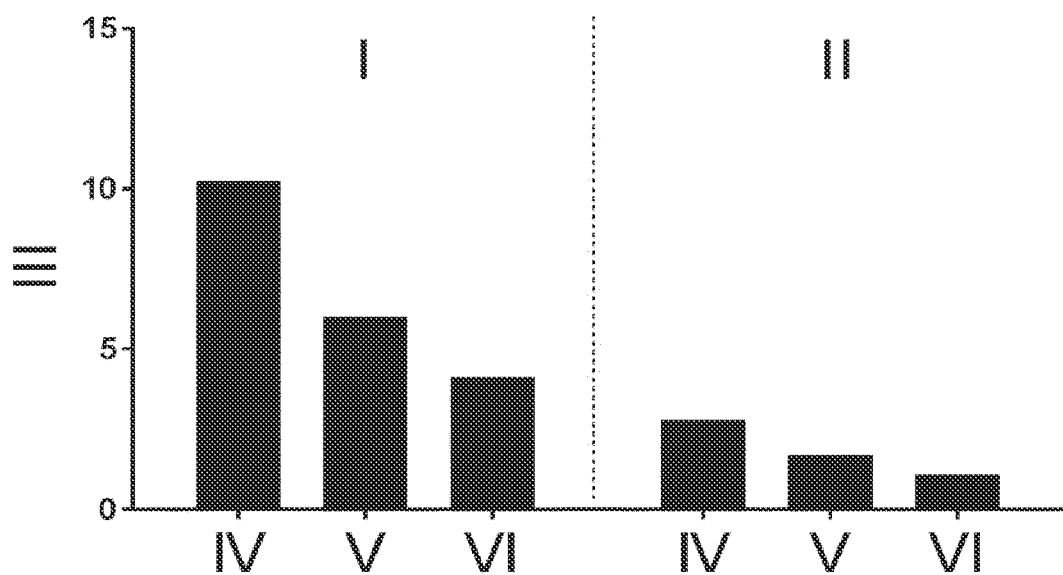
FIG. 6: Induction of apoptosis by pYV-encoded synthetic pro-apoptotic proteins. Delivery of a single or a tandem repeat of BID BH3 domain encoded on the pYV leads to apoptosis induction in 4T1 and B16F10 cancerous cells. 4T1 (I) or B16F10 (II) cells were infected with Y. enterocolitica ΔHOPEMT+IV: pYV-YopE$_{1-138}$—BH3-Bid, or V: +pYV-YopE$_{1-138}$—(BH3-Bid)$_2$ or VI: with Y. enterocolitica ΔHOPEMT pBad-MycHisA-YopE$_{1-138}$—(BH3-Bid)$_2$ for 3 hours. A titration of the bacteria added to the cells (MOI) was performed for each strain, cell counts determined and IC50 (III) calculated using non-linear regression.
Figure 7:
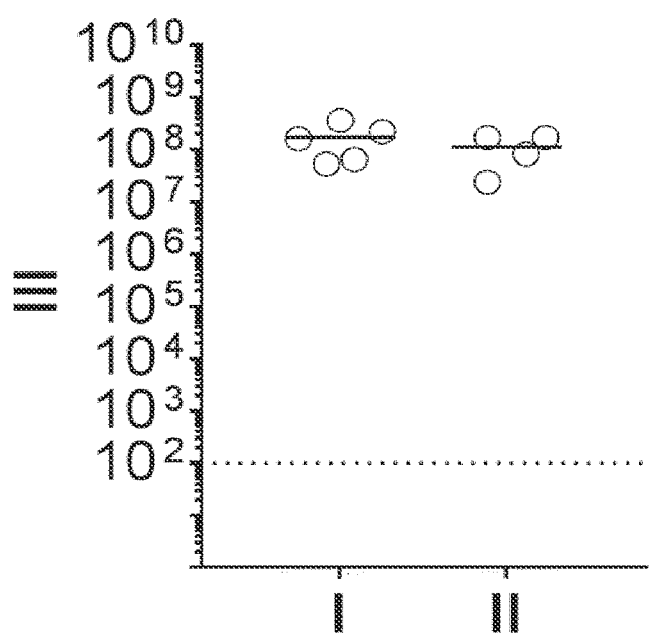
FIG. 7: Tumor colonization of i.v. injected *Y. enterocolitica* ΔyopH,O,P,E,M,T in the 4T1 breast cancer allograft model. Bacterial counts in tumors are indicated as colony forming units (CFU) per gram of tissue (III). Counts were assessed in tumors at day 8 (I) and 14 (II) post infection. Each dot represents an individual mouse. The horizontal dashed line indicates the detection limit.
Figure 8:
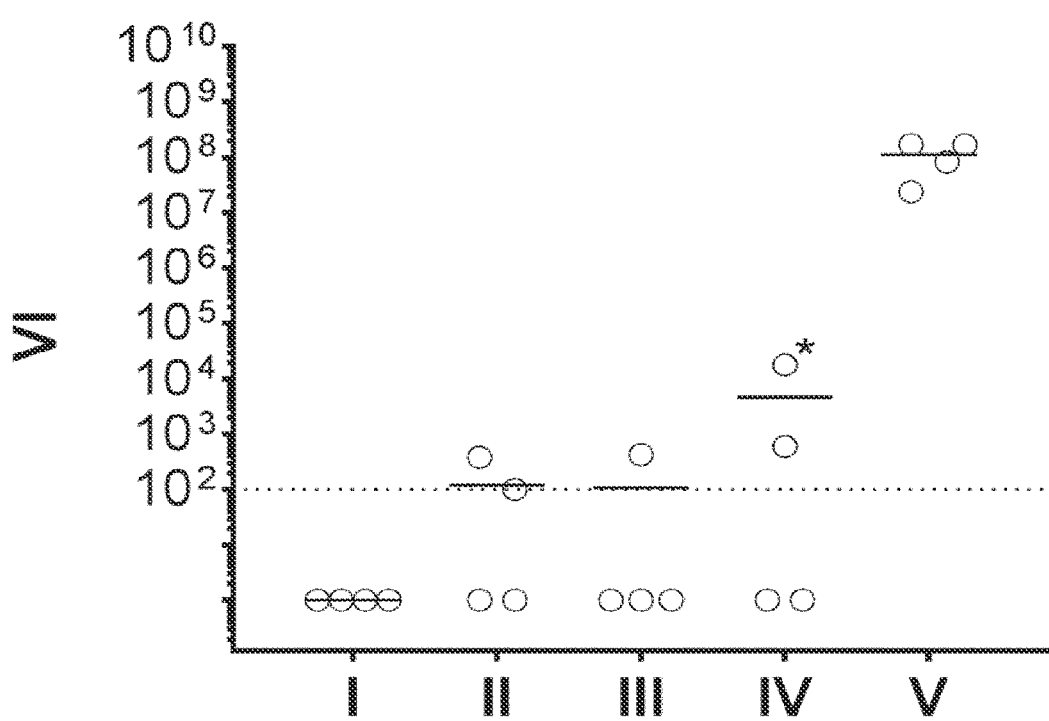
FIG. 8: Biodistribution of i.v. injected *Y. enterocolitica* ΔyopH,O,P,E,M,T in the 4T1 breast cancer allograft model. Bacterial counts in blood (I), spleen (II), liver (III), lung (IV) and tumor (V) are indicated as colony forming units (CFU) per gram of tissue or per ml of blood (VI). Counts were assessed at day 14 post infection. Each dot represents an individual mouse. The horizontal dashed line indicates the detection limit. * indicates a mouse with large metastases found on lung.

ID No. 24 and 28)) were generated. Surprisingly, tandem repeats of the same or different BH3 domains were found to result in enhanced apoptosis induction on cancerous cell lines (including 4T1 and B16F10 cells, FIG. 5). The IC50 (half maximal inhibitory concentration), referring to the number of bacteria per eukaryotic cell (MOI) needed in order to kill 50% of such cells, was found to be decreased upon delivery of tandem repeats of tBID BH3 domain as compared to a single tBID BH3 domain (FIG. 5). This finding was surprising, as the protein size is increased by fusing as second BH3 domain of t-BID. Due to this, decreased expression and delivery levels of $YopE_{1-138}$—$(tBID\ BH3)_2$ (SEQ ID No. 27) as compared to $YopE_{1-138}$—tBID BH3 (SEQ ID No. 19 and 25) would be expected, and might maximally reach equivalent levels. In order to reach an increase in cell killing activity, the fused tBID BH3 domains must simultaneously act side by side upon delivery by the T3SS into eukaryotic cells. In case only one tBID BH3 domain in the $YopE_{1-138}$—$(tBID\ BH3)_2$ construct would be functional, at best the same efficiency as with $YopE_{1-138}$—tBID BH3 might be expected.

In order to increase the genetic stability of $YopE_{1-138}$—$(tBID\ BH3)_2$ (SEQ ID No. 27) for in vivo studies, we cloned

TABLE IV

Strains transformed with different pro-apoptotic proteins

| Strain Name | Background strain | Protein to be delivred by T3SS | Backbone plasmid | Resulting plasmid name | Primers. Si_Nr.: | resistances |
|---|---|---|---|---|---|---|
| YopE1-138- (*Y. enterocolitica* codon optimized murine tBid BH3 extended part) | *Y. enterocolitica* ΔyopH, O, P, E, M, T Δasd | YopE1-138- *Y. enterocolitica* codon optimized murine tBid BH3 extended (by 4 Aa) | pBad_Si_2 | pSi_353 | | Nal Amp |
| YopE1-138- 10 Aa linker- (*Y. enterocolitica* codon optimized murine tBid BH3 part) | *Y. enterocolitica* ΔyopH, O, P, E, M, T Δasd | YopE1-138- 10 Aa linker- *Y. enterocolitica* codon optimized murine tBid BH3 | pBad_Si_2 | pSi_354 | 727/728 | Nal Amp |
| YopE1-(138- *Y. enterocolitica* a codon optimized murine Bax BH3 part- *Y. enterocolitica* codon optimized murine tBid BH3 part | *Y. enterocolitica* ΔyopH, O, P, E, M, T Δasd | YopE1-138- *Y. enterocolitica* codon optimized murine Bax BH3-. enterocolitica codon optimized murine tBid BH3 | pSi_357 | pSi_374 | 736/737 | Nal Amp |

Shortening the delivered proteins to the essential domains required for signaling (e.g. the BH3 domain of t-BID (SEQ ID No. 19)) could increase the efficiency of cell killing (FIG. 5). Without being bound by theory, this increase in efficacy is likely to be related to increased amount of protein production and following delivery via T3SS due to smaller size of the delivered protein. Introduction of a linker between the YopE part and the BH3 domain of tBID (SEQ ID No. 23) decreased efficacy, as well as extending the BH3 domain by 4 further amino acids (SEQ ID No. 22) (FIG. 5).

Additionally, synthetic cargos with repeats of such essential domains (e.g. the BH3 domain of t-BID (SEQ ID No. 27)) or combinations of these essential domains (e.g. the BH3 domain of t-BID and the BH3 domain of BAX (SEQ $YopE_{1-138}$—$(tBID\ BH3)_2$ (SEQ ID No. 27) by homologous recombination on the *Yersinia* virulence plasmid pYV at the native site of YopE and under the native YopE promoter (using mutator plamids pSI_408 and pSI_419). Such mutators contain the DNA sequence coding for the desired protein, flanked by 200-250 bp of sequences on both sides corresponding to the site of the respective gene, where the integration shall take place. These plasmids are transformed into *E. coli* Sm10 k pir, from where plasmids were mobilized into the corresponding *Y. enterocolitica* strain. Mutants carrying the integrated vector were propagated for several generations without selection pressure. Then sucrose was used to select for clones that have lost the vector. Finally mutants were identified by colony PCR. The endogenous proteins for the transport by the T3SS (called "*Yersinia* outer proteins", Yops) are encoded by *Y. enterocolitica* on this 70 kb plasmid, named plasmid of *Yersinia* Virulence (pYV), which further encodes the T3SS apparatus.

Figure 9:
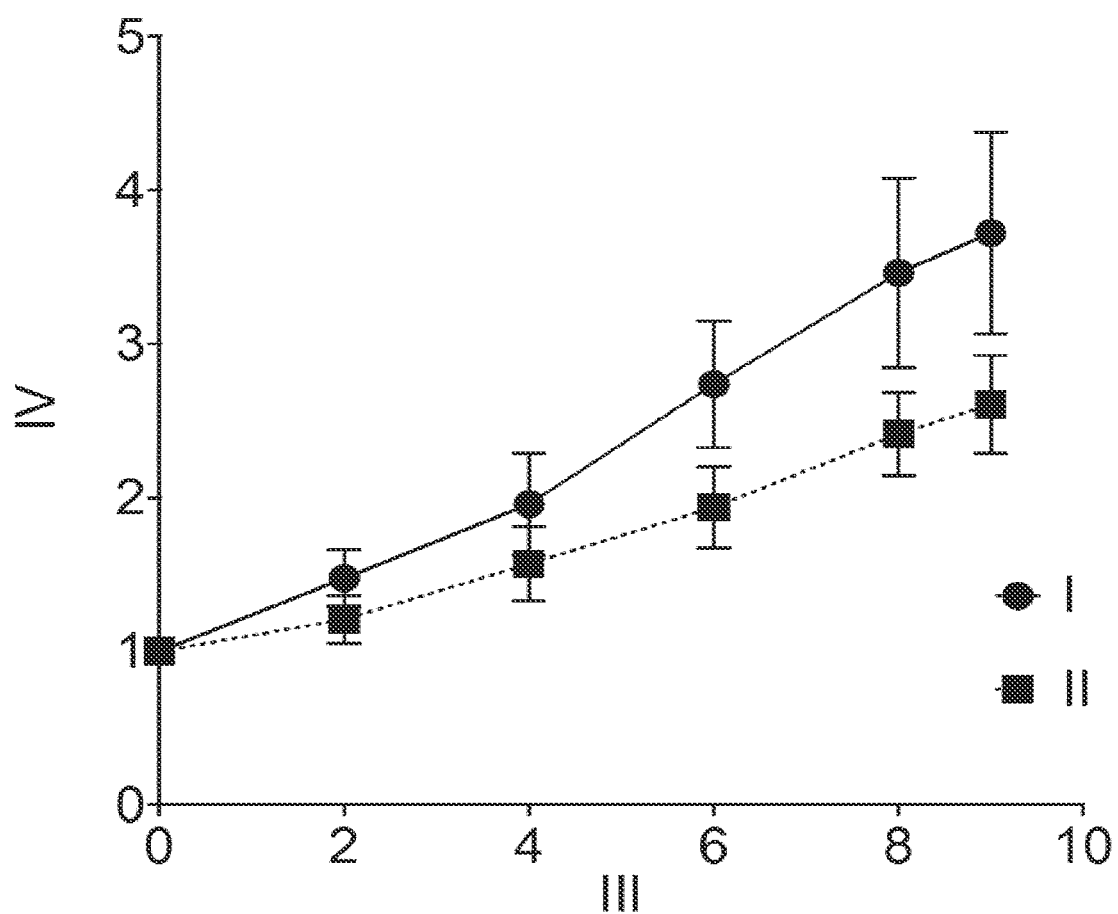
FIG. 9: Delay of tumor progression in wildtype Balb/C mice allografted s.c. with 4T1 breast cancer cells. Wildtype Balb/C mice allografted s.c. with 4T1 breast cancer cells were i.v. injected with I: PBS or II: $1*10^7$ *Y. enterocolitica* dHOPEMT ΔHairpinI-VirF+pYV-YopE$_{1-138}$(BH3-Bid)$_2$, once the tumor had reached a size of 150-250 mm3. The day of the i.v. injection of bacteria was defined as day 0. Tumor volume was measured over the following days (III; day 0 to day 9 post i.v. injection of bacteria) with calipers. The relative tumor volume, normalized to the tumor volume at day 0, is indicated (IV) as mm$^3$. The mean is indicated with symbols, error bars depicted show the standard error of the mean. Statistical significance is measured with a 2way ANOVA, * indicates p value <0.05, ** a p value <0.005.
Figure 10:
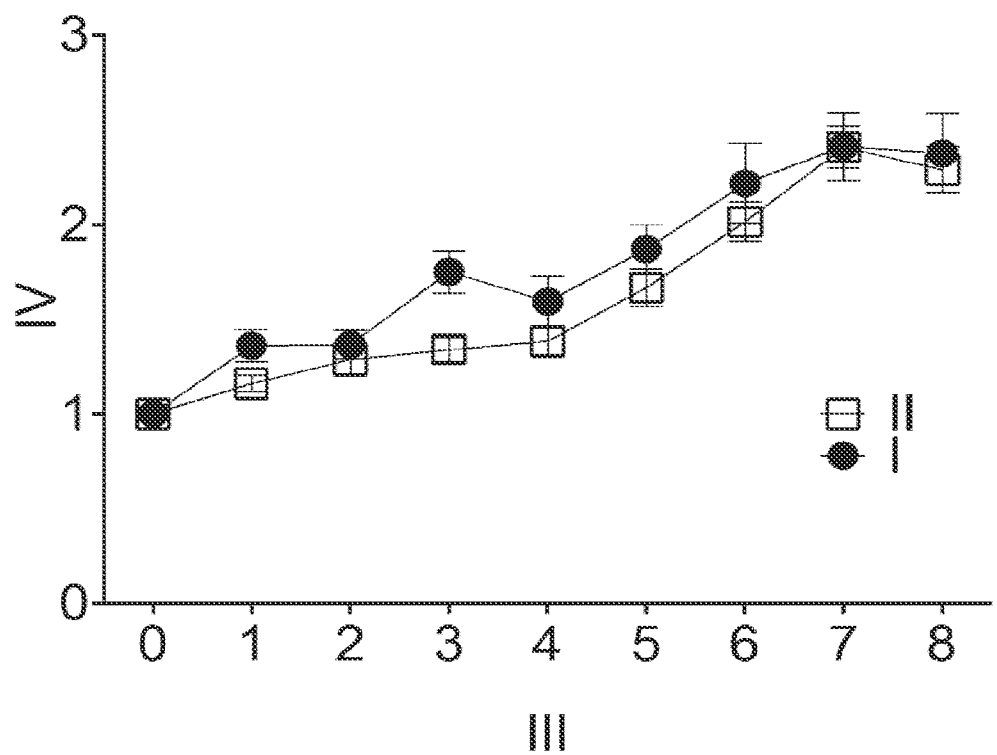
FIG. 10: Tumor progression in wildtype Balb/C mice allografted s.c. with 4T1 breast cancer cells. Wildtype Balb/C mice allografted s.c. with 4T1 breast cancer cells were i.v. injected with I: PBS or II: $1*10^7$ *Y. enterocolitica* dHOPEMT, once the tumor had reached a size of 150-250 mm3. The day of the i.v. injection of bacteria was defined as day 0. Tumor volume was measured over the following days (III; day 0 to day 9 post i.v. injection of bacteria) with calipers. The relative tumor volume, normalized to the tumor volume at day 0, is indicated (IV) as mm$^3$. The mean is indicated with symbols, error bars depicted show the standard error of the mean

*Yersinia* strains encoding YopE$_{1-138}$—(tBID BH3) (SEQ ID No. 19 and 25) or YopE$_{1-138}$—(tBID BH3)$_2$ (SEQ ID No. 27) on the *Yersinia* virulence plasmid pYV at the native site of YopE and under the native YopE promoter were assessed for their capacity of inducing apoptosis in cancerous cells (including 4T1 and B16F10 cells, FIG. 6). The IC50 (half maximal inhibitory concentration), referring to the number of bacteria per eukaryotic cell (MOI) needed in order to kill 50% of such cells, was found to be decreased upon delivery of tandem repeats of tBID BH3 domain as compared to a single tBID BH3 domain, when both proteins are encoded on the *Yersinia* virulence plasmid pYV at the native site of YopE and under the native YopE promoter (FIG. 6). This is in agreement with findings from expression plasmid borne delivery of these proteins (FIG. 5). Again, this finding was surprising, as the protein size is increased by fusing a second BH3 domain of t-BID. Due to this, decreased expression and delivery levels of $YopE_{1-138}$—$(tBID BH3)_2$ (SEQ ID No. 27) as compared to $YopE_{1-138}$—tBID BH3 (SEQ ID No. 19 and 25) would be expected, and might maximally reach equivalent levels. In order to reach an increase in cell killing activity, the fused tBID BH3 domains must simultaneously act side by side upon delivery by the T3SS into eukaryotic cells. In case only one tBID BH3 domain in the $YopE_{1-138}$—$(tBID BH3)_2$ construct would be functional, at best the same efficiency as with $YopE_{1-138}$—tBID BH3 might be expected. Furthermore, *Yersinia* strains encoding $YopE_{1-138}$—$(tBID BH3)_2$ (SEQ ID No. 27) on the *Yersinia* virulence plasmid pYV at the native site of YopE and under the native YopE promoter were compared for their capacity of inducing apoptosis in cancerous cells to expression plasmid (pBad-MycHisA based) derived delivery of $YopE_{1-138}$—$(tBID BH3)_2$. In agreement with the higher copy number of pBad-MycHisA (20-25 copies) as compared to the pYV (1-6 copies are reported), pBad-MycHisA based delivery of $YopE_{1-138}$—$(tBID BH3)_2$ (SEQ ID No. 27) resulted in a slightly decreased IC50 value on 4T1 and B16F10 cells (FIG. 6).

Biodistribution Studies in a Murine Model of Melanoma

In order to validate gram-negative bacteria with mutation(s) in key virulence determinants like the T3SS effectors as tumor specific vehicle, murine allograft tumor studies using the well-established B16F10 melanoma model (ATCC No. CRL-6475) were performed. When s.c. tumors had reached a certain size (about 100-200 $mm^3$), mice were i.v. infected with $2\times10^5$ cfu *Y. enterocolitica* subsp. *palearctica* MRS40 or *Y. enterocolitica* subsp. *palearctica* MRS40 ΔyopH,O,P,E,M,T. In order to allow bacterial growth, mice were pretreated 24 h prior to infection with desfreoxamine. Mice infected with the wt *Y. enterocolitica* subsp. *palearctica* MRS40 strain had increased scoring for physical appearance and behavior (FIGS. 47-48) and exhibited significant weight loss over the first 48 h of infection (FIG. 49), which urged us to sacrifice all of the mice in this group already at day 2 post infection. In contrast, mice infected with the virulence attenuated *Y. enterocolitica* subsp. *palearctica* MRS40 ΔyopH,O,P,E,M,T strain did not show significant weight loss and scored normally for physical appearance and behavior (FIGS. 47-49) still at day 4 post infection. In mice infected with the wt strain (*Y. enterocolitica* subsp. *palearctica* MRS40) living bacteria were detected in all organs assessed, and furthermore in the blood (FIG. 51). While wt bacteria were found present in the malignant solid tumor, equally high or higher counts were found in other organs, highest in the spleen (FIG. 51). In sharp contrast, in mice infected with *Y. enterocolitica* subsp. *palearctica* MRS40 ΔyopH,O,P,E,M,T living bacteria were mainly found in the malignant solid tumor at day 1 post infection, with low bacterial counts observed in spleen, liver and lung. Notably, at day 4 post infection, the bacterial count in the malignant solid tumor had increased by some orders of magnitude (reaching more than $10^8$ cfu/g of tumor tissue), while in all other organs assessed the bacterial counts dropped below the detection limit (FIG. 50). *Y. enterocolitica* subsp. *palearctica* MRS40 ΔyopH,O,P,E,M,T thus accumulated at day 4 post infection with a ration of about (minimally) one million fold at the site of the malignant solid tumor as compared to spleen or liver (when calculating the ration against the detection limit).

Similar high numbers of bacteria per gram of solid tumors at day 5 or 8 after intravenous administration into the lateral tail vein of B16F10 melanoma bearing mice were measured for *Y. enterocolitica* dHOPEMT, Y *Y. enterocolitica* dHOPEMT+pYV-$YopE_{1-138}$—murine RIG1 CARDs or *Y. enterocolitica* dHOPEMT ΔHairpinI-VirF+pYV-$YopE_{1-138}$—murine RIG1 CARDs (FIG. 26). These validates, that heterologous protein cargo and further mutations affecting T3SS regulation (VirF) do not influence bacterial colonization of solid tumors in murine models.

These results validate this strategy for virulence attenuation by mutation of key virulence determinants to generate a bacterial vehicle specifically targeting the malignant solid tumor.

Validation of Tumor Specific Growth In Vivo Up to Day 14 Post Bacterial Administration The experiment of tumor colonization by genetically modified *Y. enterocolitica* was repeated in a syngeneic murine allograft model (4T1 breast cancer model) and bacterial colonization was followed over two weeks. This time, mice were infected with $1*10^6$ colony forming units (CFU) of *Y. enterocolitica* ΔyopH,O,P,E,M,T. While obtaining similar results to the B16F10 model at early days post infection, we could further show that the tumor colonization is consistently found at day 8 and up to day 14 after infection (FIG. 7). Furthermore, the colonization remains highly specific with only low counts of bacteria detected in all other organs assessed (FIG. 8). These findings indicate that *Y. enterocolitica* ΔyopH,O,P,E,M,T is able to establish a persistent colonization of the tumor thereby preventing clearance by the immune system.

Efficacy of *Y. enterocolitica* ΔHOPEMT in Delaying Tumor Progression

In order to assess the impact of $YopE_{1-138}$—$(tBID BH3)_2$ delivered to tumor cells in vivo, we performed studies in wildtype Balb/C mice allografted s.c. with 4T1 breast cancer cells. We aimed at assessing the *Y. enterocolitica* ΔHOPEMT strain encoding $YopE_{1-138}$—$(tBID BH3)_2$ on the *Yersinia* virulence plasmid pYV at the native site of YopE and under the native YopE promoter, which is further optimized by deletion of hairpin I region upstream of VirF in order to increase amount of proteins delivered. Mice were i.v. injected with PBS or $1*10^7$ *Y. enterocolitica* ΔHOPEMT ΔHairpinI-virF pYV-$YopE_{1-138}$—$(tBID BH3)_2$, once the tumor had reached a size of 150-250 mm3. The day of the i.v. injection of bacteria was defined as day 0. Tumor volume was measured over the following days (day 0 to day 9 post i.v. injection of bacteria) with calipers. The tumor volume was normalized to the tumor volume at day 0 to compensate for any initial heterogeneity in tumor size. Treatment with *Y. enterocolitica* ΔHOPEMT ΔHairpinI-VirF pYV- $YopE_{1-138}$—$(tBID\ BH3)_2$ showed an impact on tumor volume progression, with statistically significant tumor reduction at day 8, 9 and 10 post bacterial administration (FIG. 9). Importantly, *Y. enterocolitica* ΔHOPEMT alone was found not to impact tumor progression in the 4T1 murine cancer model (FIG. 10). These findings highlight that such bacteria and their T3SS can be employed for interference with tumor progression.

Figure 15:
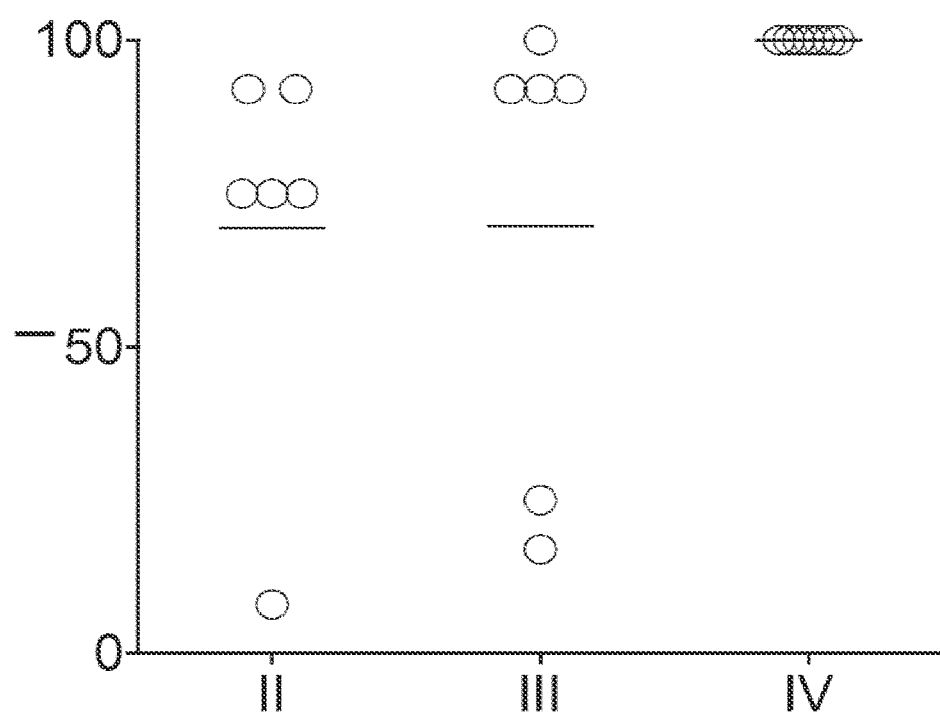
FIG. 15: Genetic stability of the pYV: Stability of native pYV or pYV-asd in solid tumors in vivo. Wildtype Balb/C mice allografted s.c. with 4T1 breast cancer cells were i.v. injected with $1*10^7$ II: *Y. enterocolitica* ΔHOPEMT+pYV-YopE$_{1-138}$—(tBID BH3)$_2$, III: *Y. enterocolitica* ΔHOPEMT ΔhairpinI-virF+pYV-YopE$_{1-138}$—(tBID BH3)$_2$ or IV: *Y. enterocolitica* ΔHOPEMT Δasd+pYV-asd-YopE$_{1-138}$—(tBID BH3)$_2$. At day 9 post i.v. injection of bacteria, tumors were isolated, homogenized, serially diluted and plated on LB-agar plates containing Nalidixic acid. After growth on these plates, single colonies from individual mice were re-picked on LB-agar plates with and without Sodium Arsenite, selective for the pYV. For each mouse, the percentage of colonies growing on the agar plates containing Arsenite to the number of colonies growing of plates not containing Arsenite is indicates (I: as %). 100% indicates, that all isolated colonies from a solid tumor still contain the pYV plasmid.

*Y. enterocolitica* ΔHOPEMT with Deletion within a RNA Thermosensor Region Upstream of a Gene Coding for a AraC-Type DNA Binding Protein Most known *Yersinia* virulence genes are not expressed outside the eukaryotic host and are only induced after entry into the host environment. Expression of these virulence genes is induced by the sudden increase in temperature related to the entry into the host. Especially, pYV encoded virulence factors as the T3SS and its effector proteins (the Yop's) are regulated this way. At room temperature (20-25° C.) the genes required for regulation of the T3SS, the T3SS formation itself and the delivered effectors are not expressed and only upon such a temperature increase to 37° C., expression is induced. Expression of the majority of pYV-encoded virulence genes (yadA and T3SS related genes) is induced by temperature and requires the AraC-type DNA-binding protein VirF in *Y. enterocolitica* (LcrF in other *Yersinia* species). Thermoregulation of the expression of LcrF is thought to happen via the melting of a RNA stem-loop in the mRNA at higher temperatures, which when not melted is sequestering the ribosomal binding site, thus preventing translation [51]. In contrast, in *Y. enterocolitica* the transcription of VirF has mainly been shown to be dependent on temperature [52]. More recent studies show a more complex picture with implication of a thermolabile regulator called YmoA [51], while the RNA thermosensor upstream of LcrF was found to be mainly responsible for temperature regulation of LcrF a thus the temperature dependent virulence genes.

In order to increase the secretion levels of a heterologous cargo expressed from the pYV under the native YopE promoter, we aimed at deleting one of these RNA hairpin structures in *Y. enterocolitica* upstream of VirF. While the importance of such RNA stem-loops was not clearly shown in *Y. enterocolitica* and the temperature induction was rather attributed to changes in transcription, we could identify hairpin I [51] upstream of *Y. enterocolitica* VirF. By homologous recombination we then removed parts of hairpin I (−111 to −57 as in [51]) and assessed secretion capacity of pYV encoded $YopE_{1-138}$—$(tBID\ BH3)_2$ (SEQ ID NO: 27) or $YopE_{1-138}$—murine RIG-1 $CARD_2$ protein (SEQ ID NO: 38) (each at the native site of YopE) in an in vitro secretion assay (FIG. 11). Surprisingly, deletion of part of hairpin region I upstream of VirF in *Y. enterocolitica* increased secretion of the heterologous proteins in vitro (FIGS. 11 A and B), which is in contrast to previous reports on *Y. enterocolitica* [52], where transcription of VirF was thought to be the main driver of thermoregulation.

In order to be able to artificially induce the expression of the T3SS and the delivery of proteins by the T3SS, we replaced in another strain the endogenous promoter of VirF on the pYV by an Arabinose inducible promoter as known from pBad-MycHisA. In addition to replacing the promoter of VirF, we introduced upstream (in inverted orientation) the complete araC gene. We then assessed secretion capacity of $YopE_{1-138}$—$(tBID\ BH3)_2$ (SEQ ID NO: 27) (pYV encoded; at the native site of YopE) in absence or presence of Arabinose in an in vitro secretion assay (FIG. 11 A). Only upon addition of Arabinose the heterologous protein was found to be secreted by the T3SS, which is in agreement with a regulation of the expression of VirF by Arabinose.

*Y. enterocolitica* ΔHOPEMT with Increased Stability of Heterologous Cargo (In Vitro and In Vivo)

*Y. enterocolitica* ΔyopH,O,P,E,M,T showed to be a highly specific strain to target solid tumors in our murine experiments, while the T3SS-dependent delivery of cytotoxic proteins was found efficacious in cell culture on cancer cells. In order to combine these two traits, solid tumor-colonizing bacteria need optimally to be engineered in order to stably encode the cytotoxic cargo over several days, or even weeks, in vivo. Due to regulatory requirements, the use of classical antibiotic resistances to maintain a foreign plasmid in bacteria is disfavored. In murine allograft studies we have thus assessed an antibiotic-resistance-free plasmid-maintenance system. This system is based on chromosomal deletion of an essential gene (such as the aspartate-semialdehyde dehydrogenase, asd) and coding for the same gene on a heterologous plasmid to maintain bacterial growth. The complementation of an asd deletion for plasmid maintenance has been shown before [53], while difficulties in reproducibility and persistence over several days have been reported [54]. We adapted this system for use in *Y. enterocolitica* ΔyopH,O,P,E,M,T, where we additionally deleted the chromosomally encoded asd (resulting in *Y. enterocolitica* ΔyopH,O,P,E,M,T Δasd), which was then brought back on a medium copy number plasmid, pBad-MycHisA (pBad-MycHisA-asd). The asd gene was cloned from *Y. enterocolitica* 8081 and inserted into the PciI site of pBad-MycHisA in forward and reverse orientation, respectively, with its endogenous promoter and transcriptional terminator. Growth behavior of the resulting strains *Y. enterocolitica* ΔyopH,O,P,E,M,T Δasd+pBad-MycHisA-asd (forward or reverse asd orientation) was compared in culture flasks in vitro (BHI medium) to wt and parent *Y. enterocolitica* ΔyopH,O,P,E,M,T Δasd strains (FIG. 12). In both orientations, pBad-MycHisA-asd rescued the phenotype observed upon deletion of asd (FIG. 12). In contrast, in the B16F10 melanoma mouse model as well as the 4T1 model, we found *Y. enterocolitica* ΔyopH,O,P,E,M,T Δasd+pBad-MycHisA-asd not to colonize solid tumors sufficiently (FIGS. 13 and 14) and from the few colonies isolated we were not able to recover the pBad-MycHisA-asd plasmid. Furthermore, the colonies isolated from the B16F10 melanoma mouse model were verified for growth on Ampicillin containing plates, which would be in favor of the presence of the pBad-MycHisA-asd plasmid coding for an Ampicillin resistance. At day 4 after i.v. injection, only a minor fraction of isolated colonies exhibited Ampicillin resistance (FIG. 13). This might reflect a of loss of pBad-MycHisA-asd, but could as well be related to loss of the Ampicillin resistance gene only or difficulties in re-starting the expression of the Ampicillin resistance gene rapid enough to avoid killing by Ampicillin. In any case, the tumor colonization with *Y. enterocolitica* ΔyopH,O,P,E,M,T Δasd+pBad-MycHisA-asd observed in the B16F10 melanoma mouse model as well as the 4T1 model show a rapid decrease of bacterial counts within the solid tumor, which is in contrast to *Y. enterocolitica* ΔyopH,O,P,E,M,T. Thus, the deletion of chromosomal asd and complementation on pBad-MycHisA leads to a drastic reduction on bacterial fitness in vivo. This observation is in agreement with reports on reduced viability upon misbalanced levels of asd [54].

The endogenous proteins for the transport by the T3SS (called "*Yersinia* outer proteins", Yops) are encoded by *Y. enterocolitica* on a 70 kb plasmid. This plasmid, named plasmid of *Yersinia* Virulence (pYV), further encodes the T3SS apparatus. We have assessed the stability of the pYV plasmid in the 4T1 murine allograft model. We have successfully isolated the pYV from strains collected at day 9 or 10 after infection of the mice (FIG. 15). We have further performed tests confirming presence and functionality of the T3SS of isolated bacterial strains after eight days of growth in a solid tumor in vivo. We thus consider the pYV as a vector of choice to encode heterologous cargo for in vivo delivery. Nevertheless, we found the percentage of bacterial colonies carrying the pYV plasmid to be heterogeneous after growth for 9-10 das in 4T1 solid tumors in mice (FIG. 15). In addition to the intrinsic instability of the pYV, the strain *Y. enterocolitica* ΔyopH,O,P,E,M,T has lost the selective advantage of the virulence increasing Yop's in vivo.

Figure 12:
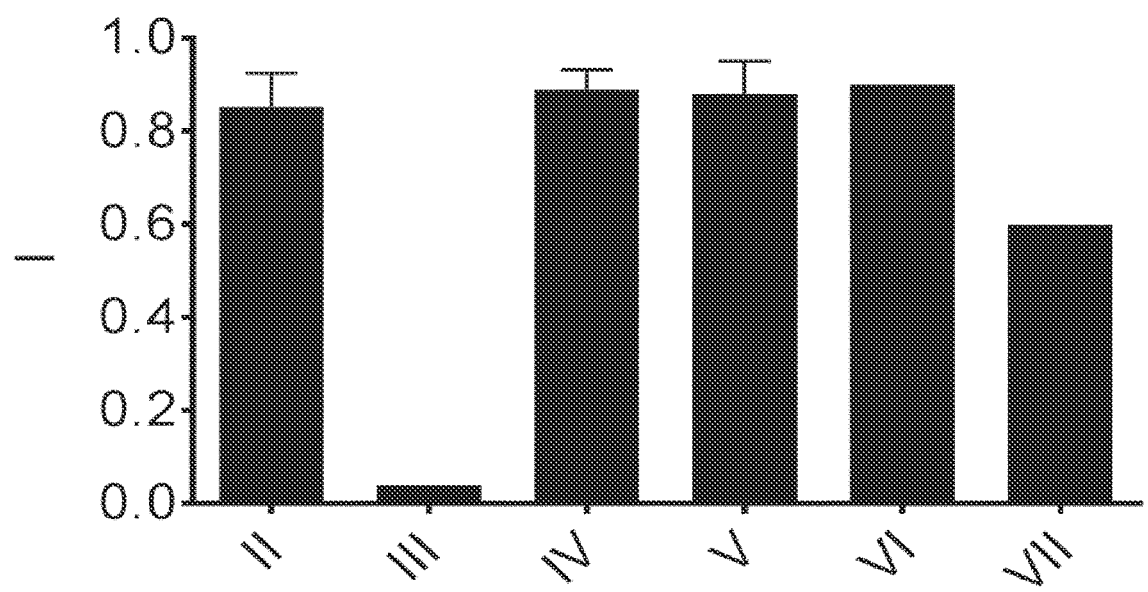
FIG. 12: Comparison of in vitro growth: Comparison of in vitro growth for II: *Y. enterocolitica* ΔHOPEMT, III: *Y. enterocolitica* ΔHOPEMT Δasd, IV: *Y. enterocolitica* ΔHOPEMT Δasd+pBAD-MycHisA-asd, V: *Y. enterocolitica* ΔHOPEMT Δasd+pBAD-MycHisA-asd (reverse orientation), VI: *Y. enterocolitica* ΔHOPEMT encoding YopE$_{1-138}$—(tBID BH3)$_2$ on the pYV and VII: *Y. enterocolitica* ΔHOPEMT Δasd+pYV-asd-YopE$_{1-138}$—(tBID BH3)$_2$. Bacteria were inoculated in liquid culture and grown for 3 hours. Subsequently, the OD600 (I) was determined for all strains.
Figure 13:
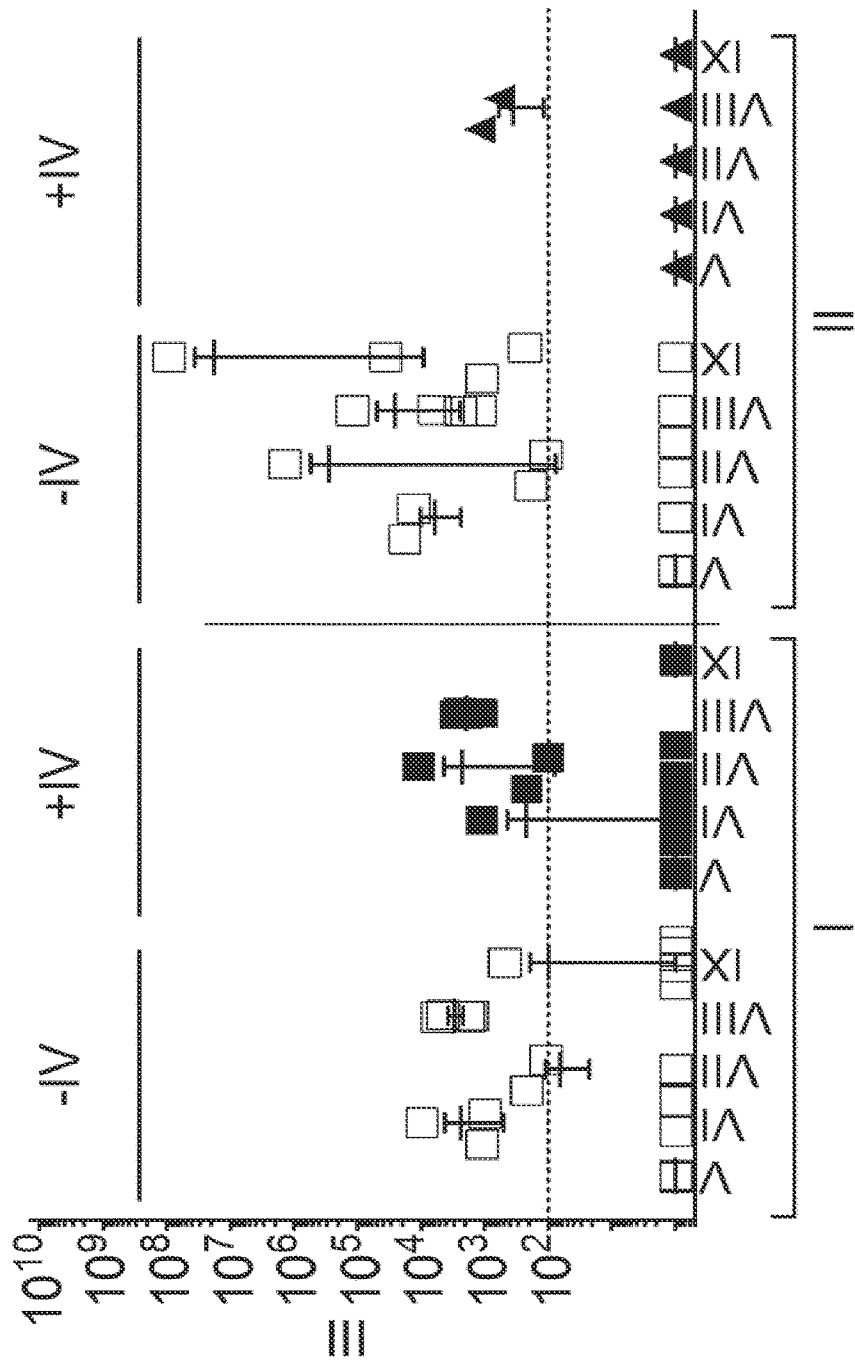
FIG. 13: Tumor colonization with *Y. enterocolitica* ΔHOPEMT Δasd+pBad-MycHisA-asd and stability of pBad-MycHisA-asd: Wildtype C57BL/6 mice allografted s.c. with B16F10 melanoma cells were i.v. injected with $1*10^6$ *Y. enterocolitica* ΔHOPEMT Δasd+pBad-MycHisA-asd. At day 1 (I) or day 4 (II) post i.v. injection of bacteria, blood (V), spleen (VI), liver (VII), lung (VIII) and tumor (IX) were isolated, homogenized, serially diluted and plated on LB-agar plates containing Nalidixic acid (and no Ampicillin, -IV) or on LB-agar plates with Ampicillin (+IV), selective for pBad-MycHisA-asd. Bacterial counts in the respective samples are indicated as colony forming units (CFU) per gram of tissue or ml of blood (III). Each dot represents an individual mouse. The horizontal dashed line indicates the detection limit.
Figure 14:
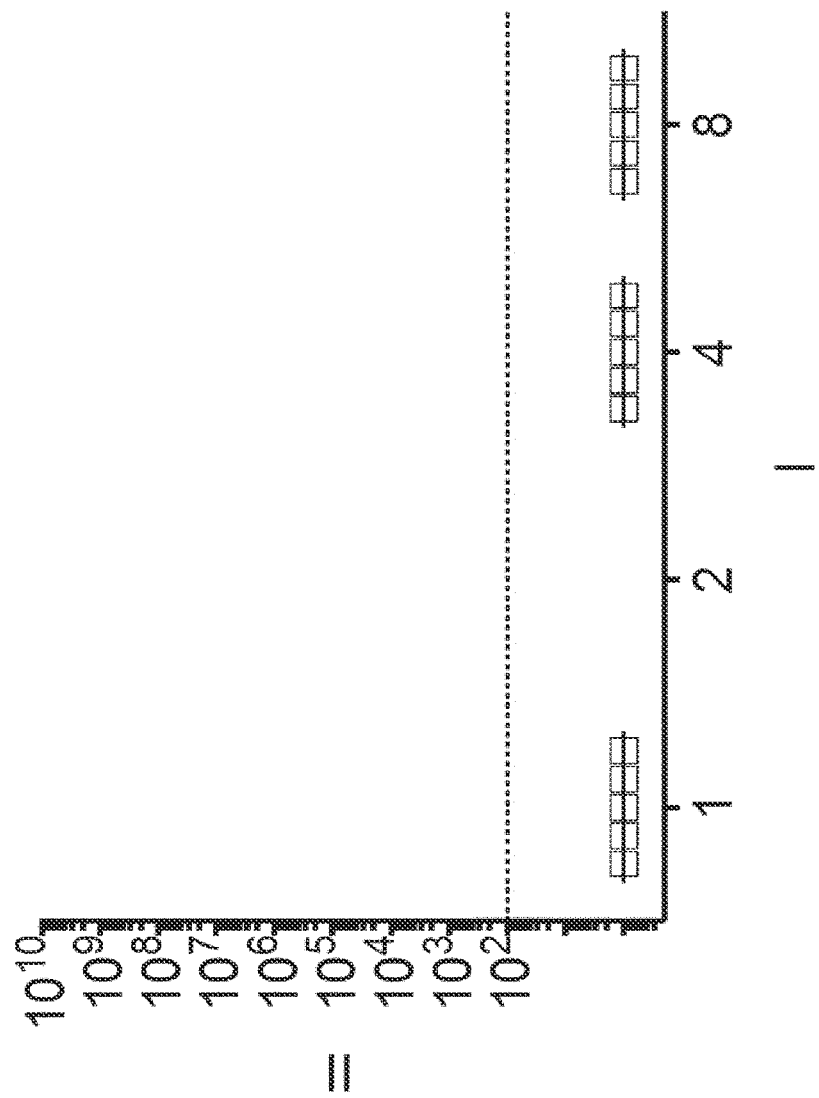
FIG. 14: Tumor colonization with *Y. enterocolitica* ΔHOPEMT Δasd+pBad-MycHisA-asd: Wildtype Balb/C mice allografted s.c. with 4T1 breast cancer cells were i.v. injected with $1*10^6$ *Y. enterocolitica* ΔHOPEMT Δasd+pBad-MycHisA-asd. At the indicated days post i.v. injection of bacteria (I), tumors were isolated, homogenized, serially diluted and plated on LB-agar plates containing Nalidixic acid. Bacterial counts in tumors are indicated as colony forming units (CFU) per gram of tissue (II). Each dot represents an individual mouse. The horizontal dashed line indicates the detection limit.
Figure 16:
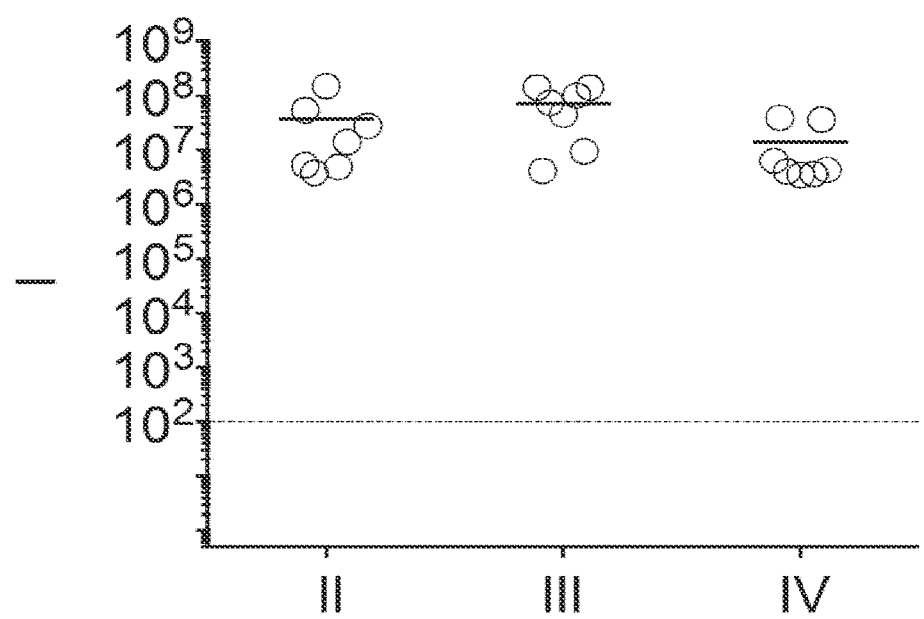
FIG. 16: Tumor colonization: Wildtype Balb/C mice allografted s.c. with 4T1 breast cancer cells were i.v. injected with $1*10^7$ II: *Y. enterocolitica* ΔHOPEMT+pYV-YopE$_{1-138}$—(tBID BH3)$_2$, III: *Y. enterocolitica* ΔHOPEMT ΔhairpinI-virF+pYV-YopE$_{1-138}$—(tBID BH3)$_2$ or IV: *Y. enterocolitica* ΔHOPEMT Δasd+pYV-asd-YopE$_{1-138}$—(tBID BH3)$_2$. At day 9 post i.v. injection of bacteria, tumors were isolated, homogenized, serially diluted and plated on LB-agar plates containing Nalidixic acid. Bacterial counts in tumors are indicated as colony forming units (CFU) per gram of tissue (I). Each dot represents an individual mouse. The horizontal dashed line indicates the detection limit.

In order to stabilize the pYV and thus the heterologous cargo encoded on the pYV, we adapted the "asd"-system for use in *Y. enterocolitica* ΔyopH,O,P,E,M,T on the pYV. We deleted the chromosomally encoded asd (resulting in *Y. enterocolitica* ΔyopH,O,P,E,M,T Δasd), which was then brought back on the pYV (called pYV-asd). The asd gene was cloned from *Y. enterocolitica* 8081 (*Y. enterocolitica* subsp. *enterocolitica* 8081; NCBI Reference Sequence: NC_008800.1) and inserted by homologous recombination onto the pYV (in to the natural insertion region before SycO) with its endogenous promoter and transcriptional terminator. Growth behavior of the resulting strains *Y. enterocolitica* ΔyopH,O,P,E,M,T Δasd+pYV-asd was compared in culture flasks in vitro (BHI medium) to wt and parent *Y. enterocolitica* ΔyopH,O,P,E,M,T Δasd strains (FIG. 12). pYV-asd was able to rescue the phenotype observed upon deletion of asd (FIG. 12), while the rescue was not complete and a slight growth reduction in vitro could be observed. In contrast, in the in vivo syngeneic 4T1 murine cancer model, we found *Y. enterocolitica* ΔyopH,O,P,E,M,T Δasd+pYV-asd to colonize solid tumors efficiently (FIG. 16). Strikingly, all the colonies isolated at day 9-10 post injection from the solid tumor were found to still contain the pYV plasmid (selection on Arsenite containing growth plates; Arsenite resistance is related to presence of arsRBC genes on the pYV [55]) (FIG. 15). Hence, pYV-asd surprisingly showed to be an in vivo stable vector for encoding heterologous proteins to be expressed in solid tumors by colonizing bacteria over several days and weeks in a *Y. enterocolitica* ΔyopH,O,P,E,M,T Δasd strain background.

Figure 45:
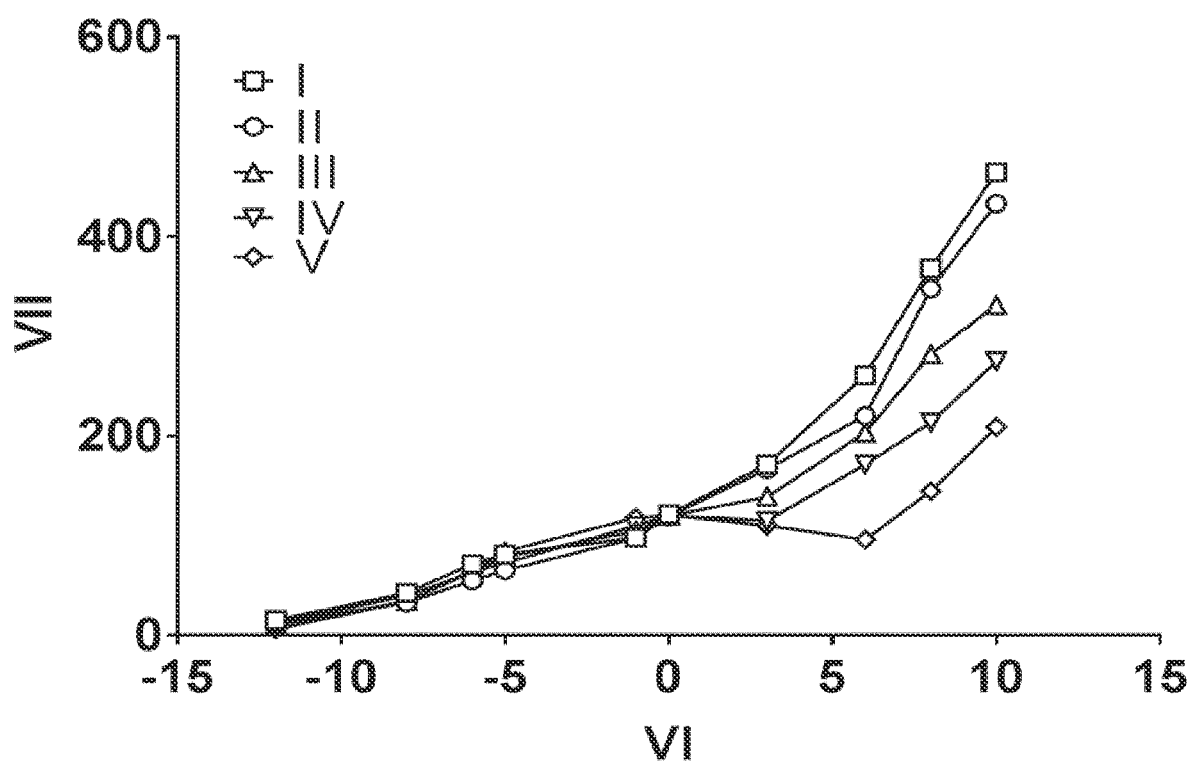
FIG. 45: Tumor progression in wildtype Balb/C mice allografted s.c. with EMT6 breast cancer cells. Wildtype Balb/C mice allografted s.c. with EMT6 breast cancer cells were i.v. injected with I: PBS, or $5*10^6$ II: *Y. enterocolitica* dHOPEMT, III: *Y. enterocolitica* dHOPEMT pYV-YopE$_{1-138}$—(tBID BH3)$_2$, IV: *Y. enterocolitica* dHOPEMT ΔHairpinI-VirF pYV-YopE$_{1-138}$—(tBID BH3)$_2$, V: *Y. enterocolitica* dHOPEMT ΔHairpinI-VirF Δasd pYV-asd-YopE$_{1-138}$—(tBID BH3)$_2$ once the tumor had reached a size of 80-250 mm3. The day of the i.v. injection of bacteria was defined as day 0, all mice were treated i.p with Desferal at d-1. Tumor volume was measured over the following days (VI: day 0 to day 15 post first injection of bacteria) with calipers. The median tumor volume is indicated (VII) as mm³.

Efficacy of *Y. enterocolitica* ΔHOPEMT in Delaying Tumor Progression and Impact of Altering VirF Activity as Well as Increasing Stability Similar experiments as with 4T1 cells (FIGS. 9 and 10) were performed in the EMT6 breast cancer mouse model, in which wildtype Balb/C mice were allografted s.c. with EMT6 breast cancer cells and treated with a single i.v. administration of bacteria once the tumor had reached a size of about 80-250 mm3. The day of the i.v. injection of bacteria was defined as day 0, all mice had an i.p injection of Desferal one day before d0. Treatment with *Y. enterocolitica* ΔHOPEMT did not impact tumor progression as compared to saline solution. *Y. enterocolitica* ΔHOPEMT pYV-YopE$_{1-138}$—(tBID BH3)$_2$ showed slight impact on tumor progression, which was reinforced by using *Y. enterocolitica* ΔHOPEMT ΔHairpinI-VirF pYV-YopE$_{1-138}$—(tBID BH3)$_2$ (FIG. 45). These findings highlight that such bacteria and their T3SS can be employed for interference with tumor progression and that manipulation of VirF activity can be used to modulate bacterial T3SS activity upon administration in vivo. Furthermore, using *Y. enterocolitica* ΔHOPEMT ΔHairpinI-VirF Δasd pYV-asd-YopE$_{1-138}$—(tBID BH3)$_2$ further strengthened the impact on tumor progression (FIG. 45), highlighting benefits of increased genetic stability upon systemic administration.

Delivery of RIG-1-Like Receptor Pathway Triggering Proteins Via the Bacterial T3SS for Induction of a Type I IFN Response Cytosolic nucleic acids are sensed by receptor as the RIG-1-like receptor (RLR) family members that detect pathogen-derived RNA in the cytosol [56]. RIG-1 and MDA5 consist of two N-terminal CARD domains and a central (DExD/H) helicase domain sensing specific nucleotides [56]. Binding to stimulatory RNA induces a structural rearrangement in RIG-I (and MDA5) that liberates its CARDs for subsequent association with unanchored K63-linked ubiquitin chains to form oligomers [56] (and in case of MDA5 to filament formation [56]). Oligomerized CARD domains of RIG-I and MDA5 interact with the CARD domain of MAVS. This interaction promotes the polymerization of the single CARD domain of MAVS, which induces downstream signaling ultimately leading to induction of type I IFN genes [56].

Figure 17:
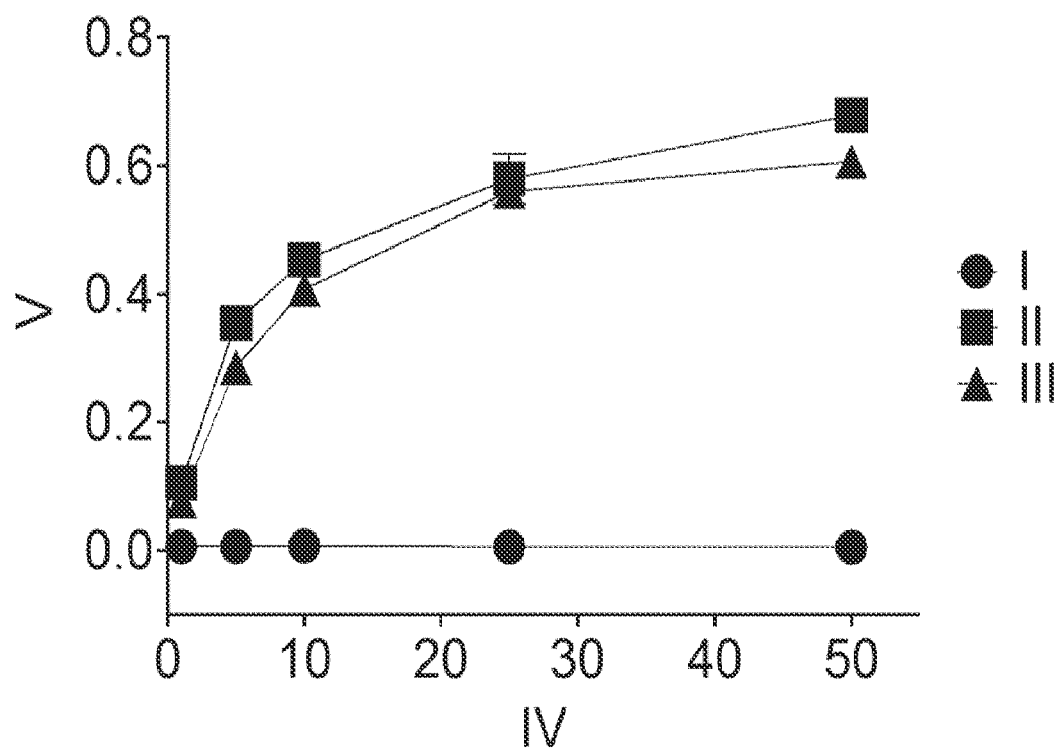
FIG. 17: Delivery of type I Interferon response inducing proteins via the bacterial T3SS-Rig1 pathway. Delivery of human and murine Rig1 CARD domains lead to type I IFN induction in a B16F10 IFN-reporter cell line. B16F10 reporter cells were infected with I: *Y. enterocolitica* ΔHOPEMT, or *Y. enterocolitica* ΔHOPEMT encoding on a pBadMycHisA derived plasmid II: YopE$_{1-138}$—human Rig1 CARD domains, III: YopE$_{1-138}$—murine Rig1 CARD domains. A titration of the bacteria added to the cells (IV: indicated as MOI) was performed for each strain, and IFN stimulation was assessed based on activity of secreted alkaline phosphatase (V: OD650) which is under the control of the I-ISG54 promoter which is comprised of the IFN-inducible ISG54 promoter enhanced by a multimeric ISRE.

We generated bacterial strains expressing the two N-terminal CARD domains of RIG-1 of human or murine origin fused to a N-terminal bacterial secretion signal for delivery by the T3SS, specifically YopE$_{1-138}$ (SEQ ID NO: 37 and 38). Delivery of the fusion protein YopE$_{1-138}$—RIG-1 CARD$_2$ was assessed by a standard in vitro secretion assay and functionality of delivered proteins were assessed on a reporter cell line for type I IFN induction. Murine B16F10 melanoma reporter cells for type I IFN stimulation are based on activity of secreted alkaline phosphatase, which is under the control of the I-ISG54 promoter, which is comprised of the IFN-inducible ISG54 promoter enhanced by a multimeric ISRE. Reporter cells were infected with various amounts (MOI) of bacterial strains expressing from a pBadMycHisA derived plasmid (pBad_Si2) and translocating the YopE$_{1-138}$—RIG-1 CARD$_2$ protein. Murine and human N-terminal CARD domains of RIG-1 showed to induce a dose-dependent type I IFN response in the reporter cell line (FIG. 17), while the bacterial background strain (*Y. enterocolitica* ΔHOPEMT) was not capable of inducing such a response (FIG. 17). Human and murine RIG-1 CARD domains induced a similar type I IFN response in the murine reporter cell line (FIG. 17), which is in agreement with the high sequence identity (76%) and similarity (88.5%).

Figure 18:
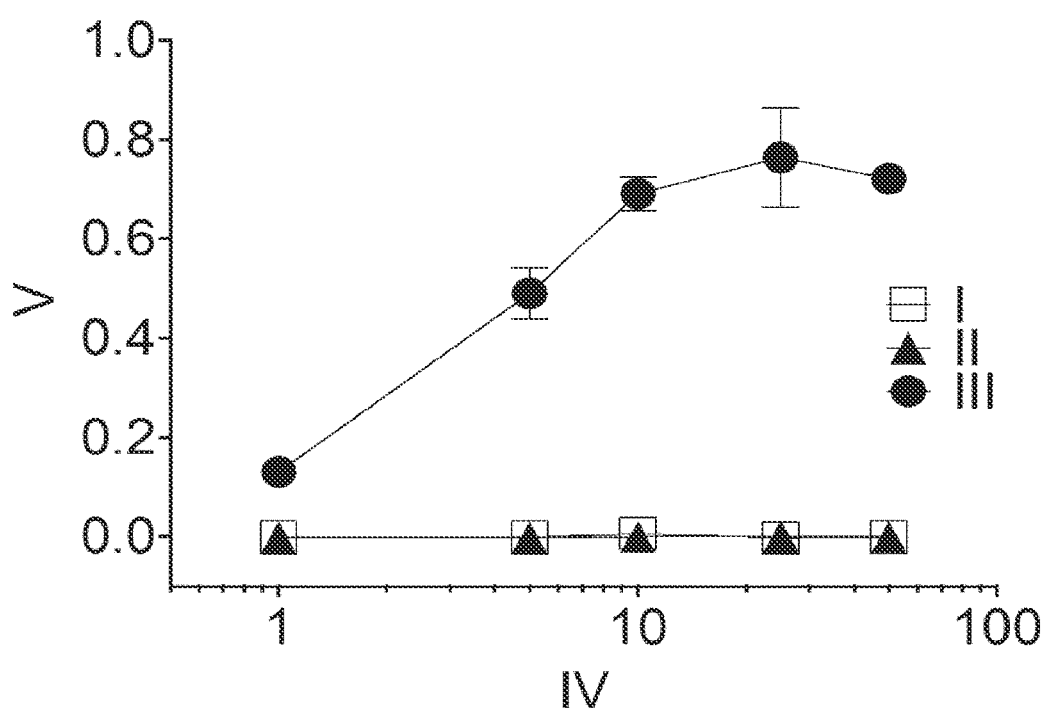
FIG. 18: Delivery of type I Interferon response inducing proteins via the bacterial T3SS-Rig1 pathway. Delivery of human Rig1 CARD domains lead to type I IFN induction in a B16F10 IFN-reporter cell line. B16F10 reporter cells were infected with I: *Y. enterocolitica* ΔHOPEMT, or *Y. enterocolitica* ΔHOPEMT encoding on a pBadMycHisA derived plasmid II: YopE$_{1-138}$—MycHis, III: YopE$_{1-138}$—human Rig1 CARD domains. A titration of the bacteria added to the cells (IV: indicated as MOI) was performed for each strain, and IFN stimulation was assessed based on activity of secreted alkaline phosphatase (V: OD650) which is under the control of the I-ISG54 promoter which is comprised of the IFN-inducible ISG54 promoter enhanced by a multimeric ISRE.
Figure 19:
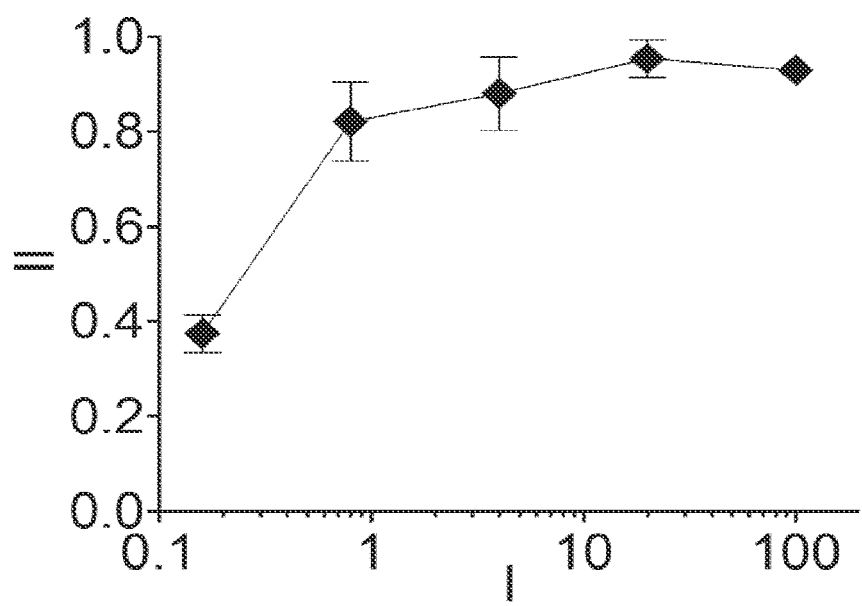
FIG. 19: Delivery of type I Interferon response inducing proteins via the bacterial T3SS-Rig1 pathway: positive control. Positive control in same experiment as FIG. 18 using IFN gamma to stimulate the B16F10 IFN-reporter cell line. B16F10 reporter cells were stimulated with murine IFN gamma. A titration of IFN gamma was added to the cells (I: indicated as U/ml), and IFN stimulation was assessed based on activity of secreted alkaline phosphatase (II: OD650) which is under the control of the I-ISG54 promoter which is comprised of the IFN-inducible ISG54 promoter enhanced by a multimeric ISRE.

Thus, the fusion to the N-terminal secretion signal of bacteria has lead to successful delivery of bacterially expressed human and murine YopE$_{1-138}$—RIG-1 CARD$_2$ proteins and has not prevented the folding and function of the RIG-1 CARD domains within the eukaryotic cell. This implies, that the YopE-fused RIG1 CARD domains are still able to multimerize themselves and induce multimerization of MAVS, which is surprising. In further experiments using this B16F10 type I IFN reporter cell line, we compared *Y. enterocolitica* ΔHOPEMT, to *Y. enterocolitica* ΔHOPEMT encoding on a pBadMycHisA derived plasmid (pBad_Si2) YopE$_{1-138}$—MycHis or YopE$_{1-138}$—human Rig1 CARD$_2$. Again, delivery of human RIG-1 CARD domains induced a dose dependent type I IFN response, while *Y. enterocolitica* ΔHOPEMT or *Y. enterocolitica* ΔHOPEMT delivering YopE$_{1-138}$—MycHis had no effect on type I IFN response (FIG. 18). In the same assay we compared the type I IFN inducing potential of bacteria delivering RIG-1 CARD domains to a positive control, murine Interferon gamma (IFNγ). Very surprisingly, bacterial delivery of RIG-1 CARD domains was able to induce a maximal response of the reporter cell line similar to the response obtained by the positive control for type I IFN induction, IFNγ (FIGS. 18 and 19).

Figure 20:
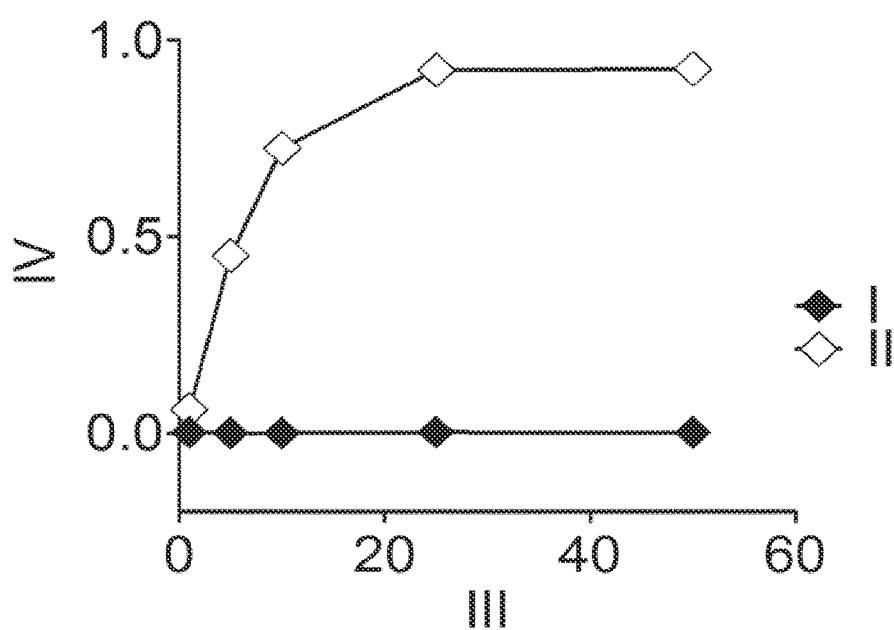
FIG. 20: Delivery of type I Interferon response inducing proteins via the bacterial T3SS-Rig1 pathway. Delivery of pYV encoded murine Rig1 CARD domains lead to type I IFN induction in the B16F10 cancer cell line. B16F10 cells were infected with I: *Y. enterocolitica* ΔHOPEMT, or *Y. enterocolitica* ΔHOPEMT encoding on the pYV II: YopE$_{1-138}$—murine Rig1 CARD domains. A titration of the bacteria added to the cells (III: indicated as MOI) was performed for each strain, and IFN stimulation was assessed by adding cellular supernatant to a IFN reporter cell line based on activity of secreted alkaline phosphatase (IV: OD650) which is under the control of the I-ISG54 promoter which is comprised of the IFN-inducible ISG54 promoter enhanced by a multimeric ISRE.
Figure 21:
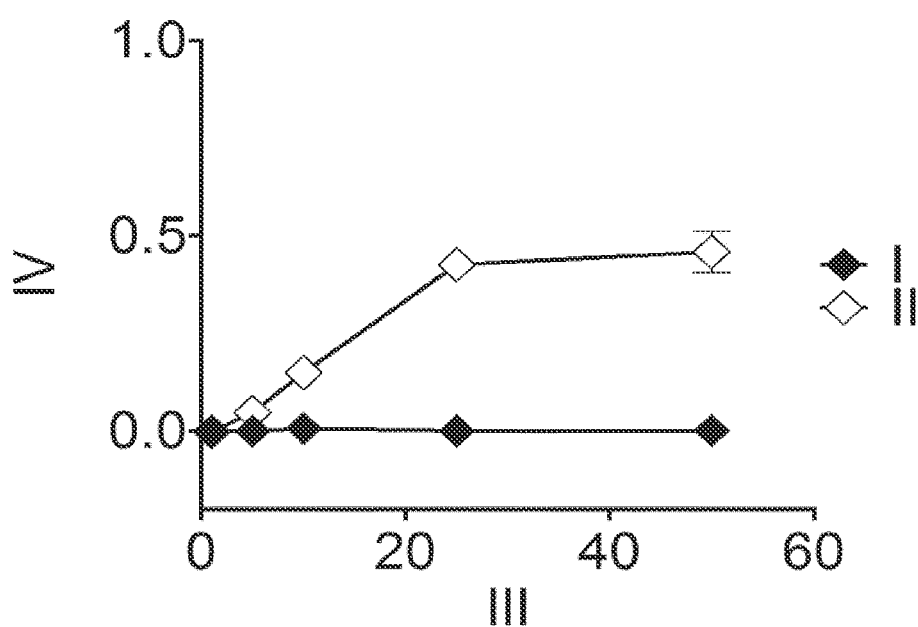
FIG. 21: Delivery of type I Interferon response inducing proteins via the bacterial T3SS-Rig1 pathway. Delivery of pYV encoded murine Rig1 CARD domains lead to type I IFN induction in the 4T1 cancer cell line. 4T1 cells were infected with I: *Y. enterocolitica* ΔHOPEMT, or *Y. enterocolitica* ΔHOPEMT encoding on the pYV II: YopE$_{1-138}$—murine Rig1 CARD domains. A titration of the bacteria added to the cells (III: indicated as MOI) was performed for each strain, and IFN stimulation was assessed by adding cellular supernatant to a IFN reporter cell line based on activity of secreted alkaline phosphatase (IV: OD650) which is under the control of the I-ISG54 promoter which is comprised of the IFN-inducible ISG54 promoter enhanced by a multimeric ISRE.

In further experiments we infected 4T1 murine breast cancer cells or wt B16F10 melanoma cells, and transferred the supernatant possibly containing IFN after 4 h onto the B16F10 type I IFN reporter cell line. This way, we compared *Y. enterocolitica* ΔHOPEMT, to *Y. enterocolitica* ΔHOPEMT encoding on the endogenous virulence plasmid (pYV) YopE$_{1-138}$—murine Rig1 CARD$_2$. Delivery of pYV encoded murine RIG-1 CARD domains induced a dose dependent type I IFN response, while *Y. enterocolitica* ΔHOPEMT had no effect on type I IFN response in wt B16F10 (FIG. 20) or 4T1 cells (FIG. 21).

Figure 27:
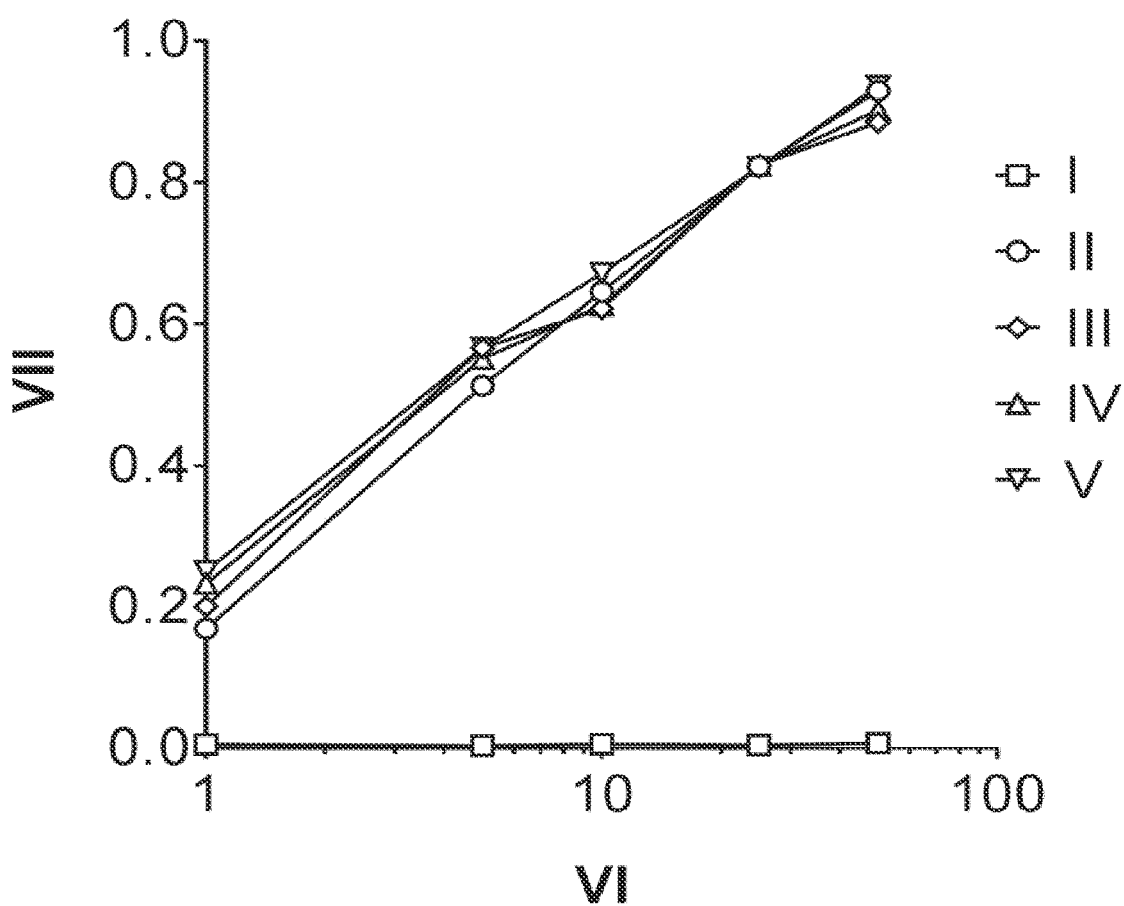
FIG. 27: Delivery of type I Interferon response inducing proteins via the bacterial T3SS—RIG1. Delivery of human and murine RIG1 CARD domains lead to type I IFN induction in a B16F10 IFN-reporter cell line. B16F10 cells were infected with I: *Y. enterocolitica* ΔHOPEMT, or *Y. enterocolitica* ΔHOPEMT encoding on a pBadMycHisA derived plasmid II: YopE$_{1-138}$—human RIG1 CARD domains$_{1-245}$, III: YopE$_{1-138}$—murine RIG1 CARD domains$_{1-246}$, IV: YopE$_{1-138}$—murine RIG1 CARD domains$_{1-229}$, V: YopE$_{1-138}$—murine RIG1 CARD domains$_{1-218}$. A titration of the bacteria added to the cells (VI: indicated as MOI) was performed for each strain, and IFN stimulation was assessed based on activity of secreted alkaline phosphatase (VII: OD650) which is under the control of the I-ISG54 promoter which is comprised of the IFN-inducible ISG54 promoter enhanced by a multimeric ISRE.
Figure 28:
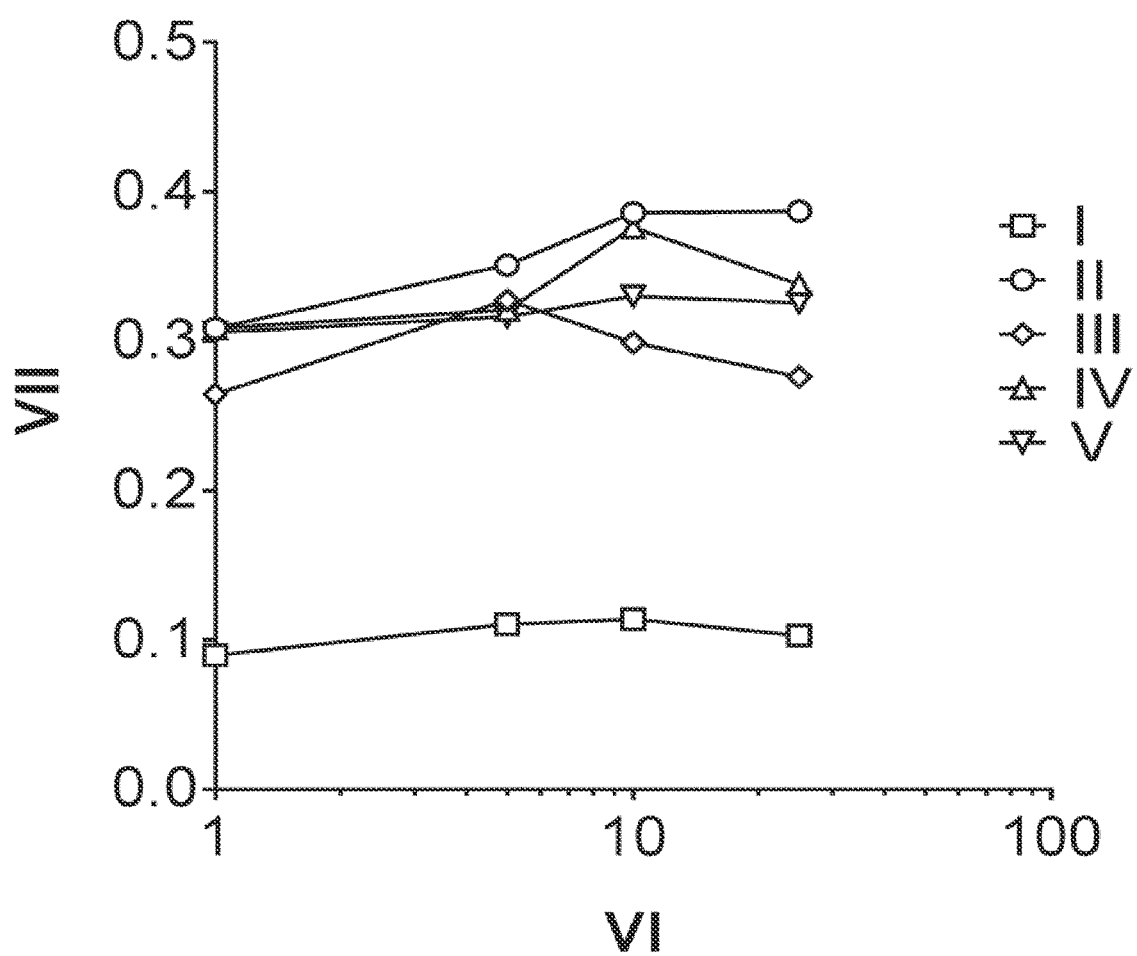
FIG. 28: Delivery of type I Interferon response inducing proteins via the bacterial T3SS—RIG1. Delivery of human and murine RIG1 CARD domains lead to type I IFN induction in a RAW IFN-reporter cell line. RAW reporter cells were infected with I: *Y. enterocolitica* ΔHOPEMT, or *Y. enterocolitica* ΔHOPEMT encoding on a pBadMycHisA derived plasmid II: YopE$_{1-138}$—human RIG1 CARD domains$_{1-245}$, III: YopE$_{1-138}$—murine RIG1 CARD domains$_{1-246}$, IV: YopE$_{1-138}$—murine RIG1 CARD domains$_{1-229}$, V: YopE$_{1-138}$—murine RIG1 CARD domains$_{1-218}$. A titration of the bacteria added to the cells (VI: indicated as MOI) was performed for each strain, and IFN stimulation was assessed based on activity of secreted alkaline phosphatase (VII: OD650) which is under the control of the I-ISG54 promoter which is comprised of the IFN-inducible ISG54 promoter enhanced by a multimeric ISRE.

In a further experiment, several versions consisting of different length of murine RIG-1 CARDs have been assessed for their potential in inducing a type I IFN response. The CARD domains of RIG-1 are predicted to be encoded by amino acids 1-172 (murine sequence, Uniprot Nr. Q6Q899). We assessed YopE$_{1-138}$—murine RIG1 CARD domains$_{1-246}$, YopE$_{1-138}$—murine RIG1 CARD domains$_{1-229}$, and YopE$_{1-138}$—murine RIG1 CARD domains$_{1-218}$ on B16F10 melanoma IFN reporter cells as well as RAW macrophage IFN reporter cells (FIG. 27-28). YopE$_{1-138}$—murine RIG1 CARD domains$_{1-246}$, YopE$_{1-138}$—murine RIG1 CARD domains$_{1-229}$ and YopE$_{1-138}$—murine RIG1 CARD domains$_{1-218}$ were found equally active.

Figure 29:
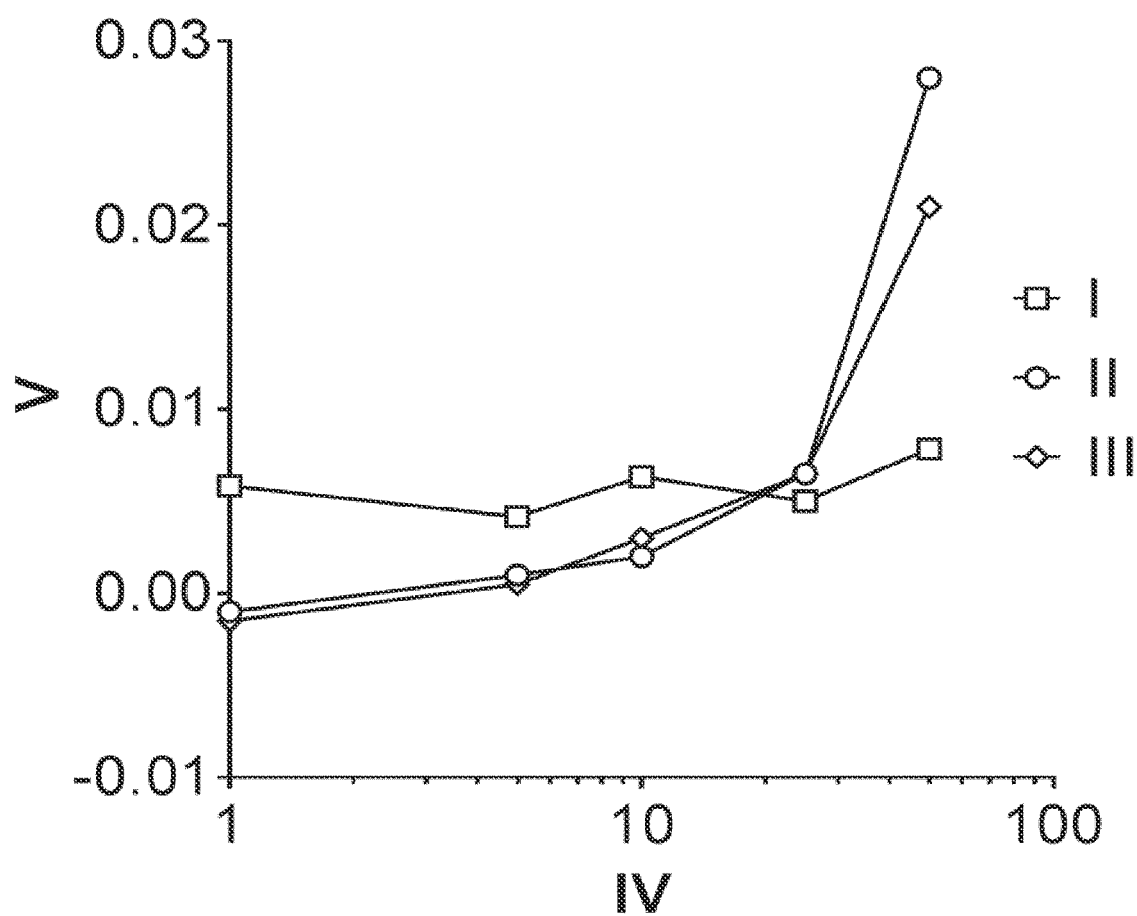
FIG. 29: Delivery of type I Interferon response inducing proteins via the bacterial T3SS-MDA5 pathway. Delivery of murine MDA5 lead to type I IFN induction in a B16F10 IFN-reporter cell line. B16F10 reporter cells were infected with I: *Y. enterocolitica* ΔHOPEMT, or *Y. enterocolitica* ΔHOPEMT encoding on a pBadMycHisA derived plasmid II: YopE$_{1-138}$—murine MDA5$_{1-294}$, III: YopE$_{1-138}$—murine MDA5$_{1-231}$. A titration of the bacteria added to the cells (IV: indicated as MOI) was performed for each strain, and IFN stimulation was assessed based on activity of secreted alkaline phosphatase (V: OD650) which is under the control of the I-ISG54 promoter which is comprised of the IFN-inducible ISG54 promoter enhanced by a multimeric ISRE.
Figure 30:
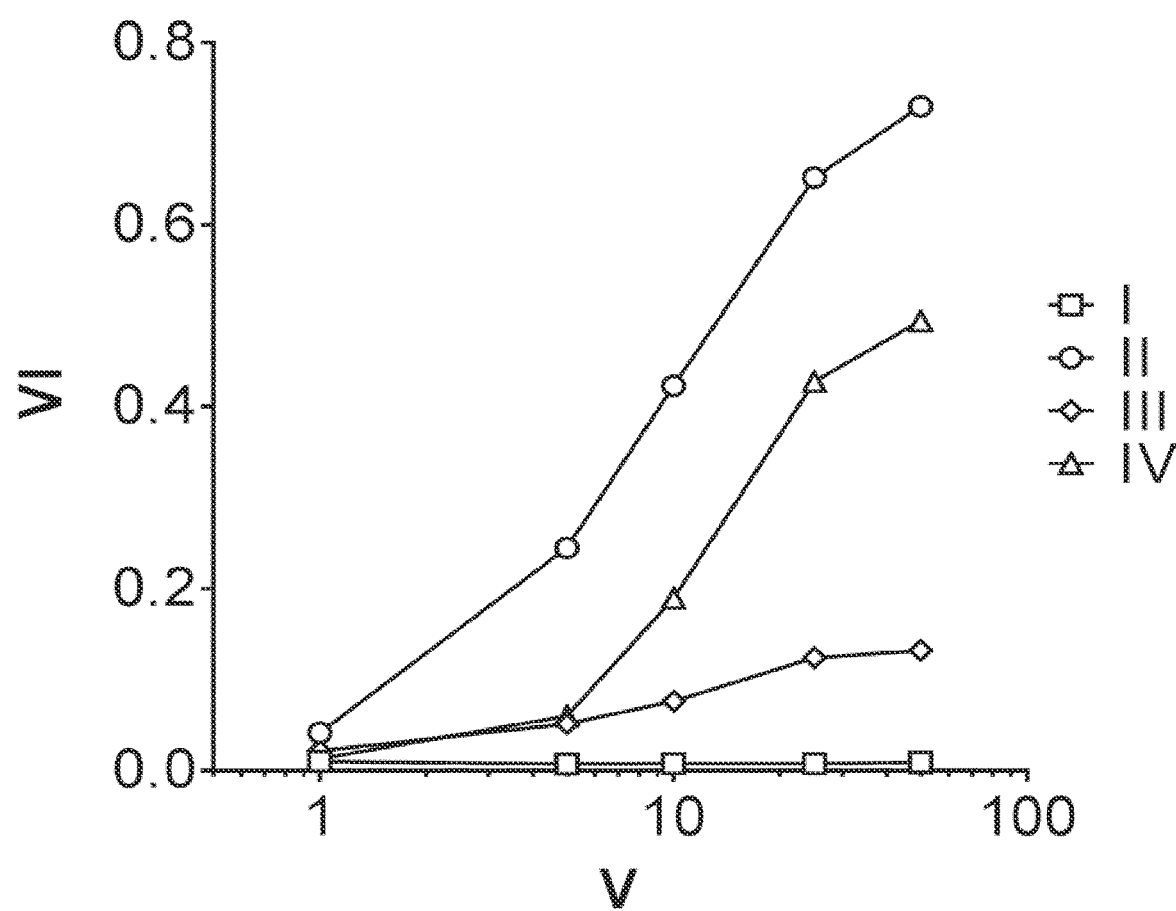
FIG. 30: Delivery of type I Interferon response inducing proteins via the bacterial T3SS—MAVS. Delivery of MAVS CARD lead to type I IFN induction in a B16F10 IFN-reporter cell line. B16F10 reporter cells were infected with I: *Y. enterocolitica* ΔHOPEMT, or *Y. enterocolitica* ΔHOPEMT encoding on a pBadMycHisA derived plasmid II: YopE$_{1-138}$—murine RIG1 CARD domains$_{1-246}$, III: YopE$_{1-138}$—human cGAS$_{161-522}$, IV: YopE$_{1-138}$—human MAVS CARD$_{1-100}$. A titration of the bacteria added to the cells (V: indicated as MOI) was performed for each strain, and IFN stimulation was assessed based on activity of secreted alkaline phosphatase (VI: OD650) which is under the control of the I-ISG54 promoter which is comprised of the IFN-inducible ISG54 promoter enhanced by a multimeric ISRE.
Figure 31:
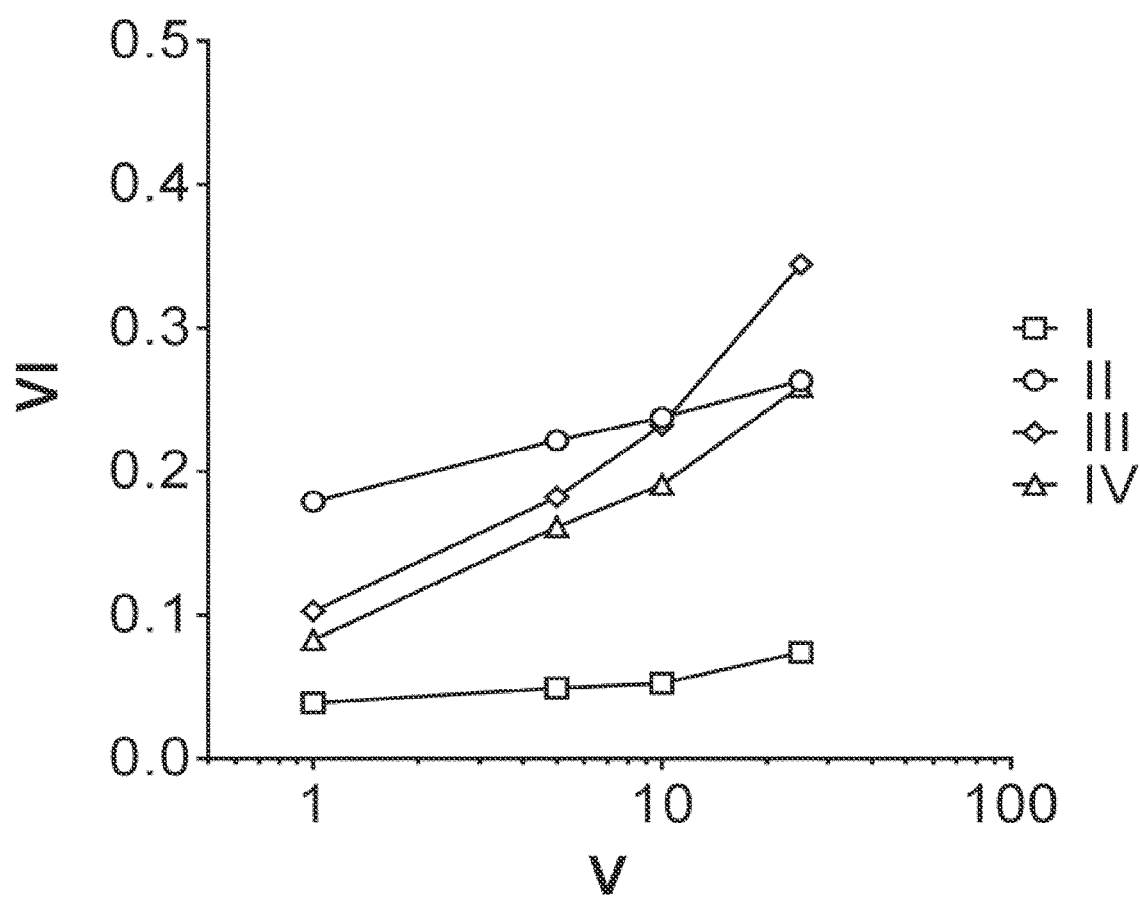
FIG. 31: Delivery of type I Interferon response inducing proteins via the bacterial T3SS—MAVS. Delivery of MAVS CARD lead to type I IFN induction in a RAW macrophage IFN-reporter cell line. RAW macrophage reporter cells were infected with I: *Y. enterocolitica* ΔHOPEMT, or *Y. enterocolitica* ΔHOPEMT encoding on a pBadMycHisA derived plasmid II: YopE$_{1-138}$—murine RIG1 CARD domains$_{1-246}$, III: YopE$_{1-138}$—human cGAS$_{161-522}$, IV: YopE$_{1-138}$—human MAVS CARD$_{1-100}$. A titration of the bacteria added to the cells (V: indicated as MOI) was performed for each strain, and IFN stimulation was assessed based on activity of secreted alkaline phosphatase (VI: OD650) which is under the control of the I-ISG54 promoter which is comprised of the IFN-inducible ISG54 promoter enhanced by a multimeric ISRE.

In a follow-on experiment we assessed potency of bacterially delivered MDA5. We cloned several versions consisting of different length of murine MDA5 CARDs and assessed them for their potential in inducing a type I IFN response on B16F10 IFN reporter cells. The CARD domains of MDA5 are predicted to be encoded by amino acids 1-190 (murine sequence, Uniprot Nr. Q8R5F7). We assessed YopE$_{1-138}$—murine MDA5 CARD domains$_{1-294}$ and YopE$_{1-138}$—murine MDA5 CARD domains$_{1-23}$1, on B16F10 melanoma IFN reporter cells. All variants were found active (FIG. 29). Surprisingly, activity of delivered MDA5 CARDs was found being by far less strong as RIG-1 CARDs, even though the proteins share very similar biological function and protein structure consisting of two N-terminal CARD domains and a central (DExD/H) helicase domain sensing specific nucleotides [56].

Delivery of cGAS/STING Pathway Triggering Proteins Via the Bacterial T3SS for Induction of a Type I IFN Response In the cGAS/STING pathway, cytosolic double-stranded DNA is detected by binding to the enzyme cyclic GMP-AMP synthase (cGAS). Upon dsDNA binding, cGAS is activated and produces a cyclic CDN second messenger, cyclic GMP-AMP (cGAMP). cGAMP then directly binds to the endoplasmic reticulum receptor protein STING (Stimulator of IFN Genes). Upon binding of cGAMP, STING is activated and induces a signaling pathway leading to transcription of type I IFN and other co-regulated genes [57]. Human cGAS produces 2',3' cGAMP (containing 2'-5' and 3'-5' phosphodiester bonds), but other CDNs have been shown to be able to induce murine or human STING at various levels. This includes 3',3' cGAMP (e.g. produced by *Vibrio cholera* DncV or some eukaryotic cGAS), cyclic di-AMP (e.g. produced by CdaA or DisA of different gram-positive species) or cyclic di-GMP (e.g. produced by *Pseudomonas aeruginosa* WspR) [57,58]. While the wt human STING (and murine STING) recognize 2',3' cGAMP, 3',3' cGAMP, cyclic di-AMP and cyclic di-GMP, several natural human STING variants respond differently to these agonists [59].

In order to activate the cGAS/STING pathway upon delivery of proteins by bacteria, we cloned *P. aeruginosa* WspR producing cyclic di-GMP to be expressed and delivered by *Y. enterocolitica* via the T3SS. In order to increase activity of WspR, only its GGDEF domain (diguanylate cyclased domain) was used and the upstream stalk domain was replaced with the leucin-zipper motif of GCN4 from yeast. Dimerization of WspR is know to be required for its activity and the leucine zipper of GCN4 has been shown to form parallel coiled-coils and, thus to serve as a strong dimerization module. The GCN4 motif was fused to the GGDEF domain of WspR including the natural linker between the GGDEF and helical stalk to allow for inter-domain flexibility comparable to wild-type WspR [60].

Figure 22:
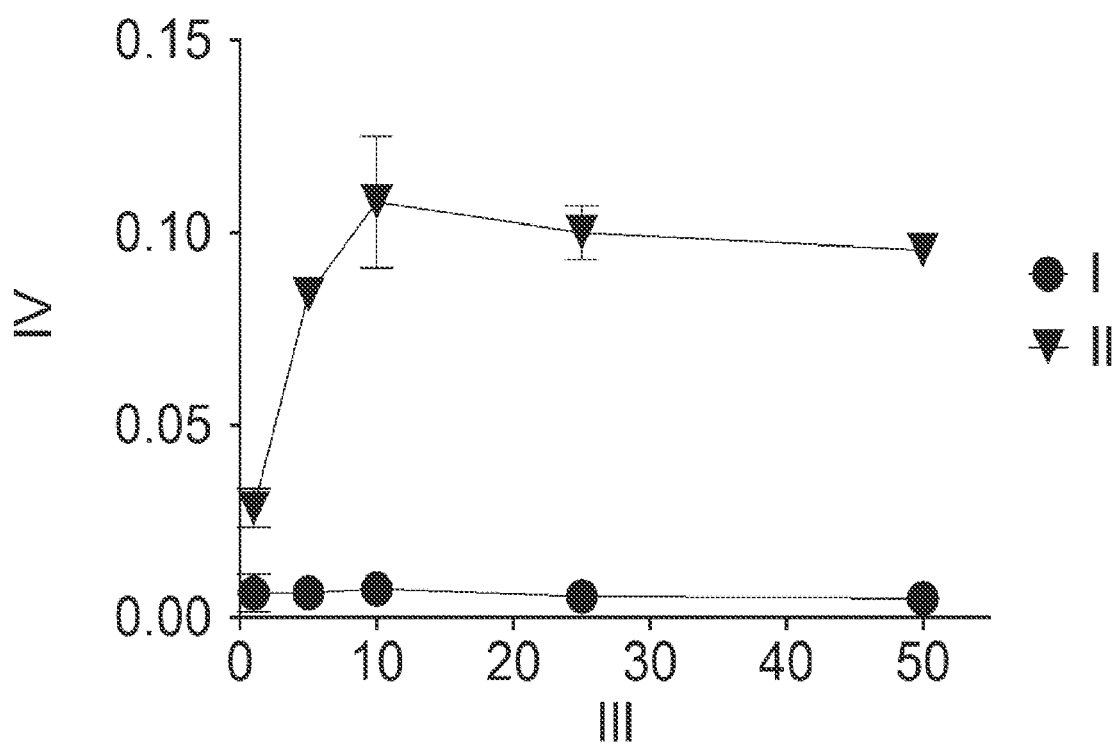
FIG. 22: Delivery of type I Interferon response inducing proteins via the bacterial T3SS—STING pathway. Delivery of cyclic dinucleotide generating enzymes lead to type I IFN induction in a B16F10 IFN-reporter cell line. B16F10 reporter cells were infected with T: *Y. enterocolitica* ΔHOPEMT, or *Y. enterocolitica* ΔHOPEMT encoding on a pBadMycHisA derived plasmid II: YopE$_{1-138}$—*P. aeruginosa* WspR (with adapted stalk domain). A titration of the bacteria added to the cells (III: indicated as MOI) was performed for each strain, and IFN stimulation was assessed based on activity of secreted alkaline phosphatase (IV: OD650) which is under the control of the I-ISG54 promoter which is comprised of the IFN-inducible ISG54 promoter enhanced by a multimeric ISRE.

Delivery of the fusion protein YopE$_{1-138}$—GCN4 leucin zipper—WspR GGDEF domain (short: YopE$_{1-138}$—WspR) (SEQ ID NO: 39) was assessed on a reporter cell line for type I IFN induction. Murine B16F10 melanoma reporter cells for type I IFN stimulation are based on activity of secreted alkaline phosphatase, which is under the control of the I-ISG54 promoter, which is comprised of the IFN-inducible ISG54 promoter enhanced by a multimeric ISRE. Reporter cells were infected with various amounts (MOI) of bacterial strains expressing from a pBadMycHisA derived plasmid (pBad_Si2) and translocating the YopE$_{1-138}$—WspR protein. *P. aeruginosa* WspR GGDEF domain fused to GCN4 leucin zipper motif showed to dose-dependently induce a type I IFN response in the reporter cell line (FIG. 22), while the bacterial background strain (*Y. enterocolitica* ΔHOPEMT) was not capable of inducing such a response (FIG. 22).

Thus, the fusion to the N-terminal secretion signal of bacteria has lead to successful delivery of bacterially expressed YopE$_{1-138}$—GCN4 leucin zipper (yeast)—WspR GGDEF (*P. aeruginosa*) protein and has not prevented the folding and function of the this tri-partite protein within the eukaryotic cell. This implies, that the YopE-fused GCN4 leucin zipper—WspR GGDEF is still able to dimerize and thus lead to active GGDEF domains, which is surprising.

For further experiments, we cloned *V. cholerae* DncV (producing 3',3' cGAMP) [57], a *Bacillus cereus* DisA-like protein (producing cyclic di-AMP) [61] and the eukaryotic Anemonae (*Nematostella vectensis*) cGAS (producing 3',3' cGAMP) [57], which has been reported to be active in absence of external stimuli, for expression and translocation by bacteria. DisA type cyclases usually form octamers [61], which might not be compatible with the N-terminal YopE fusion and bacterial delivery. *B. cereus* DisA-like (PDB code 2fb5) was identified based on structural similarity to the diadenylate cyclase (DAC) domain of classical DisA proteins [61], but it interestingly lacks all helices known from other DisA proteins to be required for multimerization. We thus decided to take advantage of the possibly monomerical active DisA-like protein from *B. cereus* (PDB code 2fb5; residues 76-205).

Figure 23:
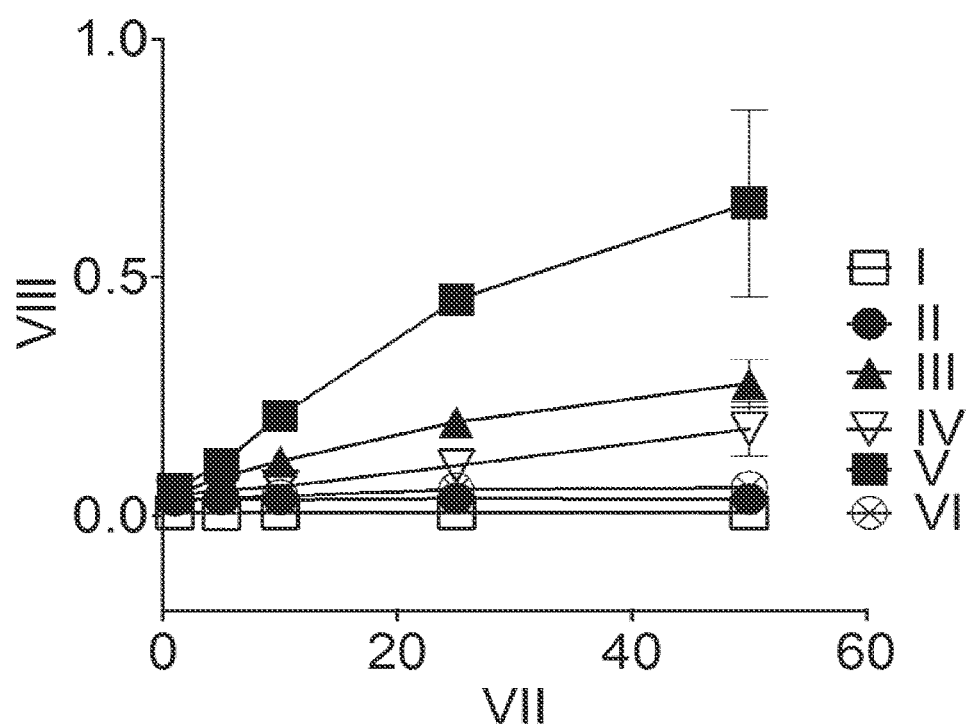
FIG. 23: Delivery of type I Interferon response inducing proteins via the bacterial T3SS—STING pathway. Delivery of cyclic dinucleotide generating enzymes lead to type I IFN induction in a B16F10 IFN-reporter cell line. B16F10 reporter cells were either left untreated (I), or infected with II: *Y. enterocolitica* ΔHOPEMT, or *Y. enterocolitica* ΔHOPEMT encoding on a pBadMycHisA derived plasmid III: YopE$_{1-138}$—*V. cholerae* DncV, IV: YopE$_{1-138}$—*B. cereus* DisA-like protein, V: YopE$_{1-138}$—Anemonae cGAS or VI: YopE$_{1-138}$—MycHis. A titration of the bacteria added to the cells (VII: indicated as MOI) was performed for each strain, and IFN stimulation was assessed based on activity of secreted alkaline phosphatase (VIII: OD650) which is under the control of the I-ISG54 promoter which is comprised of the IFN-inducible ISG54 promoter enhanced by a multimeric ISRE.

Delivery of the fusion protein YopE$_{1-138}$—*V. cholerae* DncV (SEQ ID NO: 41), YopE$_{1-138}$—*B. cereus* DisA-like protein (SEQ ID NO: 42) and YopE$_{1-138}$—Anemonae cGAS (SEQ ID NO: 43) was assessed on a reporter cell line for type I IFN induction. Murine B16F10 melanoma reporter cells for type I IFN stimulation are based on activity of secreted alkaline phosphatase, which is under the control of the I-ISG54 promoter, which is comprised of the IFN-inducible ISG54 promoter enhanced by a multimeric ISRE. Reporter cells were infected with various amounts (MOI) of bacterial strains expressing from a pBadMycHisA derived plasmid (pBad_Si2) and translocating the YopE$_{1-138}$—*V.

cholerae DncV, YopE$_{1-138}$—B. cereus DisA-like protein and YopE$_{1-138}$—Anemonae cGAS. YopE$_{1-138}$—V. cholerae DncV, YopE$_{1-138}$—B. cereus DisA-like protein and YopE$_{1-138}$—Anemonae cGAS all showed to dose-dependently induce a type I IFN response in the reporter cell line (FIG. 23), while the bacterial background strain (Y. enterocolitica ΔHOPEMT) or Y. enterocolitica ΔHOPEMT delivering YopE$_{1-138}$—MycHis were not capable of inducing such a response (FIG. 23). The 3',3' cGAMP producing Anemonae (Nematostella vectensis) cGAS showed highest activity, while V. cholerae DncV (producing 3',3' cGAMP) and Bacillus cereus DisA-like protein (producing cyclic di-AMP) were found to be similarly activating a type I IFN response. Thus, the fusion to the N-terminal secretion signal of bacteria has lead to successful deliver of bacterially expressed YopE$_{1-138}$—V. cholerae DncV, YopE$_{1-138}$—B. cereus DisA-like protein and YopE$_{1-138}$—Anemonae cGAS proteins and has not prevented the folding and function of these proteins within the eukaryotic cell, which could not have been predicted.

Alternatively, murine IRF3, a central transcription factor downstream of RLR or cGAS/STING dependent signalling [62], was cloned for expression and transport by bacteria. In the absence of activation, IRF-3 is in a latent conformation in the cytoplasm. Only upon activation of upstream receptors as RIG-1, MDA5 or STING, IRF-3 is phosphorylated via TBK1 and IKKε and thus activated. Phosphorylation of IRF-3 leads to dimerization, translocation to the nucleus, and association with co-activators [62]. In order to reach a constitutive active version of IRF3, we replaced one of the most important phosphorylation sites (Ser397 in murine IRF3) by Asp [62].

Figure 24:
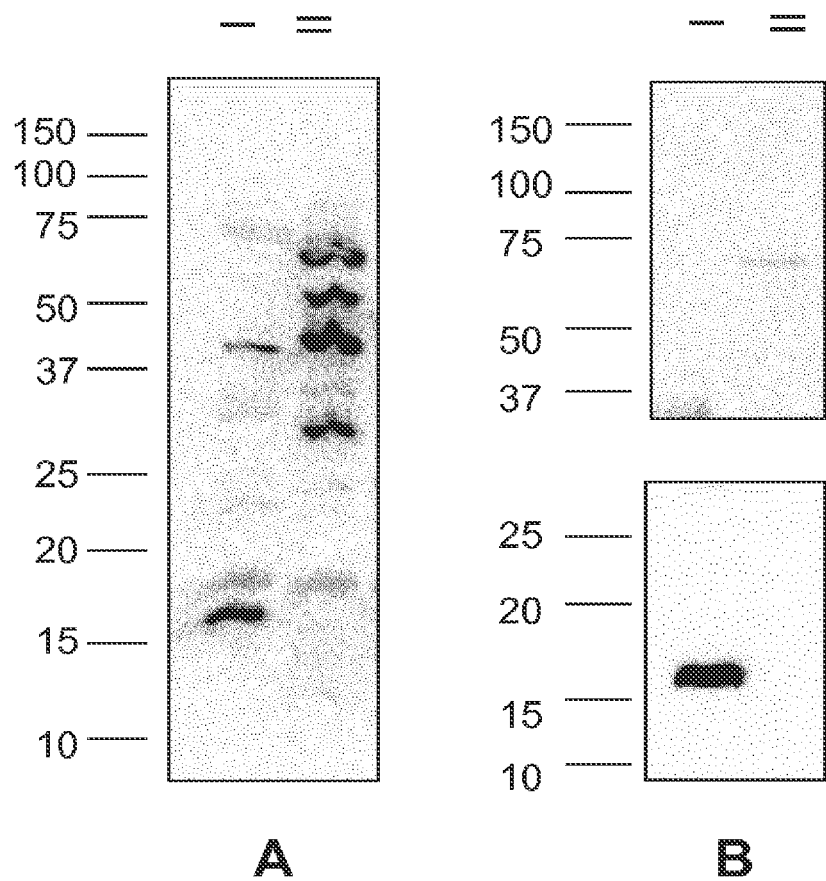
FIG. 24: T3SS dependent secretion of IRF3 into the culture supernatant. In-vitro secretion experiment of I: *Y. enterocolitica* ΔHOPEMT+YopE$_{1-138}$—murine tBID BH3 and II: *Y. enterocolitica* ΔHOPEMT+YopE$_{1-138}$—murine IRF3 Ser397Asp. Protein content of total bacterial lysates ("A") and precipitated culture supernatants ("B") was analyzed by Western blotting using an anti-YopE antibody. Numbers written indicate molecular weight in kDa at the corresponding height.

Delivery of the fusion protein YopE$_{1-138}$—murine IRF3 Ser397Asp (SEQ ID NO: 40) was assessed in an in-vitro secretion assay, where protein secretion into the surrounding liquid is artificially induced. After TCA based protein precipitation, Western blot analysis with anti-YopE antibody was used to determine protein amounts secreted (FIG. 24). While a Δ HOPEMT strains encoding YopE$_{1-138}$—murine tBID BH3 resulted in a strong band in the secreted fraction (at 15-20 kDa), YopE$_{1-138}$—murine IRF3 Ser397Asp (at 50-75 Da) was found to be secreted as well, albeit to a lesser extent (FIG. 24). Total bacterial cell fraction analysis revealed that expression levels of YopE$_{1-138}$—murine tBID BH3 and YopE$_{1-138}$—murine IRF3 Ser397Asp are comparable, while YopE$_{1-138}$—murine IRF3 Ser397Asp showed a pattern of degradation bands (FIG. 24).

Delivery of cGAS/STING and RIG-1-Like Receptor Pathway Triggering Proteins Via the Bacterial T3SS for Induction of a Type I IFN Response in Immune Cells.

Figure 25:
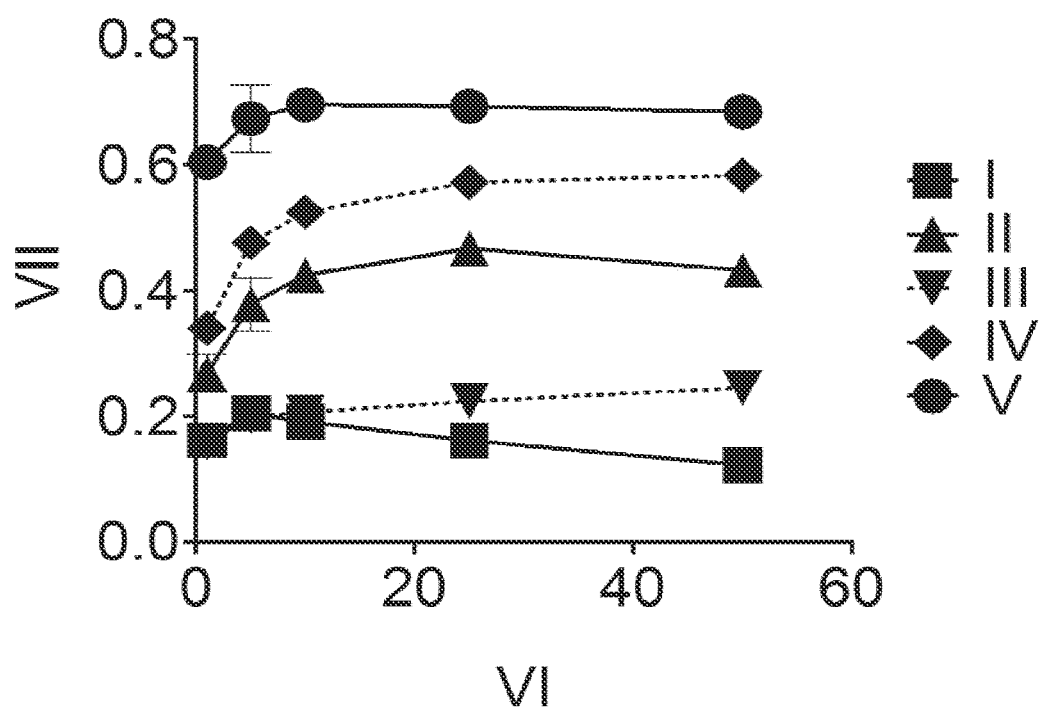
FIG. 25: Delivery of type I Interferon response inducing proteins via the bacterial T3SS to immune cells—Rig1 and STING pathway. Delivery of murine Rig1 CARD domains and cyclic dinucleotide generating enzymes lead to type I IFN induction in a RAW264.7 IFN-reporter cell line. RAW264.7 reporter cells were infected with I: *Y. enterocolitica* ΔHOPEMT, or *Y. enterocolitica* ΔHOPEMT encoding on a pBadMycHisA derived plasmid II: YopE$_{1-138}$—*V. cholerae* DncV, III: YopE$_{1-138}$—*B. cereus* DisA-like protein, IV: YopE$_{1-138}$—Anemonae cGAS or V: YopE$_{1-138}$—murine Rig1 CARD domains. A titration of the bacteria added to the cells (VI: indicated as MOI) was performed for each strain, and IFN stimulation was assessed based on activity of secreted alkaline phosphatase (VII: OD650) which is under the control of the I-ISG54 promoter which is comprised of the IFN-inducible ISG54 promoter enhanced by a multimeric ISRE.
Figure 26:
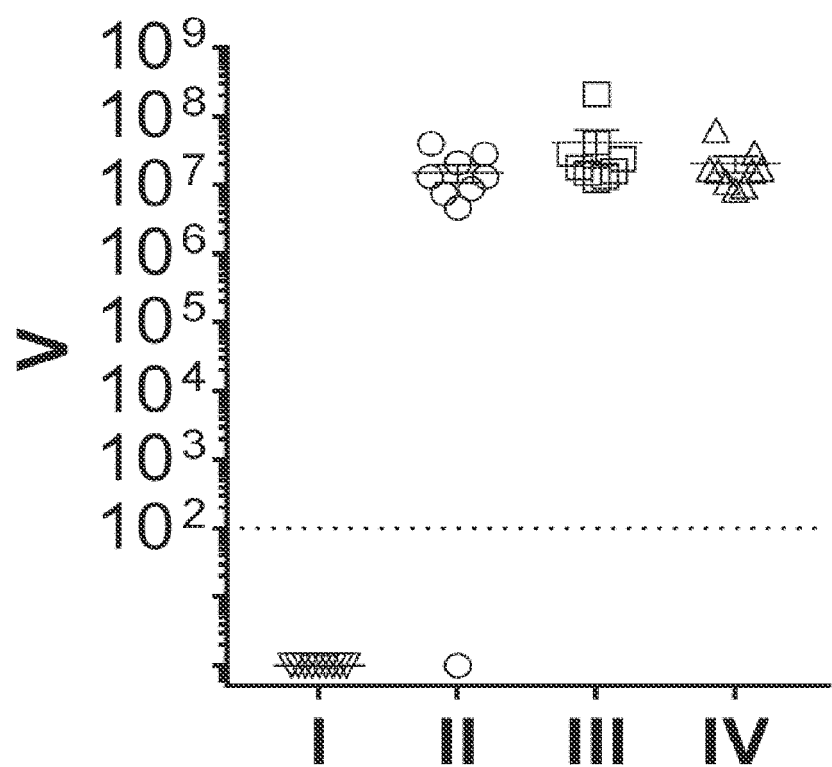
FIG. 26: Tumor colonization of i.v. injected *Y. enterocolitica* strains in the B16F10 breast cancer allograft model. Wildtype C57BL/6 mice allografted s.c. with B16F10 melanoma cancer cells were i.v. injected with I: PBS, II: $1*10^7$ *Y. enterocolitica* dHOPEMT, III: *Y. enterocolitica* dHOPEMT+pYV-YopE$_{1-138}$—murine RIG1 CARDs$_{1-246}$ or IV: *Y. enterocolitica* dHOPEMT ΔHairpinI-VirF+pYV-YopE$_{1-138}$—murine RIG1 CARDs$_{1-246}$ once the tumor had reached a size of 100-315 mm$^3$. Bacterial counts in tumors are indicated as colony forming units (CFU) per gram of tissue (V). Counts were assessed in tumors at day 5 or 8 post infection. Each dot represents an individual mouse. The horizontal dashed line indicates the detection limit.

Delivery of the fusion protein YopE$_{1-138}$—murine RIG-I CARD$_2$, YopE$_{1-138}$—V. cholerae DncV, YopE$_{1-138}$—B. cereus DisA-like protein and YopE$_{1-138}$—Anemonae cGAS was assessed on a immune reporter cell line for type I IFN induction. Murine RAW264.7 macrophage reporter cells for type I IFN stimulation are based on activity of secreted alkaline phosphatase, which is under the control of the I-ISG54 promoter, which is comprised of the IFN-inducible ISG54 promoter enhanced by a multimeric ISRE. Reporter cells were infected with various amounts (MOI) of bacterial strains expressing from a pBadMycHisA derived plasmid (pBad_Si2) and translocating the YopE$_{1-138}$—murine RIG-I CARD$_2$, YopE$_{1-138}$—V. cholerae DncV, YopE$_{1-138}$—B. cereus DisA-like protein and YopE$_{1-138}$—Anemonae cGAS. YopE$_{1-138}$—murine RIG-I CARD$_2$, YopE$_{1-138}$—V. cholerae DncV, and YopE$_{1-138}$—Anemonae cGAS all showed to dose-dependently induce a type I IFN response in this immune reporter cell line (FIG. 25), while the bacterial background strain (Y. enterocolitica ΔHOPEMT) was not capable of inducing such a response (FIG. 25). YopE$_{1-138}$—murine RIG-I CARD$_2$ showed highest activity, followed by the 3',3' cGAMP producing Anemonae (Nematostella vectensis) cGAS and V. cholerae DncV (producing 3',3' cGAMP). Bacillus cereus DisA-like protein (producing cyclic di-AMP) was found to be only weakly activating a type I IFN response.

Figure 32:
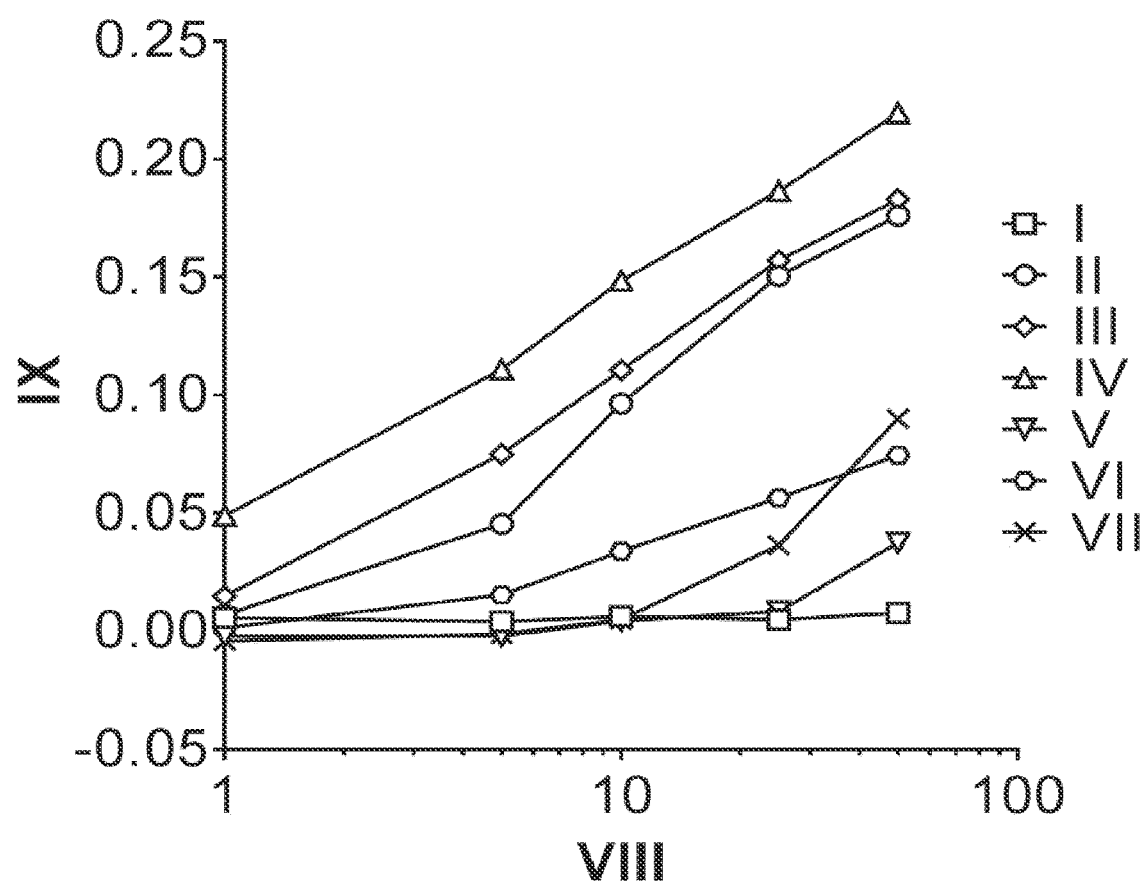
FIG. 32: Delivery of type I Interferon response inducing proteins via the bacterial T3SS—STING pathway. Delivery of cyclic dinucleotide generating enzymes lead to type I IFN induction in a B16F10 IFN-reporter cell line. B16F10 reporter cells were infected with I: *Y. enterocolitica* ΔHOPEMT, or *Y. enterocolitica* ΔHOPEMT encoding on a pBadMycHisA derived plasmid II: YopE$_{1-138}$—Anemonae cGAS, III: YopE$_{1-138}$—Anemonae cGAS$_{60-422}$, IV: YopE$_{1-138}$—human cGAS$_{161-522}$, V: YopE$_{1-138}$—*Listeria* CdaA$_{101-273}$, VI: YopE$_{1-138}$—*V. cholerae* DncV, VII: YopE$_{1-138}$—*B. cereus* DisA-like protein. A titration of the bacteria added to the cells (VIII: indicated as MOI) was performed for each strain, and IFN stimulation was assessed based on activity of secreted alkaline phosphatase (IX: OD650) which is under the control of the I-ISG54 promoter which is comprised of the IFN-inducible ISG54 promoter enhanced by a multimeric ISRE.
Figure 33:
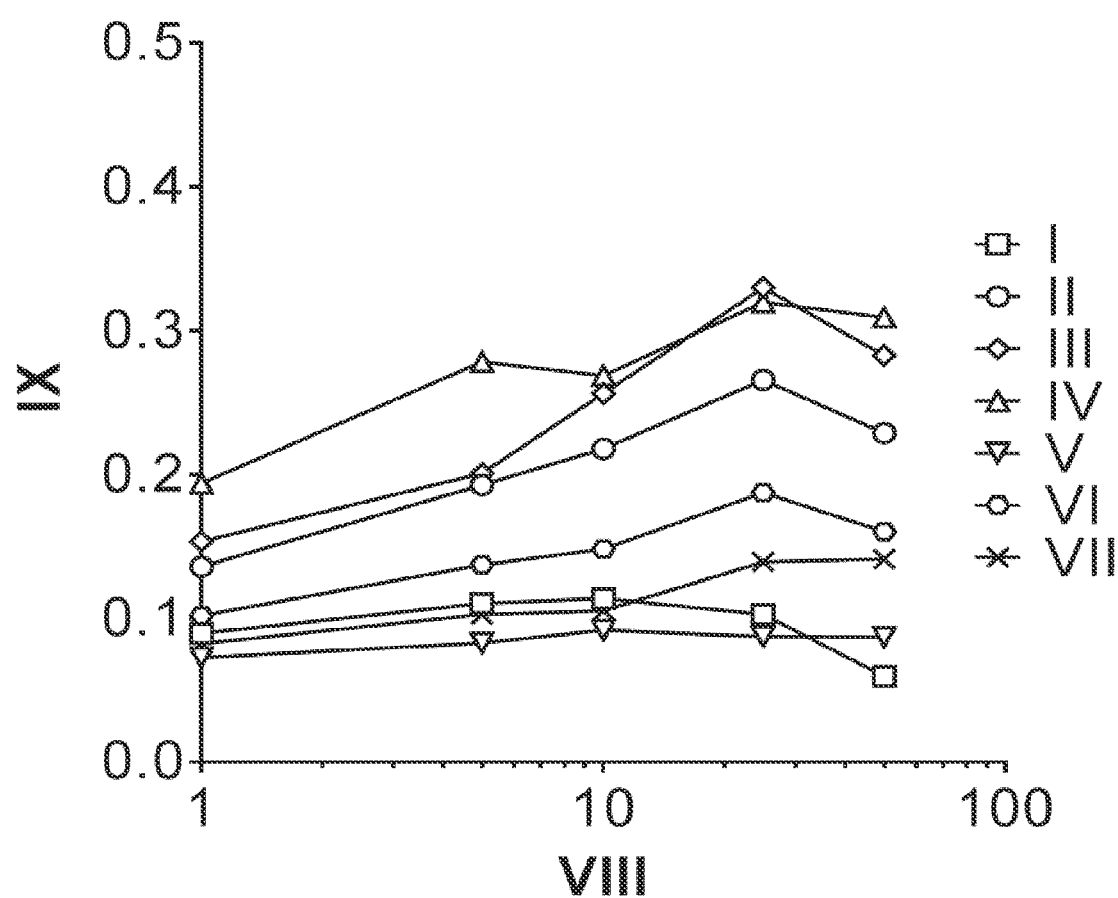
FIG. 33: Delivery of type I Interferon response inducing proteins via the bacterial T3SS—STING pathway. Delivery of cyclic dinucleotide generating enzymes lead to type I IFN induction in a RAW macrophage IFN-reporter cell line. RAW macrophage reporter cells were infected with I: *Y. enterocolitica* ΔHOPEMT, or *Y. enterocolitica* ΔHOPEMT encoding on a pBadMycHisA derived plasmid II: YopE$_{1-138}$—Anemonae cGAS, III: YopE$_{1-138}$—Anemonae cGAS$_{60-422}$, IV: YopE$_{1-138}$—human cGAS$_{161-522}$, V: YopE$_{1-138}$—*Listeria* CdaA$_{101-273}$, VI: YopE$_{1-138}$—*V. cholerae* DncV, VII: YopE$_{1-138}$—*B. cereus* DisA-like protein. A titration of the bacteria added to the cells (VIII: indicated as MOI) was performed for each strain, and IFN stimulation was assessed based on activity of secreted alkaline phosphatase (IX: OD650) which is under the control of the I-ISG54 promoter which is comprised of the IFN-inducible ISG54 promoter enhanced by a multimeric ISRE.
Figure 34:
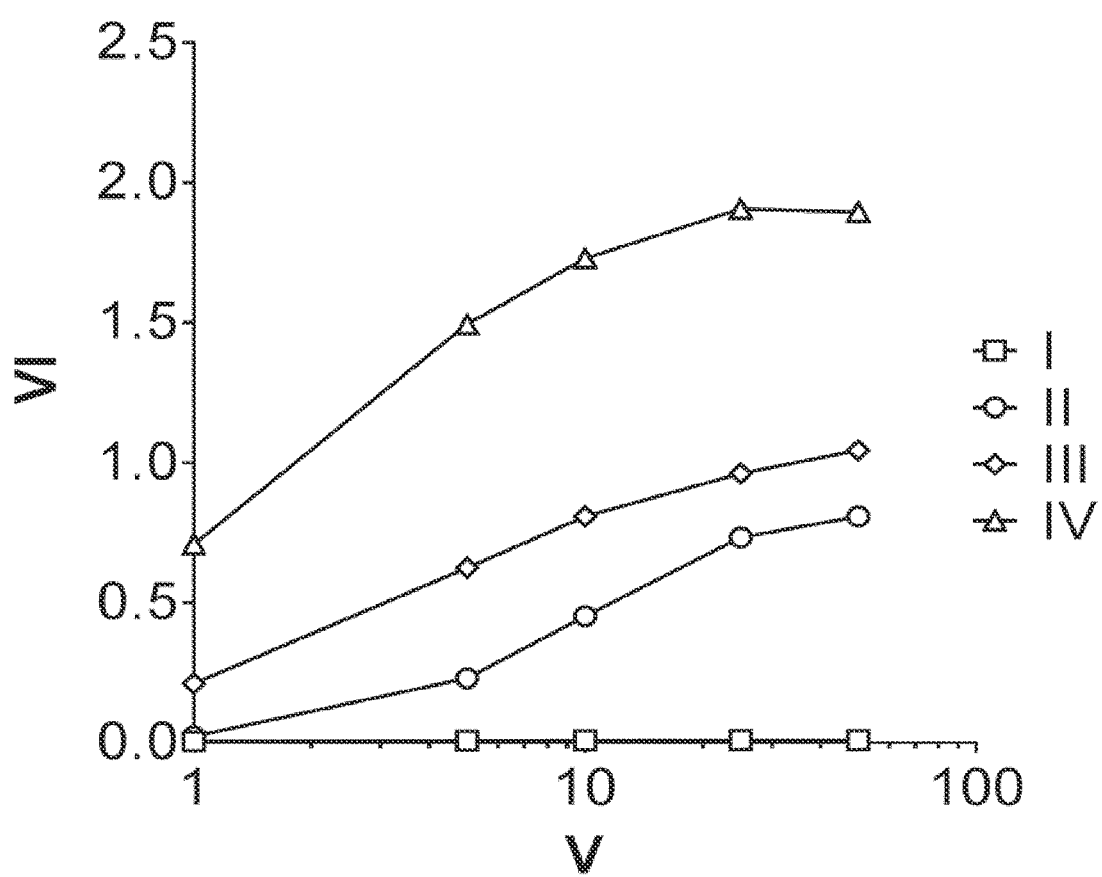
FIG. 34: Delivery of type I Interferon response inducing proteins via the bacterial T3SS and comparison to small molecular agonists of STING. Delivery of cyclic dinucleotide generating enzymes lead to type I IFN induction in a B16F10 IFN-reporter cell line. B16F10 reporter cells were infected with I: *Y. enterocolitica* ΔHOPEMT, or *Y. enterocolitica* ΔHOPEMT encoding on a pBadMycHisA derived plasmid II: YopE$_{1-138}$—Anemonae cGAS, III: YopE$_{1-138}$—human cGAS$_{161-522}$, IV: YopE$_{1-138}$—murine RIG1 CARD domains$_{1-218}$. A titration of the bacteria added to the cells (V: indicated as MOI) was performed, and IFN stimulation was assessed based on activity of secreted alkaline phosphatase (VI: OD650) which is under the control of the I-ISG54 promoter which is comprised of the IFN-inducible ISG54 promoter enhanced by a multimeric ISRE.
Figure 35:
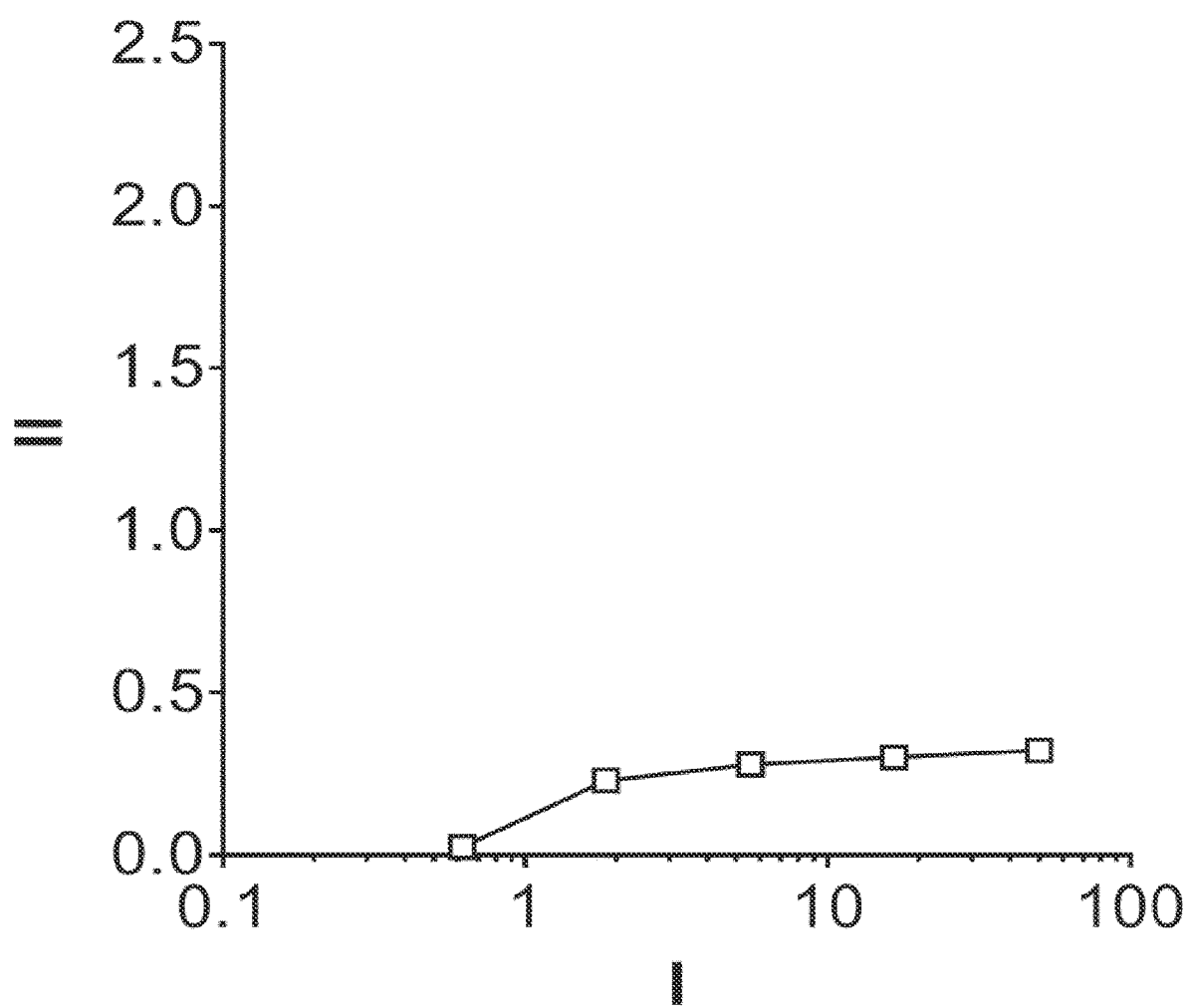
FIG. 35: Delivery of type I Interferon response inducing proteins via the bacterial T3SS and comparison to small molecular agonists of STING. Delivery of a cyclic dinucleotide lead to type I IFN induction in a B16F10 IFN-reporter cell line. B16F10 reporter cells treated with small molecular STING agonist 2'3'-c-di-AM(PS)2 (Rp,Rp). A titration of the compound (I: indicated as micromolar) was performed, and IFN stimulation was assessed based on activity of secreted alkaline phosphatase (II: OD650) which is under the control of the I-ISG54 promoter which is comprised of the IFN-inducible ISG54 promoter enhanced by a multimeric ISRE.
Figure 36:
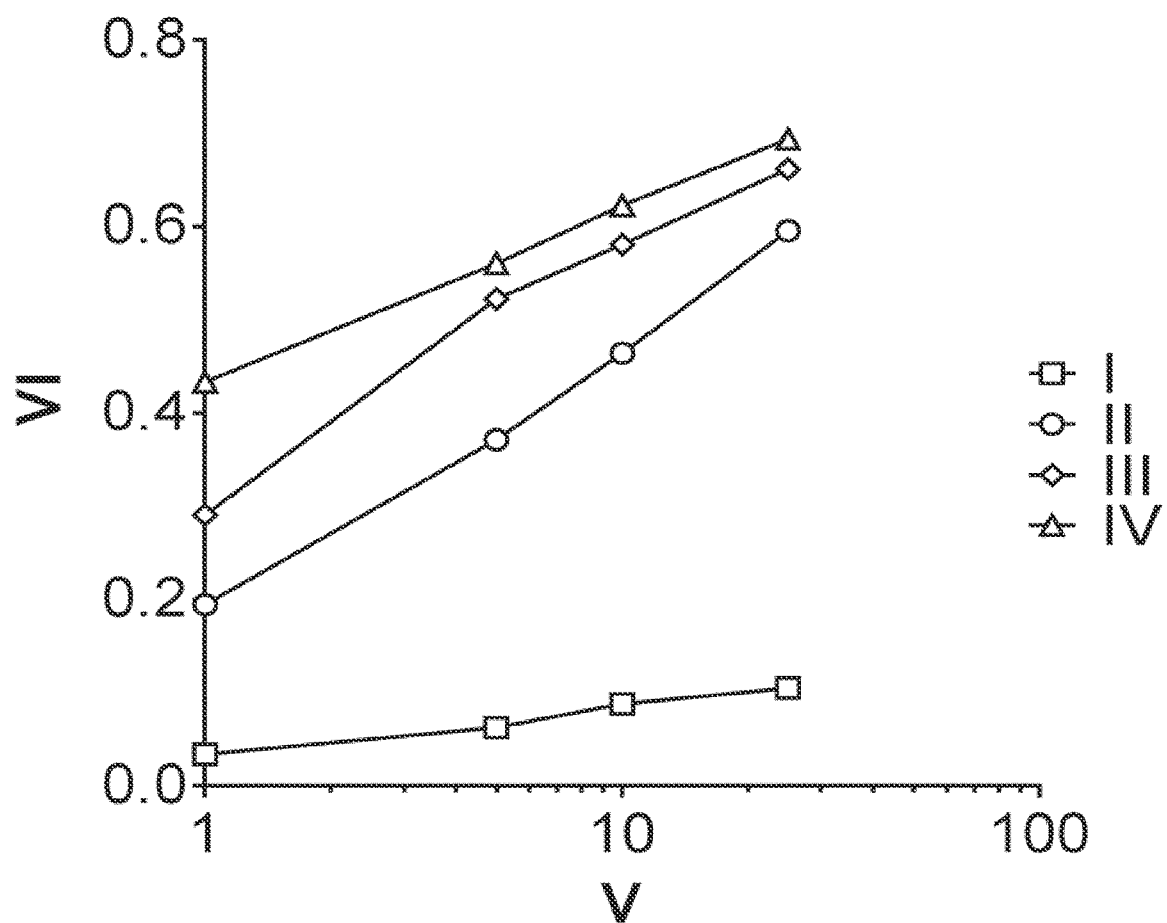
FIG. 36: Delivery of type I Interferon response inducing proteins via the bacterial T3SS and comparison to small molecular agonists of STING. Delivery of cyclic dinucleotide generating enzymes lead to type I IFN induction in a RAW IFN-reporter cell line. RAW reporter cells were infected with I: *Y. enterocolitica* ΔHOPEMT, or *Y. enterocolitica* ΔHOPEMT encoding on a pBadMycHisA derived plasmid II: YopE$_{1-138}$—Anemonae cGAS, III: YopE$_{1-138}$—human cGAS$_{161-522}$, IV: YopE$_{1-138}$—murine RIG1 CARD domains 1-218). A titration of the bacteria added to the cells (V: indicated as MOI) was performed, and IFN stimulation was assessed based on activity of secreted alkaline phosphatase (VI: OD650) which is under the control of the I-ISG54 promoter which is comprised of the IFN-inducible ISG54 promoter enhanced by a multimeric ISRE.
Figure 37:
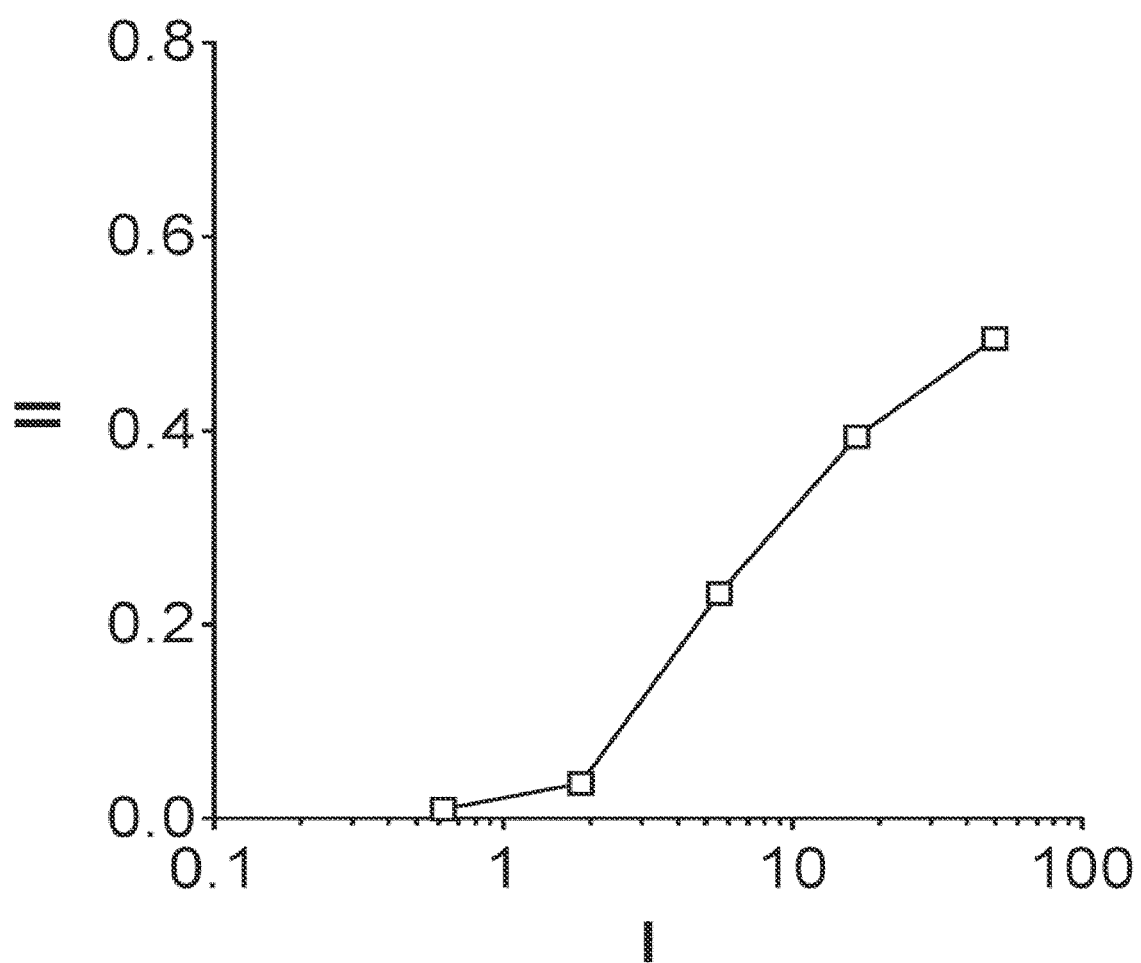
FIG. 37: Delivery of type I Interferon response inducing proteins via the bacterial T3SS and comparison to small molecular agonists of STING. Delivery of a cyclic dinucleotide lead to type I IFN induction in a RAW IFN-reporter cell line. RAW reporter cells were treated with the small molecular STING agonist 2'3'-c-di-AM(PS)2 (Rp,Rp). A titration of the compound (I: indicated as micromolar) was performed, and IFN stimulation was assessed based on activity of secreted alkaline phosphatase (II: OD650) which is under the control of the I-ISG54 promoter which is comprised of the IFN-inducible ISG54 promoter enhanced by a multimeric ISRE.
Figure 38:
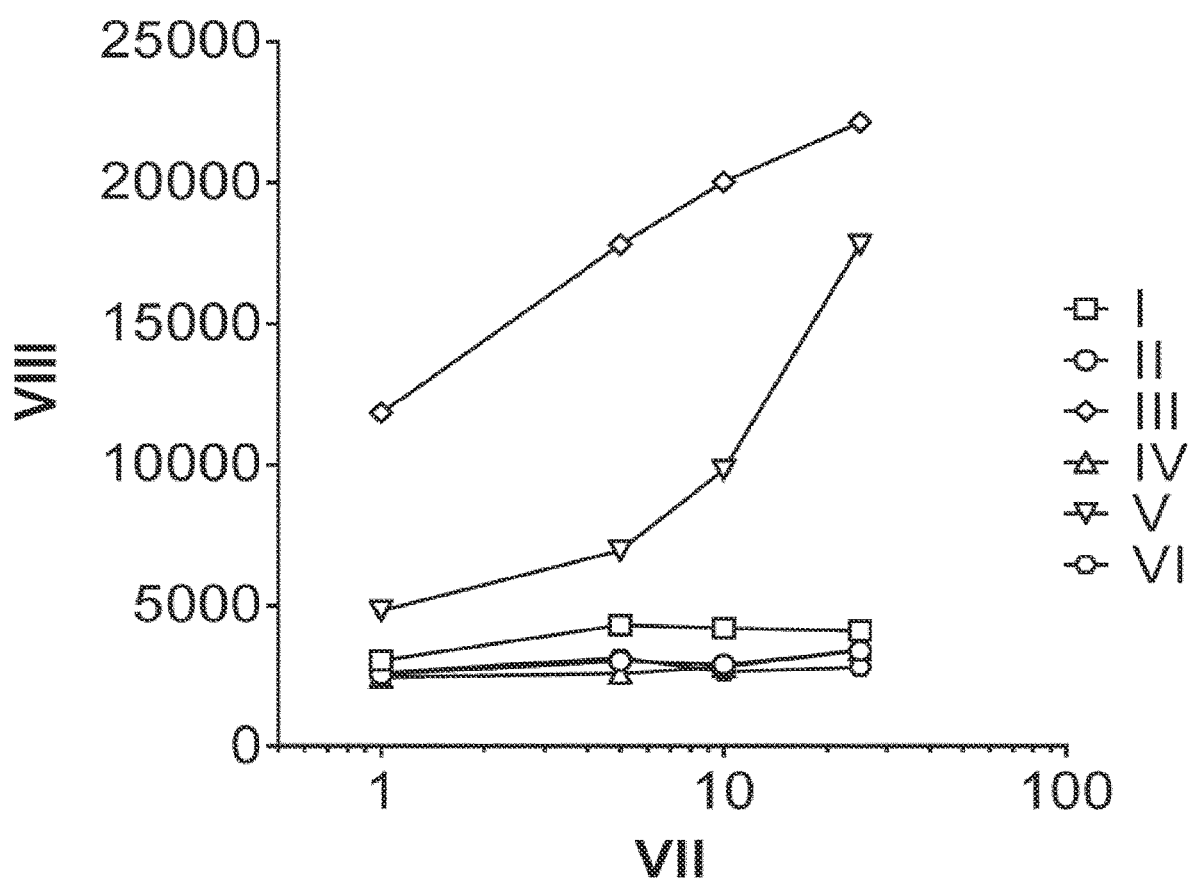
FIG. 38: Delivery of type I Interferon response inducing proteins via the bacterial T3SS and proof of T3SS dependency-RIG1 and MAVS. Delivery of RIG1 CARD domains or MAVS CARD fused to YopE$_{1-138}$ lead to type I IFN induction in a RAW IFN-reporter cell line, which is strictly T3SS dependent. RAW reporter cells were infected with I: *Y. enterocolitica* ΔHOPEMT, or II: *Y. enterocolitica* ΔHOPEMT-yopB, or *Y. enterocolitica* ΔHOPEMT encoding on a pBadMycHisA derived plasmid III: YopE$_{1-138}$—murine RIG1 CARD domains$_{1-246}$, V: YopE$_{1-138}$—human MAVS CARD$_{1-100}$ or *Y. enterocolitica* ΔHOPEMT-yopB encoding on a pBadMycHisA derived plasmid IV: YopE$_{1-138}$—murine RIG1 CARD domains$_{1-246}$, VI: YopE$_{1-138}$—human MAVS CARDs$_{1-100}$. A titration of the bacteria added to the cells (VII: indicated as MOI) was performed for each strain, and IFN stimulation was assessed based on activity of secreted lucia luciferase (VIII: OD650) which is under the control of the I-ISG54 promoter which is comprised of the IFN-inducible ISG54 promoter enhanced by a multimeric ISRE.
Figure 39:
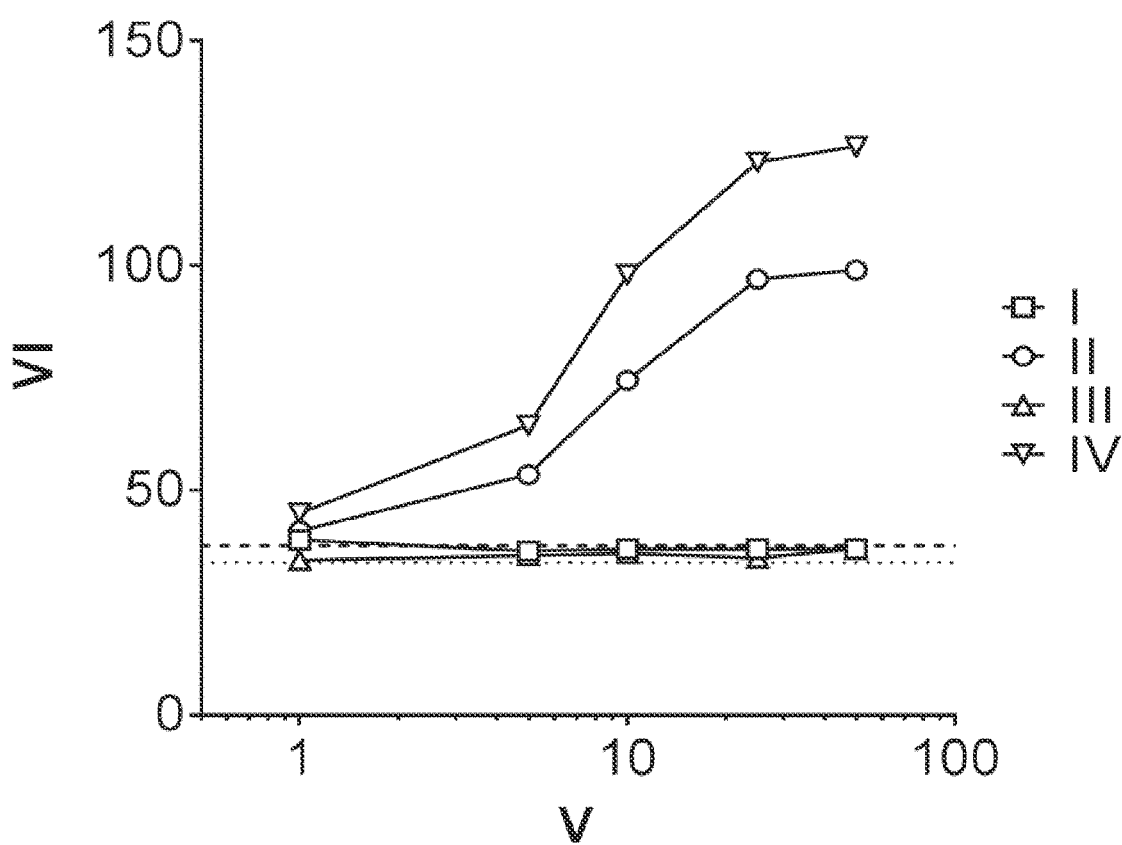
FIG. 39: Delivery of type I Interferon response inducing proteins via the bacterial T3SS in crude cell mixture from tumor isolate—RIG1. Delivery of RIG1 CARD domains fused to YopE$_{1-138}$ lead to type I IFN induction in crude tumor isolate. Wildtype Balb/C mice allografted s.c. with EMT6 breast cancer cells were sacrificed when tumor had reached a volume of >200 mm$^3$. Tumors were mashed, digested and seeded as single-cell suspension into 24-well plates. Such cells from two different tumors were infected with I and III: *Y. enterocolitica* ΔHOPEMT, or II and IV: *Y. enterocolitica* ΔHOPEMT encoding on a pBadMycHisA derived plasmid YopE$_{1-138}$—murine RIG1 CARD domains$_{1-246}$. A titration of the bacteria added to the cells (V: indicated as MOI) was performed for each strain, and IFN stimulation was assessed using an ELISA on Interferon beta (VI: picogram/millilitre). Dashed lines indicated untreated corresponding tumors, I/II and III/IV are each cells derived from the same tumor.
Figure 40:
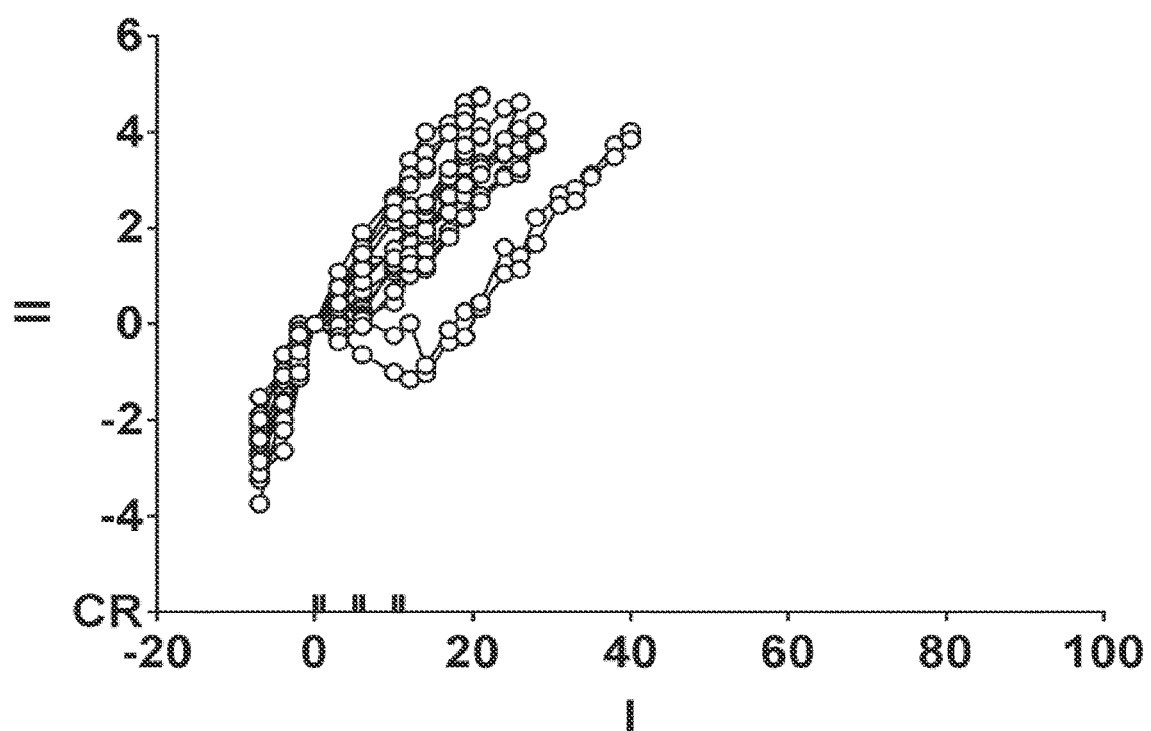
FIG. 40: Tumor progression in wildtype Balb/C mice allografted s.c. with EMT6 breast cancer cells. Wildtype Balb/C mice allografted s.c. with EMT6 breast cancer cells were intratumorally injected with PBS once the tumor had reached a size of 60-130 mm3. The day of the first intratumoral injection of PBS was defined as day 0, treatments were performed on d0, d1, d5, d6, d10 and d11. Tumor volume was measured over the following days (I: day −11 to day 80 post first injection of bacteria) with calipers. The relative tumor volume (tumor volume at corresponding day divided by tumor volume at d0) as mm$^3$, is indicated log-2 transformed (II) for each mouse. CR is complete remission.
Figure 41:
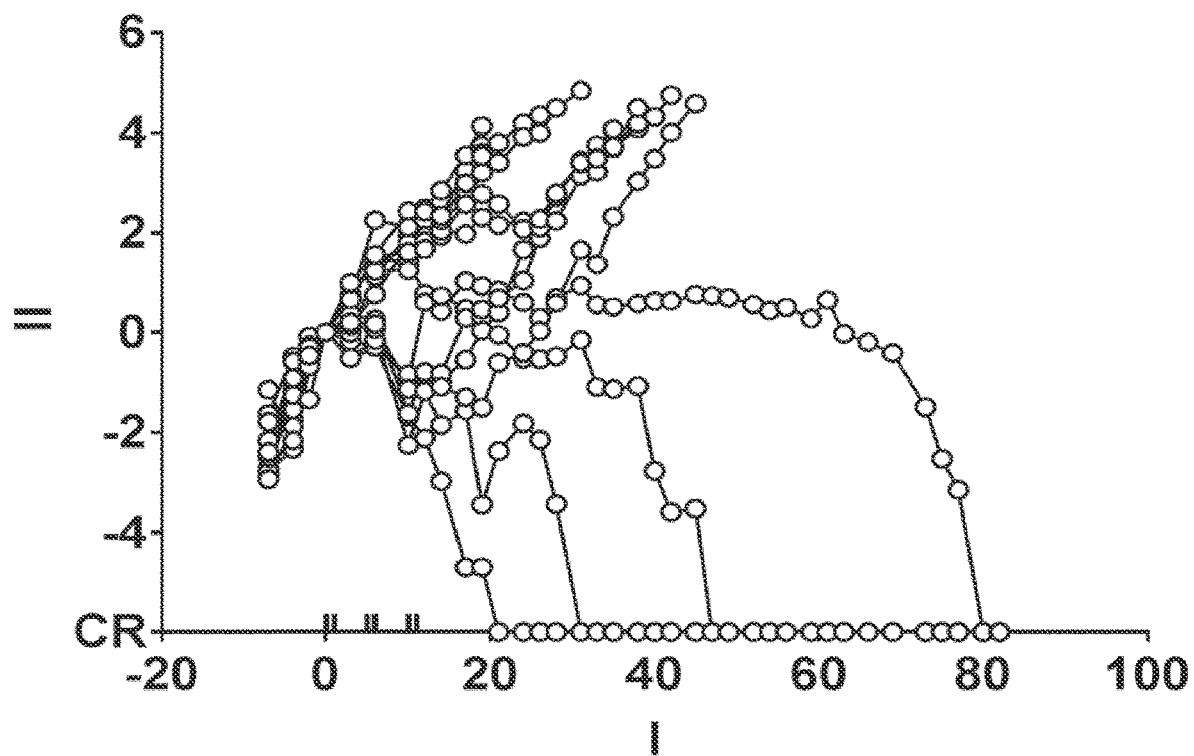
FIG. 41: Tumor progression in wildtype Balb/C mice allografted s.c. with EMT6 breast cancer cells. Wildtype Balb/C mice allografted s.c. with EMT6 breast cancer cells were intratumorally injected with 7.5*10$^7$ *Y. enterocolitica* dHOPEMT once the tumor had reached a size of 60-130 mm3. The day of the first intratumoral injection of bacteria was defined as day 0, treatments were performed on d0, d1, d5, d6, d10 and d11. Tumor volume was measured over the following days (I: day −11 to day 80 post first injection of bacteria) with calipers. The relative tumor volume (tumor volume at corresponding day divided by tumor volume at d0) as mm$^3$, is indicated log-2 transformed (II) for each mouse. CR is complete remission.

For further experiments, we cloned human cGAS amino acids 161-522 (Uniprot Nr. Q8N884 and SEQ ID No. 115; producing 2',3' cGAMP)[57], for expression and translocation by bacteria. Murine B16F10 melanoma and murine RAW macrophage reporter cells for type I IFN stimulation are based on activity of secreted alkaline phosphatase, which is under the control of the I-ISG54 promoter, which is comprised of the IFN-inducible ISG54 promoter enhanced by a multimeric ISRE. Reporter cells were infected with various amounts (MOI) of bacterial strains expressing from a pBadMycHisA derived plasmid (pBad_Si2) and translocating the YopE$_{1-138}$—human cGAS$_{161-522}$ and showed to dose-dependently induce a type I IFN response in the reporter cell line, as well as a bacterial strain expressing from a pBadMycHisA derived plasmid (pBad_Si2) and translocating YopE$_{1-138}$—Anemonae cGAS, YopE$_{1-138}$—Anemonae cGAS$_{60-422}$, YopE$_{1-138}$—Listeria CdaA$_{101-273}$, YopE$_{1-138}$—V. cholerae DncV or YopE$_{1-138}$—B. cereus DisA-like protein (FIG. 32-33). Strongest activation was observed with YopE$_{1-138}$—human cGAS$_{161-522}$, followed by YopE$_{1-138}$—Anemonae cGAS, YopE$_{1-138}$—Anemonae cGAS$_{60-422}$. Interestingly, the shorter Anemonae cGAS$_{60-422}$ variant was slightly more active. YopE$_{1-138}$—Listeria CdaA$_{101-273}$, YopE$_{1-138}$—V. cholerae DncV or YopE$_{1-138}$—B. cereus DisA-like protein as well exhibited dose-dependent IFN activation, albeit to a lesser extend than cGAS proteins (FIG. 32-33).

Delivery of MAVS Via the Bacterial T3SS for Induction of a Type I IFN Response

Cytosolic nucleic acids are sensed by receptor as the RIG-1-like receptor (RLR) family members that detect pathogen-derived RNA in the cytosol [56]. RIG-1 and MDA5 consist of two N-terminal CARD domains and a central (DExD/H) helicase domain sensing specific nucleotides [56]. Binding to stimulatory RNA induces a structural rearrangement in RIG-I (and MDA5) that liberates its CARDs for subsequent association with unanchored K63-linked ubiquitin chains to form oligomers [56] (and in case of MDA5 to filament formation [56]). Oligomerized CARD domains of RIG-I and MDA5 interact with the CARD domain of MAVS. This interaction promotes the polymerization of the single CARD domain of MAVS, which induces downstream signaling ultimately leading to induction of type I IFN genes [56].

We generated bacterial strains (based on Y. enterocolitica ΔHOPEMT) expressing the N-terminal CARD domains of MAVS of human origin fused to a N-terminal bacterial secretion signal for delivery by the T3SS, specifically YopE$_{1-138}$. Delivery of the fusion protein YopE$_{1-138}$—MAVS CARD was assessed by a standard in vitro secretion assay and functionality of delivered proteins were assessed on a reporter cell line for type I IFN induction. Murine B16F10 melanoma or murine RAW macrophage reporter cells for type I IFN stimulation are based on activity of secreted alkaline phosphatase, which is under the control of the I-ISG54 promoter, which is comprised of the IFN-inducible ISG54 promoter enhanced by a multimeric ISRE. Reporter cells were infected with various amounts (MOI) of

*Y. enterocolitica* ΔHOPEMT expressing from a pBadMycHisA derived plasmid (pBad_Si2) and translocating the YopE$_{1-138}$—human MAVS CARD protein. Murine N-terminal CARD domain of MAVS showed to dose-dependently induce a type I IFN response in the reporter cell line (FIG. 30-31), while the bacterial background strain (*Y. enterocolitica* ΔHOPEMT) was not capable of inducing such a response (FIG. 30-31). Human cGAS and murine RIG-1 CARD domains induced a type I IFN response in a similar way in the murine reporter cell lines (FIG. 30-31), with RIG-1 showing highest activation potential, followed by MAVS and cGAS.

Thus, the fusion to the N-terminal secretion signal of bacteria has led to successful deliver of bacterially expressed human $YopE_{1-138}$—MAVS CARD protein and has not prevented the folding and function of the MAVS CARD domain within the eukaryotic cell. This implies, that the YopE-fused MAVS CARD domain is still able to multimerize themselves and induce multimerization of MAVS, which is surprising. Even more surprisingly, MAVS CARD only had been shown to fail to induce IFN downstream signalling [64], whereat we found YopE-fused MAVS CARD domain to activate the type I IFN pathway strongly.

Furthermore, the C-terminal transmembrane domain of MAVS has been shown to be essential for MAVS function upon DNA transfection and MAVS CARD domain alone had been shown to be inactive when expressed from transfected DNA constructs [66]. Even more, MAVS CARD fused to the transmembrane region, which has the capacity when expressed from transfected DNA or as purified protein to activate a type I IFN response [64,66] was shown to rely on endogenous MAVS, which it started aggregating and thus activating [64]. We could show by using a MAVS KO cell line (FIG. 52), that bacterially delivered YopE-fused MAVS CARD is active without endogenous MAVS present on mitochondria. That YopE-fused MAVS CARD is able to multimerize and activate downstream partners without transmembrane domain and furthermore without endogenous MAVS is surprising.

Benchmarking to Small Molecular STING Agonist for Induction of a Type I IFN Response In Vitro Cyclic dinucleotides are well-known agonists of the STING pathway, lading to downstream induction of type I IFN signaling. STING agonists have been described in literature [59] and have been found to mainly act on immune cells, with highest activity shown on dendritic cells [59]. In contrast, RLR signaling was found to be more ubiquitously expressed [63]. We thus compared *Y. enterocolitica* ΔHOPEMT bacteria delivering cyclic dinucleotide generating enzymes ($YopE_{1-138}$—Anemonae cGAS and $YopE_{1-138}$—human cGAS) or bacteria delivering $YopE_{1-138}$—murine RIG1 CARD $domains_{1-218}$ to the small molecular STING agonist 2'3'-c-di-AM(PS)2 (Rp,Rp) (similar to ADU-S100 from Aduro Biotech) on immune cells (RAW macrophage IFN reporter cells) and non-immune cells (B16F1 melanoma IFN reporter cells) for the Interferon inducing potential. On immune cells, a similar activating potential was observed for the small molecular STING agonist 2'3'-c-di-AM(PS)2 (Rp,Rp) and all three tested bacterial strains delivering a protein ($YopE_{1-138}$—Anemonae cGAS, $YopE_{1-138}$—human cGAS or $YopE_{1-138}$—murine RIG1 CARD $domains_{1-218}$) while the *Y. enterocolitica* ΔHOPEMT bacteria not delivering a protein showed a very weak activating potential (FIG. 34-37). On non-immune cells (cancer cells, melanoma), bacterially delivered $YopE_{1-138}$—murine RIG1 CARD $domains_{1-218}$, bacterially delivered $YopE_{1-138}$—Anemonae cGAS and $YopE_{1-138}$—human cGAS worked equally well and almost outperformed small-molecular STING agonist, highlighting more ubiquitous presence of RLR as compared to STING (FIG. 34-37).

Strict T3SS-Dependency of Bacterially Delivered RIG1 CARD Domains or MAVS CARD

In order to proof strict T3SS dependent transport, one of the T3SS proteins forming the translocation pore into the eukaryotic cell membrane was deleted (YopB). Potential of such yopB deleted bacteria (called *Y. enterocolitica* ΔHOPEMT-yopB) expressing $YopE_{1-138}$—murine RIG1 CARD $domains_{1-246}$ or $YopE_{1-138}$—human MAVS $CARD_{1-100}$ was assessed on a RAW macrophage IFN reporter cell line and compared to yopB expressing *Y. enterocolitica* ΔHOPEMT bacteria expressing as well $YopE_{1-138}$—murine RIG1 CARD $domains_{1-246}$ or $YopE_{1-138}$—human MAVS $CARD_{1-100}$ (FIG. 38). While yopB-wildtype bacteria expressing $YopE_{1-138}$—murine RIG1 CARD $domains_{1-246}$ or $YopE_{1-138}$—human MAVS $CARD_{1-100}$ exhibited dose-dependent activation of a type I IFN response, yopB-deleted strains expressing the same proteins failed to induce such a response above the background level induced by the background abacterial strain not expressing a protein to be delivered (FIG. 38). This validates, that $YopE_{1-138}$—murine RIG1 CARD $domains_{1-246}$ or $YopE_{1-138}$—human MAVS $CARD_{1-100}$ are both transported through the T3SS needle into target eukaryotic cells.

Induction of Type I IFN Response in Crude Tumor Isolate

In order to verify that type I IFN response can be initiated within the tumor microenvironment, we performed analysis on crude tumor isolates infected ex vivo with bacterial strains followed by ELISA on Interferon beta. Wildtype Balb/C mice allografted s.c. with EMT6 breast cancer cells were sacrificed when tumor had reach a volume of. Tumors were mashed, digested and seeded as single-cell suspension into 24-well plates. Such cells from two different tumors were ledt uninfected (dashed lines in FIG. 39) or infected with *Y. enterocolitica* ΔHOPEMT, or *Y. enterocolitica* ΔHOPEMT encoding on a pBadMycHisA derived plasmid $YopE_{1-138}$—murine RIG1 CARD $domains_{1-246}$. IFN stimulation was assessed using an ELISA on Interferon beta and showed that while *Y. enterocolitica* ΔHOPEMT failed to induce Interferon beta secretion, infection with *Y. enterocolitica* ΔHOPEMT encoding $YopE_{1-138}$—murine RIG1 CARD $domains_{1-246}$ resulted in dose-dependent Interferon beta secretion by the crude tumor isolate of two different tumors (FIG. 39). This validates, that bacterially delivered RIG1 CARD domains are capable of inducing Interferon production in a mixed cell population consisting of cancer cells, immune cells and all other cells within the tumor microenvironment.

Efficacy of *Y. enterocolitica* ΔHOPEMT Delivering RIG1 CARDs or cGAS in Delaying Tumor Progression In order to assess the impact of $YopE_{1-138}$—murine RIG1 CARD $domains_{1-246}$ and $YopE_{1-138}$—human cGAS delivered to tumor cells in vivo, we performed studies in wildtype Balb/C mice allografted s.c. with EMT6 breast cancer cells. Mice were intratumorally (it) injected with PBS (FIG. 40) or $7.5*10^7$ *Y. enterocolitica* ΔHOPEMT, *Y. enterocolitica* ΔHOPEMT+$YopE_{1-138}$ murine RIG1 CARD $domains_{1-246}$ or *Y. enterocolitica* ΔHOPEMT+$YopE_{1-138}$ human cGAS once the tumor had reached a size of about 60-130 mm3. The day of the first it injection of bacteria was defined as day 0. Mice were it injected on d0, d1, d5, d6, d10 and d11. Tumor volume was measured over the following days with calipers. Treatment with *Y. enterocolitica* ΔHOPEMT alone showed an impact on tumor volume progression, with 4/14 mice exhibiting complete tumor regression (FIG. 41). *Y. entero-*

Figure 42:
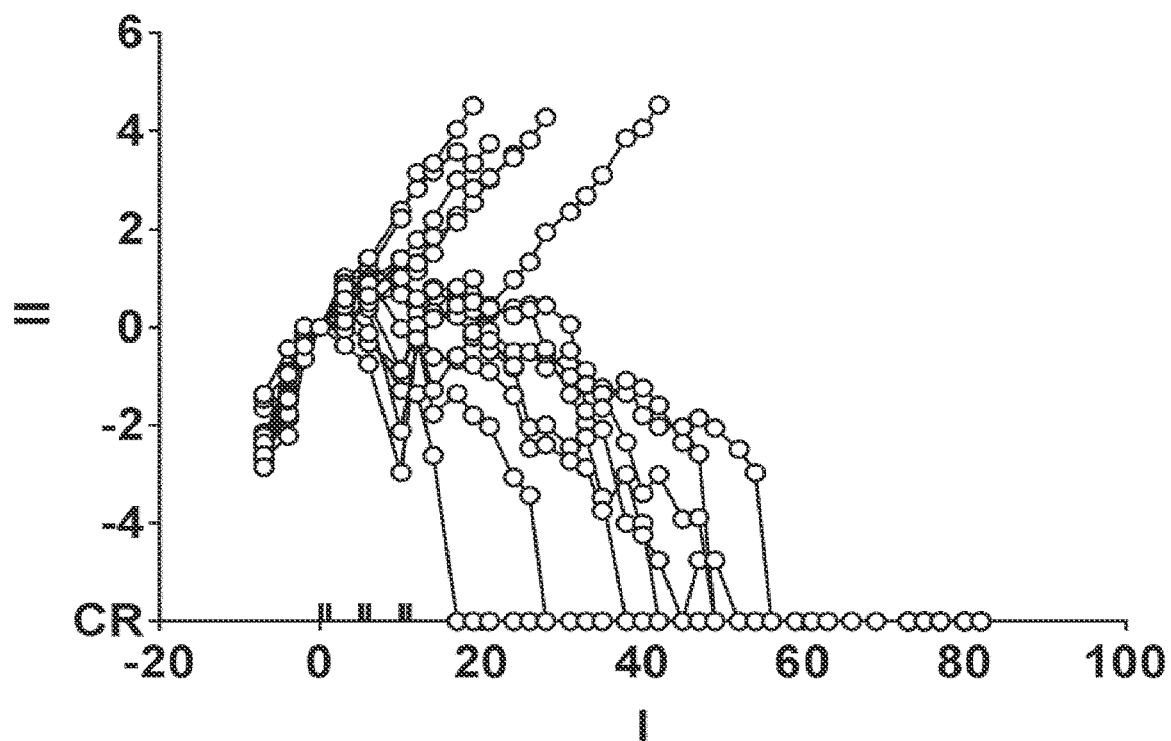
FIG. 42: Tumor progression in wildtype Balb/C mice allografted s.c. with EMT6 breast cancer cells. Wildtype Balb/C mice allografted s.c. with EMT6 breast cancer cells were intratumorally injected with 7.5*10$^7$ *Y. enterocolitica* dHOPEMT encoding on a pBadMycHisA derived plasmid YopE$_{1-138}$—murine RIG1 CARD domains$_{1-246}$ once the tumor had reached a size of 60-130 mm3. The day of the first intratumoral injection of bacteria was defined as day 0, treatments were performed on d0, d1, d5, d6, d10 and d11. Tumor volume was measured over the following days (I: day −11 to day 80 post first injection of bacteria) with calipers. The relative tumor volume (tumor volume at corresponding day divided by tumor volume at d0) as mm$^3$, is indicated log-2 transformed (II) for each mouse. CR is complete remission.
Figure 43:
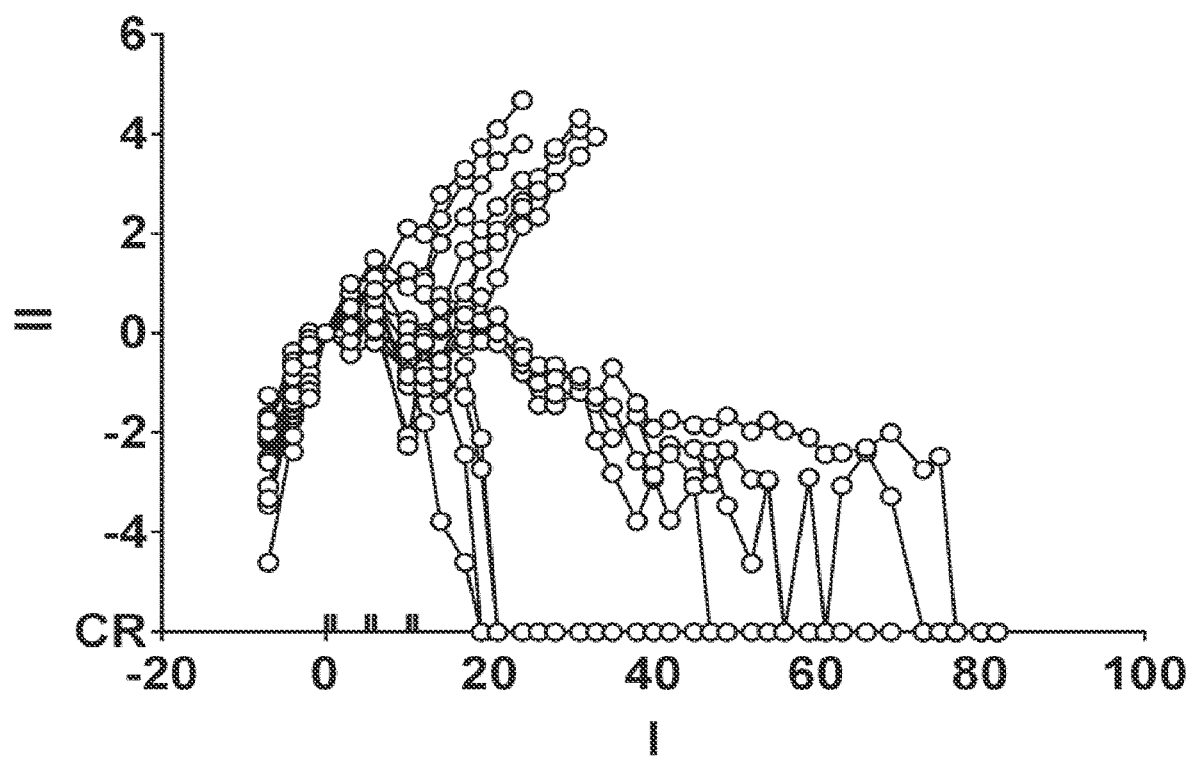
FIG. 43: Tumor progression in wildtype Balb/C mice allografted s.c. with EMT6 breast cancer cells. Wildtype Balb/C mice allografted s.c. with EMT6 breast cancer cells were intratumorally injected with 7.5*10$^7$ *Y. enterocolitica* dHOPEMT encoding on a pBadMycHisA derived plasmid YopE$_{1-138}$—human cGAS$_1$61-522 once the tumor had reached a size of 60-130 mm3. The day of the first intratumoral injection of bacteria was defined as day 0, treatments were performed on d0, d1, d5, d6, d10 and d11. Tumor volume was measured over the following days (I: day −11 to day 80 post first injection of bacteria) with calipers. The relative tumor volume (tumor volume at corresponding day divided by tumor volume at d0) as mm$^3$, is indicated log-2 transformed (II) for each mouse. CR is complete remission.

*colitica* ΔHOPEMT delivering a protein inducing a type I IFN response, being it RIG1 CARDS or cGAS, was found to lead to a more pronounced impact on tumor progression with each 8/14 (RIG1 CARDs) or 8/15 (cGAS) mice showing complete and durable tumor regression (FIG. 42-43). These findings highlight that such bacteria and their T3SS can be employed for very significant interference with tumor progression and that delivery type I IFN inducing proteins is well-suited to induce regression of primary tumor.

Figure 44:
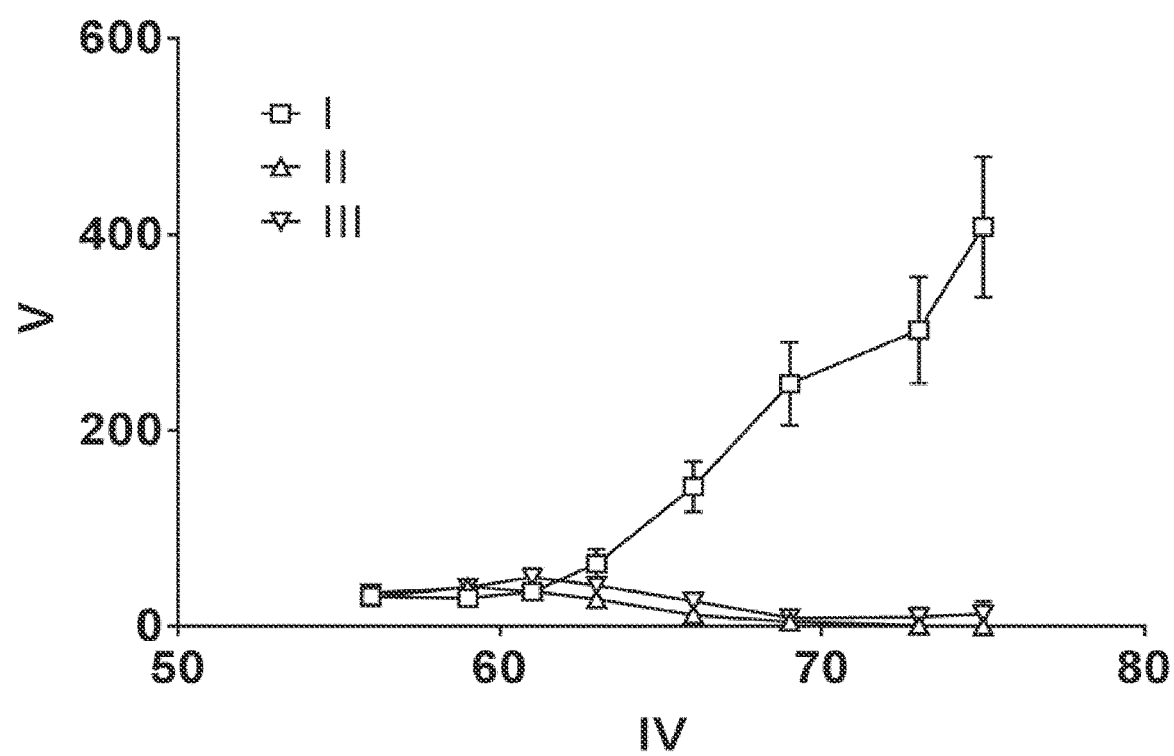
FIG. 44: Tumor progression in wildtype Balb/C mice rechallenged s.c. on the contralateral side with EMT6 breast cancer cells after a first complete remission. Wildtype Balb/C mice allografted s.c. with EMT6 breast cancer cells were treated as described above (FIG. 40-43) intratumorally with 7.5*10$^7$ II: *Y. enterocolitica* dHOPEMT encoding on a pBadMycHisA derived plasmid YopE$_{1-138}$—murine RIG1 CARD domains$_{1-246}$, III: *Y. enterocolitica* dHOPEMT encoding on a pBadMycHisA derived plasmid YopE$_{1-138}$—human cGAS$_{161-522}$, once the tumor had reached a size of 60-130 mm3. The day of the intratumoral injection of bacteria was defined as day 0. Mice with a complete tumor regression (or I: naïve mice as control) were allografted s.c. with EMT6 breast cancer cells on the contralateral flank. Tumor volume was measured over the following days (IV: up to day 80 post first injection of bacteria) with calipers. The absolute tumor volume is indicated (V) as mm³ for each mouse.

Mice with complete tumor regression were further observed up to day 65 after initial tumor allografting, followed on day 65 by a rechallenge with EMT6 breast cancer cells on the contralateral flank to assess immune-mediated memory and systemic activity towards these cancer cells. In this rechallenge study no additional treatment was administered and mice were simply observed for tumor progression on contralater flank and compared to naïve mice (mice without previous exposure to EMT6 breast cancer cells, but all other parameters as age being identical). While in naïve mice tumor cells s.c. allografted resulted in tumor growth, all mice with a previously treated EMT6 tumor on the opposite flank with complete regression were found to be protected from tumor growth (FIG. 44). Remarkably, tumors in mice with a previous complete regression induced by bacterial treatment on contralater flank started growing for several days and reached volumes of up to >100 mm3 (with peak volume at around day 10 after second grafting) and shrinkage thereafter (FIG. 44). This lag-period may be indicative of an adaptive immune system response needing several days before being fully mounted.

Figure 46:
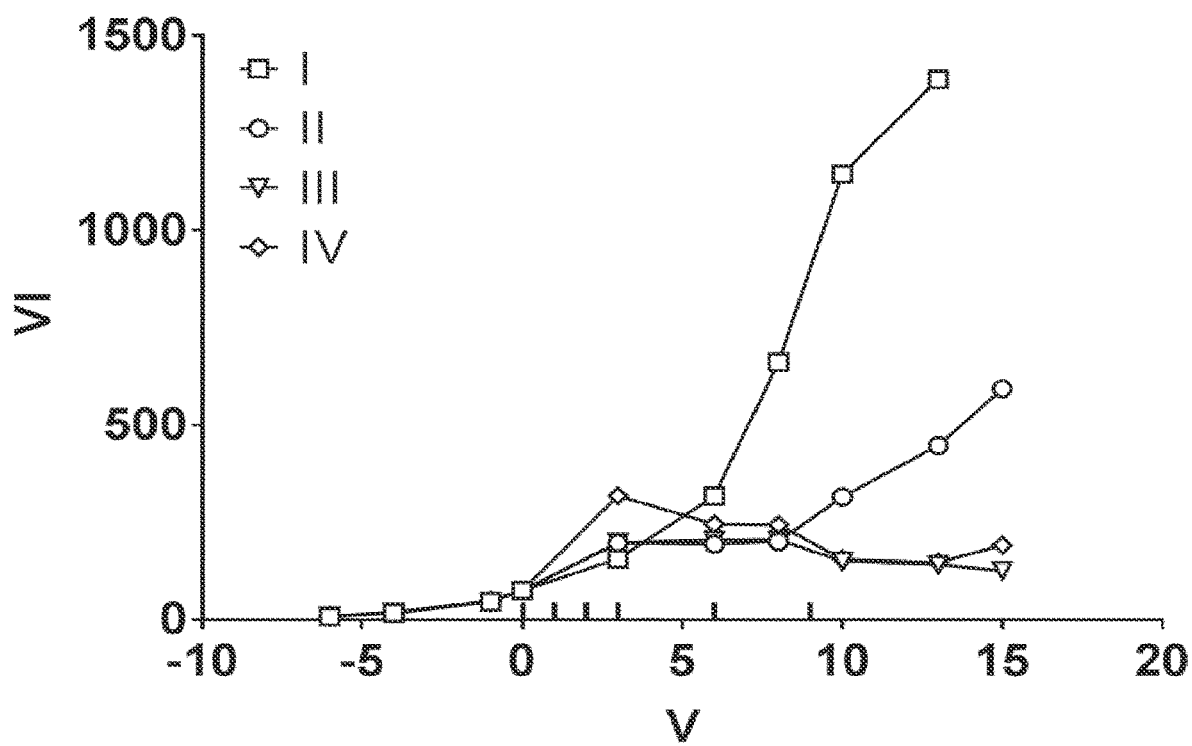
FIG. 46: Tumor progression in wildtype C57BL/6 mice allografted s.c. with B16F10 melanoma cells. Wildtype C57BL/6 mice allografted s.c. with B16F10 melanoma cells were intratumorally injected with I: PBS, or $7.5*10^7$ II: *Y. enterocolitica* dHOPEMT, III: encoding on a pBadMycHisA derived plasmid YopE$_{1-138}$—murine RIG1 CARD domains$_{1-246}$, IV: *Y. enterocolitica* dHOPEMT encoding on a pBadMycHisA derived plasmid YopE$_{1-38}$-human cGAS$_{161-522}$ once the tumor had reached a size of 60-130 mm3. The day of the first intratumoral injection of bacteria was defined as day 0, treatments were performed on d0, d1, d2, d3, d6 and d9. Tumor volume was measured over the following days (V: days) with calipers. The mean tumor volume is indicated (VI) as mm³.
Figure 47:
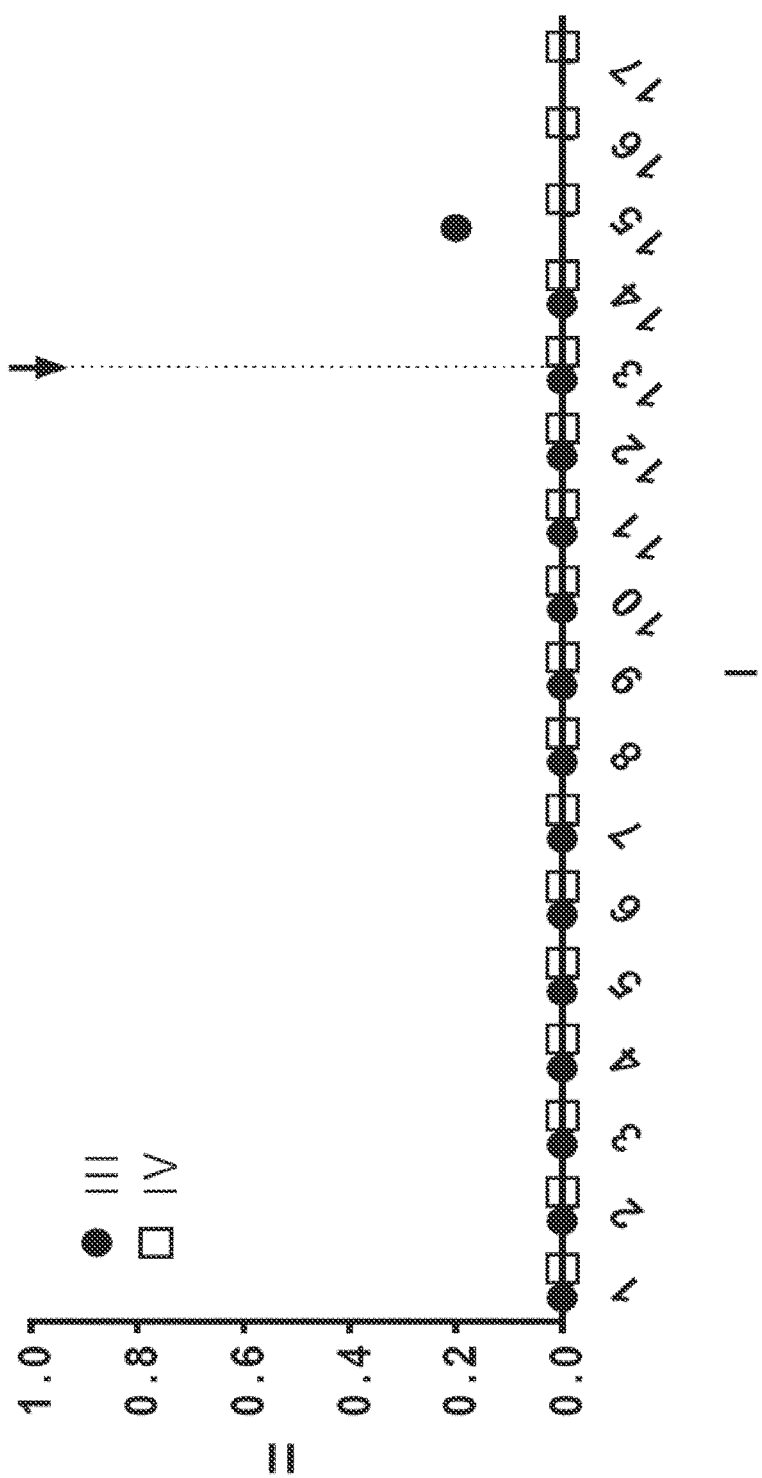
FIG. 47: Biodistribution of *Y. enterocolitica* subsp. *palearctica* in the B16F10 melanoma mouse allograft model: scoring for physical appearance. I: Days, II: fraction of mice with a score, III: *Y. enterocolitica* MRS40 wt, IV: *Y. enterocolitica* ΔyopH,O,P,E,M,T. The arrow indicates the day of i.v. injection of $2\times10^5$ bacteria.
Figure 48:
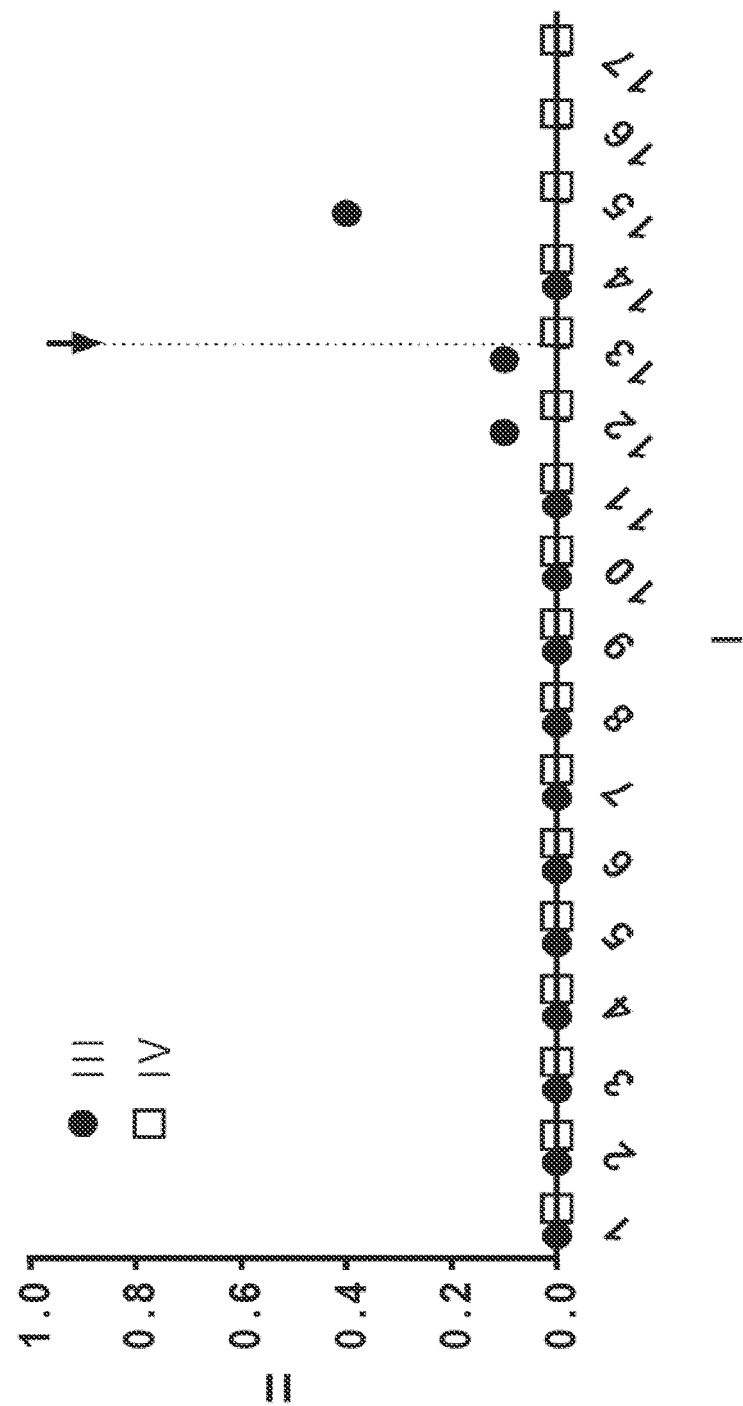
FIG. 48: Biodistribution of *Y. enterocolitica* subsp. *palearctica* in the B16F10 melanoma mouse allograft model: scoring for behavior. I: Days, II: fraction of mice with a score, III: *Y. enterocolitica* MRS40 wt, IV: *Y. enterocolitica* ΔyopH,O,P,E,M,T. The arrow indicates the day of i.v. infection with $2\times10^5$ bacteria.
Figure 49:
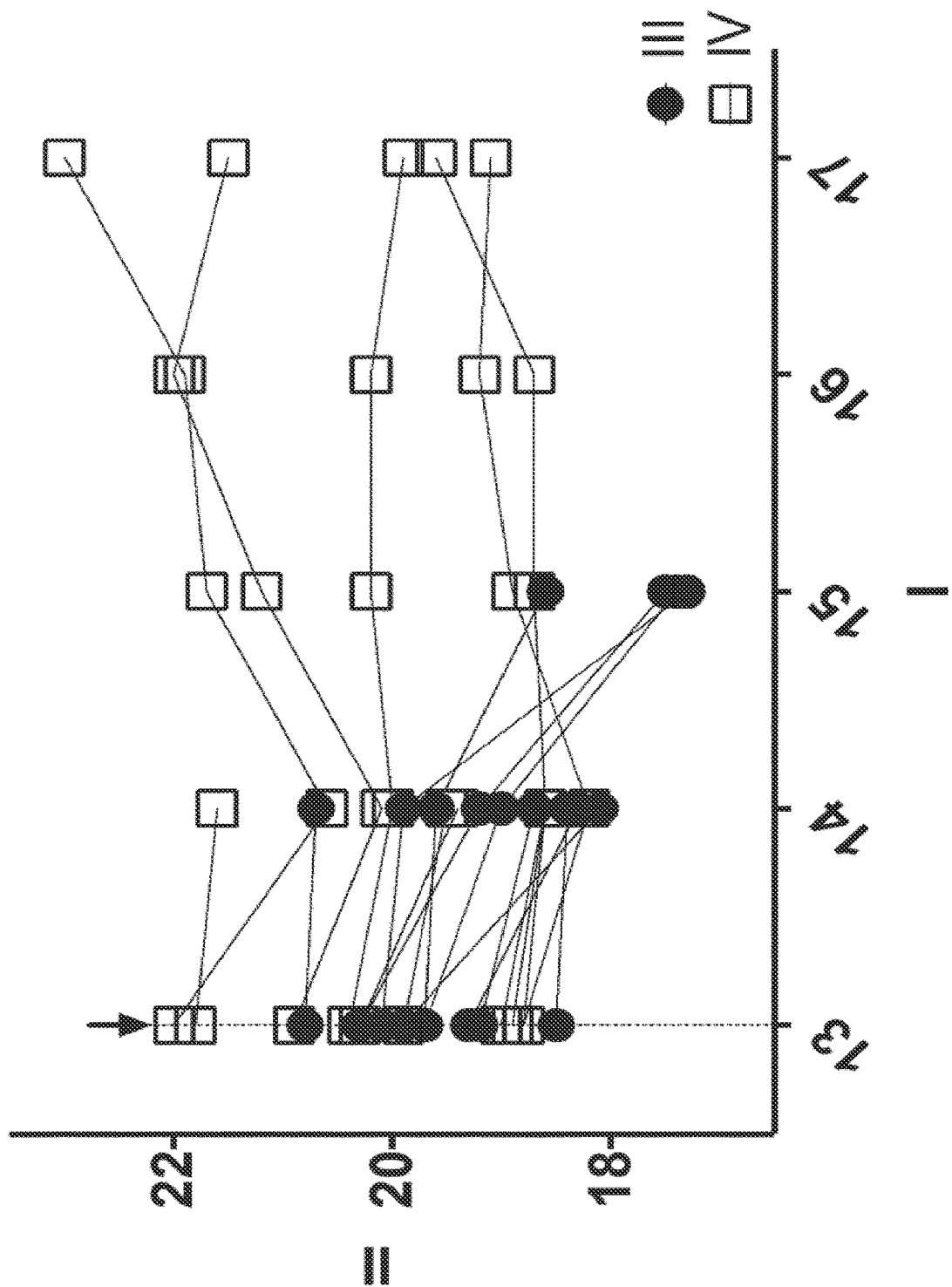
FIG. 49: Biodistribution of *Y. enterocolitica* subsp. *palearctica* in the B16F10 melanoma mouse allograft model: weights of mice. Weight of mice was assessed daily following i.v. infection with bacteria. I: Days, II: body weight in gram, III: *Y. enterocolitica* MRS40 wt, IV: *Y. enterocolitica* ΔyopH,O,P,E,M,T. The arrow indicates the day of i.v. infection with $2\times10^5$ bacteria.
Figure 50:
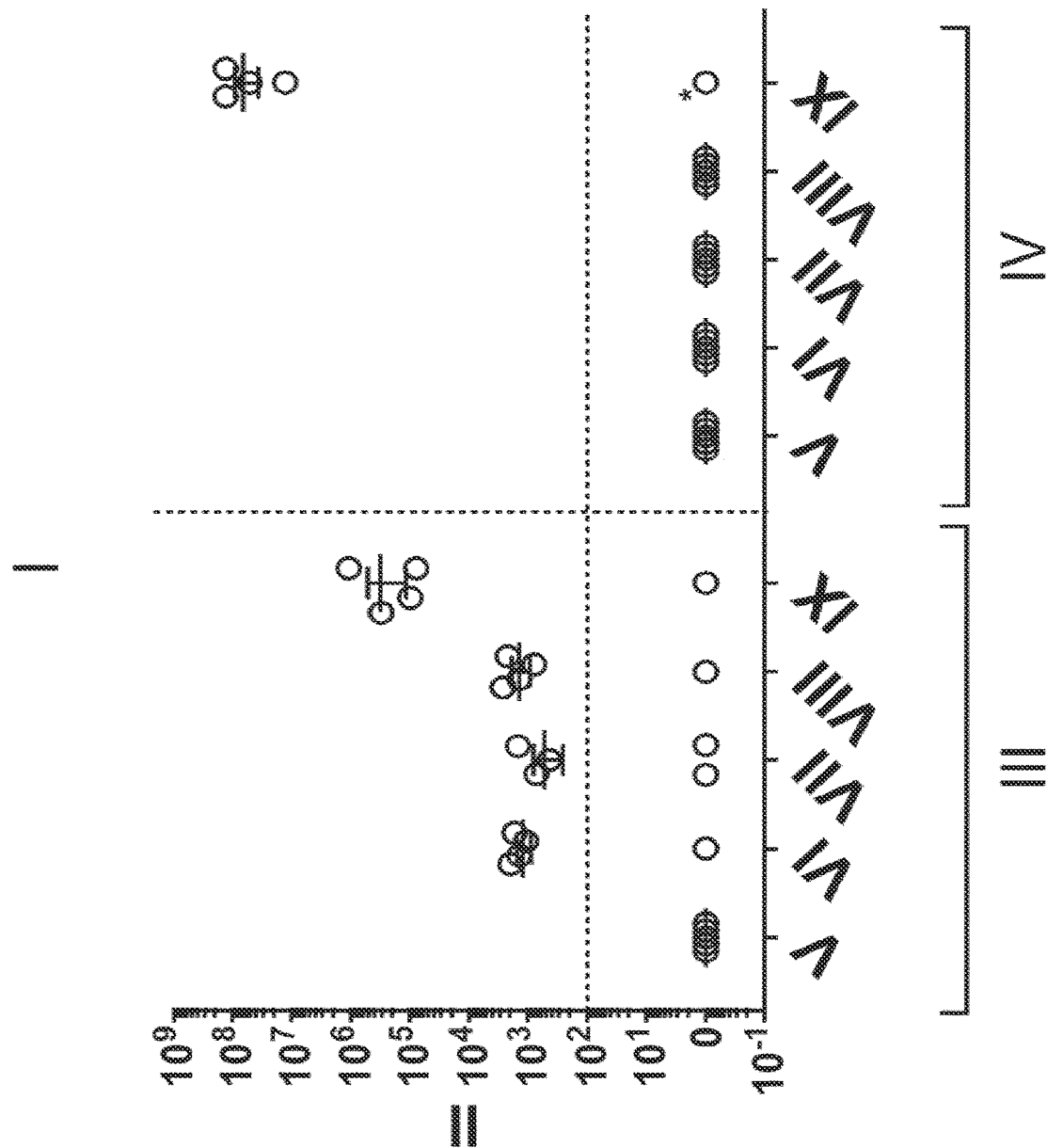
FIG. 50: Biodistribution of *Y. enterocolitica* subsp. *palearctica* in the B16F10 melanoma mouse allograft model: biodistribution of *Y. enterocolitica* ΔyopH,O,P,E,M,T. Counts in the organs at the time indicated were assessed by organ homogenization, serial dilution and counting of resulting colony forming units (CFU). The day of the i.v. injection of bacteria was defined as day 0, all mice were treated i.p ith Desferal at d-1. I: *Y. enterocolitica* ΔyopH,O,P,E,M,T, II: CFU per gram tissue or ml of blood, III: day 1, IV: day 4, V: blood, VI: spleen, VII: liver, VIII: lung, IX: tumor. * indicates a mouse with no visible tumor.
Figure 51:
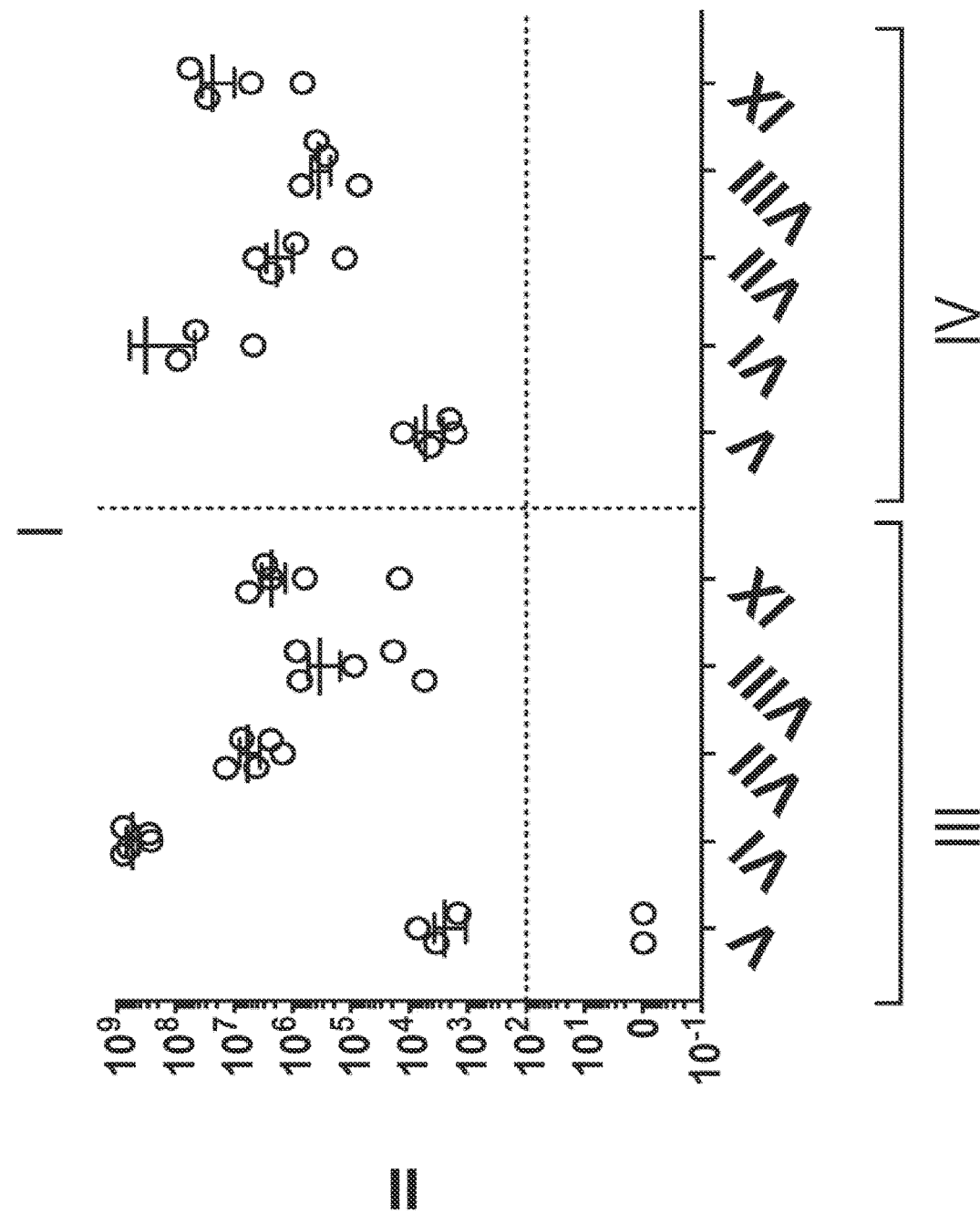
FIG. 51: Biodistribution of *Y. enterocolitica* subsp. *palearctica* in the B16F10 melanoma mouse allograft model: biodistribution of *Y. enterocolitica* MRS40 wt. Counts in the organs at the time indicated were assessed by organ homogenization, serial dilution and counting of resulting colony forming units (CFU). The day of the i.v. injection of bacteria was defined as day 0, all mice were treated i.p ith Desferal at d-1. I: *Y. enterocolitica* MRS40 wt, II: CFU per gram tissue or ml of blood, III: day 1, IV: day 4, V: blood, VI: spleen, VII: liver, VIII: lung, IX: tumor.
Figure 52:
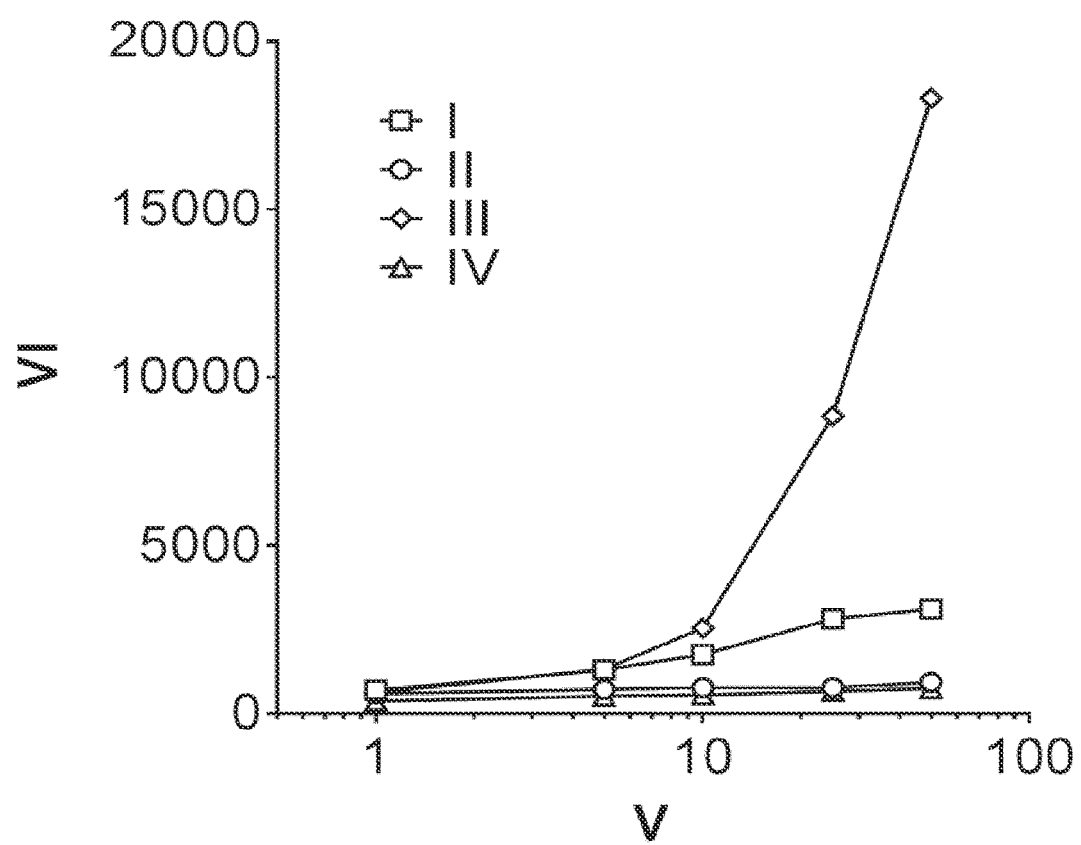
FIG. 52: Delivery of type I Interferon response inducing proteins via the bacterial T3SS—bacterially T3SS delivered MAVS works independent of endogenous MAVS. Delivery of via T3SS of MAVS CARD lead to type I IFN induction in a MAVS$^{KO}$ RAW macrophage IFN-reporter (luciferase) cell line. MAVS$^{KO}$ RAW macrophage reporter cells were infected with I: *Y. enterocolitica* ΔHOPEMT, or II: *Y. enterocolitica* ΔHOPEMT-yopB, III: *Y. enterocolitica* ΔHOPEMT encoding on a pBadMycHisA derived plasmid YopE$_{1-138}$—human MAVS CARD$_{1-100}$ or IV: *Y. enterocolitica* ΔHOPEMT-yopB encoding on a pBadMycHisA derived plasmid YopE$_{1-138}$—human MAVS CARD$_{1-100}$. A titration of the bacteria added to the cells (V: indicated as MOI) was performed for each strain, and IFN stimulation was assessed based on activity of luciferase (VI: RLU—relative luminescence units) which is under the control of the I-ISG54 promoter which is comprised of the IFN-inducible ISG54 promoter enhanced by a multimeric ISRE.

In further experiments to assess the impact of $YopE_{1-138}$—murine RIG1 CARD domains$_{1-246}$ and $YopE_{1-138}$—human cGAS delivered to tumor cells in vivo, we performed studies in wildtype C57BL/6 mice allografted s.c. with B16F10 melanoma cancer cells. Mice were intratumorally (it) injected with PBS or $7.5*10^7$ *Y. enterocolitica* ΔHOPEMT, *Y. enterocolitica* ΔHOPEMT+$YopE_{1-138}$ murine RIG1 CARD domains$_{1-246}$ or *Y. enterocolitica* ΔHOPEMT+$YopE_{1-138}$ human cGAS once the tumor had reached a size of about 75 mm3. The day of the first it injection of bacteria was defined as day 0. Mice were it injected on d0, d1, d2, d3, d6 and d9. Tumor volume was measured over the following days with calipers. Treatment with *Y. enterocolitica* ΔHOPEMT alone showed an impact on tumor volume progression, with 1/15 mice exhibiting complete tumor regression (FIG. 46). *Y. enterocolitica* ΔHOPEMT delivering a protein inducing a type I IFN response, being it RIG1 CARDS or cGAS, was found to lead to a very pronounced impact on tumor progression with each 5/15 (RIG1 CARDs) or 8/15 (cGAS) mice showing complete and durable tumor regression (FIG. 46). These findings highlight that such bacteria and their T3SS can be employed for very significant interference with tumor progression and that delivery type I IFN inducing proteins is well-suited to induce regression of primary tumor. Remarkably, especially in case of bacteria delivering $YopE_{1-38}$-human cGAS, an increase in tumor volume shortly after first administrations was observed comparing to PBS treated control, which may be induced by leukocyte influx into the tumor (pseudo-progression) induced by the intracellular delivery of the type I IFN inducing cGAS protein.

LIST OF REFERENCES

1 Hayes, C. S., Aoki, S. K. & Low, D. A. Bacterial contact-dependent delivery systems. *Annu Rev Genet* 44, 71-90, doi:10.1146/annurev.genet.42.110807.091449 (2010).

2 Cornelis, G. R. The type III secretion injectisome. *Nat Rev Microbiol* 4, 811-825, doi:nrmicro1526 [pii]10.1038/nrmicro1526 (2006).

3 Blanco-Toribio, A., Muyldermans, S., Frankel, G. & Fernandez, L. A. Direct injection of functional single-domain antibodies from *E. coli* into human cells. *PLoS One* 5, e15227, doi:10.1371/journal.pone.0015227 (2010).

4 Bichsel, C. et al. Direct reprogramming of fibroblasts to myocytes via bacterial injection of MyoD protein. *Cell Reprogram* 15, 117-125, doi:10.1089/cell.2012.0058 (2013).

5 Bichsel, C. et al. Bacterial delivery of nuclear proteins into pluripotent and differentiated cells. *PLoS One* 6, e16465, doi:10.1371/journal.pone.0016465 (2011).

6 Chamekh, M. et al. Delivery of biologically active anti-inflammatory cytokines IL-10 and IL-1ra in vivo by the *Shigella* type III secretion apparatus. *J Immunol* 180, 4292-4298 (2008).

7 Skurnik, M. & Wolf-Watz, H. Analysis of the yopA gene encoding the Yop1 virulence determinants of *Yersinia* spp. *Mol Microbiol* 3, 517-529 (1989).

8 Isberg, R. R., Voorhis, D. L. & Falkow, S. Identification of invasin: a protein that allows enteric bacteria to penetrate cultured mammalian cells. *Cell* 50, 769-778 (1987).

9 Mota, L. J. & Cornelis, G. R. The bacterial injection kit: type III secretion systems. *Ann Med* 37, 234-249, doi: R673752030212825 [pii]10.1080/07853890510037329 (2005).

10 Trosky, J. E., Liverman, A. D. & Orth, K. *Yersinia* outer proteins: Yops. *Cell Microbiol* 10, 557-565, doi:10.1111/j.1462-5822.2007.01109.x (2008).

11 Brenner, D. & Mak, T. W. Mitochondrial cell death effectors. *Curr Opin Cell Biol* 21, 871-877, doi:S0955-0674(09)00160-4 [pii]10.1016/j.ceb.2009.09.004 (2009).

12 Chalah, A. & Khosravi-Far, R. The mitochondrial death pathway. *Adv Exp Med Biol* 615, 25-45, doi:10.1007/978-1-4020-6554-5_3 (2008).

13 Fuchs, Y. & Steller, H. Programmed cell death in animal development and disease. *Cell* 147, 742-758, doi:S0092-8674(11)01283-9 [pii]10.1016/j.cell.2011.10.033 (2011).

14 Waugh, D. S. An overview of enzymatic reagents for the removal of affinity tags. *Protein Expr Purif* 80, 283-293, doi:S1046-5928(11)00203-8 [pii]10.1016/j.pep.2011.08.005 (2011).

15 Howard, S. L. et al. Application of comparative phylogenomics to study the evolution of *Yersinia enterocolitica* and to identify genetic differences relating to pathogenicity. *J Bacteriol* 188, 3645-3653, doi:10.1128/JB.188.10.3645-3653.2006 (2006).

16 Thomson, N. R. et al. The complete genome sequence and comparative genome analysis of the high pathogenicity *Yersinia enterocolitica* strain 8081. *PLoS Genet* 2, e206, doi:10.1371/journal.pgen.0020206 (2006).

17 Pelludat, C., Hogardt, M. & Heesemann, J. Transfer of the core region genes of the *Yersinia enterocolitica* WA-C serotype 0:8 high-pathogenicity island to *Y. enterocolitica* MRS40, a strain with low levels of pathogenicity, confers a yersiniabactin biosynthesis phenotype and enhanced mouse virulence. *Infect Immun* 70, 1832-1841 (2002).

18 Mulder, B., Michiels, T., Simonet, M., Sory, M. P. & Cornelis, G. Identification of additional virulence determinants on the pYV plasmid of *Yersinia enterocolitica* W227. *Infect Immun* 57, 2534-2541 (1989).

19 Sory, M. P. & Cornelis, G. R. Translocation of a hybrid YopE-adenylate cyclase from *Yersinia enterocolitica* into HeLa cells. *Mol Microbiol* 14, 583-594 (1994).

20 Sarker, M. R., Neyt, C., Stainier, I. & Cornelis, G. R. The *Yersinia* Yop virulon: LcrV is required for extrusion of the translocators YopB and YopD. *J Bacteriol* 180, 1207-1214 (1998).

21 Neubauer, H., Aleksic, S., Hensel, A., Finke, E. J. & Meyer, H. *Yersinia enterocolitica* 16S rRNA gene types belong to the same genospecies but form three homology groups. *Int J Med Microbiol* 290, 61-64, doi:10.1016/S1438-4221(00)80107-1 (2000).

22 Feldman, M. F., Muller, S., Wuest, E. & Cornelis, G. R. SycE allows secretion of YopE-DHFR hybrids by the *Yersinia enterocolitica* type III Ysc system. *Mol Microbiol* 46, 1183-1197, doi:3241 [pii] (2002).

23 Ramamurthi, K. S. & Schneewind, O. A synonymous mutation in *Yersinia enterocolitica* yopE affects the function of the YopE type III secretion signal. *J Bacteriol* 187, 707-715, doi:10.1128/JB.187.2.707-715.2005 (2005).

24 Wolke, S., Ackermann, N. & Heesemann, J. The *Yersinia enterocolitica* type 3 secretion system (T3SS) as toolbox for studying the cell biological effects of bacterial Rho GTPase modulating T3SS effector proteins. *Cell Microbiol* 13, 1339-1357, doi:10.1111/j.1462-5822.2011.01623.x (2011).

25 Forsberg, A. & Wolf-Watz, H. Genetic analysis of the yopE region of *Yersinia* spp.: identification of a novel conserved locus, yerA, regulating yopE expression. *J Bacteriol* 172, 1547-1555 (1990).

26 Sambrook, J. (ed David W. Russell) (Cold Spring Harbor Laboratory Press, Cold Spring Harbor, N.Y., 2001).

27 Alto, N. M. & Dixon, J. E. Analysis of Rho-GTPase mimicry by a family of bacterial type III effector proteins. *Methods Enzymol* 439, 131-143, doi:S0076-6879(07)00410-7 [pii]10.1016/S0076-6879(07)00410-7 (2008).

28 Alto, N. M. et al. Identification of a bacterial type III effector family with G protein mimicry functions. *Cell* 124, 133-145, doi:S0092-8674(05)01229-8 [pii]10.1016/j.cell.2005.10.031 (2006).

29 Kaniga, K., Delor, I. & Cornelis, G. R. A wide-host-range suicide vector for improving reverse genetics in gram-negative bacteria: inactivation of the blaA gene of *Yersinia enterocolitica*. *Gene* 109, 137-141, doi:0378-1119(91)90599-7 [pii] (1991).

30 Yoneda, Y. et al. A long synthetic peptide containing a nuclear localization signal and its flanking sequences of SV40 T-antigen directs the transport of IgM into the nucleus efficiently. *Exp Cell Res* 201, 313-320 (1992).

31 Metcalf, W. W., Jiang, W. & Wanner, B. L. Use of the rep technique for allele replacement to construct new *Escherichia coli* hosts for maintenance of R6K gamma origin plasmids at different copy numbers. *Gene* 138, 1-7 (1994).

32 Diepold, A. et al. Deciphering the assembly of the *Yersinia* type III secretion injectisome. *Embo J* 29, 1928-1940, doi:emboj201084 [pii]10.1038/emboj.2010.84 (2010).

33 Iriarte, M., Stainier, I. & Cornelis, G. R. The rpoS gene from *Yersinia enterocolitica* and its influence on expression of virulence factors. *Infect Immun* 63, 1840-1847 (1995).

34 Cornelis, G., Vanootegem, J. C. & Sluiters, C. Transcription of the yop regulon from *Y. enterocolitica* requires trans acting pYV and chromosomal genes. *Microb Pathog* 2, 367-379, doi:0882-4010(87)90078-7 [pii] (1987).

35 Grosdent, N., Maridonneau-Parini, I., Sory, M. P. & Cornelis, G. R. Role of Yops and adhesins in resistance of *Yersinia enterocolitica* to phagocytosis. *Infect Immun* 70, 4165-4176 (2002).

36 Boyd, A. P., Lambermont, I. & Cornelis, G. R. Competition between the Yops of *Yersinia enterocolitica* for delivery into eukaryotic cells: role of the SycE chaperone binding domain of YopE. *J Bacteriol* 182, 4811-4821 (2000).

37 Iriarte, M. & Cornelis, G. R. YopT, a new *Yersinia* Yop effector protein, affects the cytoskeleton of host cells. *Mol Microbiol* 29, 915-929 (1998).

38 Kudryashev, M. et al. In situ structural analysis of the *Yersinia enterocolitica* injectisome. *Elife* 2, e00792, doi:10.7554/eLife.0079200792 [pii] (2013).

39 Schulte, R. et al. *Yersinia enterocolitica* invasin protein triggers IL-8 production in epithelial cells via activation of Rel p65-p65 homodimers. *FASEB J* 14, 1471-1484 (2000).

40 Mota, L. J., Journet, L., Sorg, I., Agrain, C. & Cornelis, G. R. Bacterial injectisomes: needle length does matter. *Science* 307, 1278, doi:307/5713/1278 [pii]10.1126/science.1107679 (2005).

41 Carrington, J. C. & Dougherty, W. G. A viral cleavage site cassette: identification of amino acid sequences required for tobacco etch virus polyprotein processing. *Proc Natl Acad Sci USA* 85, 3391-3395 (1988).

42 Kapust, R. B., Tozser, J., Copeland, T. D. & Waugh, D. S. The P1' specificity of tobacco etch virus protease. *Biochem Biophys Res Commun* 294, 949-955, doi:10.1016/S0006-291X(02)00574-0S0006-291X(02)00574-0 [pii] (2002).

43 Liang, H., Gao, H., Maynard, C. A. & Powell, W. A. Expression of a self-processing, pathogen resistance-enhancing gene construct in *Arabidopsis*. *Biotechnol Lett* 27, 435-442, doi:10.1007/s10529-005-1884-9 (2005).

44 Weber, W. et al. Macrolide-based transgene control in mammalian cells and mice. *Nat Biotechnol* 20, 901-907, doi:10.1038/nbt731nbt731 [pii] (2002).

45 Kapust, R. B. et al. Tobacco etch virus protease: mechanism of autolysis and rational design of stable mutants with wild-type catalytic proficiency. *Protein Eng* 14, 993-1000 (2001).

46 Lee, V. T., Anderson, D. M. & Schneewind, O. Targeting of *Yersinia* Yop proteins into the cytosol of HeLa cells: one-step translocation of YopE across bacterial and eukaryotic membranes is dependent on SycE chaperone. *Mol Microbiol* 28, 593-601 (1998).

47 Gray, D. C., Mahrus, S. & Wells, J. A. Activation of specific apoptotic caspases with an engineered small-molecule-activated protease. *Cell* 142, 637-646, doi:S0092-8674(10)00783-X [pii]10.1016/j.cell.2010.07.014 (2010).

48 Henrichs, T. et al. Target-directed proteolysis at the ribosome. *Proc Natl Acad Sci USA* 102, 4246-4251, doi:102/12/4246 [pii]10.1073/pnas.0408520102 (2005).

49 Aepfelbacher, M., Trasak, C. & Ruckdeschel, K. Effector functions of pathogenic *Yersinia* species. *Thromb Haemost* 98, 521-529 (2007).

50 Trulzsch, K., Sporleder, T., Igwe, E. I., Russmann, H. & Heesemann, J. Contribution of the major secreted yops of *Yersinia enterocolitica* O:8 to pathogenicity in the mouse infection model. *Infect Immun* 72, 5227-5234, doi:10.1128/IAI.72.9.5227-5234.2004 (2004).

51 Bohme, K. et al. Concerted actions of a thermo-labile regulator and a unique intergenic RNA thermosensor control *Yersinia* virulence. *PLoS Pathog* 8, e1002518, doi:10.1371/journal.ppat.1002518 (2012).

52 Rohde, J. R., Luan, X. S., Rohde, H., Fox, J. M. & Minnich, S. A. The *Yersinia enterocolitica* pYV virulence 53 Curtiss, R., 3rd, Galan, J. E., Nakayama, K. & Kelly, S. M. Stabilization of recombinant avirulent vaccine strains in vivo. *Res Microbiol* 141, 797-805 (1990).

54 Spreng, S. & Viret, J. F. Plasmid maintenance systems suitable for GMO-based bacterial vaccines. *Vaccine* 23, 2060-2065, doi:10.1016/j.vaccine.2005.01.009 (2005).

55 Neyt, C., Iriarte, M., Thi, V. H. & Cornelis, G. R. Virulence and arsenic resistance in Yersiniae. *J Bacteriol* 179, 612-619 (1997).

56 Wu, J. & Chen, Z. J. Innate immune sensing and signaling of cytosolic nucleic acids. *Annu Rev Immunol* 32, 461-488, doi:10.1146/annurev-immunol-032713-120156 (2014).

57 Kranzusch, P. J. et al. Ancient Origin of cGAS-STING Reveals Mechanism of Universal 2',3' cGAMP Signaling. *Mol Cell* 59, 891-903, doi:10.1016/j.molcel.2015.07.022 (2015).

58 Commichau, F. M., Dickmanns, A., Gundlach, J., Ficner, R. & Stulke, J. A jack of all trades: the multiple roles of the unique essential second messenger cyclic di-AMP. *Mol Microbiol* 97, 189-204, doi:10.1111/mmi.13026 (2015).

59 Corrales, L. et al. Direct Activation of STING in the Tumor Microenvironment Leads to Potent and Systemic Tumor Regression and Immunity. *Cell Rep* 11, 1018-1030, doi:10.1016/j.celrep.2015.04.031 (2015).

60 De, N., Navarro, M. V., Raghavan, R. V. & Sondermann, H. Determinants for the activation and autoinhibition of the diguanylate cyclase response regulator WspR. *J Mol Biol* 393, 619-633, doi:10.1016/j.jmb.2009.08.030 (2009).

61 Witte, G., Hartung, S., Buttner, K. & Hopfner, K. P. Structural biochemistry of a bacterial checkpoint protein reveals diadenylate cyclase activity regulated by DNA recombination intermediates. *Mol Cell* 30, 167-178, doi: 10.1016/j.molcel.2008.02.020 (2008).

62 Panne, D., McWhirter, S. M., Maniatis, T. & Harrison, S. C. Interferon regulatory factor 3 is regulated by a dual phosphorylation-dependent switch. *J Biol Chem* 282, 22816-22822, doi:10.1074/jbc.M703019200 (2007).

63 Engel, C., G. Brugmann, S. Lambing, L. H. Muhlenbeck, S. Marx, C. Hagen, D. Horvath, M. Goldeck, J. Ludwig, A. M. Herzner, J. W. Drijfhout, D. Wenzel, C. Coch, T. Tuting, M. Schlee, V. Hornung, G. Hartmann, and J. G. Van den Boorn. 2017. RIG-I Resists Hypoxia-Induced Immunosuppression and Dedifferentiation. *Cancer Immunol Res.* 5:455-467.

64 Hou, F., L. Sun, H. Zheng, B. Skaug, Q. X. Jiang, and Z. J. Chen. 2011. MAVS forms functional prion-like aggregates to activate and propagate antiviral innate immune response. *Cell.* 146:448-461.

65 Kranzusch, P. J., A. S. Lee, J. M. Berger, and J. A. Doudna. 2013. Structure of human cGAS reveals a conserved family of second-messenger enzymes in innate immunity. *Cell Rep.* 3:1362-1368.

66 Seth, R. B., L. Sun, C. K. Ea, and Z. J. Chen. 2005. Identification and characterization of MAVS, a mitochondrial antiviral signaling protein that activates NF-kappaB and IRF 3. *Cell.* 122:669-682.

---

SEQUENCE LISTING

```
Sequence total quantity: 139
SEQ ID NO: 1           moltype = AA  length = 219
FEATURE                Location/Qualifiers
source                 1..219
                       mol_type = protein
                       organism = Yersinia enterocolitica
SEQUENCE: 1
MKISSFISTS LPLPASVSGS SSVGEMSGRS VSQQKSDQYA NNLAGRTESP QGSSLASRII  60
ERLSSMAHSV IGFIQRMFSE GSHKPVVTPA LTPAQMPSPS SFSDSIKQLA AETLPKYMQQ  120
LSSLDAETLQ KNHDQFATGS GPLRGSITQC QGLMQFCGGE LQAEASAILN TPVCGIPFSQ  180
WGTVGGAASA YVASGVDLTQ AANEIKGLGQ QMQQLLSLM                         219

SEQ ID NO: 2           moltype = AA  length = 138
FEATURE                Location/Qualifiers
source                 1..138
                       mol_type = protein
                       organism = Yersinia enterocolitica
SEQUENCE: 2
MKISSFISTS LPLPASVSGS SSVGEMSGRS VSQQKSDQYA NNLAGRTESP QGSSLASRII  60
ERLSSMAHSV IGFIQRMFSE GSHKPVVTPA LTPAQMPSPT SFSDSIKQLA AETLPKYMQQ  120
LSSLDAETLQ KNHDQFAT                                                138

SEQ ID NO: 3           moltype = AA  length = 169
FEATURE                Location/Qualifiers
REGION                 1..169
                       note = YopE1-138-MycHis
source                 1..169
                       mol_type = protein
                       organism = synthetic construct
SEQUENCE: 3
MKISSFISTS LPLPASVSGS SSVGEMSGRS VSQQKSDQYA NNLAGRTESP QGSSLASRII  60
ERLSSMAHSV IGFIQRMFSE GSHKPVVTPA LTPAQMPSPT SFSDSIKQLA AETLPKYMQQ  120
LSSLDAETLQ KNHDQFATLE SRFEKLGPEQ KLISEEDLNS AVDHHHHHH              169

SEQ ID NO: 4           moltype = AA  length = 20
FEATURE                Location/Qualifiers
source                 1..20
                       mol_type = protein
                       organism = Salmonella enterica
```

```
SEQUENCE: 4
MPYTSVSTYA RALSGNKLPH                                                         20

SEQ ID NO: 5            moltype = AA  length = 210
FEATURE                 Location/Qualifiers
source                  1..210
                        mol_type = protein
                        organism = Salmonella enterica
SEQUENCE: 5
MPYTSVSTYA RALSGNKLPH VAAGDYENKL STKIMKGILY VLTAGLAYGF TRVIEHYCNV              60
TPKVAEFCAN AGNIHNHLAD AVRDGLFTID VELSDGRMLT FEQLSLIAEG KPIVRISDGE             120
HTVEVEGTFE EICMRLEEGF FEAPAYYDYD IDEKYKTVRE RMAAYNALPQ ALGAIPCLEY             180
YIARASNMQE AKAQWAADIK ARYHNYLDNY                                             210

SEQ ID NO: 6            moltype = AA  length = 81
FEATURE                 Location/Qualifiers
source                  1..81
                        mol_type = protein
                        organism = Salmonella enterica
SEQUENCE: 6
VTKITLSPQN FRIQKQETTL LKEKSTEKNS LAKSILAVKN HFIELRSKLS ERFISHKNTE              60
SSATHFHRGS ASEGRAVLTN K                                                       81

SEQ ID NO: 7            moltype = AA  length = 105
FEATURE                 Location/Qualifiers
source                  1..105
                        mol_type = protein
                        organism = Salmonella enterica
SEQUENCE: 7
VTKITLSPQN FRIQKQETTL LKEKSTEKNS LAKSILAVKN HFIELRSKLS ERFISHKNTE              60
SSATHFHRGS ASEGRAVLTN KVVKDFMLQT LNDIDIRGSA SKDPA                             105

SEQ ID NO: 8            moltype = AA  length = 310
FEATURE                 Location/Qualifiers
REGION                  1..310
                        note = YopE1-138 - Ink4C
source                  1..310
                        mol_type = protein
                        organism = synthetic construct
SEQUENCE: 8
MKISSFISTS LPLPASVSGS SSVGEMSGRS VSQQKSDQYA NNLAGRTESP QGSSLASRII              60
ERLSSMAHSV IGFIQRMFSE GSHKPVVTPA LTPAQMPSPT SFSDSIKQLA AETLPKYMQQ             120
LSSLDAETLQ KNHDQFATLE SRMAEPWGNE LASAAARGDL EQLTSLLQNN VNVNAQNGFG             180
RTALQVMKLG NPEIARRLLL RGANPDLKDR TGFAVIHDAA RAGFLDTLQA LPEFQADVNI             240
EDNEGNLPLH LAAKEGHLRV VEFLVKHTAS NVGHRNHKGD TACDLARLYG RNEVVSLMQA             300
NGAGGATNLQ                                                                   310

SEQ ID NO: 9            moltype = AA  length = 465
FEATURE                 Location/Qualifiers
REGION                  1..465
                        note = YopE1-138 - ET1
source                  1..465
                        mol_type = protein
                        organism = synthetic construct
SEQUENCE: 9
MKISSFISTS LPLPASVSGS SSVGEMSGRS VSQQKSDQYA NNLAGRTESP QGSSLASRII              60
ERLSSMAHSV IGFIQRMFSE GSHKPVVTPA LTPAQMPSPT SFSDSIKQLA AETLPKYMQQ             120
LSSLDAETLQ KNHDQFATLE SRMPRPKLKS DDEVLEAATV VLKRCGPIEF TLSGVAKEVG             180
LSRAALIQRF TNRDTLLVRM MERGVEQVRH YLNAIPIGAG PQGLWEFLQV LVRSMNTRND             240
FSVNYLISWY ELQVPELRTL AIQRNRAVVE GIRKRLPPGA PAAAELLHHS VIAGATMQWA             300
VDPDGELADH VLAQIAAILC LMFPEHDDFQ LLQAHASAYS RARTKNNYGS TIEGLLDLPD             360
DDAPEEAGLA APRLSFLPAG HTRRLSTAPP TDVSLGDELH LDGEDVAMAH ADALDDFDLD             420
MLGDGDSPGP GFTPHDSAPY GALDMADFEF EQMFTDALGI DEYGG                            465

SEQ ID NO: 10           moltype = AA  length = 324
FEATURE                 Location/Qualifiers
REGION                  1..324
                        note = YopE1-138 - 2x TEVsite - INK4C
source                  1..324
                        mol_type = protein
                        organism = synthetic construct
SEQUENCE: 10
MKISSFISTS LPLPASVSGS SSVGEMSGRS VSQQKSDQYA NNLAGRTESP QGSSLASRII              60
ERLSSMAHSV IGFIQRMFSE GSHKPVVTPA LTPAQMPSPT SFSDSIKQLA AETLPKYMQQ             120
LSSLDAETLQ KNHDQFATLE SRENLYFQSE NLYFQSMAEP WGNELASAAA RGDLEQLTSL             180
LQNNVNVNAQ NGFGRTALQV MKLGNPEIAR RLLLRGANPD LKDRTGFAVI HDAARAGFLD             240
TLQALPEFQA DVNIEDNEGN LPLHLAAKEG HLRVVEFLVK HTASNVGHRN HKGDTACDLA             300
RLYGRNEVVS LMQANGAGGA TNLQ                                                   324
```

-continued

```
SEQ ID NO: 11           moltype = AA  length = 479
FEATURE                 Location/Qualifiers
REGION                  1..479
                        note = YopE1-138 - 2x TEVsite - ET1
source                  1..479
                        mol_type = protein
                        organism = synthetic construct
SEQUENCE: 11
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE SRENLYFQSE NLYFQSMPRP KLKSDDEVLE AATVVLKRCG   180
PIEFTLSGVA KEVGLSRAAL IQRFTNRDTL LVRMMERGVE QVRHYLNAIP IGAGPQGLWE   240
FLQVLVRSMN TRNDFSVNYL ISWYELQVPE LRTLAIQRNR AVVEGIRKRL PPGAPAAAEL   300
LLHSVIAGAT MQWAVDPDGE LADHVLAQIA AILCLMFPEH DDFQLLQAHA SAYSRARTKN   360
NYGSTIEGLL DLPDDDAPEE AGLAAPRLSF LPAGHTRRLS TAPPTDVSLG DELHLDGEDV   420
AMAHADALDD FDLDMLGDGD SPGPGFTPHD SAPYGALDMA DFEFEQMFTD ALGIDEYGG    479

SEQ ID NO: 12           moltype = AA  length = 380
FEATURE                 Location/Qualifiers
REGION                  1..380
                        note = YopE1-138 - TEV protease S219V
source                  1..380
                        mol_type = protein
                        organism = synthetic construct
SEQUENCE: 12
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE ESLFKGPRDY NPISSTICHL TNESDGHTTS LYGIGFGPFI   180
ITNKHLFRRN NGTLLVQSLH GVFKVKNTTT LQQHLIDGRD MIIIRMPKDF PPFPQKLKFR   240
EPQREERICL VTTNFQTKSM SSMVSDTSCT FPSSDGIFWK HWIQTKDGQC GSPLVSTRDG   300
FIVGIHSASN FTNTNNYFTS VPKNFMELLT NQEAQQWVSG WRLNADSVLW GGHKVFMVKP   360
EEPFQPVKEA TQLMNRRRRR                                              380

SEQ ID NO: 13           moltype = AA  length = 332
FEATURE                 Location/Qualifiers
REGION                  1..332
                        note = YopE1-138 - 2x TEVsite - Flag - INK4C
source                  1..332
                        mol_type = protein
                        organism = synthetic construct
SEQUENCE: 13
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE SRENLYFQSE NLYFQSDYKD DDDKMAEPWG NELASAAARG   180
DLEQLTSLLQ NNVNVNAQNG FGRTALQVMK LGNPEIARRL LLRGANPDLK DRTGFAVIHD   240
AARAGFLDTL QALPEFQADV NIEDNEGNLP LHLAAKEGHL RVVEFLVKHT ASNVGHRNHK   300
GDTACDLARL YGRNEVVSLM QANGAGGATN LQ                                332

SEQ ID NO: 14           moltype = AA  length = 245
FEATURE                 Location/Qualifiers
REGION                  1..245
                        note = YopE1-138-Ubiquitin
source                  1..245
                        mol_type = protein
                        organism = synthetic construct
SEQUENCE: 14
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE MQIFVKTLTG KTITLEVEPS DTIENVKAKI QDKEGIPPDQ   180
QRLIFAGKQL EDGRTLSDYN IQKESTLHLV LRLRGGFEAS KLGPEQKLIS EEDLNSAVDH   240
HHHHH                                                              245

SEQ ID NO: 15           moltype = AA  length = 419
FEATURE                 Location/Qualifiers
REGION                  1..419
                        note = YopE1-138-Ubiquitin-Flag-INK4C-MycHis
source                  1..419
                        mol_type = protein
                        organism = synthetic construct
SEQUENCE: 15
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE MQIFVKTLTG KTITLEVEPS DTIENVKAKI QDKEGIPPDQ   180
QRLIFAGKQL EDGRTLSDYN IQKESTLHLV LRLRGGFEDY KDDDDKMAEP WGNELASAAA   240
RGDLEQLTSL LQNNVNVNAQ NGFGRTALQV MKLGNPEIAR RLLLRGANPD LKDRTGFAVI   300
HDAARAGFLD TLQALPEFQA DVNIEDNEGN LPLHLAAKEG HLRVVEFLVK HTASNVGHRN   360
HKGDTACDLA RLYGRNEVVS LMQANGAGGA TNLQKLGPEQ KLISEEDLNS AVDHHHHHH   419

SEQ ID NO: 16           moltype = AA  length = 318
```

```
FEATURE                 Location/Qualifiers
REGION                  1..318
                        note = YopE1-138 - z-BIM
source                  1..318
                        mol_type = protein
                        organism = synthetic construct
SEQUENCE: 16
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE SRMSDTSREQ TLANGPASQG SGESTGGGVV LPAGHFDFPQ   180
PGEGDPLRGG ISMSNNQSRS PMNRTFSRSS SGYFSVDSDS VPGSPLMPNI SEAQDGQNDE   240
VWLSEHSHQH LQMAAPVAAL PPEMVVAREL RRIGDEFNRL YCEAGAGVNQ LRAPNEHAIV   300
LWMNVIIGRL VHFFLRRR                                                 318

SEQ ID NO: 17           moltype = AA  length = 337
FEATURE                 Location/Qualifiers
REGION                  1..337
                        note = YopE1-138 - human Bid
source                  1..337
                        mol_type = protein
                        organism = synthetic construct
SEQUENCE: 17
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE SRMDCEVNNG SSLRDECITN LLVFGFLQSC DNSFRRELD    180
ALGHELPVLA PQWEGYDELQ TDGNRSSHSR LGRIEADSES QEDIIRNIAR HLAQVGDSMD   240
RSIPPGLVNG LALQLRNTSR SEEDRNRDLA TALEQLLQAY PRDMEKEKTM LVLALLLAKK   300
VASHTPSLLR DVFHTTVNFI NQNLRTYVRS LARNGMD                            337

SEQ ID NO: 18           moltype = AA  length = 277
FEATURE                 Location/Qualifiers
REGION                  1..277
                        note = YopE1-138 - human t-Bid
source                  1..277
                        mol_type = protein
                        organism = synthetic construct
SEQUENCE: 18
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE SRGNRSSHSR LGRIEADSES QEDIIRNIAR HLAQVGDSMD   180
RSIPPGLVNG LALQLRNTSR SEEDRNRDLA TALEQLLQAY PRDMEKEKTM LVLALLLAKK   240
VASHTPSLLR DVFHTTVNFI NQNLRTYVRS LARNGMD                            277

SEQ ID NO: 19           moltype = AA  length = 163
FEATURE                 Location/Qualifiers
REGION                  1..163
                        note = YopE1-138 - Y. enterocolitica codon optimized murine
                         BID BH3 part
source                  1..163
                        mol_type = protein
                        organism = synthetic construct
SEQUENCE: 19
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE SRFEEIIHNI ARHLAQIGDE MDH                     163

SEQ ID NO: 20           moltype = AA  length = 156
FEATURE                 Location/Qualifiers
REGION                  1..156
                        note = YopE1-138 - Y. enterocolitica codon optimized murine
                         Bax BH3 part
source                  1..156
                        mol_type = protein
                        organism = synthetic construct
SEQUENCE: 20
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE KKLSECLRRI GDELDS                             156

SEQ ID NO: 21           moltype = AA  length = 276
FEATURE                 Location/Qualifiers
REGION                  1..276
                        note = YopE1-138-Y. enterocolitica codon optimized murine
                         tBid
source                  1..276
                        mol_type = protein
                        organism = synthetic construct
SEQUENCE: 21
MKISSFISTS LPLPASVSGS SSVGEMSGRS VSQQKSDQYA NNLAGRTESP QGSSLASRII    60
```

```
ERLSSMAHSV IGFIQRMFSE GSHKPVVTPA LTPAQMPSPT SFSDSIKQLA AETLPKYMQQ    120
LSSLDAETLQ KNHDQFATLE GSQASRSFNQ GRIEPDSESQ EEIIHNIARH LAQIGDEMDH    180
NIQPTLVRQL AAQFMNGSLS EEDKRNCLAK ALDEVKTAFP RDMENDKAML IMTMLLAKKV    240
ASHAPSLLRD VFHTTVNFIN QNLFSYVRNL VRNEMD                              276

SEQ ID NO: 22           moltype = AA   length = 167
FEATURE                 Location/Qualifiers
REGION                  1..167
                        note = YopE1-138- codon optimized murine tBid BH3 extended
                         part
source                  1..167
                        mol_type = protein
                        organism = synthetic construct
SEQUENCE: 22
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE SRFEEIIHNI ARHLAQIGDE MDHNIQP                 167

SEQ ID NO: 23           moltype = AA   length = 168
FEATURE                 Location/Qualifiers
REGION                  1..168
                        note = YopE1-138-10 Aa linker - Y. enterocolitica codon
                         optimized murine tBid BH3 part
source                  1..168
                        mol_type = protein
                        organism = synthetic construct
SEQUENCE: 23
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE SRFEAGGAEE IIHNIARHLA QIGDEMDH                168

SEQ ID NO: 24           moltype = AA   length = 186
FEATURE                 Location/Qualifiers
REGION                  1..186
                        note = YopE1-138-Y. enterocolitica codon optimized murine
                         Bax BH3 part- Y. enterocolitica codon optimized murine
                         tBid BH3 part
source                  1..186
                        mol_type = protein
                        organism = synthetic construct
SEQUENCE: 24
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE GAIDAKKLSE CLRRIGDELD SGAFDAEEII HNIARHLAQI   180
GDEMDH                                                              186

SEQ ID NO: 25           moltype = AA   length = 165
FEATURE                 Location/Qualifiers
REGION                  1..165
                        note = YopE1-138 - Y. enterocolitica codon optimized murine
                         BID BH3 part (ready for insertion of further domains)
source                  1..165
                        mol_type = protein
                        organism = synthetic construct
SEQUENCE: 25
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE GAIDAEEIIH NIARHLAQIG DEMDH                   165

SEQ ID NO: 26           moltype = AA   length = 161
FEATURE                 Location/Qualifiers
REGION                  1..161
                        note = YopE1-138 - Y. enterocolitica codon optimized murine
                         Bax BH3 part (ready for insertion of further domains)
source                  1..161
                        mol_type = protein
                        organism = synthetic construct
SEQUENCE: 26
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE GAIDAKKLSE CLRRIGDELD S                       161

SEQ ID NO: 27           moltype = AA   length = 190
FEATURE                 Location/Qualifiers
REGION                  1..190
                        note = YopE1-138 - (Y. enterocolitica codon optimized
                         murine BID BH3 part)2
source                  1..190
                        mol_type = protein
```

```
                       organism = synthetic construct
SEQUENCE: 27
MKISSFISTS LPLPASVSGS SSVGEMSGRS VSQQKSDQYA NNLAGRTESP QGSSLASRII  60
ERLSSMAHSV IGFIQRMFSE GSHKPVVTPA LTPAQMPSPT SFSDSIKQLA AETLPKYMQQ  120
LSSLDAETLQ KNHDQFATLE GAIDAEEIIH NIARHLAQIG DEMDHGAFDA EEIIHNIARH  180
LAQIGDEMDH                                                        190

SEQ ID NO: 28          moltype = AA  length = 186
FEATURE                Location/Qualifiers
REGION                 1..186
                       note = YopE1-138 - (Y. enterocolitica codon optimized
                        murine BID BH3 part)(Y. enterocolitica codon optimized
                        murine Bax BH3 part)
source                 1..186
                       mol_type = protein
                       organism = synthetic construct
SEQUENCE: 28
MKISSFISTS LPLPASVSGS SSVGEMSGRS VSQQKSDQYA NNLAGRTESP QGSSLASRII  60
ERLSSMAHSV IGFIQRMFSE GSHKPVVTPA LTPAQMPSPT SFSDSIKQLA AETLPKYMQQ  120
LSSLDAETLQ KNHDQFATLE GAIDAEEIIH NIARHLAQIG DEMDHGAFDA KKLSECLRRI  180
GDELDS                                                            186

SEQ ID NO: 29          moltype = AA  length = 20
FEATURE                Location/Qualifiers
source                 1..20
                       mol_type = protein
                       organism = Mus musculus
SEQUENCE: 29
EEIIHNIARH LAQIGDEMDH                                             20

SEQ ID NO: 30          moltype = AA  length = 14
FEATURE                Location/Qualifiers
source                 1..14
                       mol_type = protein
                       organism = Mus musculus
SEQUENCE: 30
IARHLAQIGD EMDH                                                   14

SEQ ID NO: 31          moltype = AA  length = 20
FEATURE                Location/Qualifiers
source                 1..20
                       mol_type = protein
                       organism = Homo sapiens
SEQUENCE: 31
EDIIRNIARH LAQVGDSMDR                                             20

SEQ ID NO: 32          moltype = AA  length = 15
FEATURE                Location/Qualifiers
source                 1..15
                       mol_type = protein
                       organism = Homo sapiens
SEQUENCE: 32
IARHLAQVGD SMDRS                                                  15

SEQ ID NO: 33          moltype = AA  length = 17
FEATURE                Location/Qualifiers
source                 1..17
                       mol_type = protein
                       organism = Mus musculus
SEQUENCE: 33
KKLSECLRRI GDELDSN                                                17

SEQ ID NO: 34          moltype = AA  length = 14
FEATURE                Location/Qualifiers
source                 1..14
                       mol_type = protein
                       organism = Mus musculus
SEQUENCE: 34
LSECLRRIGD ELDS                                                   14

SEQ ID NO: 35          moltype = AA  length = 17
FEATURE                Location/Qualifiers
source                 1..17
                       mol_type = protein
                       organism = Homo sapiens
SEQUENCE: 35
KKLSECLKRI GDELDSN                                                17

SEQ ID NO: 36          moltype = AA  length = 14
```

```
FEATURE                 Location/Qualifiers
source                  1..14
                        mol_type = protein
                        organism = Homo sapiens
SEQUENCE: 36
LSECLKRIGD ELDS                                                       14

SEQ ID NO: 37           moltype = AA  length = 387
FEATURE                 Location/Qualifiers
REGION                  1..387
                        note = YopE1-138 - Y. enterocolitica codon optimized human
                        RIG-1 two CARD domains (Aa. 1-245)
source                  1..387
                        mol_type = protein
                        organism = synthetic construct
SEQUENCE: 37
MKISSFISTS LPLPASVSGS SSVGEMSGRS VSQQKSDQYA NNLAGRTESP QGSSLASRII      60
ERLSSMAHSV IGFIQRMFSE GSHKPVVTPA LTPAQMPSPT SFSDSIKQLA AETLPKYMQQ     120
LSSLDAETLQ KNHDQFATLE SRMTTEQRRS LQAFQDYIRK TLDPTYILSY MAPWFREEEV     180
QYIQAEKNNK GPMEAATLFL KFLLELQEEG WFRGFLDALD HAGYSGLYEA IESWDFKKIE     240
KLEEYRLLLK RLQPEFKTRI IPTDIISDLS ECLINQECEE ILQICSTKGM MAGAEKLVEC     300
LLRSDKENWP KTLKLALEKE RNKFSELWIV EKGIKDVETE DLEDKMETSD IQIFYQEDPE     360
CQNLSENSCP PSEVSDTNLY SPFKPRN                                         387

SEQ ID NO: 38           moltype = AA  length = 388
FEATURE                 Location/Qualifiers
REGION                  1..388
                        note = YopE1-138 - Y. enterocolitica codon optimized murine
                        RIG-1 two CARD domains (Aa. 1-246)
source                  1..388
                        mol_type = protein
                        organism = synthetic construct
SEQUENCE: 38
MKISSFISTS LPLPASVSGS SSVGEMSGRS VSQQKSDQYA NNLAGRTESP QGSSLASRII      60
ERLSSMAHSV IGFIQRMFSE GSHKPVVTPA LTPAQMPSPT SFSDSIKQLA AETLPKYMQQ     120
LSSLDAETLQ KNHDQFATLE SRMTAEQRQN LQAFRDYIKK ILDPTYILSY MSSWLEDEEV     180
QYIQAEKNNK GPMEAASLFL QYLLKLQSEG WFQAFLDALY HAGYCGLCEA IESWDFQKIE     240
KLEEHRLLLR RLEPEFKATV DPNDILSELS ECLINQECEE IRQIRDTKGR MAGAEKMAEC     300
LIRSDKENWP KVLQLALEKD NSKFSELWIV DKGFKRAESK ADEDDGAEAS SIQIFIQEEP     360
ECQNLSQNPG PPSEASSNNL HSPLKPRN                                        388

SEQ ID NO: 39           moltype = AA  length = 348
FEATURE                 Location/Qualifiers
REGION                  1..348
                        note = YopE1-138 - Y. enterocolitica codon optimized S.
                        cerevisiae GCN4 (Aa. 249-278) - Y. enterocolitica codon
                        optimized P. aeruginosa WspR (Aa. 172-347)
source                  1..348
                        mol_type = protein
                        organism = synthetic construct
SEQUENCE: 39
MKISSFISTS LPLPASVSGS SSVGEMSGRS VSQQKSDQYA NNLAGRTESP QGSSLASRII      60
ERLSSMAHSV IGFIQRMFSE GSHKPVVTPA LTPAQMPSPT SFSDSIKQLA AETLPKYMQQ     120
LSSLDAETLQ KNHDQFATLE SRRMKQLEDK VEELLSKNYH LENEVARLKK LVNSDGLTGL     180
SNRRHDEYL EMEWRRSLRE QSQLSLLMID VDYFKSYNDT FGHVAGDEAL RQVAGAIREG     240
CSRSSDLAAR YGGEEFAMVL PGTSPGGARL LAEKVRRTVE SLQISHDQPR PGSHLTVSIG     300
VSTLVPGGGG QTFRVLIEMA DQALYQAKNN GRNQVGLMEQ PVPPAPAG                  348

SEQ ID NO: 40           moltype = AA  length = 561
FEATURE                 Location/Qualifiers
REGION                  1..561
                        note = YopE1-138 - Y. enterocolitica codon optimized murine
                        IRF3 S397D
source                  1..561
                        mol_type = protein
                        organism = synthetic construct
SEQUENCE: 40
MKISSFISTS LPLPASVSGS SSVGEMSGRS VSQQKSDQYA NNLAGRTESP QGSSLASRII      60
ERLSSMAHSV IGFIQRMFSE GSHKPVVTPA LTPAQMPSPT SFSDSIKQLA AETLPKYMQQ     120
LSSLDAETLQ KNHDQFATLE SRMETPKPRI LPWLVSQLDL GQLEGVAWLD ESRTRFRIPW     180
KHGLRQDAQM ADFGIFQAWA EASGAYTPGK DKPDVSTWKR NFRSALNRKE VLRLAADNSK     240
DPYDPHKVYE FVTPGARDFV HLGASPDTNG KSSLPHSQEN LPKLFDGLIL GPLKDEGSSD     300
LAIVSDPSQQ LPSPNVNNFL NPAPQENPLK QLLAEEQWEF EVTAFYRGRQ VFQQTLFCPG     360
GLRLVGSTAD MTLPWQPVTL PDPEGFLTDK LVKEYVGQVL KGLGNGLALW QAGQCLWAQR     420
LGHSHAFWAL GEELLPDSGR GPDGEVHKDK DGAVFDLRPF VADLIAFMEG SGHSPRYTLW     480
FCMGEMWPQD QPWVKRLVMV KVVPTCLKEL LEMAREGGAS SLKTVDLHID NSQPISLTSD     540
QYKAYLQDLV EDMDFQATGN I                                               561

SEQ ID NO: 41           moltype = AA  length = 553
```

```
FEATURE                 Location/Qualifiers
REGION                  1..553
                        note = YopE1-138 - Y. enterocolitica codon optimized V.
                         Cholerae DncV (M3toL413)
source                  1..553
                        mol_type = protein
                        organism = synthetic construct
SEQUENCE: 41
MKISSFIS

```
MKISSFISTS LPLPASVSGS SSVGEMSGRS VSQQKSDQYA NNLAGRTESP QGSSLASRII  60
ERLSSMAHSV IGFIQRMFSE GSHKPVVTPA LTPAQMPSPT SFSDSIKQLA AETLPKYMQQ  120
LSSLDAETLQ KNHDQFATLE SRMSIVCSAE DSFRNLILFF RPRLKMYIQV EPVLDHLIFL  180
SAETKEQILK KINTCGNTSA AELLLSTLEQ GQWPLGWTQM FVEALEHSGN PLAARYVKPT  240
LTDLPSPSSE TAHDECLHLL TLLQPTLVDK LLINDVLDTC FEKGLLTVED RNRISAAGNS  300
GNESGVRELL RRIVQKENWF STFLDVLRQT GNDALFQELT GGGCPEDNTD LANSSHRDGP  360
AANECLLPAV DESSLETEAW NVDDILPEAS CTDSSVTTES DTSLAEGSVS CFDESLGHNS  420
NMGRDSGTMG SDSDESVIQT KRVSPEPELQ LRPYQME                           457

SEQ ID NO: 46          moltype = AA  length = 332
FEATURE                Location/Qualifiers
REGION                 1..332
                       note = YopE1-138 - Y. enterocolitica codon optimized human
                        MDA5 two CARD domains (minimal: Aa 1-190)
source                 1..332
                       mol_type = protein
                       organism = synthetic construct
SEQUENCE: 46
MKISSFISTS LPLPASVSGS SSVGEMSGRS VSQQKSDQYA NNLAGRTESP QGSSLASRII  60
ERLSSMAHSV IGFIQRMFSE GSHKPVVTPA LTPAQMPSPT SFSDSIKQLA AETLPKYMQQ  120
LSSLDAETLQ KNHDQFATLE SRMSNGYSTD ENFRYLISCF RARVKMYIQV EPVLDYLTFL  180
PAEVKEQIQR TVATSGNMQA VELLLSTLEK GVWHLGWTRE FVEALRRTGS PLAARYMNPE  240
LTDLPSPSFE NAHDEYLQLL NLLQPTLVDK LLVRDVLDKC MEEELLTIED RNRIAAAENN  300
GNESGVRELL KRIVQKENWF SAFLNVLRQT GN                                332

SEQ ID NO: 47          moltype = AA  length = 456
FEATURE                Location/Qualifiers
REGION                 1..456
                       note = YopE1-138 - Y. enterocolitica codon optimized human
                        MDA5 two CARD domains (extended: Aa 1-314)
source                 1..456
                       mol_type = protein
                       organism = synthetic construct
SEQUENCE: 47
MKISSFISTS LPLPASVSGS SSVGEMSGRS VSQQKSDQYA NNLAGRTESP QGSSLASRII  60
ERLSSMAHSV IGFIQRMFSE GSHKPVVTPA LTPAQMPSPT SFSDSIKQLA AETLPKYMQQ  120
LSSLDAETLQ KNHDQFATLE SRMSNGYSTD ENFRYLISCF RARVKMYIQV EPVLDYLTFL  180
PAEVKEQIQR TVATSGNMQA VELLLSTLEK GVWHLGWTRE FVEALRRTGS PLAARYMNPE  240
LTDLPSPSFE NAHDEYLQLL NLLQPTLVDK LLVRDVLDKC MEEELLTIED RNRIAAAENN  300
GNESGVRELL KRIVQKENWF SAFLNVLRQT GNNELVQELT GSDCSESNAE IENLSQVDGP  360
QVEEQLLSTT VQPNLEKEVW GMENNSSESS FADSSVVSES DTSLAEGSVS CLDESLGHNS  420
NMGSDSGTMG SDSDEENVAA RASPEPELQL RPYQME                            456

SEQ ID NO: 48          moltype = AA  length = 219
FEATURE                Location/Qualifiers
REGION                 1..219
                       note = YopE1-138 - Y. enterocolitica codon optimized human
                        MAVS CARD domain (minimal: Aa 1-77)
source                 1..219
                       mol_type = protein
                       organism = synthetic construct
SEQUENCE: 48
MKISSFISTS LPLPASVSGS SSVGEMSGRS VSQQKSDQYA NNLAGRTESP QGSSLASRII  60
ERLSSMAHSV IGFIQRMFSE GSHKPVVTPA LTPAQMPSPT SFSDSIKQLA AETLPKYMQQ  120
LSSLDAETLQ KNHDQFATLE SRMPFAEDKT YKYICRNFSN FCNVDVVEIL PYLPCLTARD  180
QDRLRATCTL SGNRDTLWHL FNTLQRRPGW VEYFIAALR                         219

SEQ ID NO: 49          moltype = AA  length = 142
FEATURE                Location/Qualifiers
REGION                 1..142
                       note = YopE1-138 - Y. enterocolitica codon optimized murine
                        MAVS CARD domain (minimal: Aa 1-77)
source                 1..142
                       mol_type = protein
                       organism = synthetic construct
SEQUENCE: 49
MKISSFISTS LPLPASVSGS SSVGEMSGRS VSQQKSDQYA NNLAGRTESP QGSSLASRII  60
ERLSSMAHSV IGFIQRMFSE GSHKPVVTPA LTPAQMPSPT SFSDSIKQLA AETLPKYMQQ  120
LSSLDAETLQ KNHDQFATLE SR                                           142

SEQ ID NO: 50          moltype = DNA  length = 1675
FEATURE                Location/Qualifiers
misc_feature           1..1675
                       note = Mutator sequence for generation of YopE1-138 - Y.
                        enterocolitica codon optimized murine RIG-1 two CARD
                        domains (Aa. 1-246) integrated on the pYV plasmid
source                 1..1675
                       mol_type = other DNA
                       organism = synthetic construct
```

```
SEQUENCE: 50
gaatagacag cgaaagttgt tgaaataatt gagtgatagc ttgttcaaat gaatacattt    60
gatctcctaa tagttagata aaatatcaac ttaaccaaag cactctcggc agaccatcaa   120
ttttagccta taattttag ttttattt gtcaatata acaacaaaaa cagcagcggt      180
tttttatata accaccggct attttcccac taagataacc ttgttttaat agccaaggga  240
ataaatagtc atgaaaatat catcatttat ttctacatca ctgccctgc cggcatcagt   300
gtcaggatct agcagcgtag gagaaatgtc tgggcgctca gtctcacagc aaaaaagtga  360
tcaatatgca aacaatctgg ccgggcgcac tgaaagccct cagggttcca gcttagccag  420
ccgtatcatt gagaggttat catcaatggc ccactctgtg attggattta tccaacgcat  480
gttctcggag gggagccata accggtggt gacaccggctg cacaaatgcc                540
aagccctacg tctttcagtg atagtatcaa gcaacttgct gctgagacgc tgccaaaata  600
catgcagcag ttgagtagct tggatgcaga acgctgcag aaaaatcatg accagttcgc   660
cacgctcgag tctagaatga ccgccgaaca acgccaaaat ctgcaagcct ttcgcgatta  720
tattaaaaaa attctggatc cgacctatat tctgagctat atgagcagct ggctggaaga  780
tgaagaagtg caatatattc aagccgaaaa aaataataaa ggtccgatgg aagccgccag  840
cctgtttctg caatatctgc tgaaactgca agcgaaggt tggtttcaag cctttctgga   900
tgccctgtat catgccggtt attgtggtct gtgtgaagcc attgaaagct gggattttca  960
aaaaattgaa aaactggaag aacatcgcct gctgctgcgc cgcctggaac cggaatttaa 1020
agccaccgtg gatccgaatg atattctgag cgaactgagc gaatgtctga ttaatcaaga 1080
atgtgaagaa attcgccaaa ttcgcgatac caaaggtcgc atggccggtg ccgaaaaaat 1140
ggccgaatgt ctgattcgca gcgataaga aaattggccg aaagtgctgc aactggccct  1200
ggaaaaagat aatagcaaat ttagcgaact gtggattgtg gataaaggtt ttaaacgcgc 1260
cgaaagcaaa gccgatgaag atgatggtgc cgaagccagc agcattcaaa tttttattca 1320
agaagaaccg gaatgtcaaa atctgagcca aaatccgggt ccgccgagcg aagccagcag 1380
caataatctg catagcccgc tgaaaccgcg caattaatat ggataaaaac aagggggtag 1440
tgtttccccc tttttctatc aatattgcga atatcttgct ccctgatctt tcagggcga  1500
atcgtttttt agcatgctca ttgttagaat ttctgactta tctctcttct gtattactac 1560
tcatactctg gaaaatcctg agcatttata tctatggatt gatgcagcac tcgagaaatc 1620
aaaatatcat tgctaagcgt tatatagtat ataccgtgct ttttatactg aaaac      1675

SEQ ID NO: 51           moltype = DNA   length = 27
FEATURE                 Location/Qualifiers
misc_feature            1..27
                        note = Primer No. : Si_285
source                  1..27
                        mol_type = other DNA
                        organism = synthetic construct
SEQUENCE: 51
cataccatgg gagtgagcaa gggcgag                                       27

SEQ ID NO: 52           moltype = DNA   length = 30
FEATURE                 Location/Qualifiers
misc_feature            1..30
                        note = Primer No. : Si_286
source                  1..30
                        mol_type = other DNA
                        organism = synthetic construct
SEQUENCE: 52
ggaagatctt tacttgtaca gctcgtccat                                    30

SEQ ID NO: 53           moltype = DNA   length = 29
FEATURE                 Location/Qualifiers
misc_feature            1..29
                        note = Primer No. : Si_287
source                  1..29
                        mol_type = other DNA
                        organism = synthetic construct
SEQUENCE: 53
cggggtacct caactaaatg accgtggtg                                     29

SEQ ID NO: 54           moltype = DNA   length = 43
FEATURE                 Location/Qualifiers
misc_feature            1..43
                        note = Primer No. : Si_288
source                  1..43
                        mol_type = other DNA
                        organism = synthetic construct
SEQUENCE: 54
gttaaagctt ttcgaatcta gactcgagcg tggcgaactg gtc                     43

SEQ ID NO: 55           moltype = DNA   length = 30
FEATURE                 Location/Qualifiers
misc_feature            1..30
                        note = Primer No. : Si_387
source                  1..30
                        mol_type = other DNA
                        organism = synthetic construct
SEQUENCE: 55
cgtatctaga atgactgtg aggtcaacaa                                     30
```

```
SEQ ID NO: 56          moltype = DNA  length = 23
FEATURE                Location/Qualifiers
misc_feature           1..23
                       note = Primer No. : Si_391
source                 1..23
                       mol_type = other DNA
                       organism = synthetic construct
SEQUENCE: 56
cgtatctaga ggcaaccgca gca                                                23

SEQ ID NO: 57          moltype = DNA  length = 29
FEATURE                Location/Qualifiers
misc_feature           1..29
                       note = Primer No. : Si_389
source                 1..29
                       mol_type = other DNA
                       organism = synthetic construct
SEQUENCE: 57
gttaaagctt tcagtccatc ccatttctg                                          29

SEQ ID NO: 58          moltype = DNA  length = 22
FEATURE                Location/Qualifiers
misc_feature           1..22
                       note = Primer No. : Si_436
source                 1..22
                       mol_type = other DNA
                       organism = synthetic construct
SEQUENCE: 58
cgtatctaga atgccccgcc cc                                                 22

SEQ ID NO: 59          moltype = DNA  length = 31
FEATURE                Location/Qualifiers
misc_feature           1..31
                       note = Primer No. : Si_437
source                 1..31
                       mol_type = other DNA
                       organism = synthetic construct
SEQUENCE: 59
gttaaagctt ctacccaccg tactcgtcaa t                                       31

SEQ ID NO: 60          moltype = DNA  length = 31
FEATURE                Location/Qualifiers
misc_feature           1..31
                       note = Primer No. : Si_438
source                 1..31
                       mol_type = other DNA
                       organism = synthetic construct
SEQUENCE: 60
cgtatctaga atgtctgaca cgtccagaga g                                       31

SEQ ID NO: 61          moltype = DNA  length = 32
FEATURE                Location/Qualifiers
misc_feature           1..32
                       note = Primer No. : Si_439
source                 1..32
                       mol_type = other DNA
                       organism = synthetic construct
SEQUENCE: 61
gttaaagctt tcatcttctt cgcaggaaaa ag                                      32

SEQ ID NO: 62          moltype = DNA  length = 29
FEATURE                Location/Qualifiers
misc_feature           1..29
                       note = Primer No. : Si_463
source                 1..29
                       mol_type = other DNA
                       organism = synthetic construct
SEQUENCE: 62
cagtctcgag gaaagcttgt ttaaggggc                                          29

SEQ ID NO: 63          moltype = DNA  length = 25
FEATURE                Location/Qualifiers
misc_feature           1..25
                       note = Primer No. : Si_464
source                 1..25
                       mol_type = other DNA
                       organism = synthetic construct
SEQUENCE: 63
```

```
cagtttcgaa ttagcgacgg cgacg                                              25

SEQ ID NO: 64           moltype = DNA   length = 31
FEATURE                 Location/Qualifiers
misc_feature            1..31
                        note = Primer No. : Si_476
source                  1..31
                        mol_type = other DNA
                        organism = synthetic construct
SEQUENCE: 64
gttaaagctt ttacttgtac agctcgtcca t                                       31

SEQ ID NO: 65           moltype = DNA   length = 24
FEATURE                 Location/Qualifiers
misc_feature            1..24
                        note = Primer No. : Si_494
source                  1..24
                        mol_type = other DNA
                        organism = synthetic construct
SEQUENCE: 65
cgtatctaga atggccgagc cttg                                               24

SEQ ID NO: 66           moltype = DNA   length = 31
FEATURE                 Location/Qualifiers
misc_feature            1..31
                        note = Primer No. : Si_495
source                  1..31
                        mol_type = other DNA
                        organism = synthetic construct
SEQUENCE: 66
gttaaagctt ttattgaaga tttgtggctc c                                       31

SEQ ID NO: 67           moltype = DNA   length = 64
FEATURE                 Location/Qualifiers
misc_feature            1..64
                        note = Primer No. : Si_504
source                  1..64
                        mol_type = other DNA
                        organism = synthetic construct
SEQUENCE: 67
cgtatctaga gaaaatctgt attttcaaag tgaaatctg tattttcaaa gtatgccccg         60
cccc                                                                     64

SEQ ID NO: 68           moltype = DNA   length = 30
FEATURE                 Location/Qualifiers
misc_feature            1..30
                        note = Primer No. : Si_505
source                  1..30
                        mol_type = other DNA
                        organism = synthetic construct
SEQUENCE: 68
gttaaagctt cccaccgtac tcgtcaattc                                         30

SEQ ID NO: 69           moltype = DNA   length = 66
FEATURE                 Location/Qualifiers
misc_feature            1..66
                        note = Primer No. : Si_508
source                  1..66
                        mol_type = other DNA
                        organism = synthetic construct
SEQUENCE: 69
cgtatctaga gaaaatctgt attttcaaag tgaaatctg tattttcaaa gtatggcga          60
gccttg                                                                   66

SEQ ID NO: 70           moltype = DNA   length = 29
FEATURE                 Location/Qualifiers
misc_feature            1..29
                        note = Primer No. : Si_509
source                  1..29
                        mol_type = other DNA
                        organism = synthetic construct
SEQUENCE: 70
gttaaagctt ttgaagattt gtggctccc                                          29

SEQ ID NO: 71           moltype = DNA   length = 67
FEATURE                 Location/Qualifiers
misc_feature            1..67
                        note = Primer No. : Si_511
source                  1..67
```

```
                    mol_type = other DNA
                    organism = synthetic construct
SEQUENCE: 71
cgtatctaga gaaaatctgt attttcaaag tgaaatctg tattttcaaa gtgtgagcaa    60
gggcgag                                                             67

SEQ ID NO: 72          moltype = DNA   length = 91
FEATURE                Location/Qualifiers
misc_feature           1..91
                       note = Primer No. : Si_512
source                 1..91
                       mol_type = other DNA
                       organism = synthetic construct
SEQUENCE: 72
cgtatctaga gaaaatctgt attttcaaag tgaaatctg tattttcaaa gtccgccgaa    60
aaaaaaacgt aaagttgtga gcaagggcga g                                  91

SEQ ID NO: 73          moltype = DNA   length = 55
FEATURE                Location/Qualifiers
misc_feature           1..55
                       note = Primer No. : Si_513
source                 1..55
                       mol_type = other DNA
                       organism = synthetic construct
SEQUENCE: 73
gttaaagctt ttaaacttta cgttttttt tcggcggctt gtacagctcg tccat         55

SEQ ID NO: 74          moltype = DNA   length = 90
FEATURE                Location/Qualifiers
misc_feature           1..90
                       note = Primer No. : Si_515
source                 1..90
                       mol_type = other DNA
                       organism = synthetic construct
SEQUENCE: 74
cgtatctaga gaaaatctgt attttcaaag tgaaatctg tattttcaaa gtgattataa    60
agatgatgat gataaaatgg ccgagccttg                                    90

SEQ ID NO: 75          moltype = DNA   length = 82
FEATURE                Location/Qualifiers
misc_feature           1..82
                       note = Primer No. : Si_677
source                 1..82
                       mol_type = other DNA
                       organism = synthetic construct
SEQUENCE: 75
ttactattcg aagaaattat tcataatatt gcccgccatc tggcccaaat tggtgatgaa    60
atggatcatt aagcttggag ta                                            82

SEQ ID NO: 76          moltype = DNA   length = 82
FEATURE                Location/Qualifiers
misc_feature           1..82
                       note = Primer No. : Si_678
source                 1..82
                       mol_type = other DNA
                       organism = synthetic construct
SEQUENCE: 76
tactccaagc ttaatgatcc atttcatcac caatttgggc cagatggcgg gcaatattat    60
gaataatttc ttcgaatagt aa                                            82

SEQ ID NO: 77          moltype = DNA   length = 73
FEATURE                Location/Qualifiers
misc_feature           1..73
                       note = Primer No. : Si_682
source                 1..73
                       mol_type = other DNA
                       organism = synthetic construct
SEQUENCE: 77
ttactactcg agaaaaaact gagcgaatgt ctgcgccgca ttggtgatga actggatagc    60
taagcttgga gta                                                      73

SEQ ID NO: 78          moltype = DNA   length = 73
FEATURE                Location/Qualifiers
misc_feature           1..73
                       note = Primer No. : Si_683
source                 1..73
                       mol_type = other DNA
                       organism = synthetic construct
SEQUENCE: 78
```

```
tactccaagc ttagctatcc agttcatcac caatgcggcg cagacattcg ctcagttttt    60
tctcgagtag taa                                                       73

SEQ ID NO: 79          moltype = DNA   length = 34
FEATURE                Location/Qualifiers
misc_feature           1..34
                       note = Primer No. : Si_580
source                 1..34
                       mol_type = other DNA
                       organism = synthetic construct
SEQUENCE: 79
catgccatgg atttatggtc atagatatga cctc                                34

SEQ ID NO: 80          moltype = DNA   length = 35
FEATURE                Location/Qualifiers
misc_feature           1..35
                       note = Primer No. : Si_612
source                 1..35
                       mol_type = other DNA
                       organism = synthetic construct
SEQUENCE: 80
cggggtacca tgaggtagct tatttcctga taaag                               35

SEQ ID NO: 81          moltype = DNA   length = 35
FEATURE                Location/Qualifiers
misc_feature           1..35
                       note = Primer No. : Si_613
source                 1..35
                       mol_type = other DNA
                       organism = synthetic construct
SEQUENCE: 81
cggggtacca taattgtcca aatagttatg gtagc                               35

SEQ ID NO: 82          moltype = DNA   length = 24
FEATURE                Location/Qualifiers
misc_feature           1..24
                       note = Primer No. : Si_614
source                 1..24
                       mol_type = other DNA
                       organism = synthetic construct
SEQUENCE: 82
catgccatgg cggcaaggct cctc                                           24

SEQ ID NO: 83          moltype = DNA   length = 29
FEATURE                Location/Qualifiers
misc_feature           1..29
                       note = Primer No. : Si_615
source                 1..29
                       mol_type = other DNA
                       organism = synthetic construct
SEQUENCE: 83
cggggtacct ttatttgtca acactgccc                                      29

SEQ ID NO: 84          moltype = DNA   length = 26
FEATURE                Location/Qualifiers
misc_feature           1..26
                       note = Primer No. : Si_616
source                 1..26
                       mol_type = other DNA
                       organism = synthetic construct
SEQUENCE: 84
cggggtacct gcgggtctt tactcg                                          26

SEQ ID NO: 85          moltype = DNA   length = 30
FEATURE                Location/Qualifiers
misc_feature           1..30
                       note = Primer No. : Si_585
source                 1..30
                       mol_type = other DNA
                       organism = synthetic construct
SEQUENCE: 85
cagtctcgag atgcagatct tcgtcaagac                                     30

SEQ ID NO: 86          moltype = DNA   length = 43
FEATURE                Location/Qualifiers
misc_feature           1..43
                       note = Primer No. : Si_586
source                 1..43
                       mol_type = other DNA
```

```
                            organism = synthetic construct
SEQUENCE: 86
gttaaagctt gctagcttcg aaaccaccac gtagacgtaa gac                    43

SEQ ID NO: 87               moltype = DNA   length = 48
FEATURE                     Location/Qualifiers
misc_feature                1..48
                            note = Primer No. : Si_588
source                      1..48
                            mol_type = other DNA
                            organism = synthetic construct
SEQUENCE: 87
cagtttcgaa gattataaag atgatgatga taaaatggcc gagccttg               48

SEQ ID NO: 88               moltype = DNA   length = 53
FEATURE                     Location/Qualifiers
misc_feature                1..53
                            note = primer No. 733
source                      1..53
                            mol_type = other DNA
                            organism = synthetic construct
SEQUENCE: 88
ttactactcg agggtgccat cgatgccgaa gaaattattc ataatattgc ccg          53

SEQ ID NO: 89               moltype = DNA   length = 39
FEATURE                     Location/Qualifiers
misc_feature                1..39
                            note = primer No. 735
source                      1..39
                            mol_type = other DNA
                            organism = synthetic construct
SEQUENCE: 89
tactccttcg aattaatgat ccatttcatc accaatttg                         39

SEQ ID NO: 90               moltype = DNA   length = 50
FEATURE                     Location/Qualifiers
misc_feature                1..50
                            note = primer No. 736
source                      1..50
                            mol_type = other DNA
                            organism = synthetic construct
SEQUENCE: 90
ttactactcg agggtgccat cgatgccaaa aaactgagcg aatgtctgcg              50

SEQ ID NO: 91               moltype = DNA   length = 37
FEATURE                     Location/Qualifiers
misc_feature                1..37
                            note = primer No. 738
source                      1..37
                            mol_type = other DNA
                            organism = synthetic construct
SEQUENCE: 91
tactccttcg aattagctat ccagttcatc accaatg                           37

SEQ ID NO: 92               moltype = DNA   length = 43
FEATURE                     Location/Qualifiers
misc_feature                1..43
                            note = primer No. 734
source                      1..43
                            mol_type = other DNA
                            organism = synthetic construct
SEQUENCE: 92
tactccttcg aaggcaccat gatccatttc atcaccaatt tgg                    43

SEQ ID NO: 93               moltype = DNA   length = 33
FEATURE                     Location/Qualifiers
misc_feature                1..33
                            note = primer No. 725
source                      1..33
                            mol_type = other DNA
                            organism = synthetic construct
SEQUENCE: 93
ttactattcg aagaaattat tcataatatt gcc                               33

SEQ ID NO: 94               moltype = DNA   length = 50
FEATURE                     Location/Qualifiers
misc_feature                1..50
                            note = primer No. 726
source                      1..50
```

```
                              mol_type = other DNA
                              organism = synthetic construct
SEQUENCE: 94
tactccaagc ttacggttga atattatgat ccatttcatc accaatttgg          50

SEQ ID NO: 95              moltype = DNA  length = 49
FEATURE                    Location/Qualifiers
misc_feature               1..49
                              note = primer No. 727
source                     1..49
                              mol_type = other DNA
                              organism = synthetic construct
SEQUENCE: 95
ttactattcg aagccggtgg tgccgaagaa attattcata atattgccc            49

SEQ ID NO: 96              moltype = DNA  length = 29
FEATURE                    Location/Qualifiers
misc_feature               1..29
                              note = primer No. 728
source                     1..29
                              mol_type = other DNA
                              organism = synthetic construct
SEQUENCE: 96
tactccaagc ttaatgatcc atttcatca                                 29

SEQ ID NO: 97              moltype = DNA  length = 40
FEATURE                    Location/Qualifiers
misc_feature               1..40
                              note = primer No. 737
source                     1..40
                              mol_type = other DNA
                              organism = synthetic construct
SEQUENCE: 97
tactccttcg aaggcaccgc tatccagttc atcaccaatg                     40

SEQ ID NO: 98              moltype = AA  length = 394
FEATURE                    Location/Qualifiers
REGION                     1..394
                              note = YopE1-138 2xTEVsite - EGFP
source                     1..394
                              mol_type = protein
                              organism = synthetic construct
SEQUENCE: 98
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE SRENLYFQSE NLYFQSVSKG EELFTGVVPI LVELDGDVNG   180
HKFSVSGEGE GDATYGKLTL KFICTTGKLP VPWPTLVTTL TYGVQCFSRY PDHMKQHDFF   240
KSAMPEGYVQ ERTIFFKDDG NYKTRAEVKF EGDTLVNRIE LKGIDFKEDG NILGHKLEYN   300
YNSHNVYIMA DKQKNGIKVN FKIRHNIEDG SVQLADHYQQ NTPIGDGPVL LPDNHYLSTQ   360
SALSKDPNEK RDHMVLLEFV TAAGITLGMD ELYK                              394

SEQ ID NO: 99              moltype = AA  length = 401
FEATURE                    Location/Qualifiers
REGION                     1..401
                              note = YopE1-138 - 2xTEVsite - NLS - EGFP
source                     1..401
                              mol_type = protein
                              organism = synthetic construct
SEQUENCE: 99
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE SRENLYFQSV SKGQSPPKKK RKVVSKGEEL FTGVVPILVE   180
LDGDVNGHKF SVSGEGEGDA TYGKLTLKFI CTTGKLPVPW PTLVTTLTYG VQCFSRYPDH   240
MKQHDFFKSA MPEGYVQERT IFFKDDGNYK TRAEVKFEGD TLVNRIELKG IDFKEDGNIL   300
GHKLEYNYNS HNVYIMADKQ KNGIKVNFKI RHNIEDGSVQ LADHYQQNTP IGDGPVLLPD   360
NHYLSTQSAL SKDPNEKRDH MVLLEFVTAA GITLGMDELY K                      401

SEQ ID NO: 100             moltype = AA  length = 402
FEATURE                    Location/Qualifiers
REGION                     1..402
                              note = YopE1-138 - 2xTEVsite - EGFP - NLS
source                     1..402
                              mol_type = protein
                              organism = synthetic construct
SEQUENCE: 100
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE SRENLYFQSE NLYFQSVSKG EELFTGVVPI LVELDGDVNG   180
HKFSVSGEGE GDATYGKLTL KFICTTGKLP VPWPTLVTTL TYGVQCFSRY PDHMKQHDFF   240
```

```
KSAMPEGYVQ ERTIFFKDDG NYKTRAEVKF EGDTLVNRIE LKGIDFKEDG NILGHKLEYN    300
YNSHNVYIMA DKQKNGIKVN FKIRHNIEDG SVQLADHYQQ NTPIGDGPVL LPDNHYLSTQ    360
SALSKDPNEK RDHMVLLEFV TAAGITLGMD ELYKPPKKKR KV                       402

SEQ ID NO: 101           moltype = DNA   length = 36
FEATURE                  Location/Qualifiers
misc_feature             1..36
                         note = primer No. 869
source                   1..36
                         mol_type = other DNA
                         organism = synthetic construct
SEQUENCE: 101
gatcgtcgac ttaagttcaa tggagcgttt aatatc                                36

SEQ ID NO: 102           moltype = DNA   length = 41
FEATURE                  Location/Qualifiers
misc_feature             1..41
                         note = primer No. 870
source                   1..41
                         mol_type = other DNA
                         organism = synthetic construct
SEQUENCE: 102
ctttgactgg cgagaaacgc tcttaacatg aggctgagct c                          41

SEQ ID NO: 103           moltype = DNA   length = 41
FEATURE                  Location/Qualifiers
misc_feature             1..41
                         note = primer No. 871
source                   1..41
                         mol_type = other DNA
                         organism = synthetic construct
SEQUENCE: 103
gagctcagcc tcatgttaag agcgtttctc gccagtcaaa g                          41

SEQ ID NO: 104           moltype = DNA   length = 40
FEATURE                  Location/Qualifiers
misc_feature             1..40
                         note = primer No. 872
source                   1..40
                         mol_type = other DNA
                         organism = synthetic construct
SEQUENCE: 104
gatagccccc gagcctgtgc actttgtcat taacctcagc                            40

SEQ ID NO: 105           moltype = DNA   length = 40
FEATURE                  Location/Qualifiers
misc_feature             1..40
                         note = primer No. 873
source                   1..40
                         mol_type = other DNA
                         organism = synthetic construct
SEQUENCE: 105
gctgaggtta atgacaaagt gcacaggctc gggggctatc                            40

SEQ ID NO: 106           moltype = DNA   length = 31
FEATURE                  Location/Qualifiers
misc_feature             1..31
                         note = primer No. 874
source                   1..31
                         mol_type = other DNA
                         organism = synthetic construct
SEQUENCE: 106
catgtctaga ccctcagcat aataacgact c                                     31

SEQ ID NO: 107           moltype = DNA   length = 24
FEATURE                  Location/Qualifiers
misc_feature             1..24
                         note = primer No. 600
source                   1..24
                         mol_type = other DNA
                         organism = synthetic construct
SEQUENCE: 107
catgacatgt tggcgtttct cgcc                                             24

SEQ ID NO: 108           moltype = DNA   length = 34
FEATURE                  Location/Qualifiers
misc_feature             1..34
                         note = primer No. 601
source                   1..34
```

-continued

```
                        mol_type = other DNA
                        organism = synthetic construct
SEQUENCE: 108
catgacatgt attaacctca gccctgacta taag                             34

SEQ ID NO: 109          moltype = DNA   length = 138
FEATURE                 Location/Qualifiers
misc_feature            1..138
                        note = Multiple cloning site of pBad_Si_1 and pBad_Si_2
source                  1..138
                        mol_type = other DNA
                        organism = synthetic construct
SEQUENCE: 109
gttcgccacg ctcgagtcta gattcgaaaa gcttgggccc gaacaaaaac tcatctcaga      60
agaggatctg aatagcgccg tcgaccatca tcatcatcat cattgagttt aaacggtctc     120
cagcttggct gttttggc                                                  138

SEQ ID NO: 110          moltype = AA   length = 371
FEATURE                 Location/Qualifiers
REGION                  1..371
                        note = YopE1-138 - Y. enterocolitica codon optimized murine
                        RIG1 CARD domains (Aa. 1-229)
source                  1..371
                        mol_type = protein
                        organism = synthetic construct
SEQUENCE: 110
MKISSFISTS LPLPASVSGS SSVGEMSGRS VSQQKSDQYA NNLAGRTESP QGSSLASRII      60
ERLSSMAHSV IGFIQRMFSE GSHKPVVTPA LTPAQMPSPT SFSDSIKQLA AETLPKYMQQ     120
LSSLDAETLQ KNHDQFATLE SRMTAEQRQN LQAFRDYIKK ILDPTYILSY MSSWLEDEEV     180
QYIQAEKNNK GPMEAASLFL QYLLKLQSEG WFQAFLDALY HAGYCGLCEA IESWDFQKIE     240
KLEEHRLLLR RLEPEFKATV DPNDILSELS ECLINQECEE IRQIRDTKGR MAGAEKMAEC     300
LIRSDKENWP KVLQLALEKD NSKFSELWIV DKGFKRAESK ADEDDGAEAS SIQIFIQEEP     360
ECQNLSQNPG P                                                         371

SEQ ID NO: 111          moltype = AA   length = 360
FEATURE                 Location/Qualifiers
REGION                  1..360
                        note = YopE1-138 - Y. enterocolitica codon optimized murine
                        RIG1 CARD domains (Aa. 1-218)
source                  1..360
                        mol_type = protein
                        organism = synthetic construct
SEQUENCE: 111
MKISSFISTS LPLPASVSGS SSVGEMSGRS VSQQKSDQYA NNLAGRTESP QGSSLASRII      60
ERLSSMAHSV IGFIQRMFSE GSHKPVVTPA LTPAQMPSPT SFSDSIKQLA AETLPKYMQQ     120
LSSLDAETLQ KNHDQFATLE SRMTAEQRQN LQAFRDYIKK ILDPTYILSY MSSWLEDEEV     180
QYIQAEKNNK GPMEAASLFL QYLLKLQSEG WFQAFLDALY HAGYCGLCEA IESWDFQKIE     240
KLEEHRLLLR RLEPEFKATV DPNDILSELS ECLINQECEE IRQIRDTKGR MAGAEKMAEC     300
LIRSDKENWP KVLQLALEKD NSKFSELWIV DKGFKRAESK ADEDDGAEAS SIQIFIQEEP     360

SEQ ID NO: 112          moltype = AA   length = 436
FEATURE                 Location/Qualifiers
REGION                  1..436
                        note = YopE1-138 - Y. enterocolitica codon optimized murine
                        MDA5 (Aa. 1-294)
source                  1..436
                        mol_type = protein
                        organism = synthetic construct
SEQUENCE: 112
MKISSFISTS LPLPASVSGS SSVGEMSGRS VSQQKSDQYA NNLAGRTESP QGSSLASRII      60
ERLSSMAHSV IGFIQRMFSE GSHKPVVTPA LTPAQMPSPT SFSDSIKQLA AETLPKYMQQ     120
LSSLDAETLQ KNHDQFATLE SRMSIVCSAE DSFRNLILFF RPRLKMYIQV EPVLDHLIFL     180
SAETKEQILK KINTCGNTSA AELLLSTLEQ GQWPLGWTQM FVEALEHSGN PLAARYVKPT     240
LTDLPSPSSE TAHDECLHLL TLLQPTLVDK LLINDVLDTC FEKGLLTVED RNRISAAGNS     300
GNESGVRELL RRIVQKENWF STFLDVLRQT GNDALFQELT GGGCPEDNTD LANSSHRDGP     360
AANECLLPAV DESSLETEAW NVDDILPEAS CTDSSVTTES DTSLAEGSVS CFDESLGHNS     420
NMGRDSGTMG SDSDES                                                    436

SEQ ID NO: 113          moltype = AA   length = 373
FEATURE                 Location/Qualifiers
REGION                  1..373
                        note = YopE1-138 - Y. enterocolitica codon optimized murine
                        MDA5 (Aa. 1-231)
source                  1..373
                        mol_type = protein
                        organism = synthetic construct
SEQUENCE: 113
MKISSFISTS LPLPASVSGS SSVGEMSGRS VSQQKSDQYA NNLAGRTESP QGSSLASRII      60
ERLSSMAHSV IGFIQRMFSE GSHKPVVTPA LTPAQMPSPT SFSDSIKQLA AETLPKYMQQ     120
```

```
LSSLDAETLQ KNHDQFATLE SRMSIVCSAE DSFRNLILFF RPRLKMYIQV EPVLDHLIFL    180
SAETKEQILK KINTCGNTSA AELLLSTLEQ GQWPLGWTQM FVEALEHSGN PLAARYVKPT    240
LTDLPSPSSE TAHDECLHLL TLLQPTLVDK LLINDVLDTC FEKGLLTVED RNRISAAGNS    300
GNESGVRELL RRIVQKENWF STFLDVLRQT GNDALFQELT GGGCPEDNTD LANSSHRDGP    360
AANECLLPAV DES                                                       373

SEQ ID NO: 114           moltype = AA  length = 349
FEATURE                  Location/Qualifiers
REGION                   1..349
                         note = YopE1-138- Y. enterocolitica codon optimized B.
                         subtilis CdaS L44F constitutive active version
source                   1..349
                         mol_type = protein
                         organism = synthetic construct
SEQUENCE: 114
MKISSFISTS LPLPASVSGS SSVGEMSGRS VSQQKSDQYA NNLAGRTESP QGSSLASRII     60
ERLSSMAHSV IGFIQRMFSE GSHKPVVTPA LTPAQMPSPT SFSDSIKQLA AETLPKYMQQ    120
LSSLDAETLQ KNHDQFATLE SRMKAMRYEQ ISENAFKGKI QVYLEQILGD ASLILKTLHE    180
KDQCLFCELD DLGHVFQDMQ GIASSFYLQS YIEEFTPAFI ELAKAIKALS EHKHGALIVI    240
ERADPVERFI QKGTSLHAEI SSSLIESIFF PGNPLHDGAL LVRENKLVSA ANVLPLTTKE    300
VDIHLGTRHR AALGMSGYTD ALVLVVSEET GKMSFAKDGV LYPLISPRT                349

SEQ ID NO: 115           moltype = AA  length = 504
FEATURE                  Location/Qualifiers
REGION                   1..504
                         note = YopE1-138- Y. enterocolitica codon optimized human
                         cGAS (Aa. 161-522)
source                   1..504
                         mol_type = protein
                         organism = synthetic construct
SEQUENCE: 115
MKISSFISTS LPLPASVSGS SSVGEMSGRS VSQQKSDQYA NNLAGRTESP QGSSLASRII     60
ERLSSMAHSV IGFIQRMFSE GSHKPVVTPA LTPAQMPSPT SFSDSIKQLA AETLPKYMQQ    120
LSSLDAETLQ KNHDQFATLE SRGASKLRAV LEKLKLSRDD ISTAAGMVKG VVDHLLLRLK    180
CDSAFRGVGL LNTGSYYEHV KISAPNEFDV MPFKLEVPRIQ LEEYSNTRAY YFVKFKRNPK   240
ENPLSQFLEG EILSASKMLS KFRKIIKEEI NDIKDTDVIM KRKRGGSPAV TLLISEKISV    300
DITLALESKS SWPASTQEGL RIQNWLSAKV RKQLRLKPFY LVPKHAKEGN GFQEETWRLS    360
FSHIEKEILN NHGKSKTCCE NKEEKCCRKD CLKLMKYLLE QLKERFKDKK HLDKFSSYHV    420
KTAFFHVCTQ NPQDSQWDRK DLGLCFDNCV TYFLQCLRTE KLENYFIPEF NLFSSNLIDK    480
RSKEFLTKQI EYERNNEFPV FDEF                                           504

SEQ ID NO: 116           moltype = AA  length = 242
FEATURE                  Location/Qualifiers
REGION                   1..242
                         note = YopE1-138- Y. enterocolitica codon optimized human
                         MAVS CARD (Aa. 1-100)
source                   1..242
                         mol_type = protein
                         organism = synthetic construct
SEQUENCE: 116
MKISSFISTS LPLPASVSGS SSVGEMSGRS VSQQKSDQYA NNLAGRTESP QGSSLASRII     60
ERLSSMAHSV IGFIQRMFSE GSHKPVVTPA LTPAQMPSPT SFSDSIKQLA AETLPKYMQQ    120
LSSLDAETLQ KNHDQFATLE SRMPFAEDKT YKYICRNFSN FCNVDVVEIL PYLPCLTARD    180
QDRLRATCTL SGNRDTLWHL FNTLQRRPGW VEYFIAALRG CELVDLADEV ASVYESYQPR    240
TS                                                                    242

SEQ ID NO: 117           moltype = AA  length = 505
FEATURE                  Location/Qualifiers
REGION                   1..505
                         note = YopE1-138- Y. enterocolitica codon optimized
                         Anemonae (N. vectensis) cGAS (Aa. 60-422) (Ensembl:
                         A7SFB5.1)
source                   1..505
                         mol_type = protein
                         organism = synthetic construct
SEQUENCE: 117
MKISSFISTS LPLPASVSGS SSVGEMSGRS VSQQKSDQYA NNLAGRTESP QGSSLASRII     60
ERLSSMAHSV IGFIQRMFSE GSHKPVVTPA LTPAQMPSPT SFSDSIKQLA AETLPKYMQQ    120
LSSLDAETLQ KNHDQFATLE SRQPFPKGDL ETLRRFSVTD VKISKQSTKW AKKMADKHLE    180
IIRKHCKTNS IKLFNHFEYT GSFYEHLKTI DADELDIMVA LSIKMDELEV EQVTPGYAGL    240
KLRDTPSNRN KYNDLTIADN YGRYLSPEKV SRWFFSLVQK AVNTYKDEIP QTEVKLTDNG    300
PATTLVITYR EGDKPQEKNR RLSIDLVPAL LFKDKTKPAG DDLRAWHYVA KTIPKGARLK    360
EPLPFRSELL WRQSFSLKEK HLMDKLDKDD NGCRREMVRI VKTIVKKDPT LAQLSSYHIK    420
TAFLQYNFSD VKLDWEGKKL AERFLHFLEF LRDRVKDKTL NNYFITDLNL LDDLNDSNID    480
NIANRLDKII QNETERAKIF TTQRQ                                          505

SEQ ID NO: 118           moltype = AA  length = 315
FEATURE                  Location/Qualifiers
REGION                   1..315
```

```
                         note = YopE1-138- Y. enterocolitica codon optimized
                          Listeria CdaA (Aa. 101-273)
source                   1..315
                         mol_type = protein
                         organism = synthetic construct
SEQUENCE: 118
MKISSFISTS LPLPASVSGS SSVGEMSGRS VSQQKSDQYA NNLAGRTESP QGSSLASRII  60
ERLSSMAHSV IGFIQRMFSE GSHKPVVTPA LTPAQMPSPT SFSDSIKQLA AETLPKYMQQ  120
LSSLDAETLQ KNHDQFATLE SRYGSRIERE QHHLIESIEK STQYMAKRRI GALISVARDT  180
GMDDYIETGI PLNAKISSQL LINIFIPNTP LHDGAVIIKG NEIASAASYL PLSDSPFLSK  240
ELGTRHRAAL GISEVTDSIT IVVSEETGGI SLTKGGELFR DVSEEELHKI LLKELVTVTA  300
KKPSIFSKWK GGKSE                                                   315

SEQ ID NO: 119           moltype = DNA  length = 36
FEATURE                  Location/Qualifiers
misc_feature             1..36
                         note = primer No. 1010
source                   1..36
                         mol_type = other DNA
                         organism = synthetic construct
SEQUENCE: 119
cacatgtcta gacaaccgtt tccgaaaggt gatctg                           36

SEQ ID NO: 120           moltype = DNA  length = 37
FEATURE                  Location/Qualifiers
misc_feature             1..37
                         note = primer No. 1012
source                   1..37
                         mol_type = other DNA
                         organism = synthetic construct
SEQUENCE: 120
atcccaagct tattggcgtt gggtggtaaa aattttg                          37

SEQ ID NO: 121           moltype = DNA  length = 30
FEATURE                  Location/Qualifiers
misc_feature             1..30
                         note = primer No. 1021
source                   1..30
                         mol_type = other DNA
                         organism = synthetic construct
SEQUENCE: 121
cacatgtcta gaatgaccgc cgaacaacgc                                  30

SEQ ID NO: 122           moltype = DNA  length = 30
FEATURE                  Location/Qualifiers
misc_feature             1..30
                         note = primer No. 1022
source                   1..30
                         mol_type = other DNA
                         organism = synthetic construct
SEQUENCE: 122
catgaagctt acggacccgg attttggctc                                  30

SEQ ID NO: 123           moltype = DNA  length = 39
FEATURE                  Location/Qualifiers
misc_feature             1..39
                         note = primer No. 1023
source                   1..39
                         mol_type = other DNA
                         organism = synthetic construct
SEQUENCE: 123
catgaagctt acggttcttc ttgaataaaa atttgaatg                        39

SEQ ID NO: 124           moltype = DNA  length = 33
FEATURE                  Location/Qualifiers
misc_feature             1..33
                         note = primer No. 1024
source                   1..33
                         mol_type = other DNA
                         organism = synthetic construct
SEQUENCE: 124
catgaagctt attgcagcac tttcggccaa ttt                              33

SEQ ID NO: 125           moltype = DNA  length = 32
FEATURE                  Location/Qualifiers
misc_feature             1..32
                         note = primer No. 1025
source                   1..32
                         mol_type = other DNA

```
                        organism = synthetic construct
SEQUENCE: 125
cacatgtcta gaatgagcat tgtgtgtagc gc                              32

SEQ ID NO: 126          moltype = DNA  length = 29
FEATURE                 Location/Qualifiers
misc_feature            1..29
                        note = primer No. 1026
source                  1..29
                        mol_type = other DNA
                        organism = synthetic construct
SEQUENCE: 126
catgaagctt agctttcatc cacggccgg                                  29

SEQ ID NO: 127          moltype = DNA  length = 30
FEATURE                 Location/Qualifiers
misc_feature            1..30
                        note = primer No. 1027
source                  1..30
                        mol_type = other DNA
                        organism = synthetic construct
SEQUENCE: 127
catgaagctt aattaccggt ttggcgcagc                                 30

SEQ ID NO: 128          moltype = AA  length = 370
FEATURE                 Location/Qualifiers
REGION                  1..370
                        note = YopE1-138 - Y. enterocolitica codon optimized human
                         RIG1 CARD domains (Aa. 1-228)
source                  1..370
                        mol_type = protein
                        organism = synthetic construct
SEQUENCE: 128
MKISSFISTS LPLPASVSGS SSVGEMSGRS VSQQKSDQYA NNLAGRTESP QGSSLASRII   60
ERLSSMAHSV IGFIQRMFSE GSHKPVVTPA LTPAQMPSPT SFSDSIKQLA AETLPKYMQQ  120
LSSSLDAETLQ KNHDQFATLE SRMTTEQRRS LQAFQDYIRK TLDPTYILSY MAPWFREEEV  180
QYIQAEKNNK GPMEAATLFL KFLLELQEEG WFRGFLDALD HAGYSGLYEA IESWDFKKIE  240
KLEEYRLLLK RLQPEFKTRI IPTDIISDLS ECLINQECEE ILQICSTKGM MAGAEKLVEC  300
LLRSDKENWP KTLKLALEKE RNKFSELWIV EKGIKDVETE DLEDKMETSD IQIFYQEDPE  360
CQNLSENSCP                                                        370

SEQ ID NO: 129          moltype = AA  length = 358
FEATURE                 Location/Qualifiers
REGION                  1..358
                        note = YopE1-138 - Y. enterocolitica codon optimized human
                         RIG1 CARD domains (Aa. 1-217)
source                  1..358
                        mol_type = protein
                        organism = synthetic construct
SEQUENCE: 129
KISSFISTSL PLPASVSGSS SVGEMSGRSV SQQKSDQYAN NLAGRTESPQ GSSLASRIIE   60
RLSSMAHSVI GFIQRMFSEG SHKPVVTPAL TPAQMPSPTS FSDSIKQLAA ETLPKYMQQL  120
SSSLDAETLQK NHDQFATLES RMTTEQRRSL QAFQDYIRKT LDPTYILSYM APWFREEEVQ  180
YIQAEKNNKG PMEAATLFLK FLLELQEEGW FRGFLDALDH AGYSGLYEAI ESWDFKKIEK  240
LEEYRLLLKR LQPEFKTRII PTDIISDLSE CLINQECEEI LQICSTKGMM AGAEKLVECL  300
LRSDKENWPK TLKLALEKER NKFSELWIVE KGIKDVETED LEDKMETSDI QIFYQEDP   358

SEQ ID NO: 130          moltype = AA  length = 243
FEATURE                 Location/Qualifiers
REGION                  1..243
                        note = YopE1-138 - Y. enterocolitica codon optimized murine
                         MAVS CARD domain (Aa. 1-101)
source                  1..243
                        mol_type = protein
                        organism = synthetic construct
SEQUENCE: 130
MKISSFISTS LPLPASVSGS SSVGEMSGRS VSQQKSDQYA NNLAGRTESP QGSSLASRII   60
ERLSSMAHSV IGFIQRMFSE GSHKPVVTPA LTPAQMPSPT SFSDSIKQLA AETLPKYMQQ  120
LSSSLDAETLQ KNHDQFATLE SRMTFAEDKT YKYIRDNHSK FCCVDVLEIL PYLSCLTASD  180
QDRLRASYRQ IGNRDTLWGL FNNLQRRPGW VEVFIRALQI CELPGLADQV TRVYQSYLPP  240
GTS                                                               243

SEQ ID NO: 131          moltype = AA  length = 504
FEATURE                 Location/Qualifiers
REGION                  1..504
                        note = YopE1-138- Y. enterocolitica codon optimized murine
                         cGAS (Aa. 146-507)
source                  1..504
                        mol_type = protein
```

```
                        organism = synthetic construct
SEQUENCE: 131
MKISSFISTS LPLPASVSGS SSVGEMSGRS VSQQKSDQYA NNLAGRTESP QGSSLASRII    60
ERLSSMAHSV IGFIQRMFSE GSHKPVVTPA LTPAQMPSPT SFSDSIKQLA AETLPKYMQQ   120
LSSLDAETLQ KNHDQFATLE SREPDKLKKV LDKLRLKRKD ISEAAETVNK VVERLLRRMQ   180
KRESEFKGVE QLNTGSYYEH VKISAPNEFD VMFKLEVPRI ELQEYYETGA FYLVKFKRIP   240
RGNPLSHFLE GEVLSATKML SKFRKIIKEE VKEIKDIDVS VEKEKPGSPA VTLLIRNPEE   300
ISVDIILALE SKGSWPISTK EGLPIQGWLG TKVRTNLRRE PFYLVPKNAK DGNSFQGETW   360
RLSFSHTEKY ILNNHGIEKT CCESSGAKCC RKECLKLMKY LLEQLKKEFQ ELDAFCSYHV   420
KTAIFHMWTQ DPQDSQWDPR NLSSCFDKLL AFFLECLRTE KLDHYFIPKF NLFSQELIDR   480
KSKEFLSKKI EYERNNGFPI FDKL                                         504

SEQ ID NO: 132          moltype = AA   length = 5
FEATURE                 Location/Qualifiers
source                  1..5
                        mol_type = protein
                        organism = synthetic construct
SEQUENCE: 132
DDDDK                                                                5

SEQ ID NO: 133          moltype = AA   length = 8
FEATURE                 Location/Qualifiers
source                  1..8
                        mol_type = protein
                        organism = synthetic construct
SEQUENCE: 133
LEVLFQGP                                                             8

SEQ ID NO: 134          moltype = AA   length = 7
FEATURE                 Location/Qualifiers
source                  1..7
                        mol_type = protein
                        organism = synthetic construct
SEQUENCE: 134
ENLYFQS                                                              7

SEQ ID NO: 135          moltype = AA   length = 8
FEATURE                 Location/Qualifiers
source                  1..8
                        mol_type = protein
                        organism = synthetic construct
VARIANT                 2..3
                        note = Wherein X at positions 2 and 3 can independently be
                         any amino acid
VARIANT                 5
                        note = Wherein X at position 5 can be any amino acid
SEQUENCE: 135
EXXYXQGS                                                             8

SEQ ID NO: 136          moltype = AA   length = 7
FEATURE                 Location/Qualifiers
source                  1..7
                        mol_type = protein
                        organism = synthetic construct
SEQUENCE: 136
ETVRFQS                                                              7

SEQ ID NO: 137          moltype = AA   length = 4
FEATURE                 Location/Qualifiers
source                  1..4
                        mol_type = protein
                        organism = synthetic construct
VARIANT                 2
                        note = Where the E at position 2 can also be D
SEQUENCE: 137
IEGR                                                                 4

SEQ ID NO: 138          moltype = AA   length = 6
FEATURE                 Location/Qualifiers
source                  1..6
                        mol_type = protein
                        organism = synthetic construct
SEQUENCE: 138
LVPRGS                                                               6
```

```
SEQ ID NO: 139        moltype = AA  length = 8
FEATURE               Location/Qualifiers
source                1..8
                      mol_type = protein
                      organism = synthetic construct
SEQUENCE: 139
PPKKKRKV                                                              8
```

The invention claimed is:

1. A recombinant virulence attenuated Gram-negative bacterial strain which comprises a nucleotide molecule comprising:
- a nucleotide sequence encoding a heterologous protein fused in frame to the 3'end of a nucleotide sequence encoding a delivery signal from a bacterial effector protein, and a nucleotide sequence encoding a promoter operably linked to the nucleotide sequence encoding the delivery signal from a bacterial effector protein, and wherein the heterologous protein is a protein involved in induction or regulation of an interferon (IFN) response.

2. The recombinant virulence attenuated Gram-negative bacterial strain of claim 1, wherein the protein involved in induction or regulation of an IFN response is a protein involved in induction or regulation of a type I IFN response, wherein the heterologous protein involved in induction or regulation of a type I IFN response is selected from the group consisting of the RIG-I-like receptor (RLR) family, CARD domain containing proteins involved in antiviral signaling and type I IFN induction, and cyclic dinucleotide generating enzymes such as cyclic-di-AMP, cyclic-di-GMP and cyclic-di-GAMP cyclases selected from the group consisting of WspR, DncV, DisA and DisA-like, CdaA, CdaS and cGAS, leading to stimulation of STING.

3. The recombinant virulence attenuated Gram-negative bacterial strain of claim 1, wherein the protein involved in induction or regulation of an IFN response is a protein involved in induction or regulation of a type I IFN response wherein the protein involved in induction or regulation of a type I IFN response is selected from the group consisting of RIG 1, MDA5, MAVS/IPS-1, WspR, DncV, DisA and DisA-like, CdaA, and cGAS or a fragment thereof.

4. The recombinant virulence attenuated Gram-negative bacterial strain of claim 1, wherein the recombinant virulence attenuated Gram-negative bacterial strain further comprises:

a deletion of a chromosomal gene coding for an endogenous protein essential for growth; and an endogenous virulence plasmid which comprises a nucleotide sequence comprising a gene coding for said endogenous protein essential for growth operably linked to a promoter.

5. The recombinant virulence attenuated Gram-negative bacterial strain of claim 4, wherein said virulence attenuated recombinant Gram-negative bacterial strain is deficient in producing at least one bacterial effector protein.

6. The recombinant virulence attenuated Gram-negative bacterial strain of claim 4, wherein the gene coding for an endogenous protein essential for growth is selected from a gene coding for an enzyme essential for amino acid production, a gene coding for an enzyme involved in peptidoglycan biosynthesis, a gene coding for an enzyme involved in LPS biosynthesis, a gene coding for an enzyme involved in nucleotide synthesis and a gene coding for a translation initiation factor.

7. The recombinant virulence attenuated Gram-negative bacterial strain of claim 4, wherein the gene coding for an endogenous enzyme essential for growth is a gene coding for an enzyme essential for amino acid production, wherein the enzyme essential for amino acid production is aspartate-beta-semialdehyde dehydrogenase (asd).

8. The recombinant virulence attenuated Gram-negative bacterial strain of claim 1, wherein the recombinant virulence attenuated Gram-negative bacterial strain is a *Yersinia* strain.

9. The recombinant virulence attenuated Gram-negative bacterial strain of claim 4, wherein the gene coding for the endogenous enzyme essential for growth located on the endogenous virulence plasmid comprises its endogenous promoter and its endogenous transcriptional terminator.

10. The recombinant virulence attenuated Gram-negative bacterial strain of claim 9, wherein the gene coding for the endogenous enzyme essential for growth, its endogenous promoter and its endogenous transcriptional terminator are located 122 bp upstream of the start of orf155 (SycO) on the endogenous virulence plasmid.

11. The recombinant virulence attenuated Gram-negative bacterial strain of claim 1, wherein the recombinant virulence attenuated Gram-negative bacterial strain further comprises a modulation within a RNA thermosensor region upstream of a gene coding for an endogenous AraC-type DNA binding protein.

12. The recombinant virulence attenuated Gram-negative bacterial strain of claim 11, wherein the modulation within a RNA thermosensor region upstream of a gene coding for an endogenous AraC-type DNA binding protein comprises a deletion which removes a RNA hairpin structure or parts thereof upstream of the gene coding for an endogenous AraC-type DNA binding protein.

13. The recombinant virulence attenuated Gram-negative bacterial strain of claim 11, wherein the AraC-type DNA binding protein is VirF.

14. The recombinant virulence attenuated Gram-negative bacterial strain of claim 1, wherein the recombinant virulence attenuated Gram-negative bacterial strain is *Yersinia enterolitica.*

15. A recombinant virulence attenuated Gram-negative bacterial strain which comprises a nucleotide molecule comprising:

a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a deletion of a chromosomal gene coding for an endogenous protein essential for growth and an endogenous virulence plasmid which comprises a nucleotide sequence comprising a gene coding for said endogenous protein essential for growth operably linked to a promoter.

16. The recombinant virulence attenuated Gram-negative bacterial strain of claim 15, wherein said virulence attenuated recombinant Gram-negative bacterial strain is deficient in producing at least one bacterial effector protein.

17. The recombinant virulence attenuated Gram-negative bacterial strain of claim 15, wherein the gene coding for an endogenous protein essential for growth is selected from a gene coding for an enzyme essential for amino acid production, a gene coding for an enzyme involved in peptidoglycan biosynthesis, a gene coding for an enzyme involved in LPS biosynthesis, a gene coding for an enzyme involved in nucleotide synthesis and a gene coding for a translation initiation factor.

18. The recombinant virulence attenuated Gram-negative bacterial strain of claim 15, wherein the gene coding for an endogenous enzyme essential for growth is a gene coding for an enzyme essential for amino acid production, wherein the enzyme essential for amino acid production is aspartate-beta-semialdehyde dehydrogenase (asd).

19. The recombinant virulence attenuated Gram-negative bacterial strain of claim 15, wherein the recombinant virulence attenuated Gram-negative bacterial strain is a *Yersinia* strain.

20. The recombinant virulence attenuated Gram-negative bacterial strain of claim 15, wherein the gene coding for an endogenous enzyme essential for growth located on the endogenous virulence plasmid comprises its endogenous promoter and its endogenous transcriptional terminator.

21. The recombinant virulence attenuated Gram-negative bacterial strain of claim 20, wherein the gene coding for the endogenous enzyme essential for growth, its endogenous promoter and its endogenous transcriptional terminator are located 122 bp upstream of the start of orf155 (SycO) on the endogenous virulence plasmid.

22. The recombinant virulence attenuated Gram-negative bacterial strain of claim 15, wherein the recombinant virulence attenuated Gram-negative bacterial strain further comprises a modulation within a RNA thermosensor region upstream of a gene coding for an endogenous AraC-type DNA binding protein.

23. A recombinant virulence attenuated Gram-negative bacterial strain which comprises a nucleotide molecule comprising:

a nucleotide sequence encoding a heterologous protein fused in frame to the 3'end of a nucleotide sequence encoding a delivery signal from a bacterial effector protein, and a nucleotide sequence encoding a promoter operably linked to the nucleotide sequence encoding the delivery signal from a bacterial effector protein, wherein the recombinant virulence attenuated Gram-negative bacterial strain further comprises a modulation within a RNA thermosensor region upstream of a gene coding for an endogenous AraC-type DNA binding protein.

24. The recombinant virulence attenuated Gram-negative bacterial strain of claim 22, wherein the modulation within a RNA thermosensor region upstream of a gene coding for an endogenous AraC-type DNA binding protein comprises a deletion which removes a RNA hairpin structure or parts thereof upstream of the gene coding for an endogenous AraC-type DNA binding protein.

25. The recombinant virulence attenuated Gram-negative bacterial strain of claim 22, wherein the AraC-type DNA binding protein is a bacterial transcription regulation protein which binds DNA through a helix-turn-helix motif.

26. The recombinant virulence attenuated Gram-negative bacterial strain of claim 22, wherein the AraC-type DNA binding protein is selected from the group consisting of VirF, LcrF, YbtA, Rns, MxiE, AraC, XylS, ExsA, PerA, MmsR, RhaS, TcpN, HrpX, HrpB, GadX, HilC, HilD, MarA, CafR, FapR and InvF.

27. The recombinant virulence attenuated Gram-negative bacterial strain of claim 22, wherein the recombinant virulence attenuated Gram-negative bacterial strain is *Yersinia enterolitica* and the AraC-type DNA binding protein is VirF.

28. The recombinant virulence attenuated Gram-negative bacterial strain of claim 15, wherein the heterologous protein is selected from the group consisting of proteins involved in induction or regulation of an interferon (IFN) response, proteins involved in apoptosis or apoptosis regulation, cell cycle regulators, ankyrin repeat proteins, cell signalling proteins, reporter proteins, transcription factors, proteases, small GTPases, GPCR related proteins, nanobody fusion constructs and nanobodies, bacterial T3SS effectors, bacterial T4SS effectors and viral proteins.

29. A method of treating cancer in a subject, the method comprising: administering to the subject the recombinant virulence attenuated Gram-negative bacterial strain of claim 1, wherein the recombinant virulence attenuated Gram-negative bacterial strain is administered in an amount that is sufficient to treat the subject, wherein the cancer is breast cancer or melanoma.

* * * * *